United States Patent
Chu et al.

(10) Patent No.: US 10,117,733 B2
(45) Date of Patent: Nov. 6, 2018

(54) SYSTEMS, METHODS AND DEVICES RELATING TO DELIVERY OF MEDICAL IMPLANTS

(71) Applicant: Boston Scientific Scimed, Inc., Maple Grove, MN (US)

(72) Inventors: Michael S. H. Chu, Brookline, MA (US); Alfred P. Intoccia, Nashua, NH (US); Barry N. Gellman, N. Easton, MA (US); Joseph John Raneri, Tewksbury, MA (US); Michael Frank Weiser, Tewksbury, MA (US); Kenneth J. Daignault, Holden, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 68 days.

(21) Appl. No.: 14/875,257

(22) Filed: Oct. 5, 2015

(65) Prior Publication Data

US 2016/0022401 A1    Jan. 28, 2016

Related U.S. Application Data

(63) Continuation of application No. 10/642,365, filed on Aug. 14, 2003, now Pat. No. 9,149,261, which is a
(Continued)

(51) Int. Cl.
*A61B 17/08* (2006.01)
*A61F 2/00* (2006.01)
(Continued)

(52) U.S. Cl.
CPC ...... *A61F 2/0045* (2013.01); *A61B 17/00234* (2013.01); *A61B 17/06109* (2013.01);
(Continued)

(58) Field of Classification Search
CPC .......... A61B 17/00234; A61B 17/3468; A61B 2017/06019; A61B 2017/06042;
(Continued)

(56) References Cited

U.S. PATENT DOCUMENTS

| 568,077 A | 9/1896 | Michel et al. |
| 2,738,790 A | 3/1956 | Todt, Sr. et al. |

(Continued)

FOREIGN PATENT DOCUMENTS

| CA | 2407001 A1 | 10/2001 |
| CA | 2705609 A1 | 2/2004 |

(Continued)

OTHER PUBLICATIONS

Non-Final Office Action for U.S. Appl. No. 10/642,395, dated Oct. 7, 2013, 12 pages.
(Continued)

*Primary Examiner* — Robert Lynch
(74) *Attorney, Agent, or Firm* — Brake Hughes Bellermann LLP

(57) ABSTRACT

Implant delivery systems are disclosed. In general overview, an exemplary system includes any number of the following: a delivery device, a sling assembly, guide members, and connectors that interconnect the above. Embodiments of all the above components and their combinations are disclosed. Methods of using the above system in suprapubic, prepubic, transvaginal, trans-obturator and other approaches are also disclosed.

16 Claims, 92 Drawing Sheets

Related U.S. Application Data continuation-in-part of application No. 10/093,371, filed on Mar. 7, 2002, now Pat. No. 6,991,597, and a continuation-in-part of application No. 10/093,398, filed on Mar. 7, 2002, now Pat. No. 8,162,816, and a continuation-in-part of application No. 10/093,424, filed on Mar. 7, 2002, now Pat. No. 6,936,052, and a continuation-in-part of application No. 10/093,450, filed on Mar. 7, 2002, now Pat. No. 8,617,048, and a continuation-in-part of application No. 10/093,498, filed on Mar. 7, 2002, now Pat. No. 7,025,772, and a continuation-in-part of application No. 10/094,352, filed on Mar. 7, 2002, now Pat. No. 7,235,043.

(60) Provisional application No. 60/403,555, filed on Aug. 14, 2002, provisional application No. 60/418,827, filed on Oct. 15, 2002, provisional application No. 60/418,642, filed on Oct. 15, 2002, provisional application No. 60/434,167, filed on Dec. 17, 2002, provisional application No. 60/449,465, filed on Feb. 24, 2003, provisional application No. 60/465,722, filed on Apr. 25, 2003, provisional application No. 60/483,534, filed on Jun. 27, 2003, provisional application No. 60/274,843, filed on Mar. 9, 2001, provisional application No. 60/286,863, filed on Feb. 26, 2001.

(51) Int. Cl.
  *A61B 17/00* (2006.01)
  *A61B 17/06* (2006.01)
  *A61B 17/34* (2006.01)

(52) U.S. Cl.
  CPC ............ *A61B 17/3468* (2013.01); *A61B 2017/00805* (2013.01); *A61B 2017/06019* (2013.01); *A61B 2017/06042* (2013.01); *A61B 2017/06052* (2013.01); *A61B 2017/06076* (2013.01); *A61B 2017/06171* (2013.01); *A61F 2002/0072* (2013.01); *A61F 2220/0083* (2013.01)

(58) Field of Classification Search
  CPC ......... A61B 2017/06052; A61F 2/0045; A61F 2002/0072; A61F 2220/0083
  See application file for complete search history.

(56) References Cited

U.S. PATENT DOCUMENTS

| | | |
|---|---|---|
| 2,751,903 A | 6/1956 | Ivory et al. |
| 2,917,878 A | 12/1959 | Carnarius et al. |
| 3,372,477 A | 3/1968 | Hoppe |
| 3,472,232 A | 10/1969 | Earl |
| 3,565,073 A | 2/1971 | Giesy |
| 3,699,969 A | 10/1972 | Allen |
| 3,704,712 A | 12/1972 | Giesy et al. |
| 3,710,795 A | 1/1973 | Higuchi et al. |
| 3,802,074 A | 4/1974 | Hoppe et al. |
| 3,875,937 A | 4/1975 | Schmitt et al. |
| 3,877,434 A | 4/1975 | Ferguson et al. |
| 3,937,223 A | 2/1976 | Roth |
| 3,995,619 A | 12/1976 | Glatzer et al. |
| 4,172,458 A | 10/1979 | Pereyra |
| 4,363,319 A | 12/1982 | Altshuler et al. |
| 4,367,816 A | 1/1983 | Wilkes |
| 4,422,567 A | 12/1983 | Haynes et al. |
| 4,445,898 A | 5/1984 | Jensen |
| 4,535,768 A | 8/1985 | Hourahane et al. |
| 4,583,450 A | 4/1986 | Rost et al. |
| 4,583,540 A | 4/1986 | Malmin |
| 4,592,339 A | 6/1986 | Kuzmak et al. |
| 4,606,335 A | 8/1986 | Wedeen et al. |
| 4,739,751 A | 4/1988 | Sapega et al. |
| 4,741,330 A | 5/1988 | Hayhurst |
| 4,744,353 A | 5/1988 | Mcfarland |
| 4,776,337 A | 10/1988 | Palmaz et al. |
| 4,784,137 A | 11/1988 | Shmyrin et al. |
| 4,784,138 A | 11/1988 | Sinnett et al. |
| 4,798,193 A | 1/1989 | Geisy et al. |
| 4,824,435 A | 4/1989 | Giesy et al. |
| 4,872,451 A | 10/1989 | Moore et al. |
| 4,873,977 A | 10/1989 | Avant et al. |
| 4,874,375 A | 10/1989 | Ellison |
| 4,896,668 A | 1/1990 | Popoff et al. |
| 4,920,958 A | 5/1990 | Walt et al. |
| 4,927,420 A | 5/1990 | Newkirk et al. |
| 4,938,760 A | 7/1990 | Burton et al. |
| 4,946,468 A | 8/1990 | Li |
| 4,983,168 A | 1/1991 | Moorehead |
| 4,988,339 A | 1/1991 | Vadher |
| 5,002,550 A | 3/1991 | Li |
| 5,013,292 A | 5/1991 | Lemay |
| 5,064,435 A | 11/1991 | Porter |
| 5,078,730 A | 1/1992 | Li et al. |
| 5,084,058 A | 1/1992 | Li |
| 5,085,661 A | 2/1992 | Moss |
| 5,087,263 A | 2/1992 | Li |
| 5,089,013 A | 2/1992 | Bezwada et al. |
| 5,112,344 A | 5/1992 | Petros |
| 5,133,723 A | 7/1992 | Li et al. |
| 5,149,329 A | 9/1992 | Richardson |
| 5,152,749 A | 10/1992 | Giesy et al. |
| 5,163,946 A | 11/1992 | Li et al. |
| 5,167,634 A | 12/1992 | Corrigan et al. |
| 5,188,636 A | 2/1993 | Fedotov |
| 5,203,784 A | 4/1993 | Ross et al. |
| 5,207,679 A | 5/1993 | Li |
| 5,222,508 A | 6/1993 | Contarini et al. |
| 5,234,457 A | 8/1993 | Andersen |
| 5,250,033 A | 10/1993 | Evans et al. |
| 5,250,054 A | 10/1993 | Li |
| 5,256,133 A | 10/1993 | Spitz |
| 5,279,311 A | 1/1994 | Snyder |
| 5,281,237 A | 1/1994 | Gimpelson |
| 5,282,812 A | 2/1994 | Suarez, Jr. |
| 5,324,306 A | 6/1994 | Makower et al. |
| 5,334,185 A | 8/1994 | Giesy et al. |
| 5,337,736 A | 8/1994 | Reddy |
| 5,354,292 A | 10/1994 | Braeuer et al. |
| 5,368,595 A | 11/1994 | Lewis |
| 5,409,469 A | 4/1995 | Schaerf |
| 5,417,226 A | 5/1995 | Juma |
| 5,431,173 A | 7/1995 | Chin et al. |
| 5,437,682 A | 8/1995 | Grice et al. |
| 5,439,467 A | 8/1995 | Benderev et al. |
| 5,441,502 A | 8/1995 | Bartlett |
| 5,474,543 A | 12/1995 | Mckay |
| 5,499,991 A | 3/1996 | Garman et al. |
| 5,505,735 A | 4/1996 | Li |
| 5,520,703 A | 5/1996 | Essig et al. |
| 5,536,273 A | 7/1996 | Lehrer et al. |
| 5,544,664 A | 8/1996 | Benderev et al. |
| 5,549,623 A | 8/1996 | Sharpe et al. |
| 5,562,717 A | 10/1996 | Tippey et al. |
| 5,579,978 A | 12/1996 | Green et al. |
| 5,582,188 A | 12/1996 | Benderev et al. |
| 5,591,163 A | 1/1997 | Thompson |
| 5,611,515 A | 3/1997 | Benderev et al. |
| 5,620,012 A | 4/1997 | Benderev et al. |
| 5,624,446 A | 4/1997 | Harryman, II |
| 5,626,614 A | 5/1997 | Hart et al. |
| 5,637,112 A | 6/1997 | Moore et al. |
| 5,643,288 A | 7/1997 | Thompson |
| 5,647,857 A | 7/1997 | Anderson et al. |
| 5,683,418 A | 11/1997 | Luscombe et al. |
| 5,690,649 A | 11/1997 | Li |
| 5,697,931 A | 12/1997 | Thompson |
| 5,700,266 A | 12/1997 | Harryman, II |
| 5,700,286 A | 12/1997 | Tartalin et al. |
| 5,702,215 A | 12/1997 | Li |
| 5,742,943 A | 4/1998 | Chen |

(56) References Cited

U.S. PATENT DOCUMENTS

| | | |
|---|---|---|
| 5,749,884 A | 5/1998 | Benderev et al. |
| 5,766,221 A | 6/1998 | Benderev et al. |
| 5,776,184 A | 7/1998 | Tuch et al. |
| 5,813,408 A | 9/1998 | Benderev et al. |
| 5,814,072 A | 9/1998 | Bonutti |
| 5,816,258 A | 10/1998 | Jervis |
| 5,824,049 A | 10/1998 | Ragheb et al. |
| 5,830,220 A | 11/1998 | Wan et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,993 A | 1/1999 | Thompson et al. |
| 5,885,291 A | 3/1999 | Moskovitz et al. |
| 5,899,909 A | 5/1999 | Claren et al. |
| 5,904,692 A | 5/1999 | Steckel et al. |
| 5,935,122 A | 8/1999 | Fourkas et al. |
| 5,954,057 A | 9/1999 | Li |
| 5,997,541 A | 12/1999 | Schenk |
| 6,001,104 A | 12/1999 | Benderev et al. |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,050,937 A | 4/2000 | Benderev |
| 6,056,688 A | 5/2000 | Benderev et al. |
| 6,059,801 A | 5/2000 | Samimi |
| 6,077,216 A | 6/2000 | Benderev et al. |
| 6,096,041 A | 8/2000 | Gellman et al. |
| 6,099,538 A | 8/2000 | Moses et al. |
| 6,099,547 A | 8/2000 | Gellman et al. |
| 6,110,101 A | 8/2000 | Tihon et al. |
| 6,110,184 A | 8/2000 | Weadock |
| 6,117,067 A | 9/2000 | Gil-Vernet |
| 6,200,330 B1 | 3/2001 | Benderev et al. |
| 6,245,082 B1 | 6/2001 | Gellman et al. |
| 6,254,620 B1 | 7/2001 | Koh et al. |
| 6,264,676 B1 | 7/2001 | Gellman et al. |
| 6,273,852 B1 | 8/2001 | Lehe et al. |
| 6,299,607 B1 | 10/2001 | Osborn et al. |
| 6,312,448 B1 | 11/2001 | Bonutti et al. |
| 6,328,686 B1 | 12/2001 | Kovac |
| 6,382,214 B1 | 5/2002 | Raz et al. |
| 6,406,423 B1 | 6/2002 | Scetbon |
| 6,423,080 B1 | 7/2002 | Gellman et al. |
| 6,440,154 B2 | 8/2002 | Gellman et al. |
| D466,213 S | 11/2002 | Snitkin et al. |
| 6,478,727 B2 | 11/2002 | Scetbon |
| 6,478,763 B1 | 11/2002 | Simonsen et al. |
| 6,491,703 B1 | 12/2002 | Ulmsten |
| 6,494,887 B1 | 12/2002 | Kaladelfos |
| 6,500,194 B2 | 12/2002 | Benderev et al. |
| 6,502,578 B2 | 1/2003 | Raz et al. |
| 6,530,943 B1 | 3/2003 | Hoepffner et al. |
| 6,605,097 B1 | 8/2003 | Lehe et al. |
| 6,612,977 B2 | 9/2003 | Staskin et al. |
| 6,638,209 B2 | 10/2003 | Landgrebe |
| 6,638,210 B2 | 10/2003 | Berger |
| 6,638,211 B2 | 10/2003 | Suslian et al. |
| 6,648,921 B2 | 11/2003 | Anderson et al. |
| 6,652,450 B2 | 11/2003 | Neisz et al. |
| 6,685,629 B2 | 2/2004 | Therin |
| 6,691,711 B2 | 2/2004 | Raz et al. |
| 6,723,107 B1 | 4/2004 | Skiba et al. |
| 6,911,003 B2 | 6/2005 | Anderson et al. |
| 6,936,054 B2 | 8/2005 | Chu |
| 6,960,160 B2 | 11/2005 | Browning |
| 6,991,635 B2 | 1/2006 | Takamoto et al. |
| 7,160,314 B2 | 1/2007 | Sgro et al. |
| 7,527,633 B2 | 5/2009 | Rioux |
| 8,602,965 B2 | 12/2013 | Chu et al. |
| 8,915,927 B2 | 12/2014 | Chu et al. |
| 9,149,261 B2 | 10/2015 | Chu et al. |
| 2001/0000533 A1 | 4/2001 | Kovac et al. |
| 2001/0018549 A1 | 8/2001 | Scetbon |
| 2001/0023356 A1 | 9/2001 | Raz et al. |
| 2001/0049467 A1 | 12/2001 | Lehe et al. |
| 2001/0053916 A1 | 12/2001 | Rioux et al. |
| 2002/0013590 A1 | 1/2002 | Therin et al. |
| 2002/0022841 A1 | 2/2002 | Kovac |
| 2002/0055748 A1 | 5/2002 | Gellman et al. |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |
| 2002/0082619 A1 | 6/2002 | Cabak et al. |
| 2002/0091298 A1 | 7/2002 | Landgrebe |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0099260 A1 | 7/2002 | Suslian et al. |
| 2002/0116025 A1 | 8/2002 | Haab et al. |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |
| 2002/0151910 A1 | 10/2002 | Gellman et al. |
| 2002/0156488 A1* | 10/2002 | Gellman .......... A61B 17/00234 606/139 |
| 2002/0161382 A1 | 10/2002 | Neisz et al. |
| 2002/0165566 A1 | 11/2002 | Ulmsten et al. |
| 2002/0188169 A1 | 12/2002 | Kammerer et al. |
| 2003/0004395 A1 | 1/2003 | Therin |
| 2003/0004580 A1 | 1/2003 | Sump et al. |
| 2003/0010929 A1 | 1/2003 | Priewe et al. |
| 2003/0018350 A1 | 1/2003 | Zucherman et al. |
| 2003/0023138 A1 | 1/2003 | Luscombe |
| 2003/0036676 A1 | 2/2003 | Scetbon et al. |
| 2003/0045774 A1 | 3/2003 | Staskin et al. |
| 2003/0045892 A1 | 3/2003 | Kaladelfos et al. |
| 2003/0050530 A1 | 3/2003 | Neisz et al. |
| 2003/0100954 A1 | 5/2003 | Schuldthempe et al. |
| 2003/0130670 A1 | 7/2003 | Anderson et al. |
| 2003/0181926 A1 | 9/2003 | Dana et al. |
| 2003/0191480 A1 | 10/2003 | Ulmsten et al. |
| 2004/0015048 A1 | 1/2004 | Neisz et al. |
| 2004/0097974 A1 | 5/2004 | De Leval |
| 2004/0106845 A1 | 6/2004 | Anderson et al. |
| 2004/0176802 A1 | 9/2004 | Skiba et al. |
| 2005/0021055 A1 | 1/2005 | Toubia et al. |
| 2005/0131393 A1 | 6/2005 | Chu et al. |
| 2005/0203562 A1 | 9/2005 | Palmer et al. |
| 2005/0222601 A1 | 10/2005 | Erhard et al. |

FOREIGN PATENT DOCUMENTS

| | | |
|---|---|---|
| DE | 2305815 A1 | 8/1974 |
| DE | 2532242 A1 | 2/1977 |
| DE | 4334419 A1 | 4/1995 |
| DE | 20-2006-016866 U1 | 2/2007 |
| EP | 0140557 A3 | 9/1986 |
| EP | 0437063 A2 | 7/1991 |
| EP | 0437063 A3 | 8/1991 |
| EP | 0506920 A1 | 10/1992 |
| EP | 0599772 A1 | 6/1994 |
| EP | 0668056 A1 | 8/1995 |
| EP | 0677297 A1 | 10/1995 |
| EP | 0417189 B1 | 10/1997 |
| EP | 0628288 B1 | 4/2000 |
| EP | 1159920 A2 | 12/2001 |
| EP | 1201189 A2 | 5/2002 |
| EP | 0831751 B1 | 11/2002 |
| EP | 1321111 A2 | 6/2003 |
| EP | 1342450 B1 | 1/2007 |
| FR | 1539593 A | 9/1968 |
| FR | 2739016 A1 | 3/1997 |
| GB | 2268690 A | 1/1994 |
| JP | 2001-511684 A | 8/2001 |
| JP | 2001-517999 A | 10/2001 |
| SE | 503271 C2 | 4/1996 |
| SE | 506164 C2 | 11/1997 |
| SU | 1225547 A1 | 4/1986 |
| SU | 1443873 A1 | 12/1988 |
| WO | 1993/010715 A2 | 6/1993 |
| WO | 1993/019678 A2 | 10/1993 |

(56) References Cited

FOREIGN PATENT DOCUMENTS

| | | |
|---|---|---|
| WO | 1996/001597 A2 | 1/1996 |
| WO | 1996/034587 A1 | 11/1996 |
| WO | 1996/039227 A1 | 12/1996 |
| WO | 1997/013465 A1 | 4/1997 |
| WO | 1998/012971 A1 | 4/1998 |
| WO | 1998/019606 A1 | 5/1998 |
| WO | 1998/035632 A1 | 8/1998 |
| WO | 1999/037216 A1 | 7/1999 |
| WO | 1999/059477 A1 | 11/1999 |
| WO | 2000/074594 A1 | 12/2000 |
| WO | 2001/078609 A2 | 10/2001 |
| WO | 2002/019945 A2 | 3/2002 |
| WO | 2002/039905 A1 | 5/2002 |
| WO | 2002/058564 A2 | 8/2002 |
| WO | 2003/007847 A1 | 1/2003 |

OTHER PUBLICATIONS

Response to Non-Final Office Action for U.S. Appl. No. 10/642,395, filed Jan. 7, 2014, 9 pages.
Final Office Action for U.S. Appl. No. 10/642,395, dated Jan. 29, 2014, 12 pages.
Response to Final Office Action for U.S. Appl. No. 10/642,395, filed Apr. 29, 2014, 9 pages.
Notice of Allowance received for U.S. Appl. No. 10/642,395, dated Aug. 15, 2014, 9 pages.
Non-Final Office Action received for U.S. Appl. No. 10/642,365, dated Sep. 10, 2013, 11 pages.
Response to Non-Final Office Action for U.S. Appl. No. 10/642,365, filed Dec. 10, 2013, 8 pages.
Final Office Action received for U.S. Appl. No. 10/642,365, dated Feb. 13, 2014, 16 pages.
Response to Final Office Action for U.S. Appl. No. 10/642,365, filed Apr. 8, 2014, 8 pages.
Non-Final Office Action received for U.S. Appl. No. 10/642,365, dated Jun. 19, 2014, 12 pages.
Response to Non-Final Office Action for U.S. Appl. No. 10/642,365, filed Sep. 17, 2014, 9 pages.
Final Office Action received for U.S. Appl. No. 10/642,365, dated Oct. 31, 2014, 12 pages.
Response to Non-Final Office Action for U.S. Appl. No. 10/642,365, filed Jan. 16, 2015, 9 pages.
Notice of Allowance received for U.S. Appl. No. 10/642,365, dated Jan. 27, 2015, 9 pages.
Notice of Allowance received for U.S. Appl. No. 10/642,365, dated May 26, 2015, 9 pages.
Non-Final Office Action received for U.S. Appl. No. 12/012,270, dated Jan. 17, 2013, 12 pages.
Response to Non-Final Office Action Filed for U.S. Appl. No. 12/012,270, dated Apr. 2, 2013, 10 pages.
Final Office Action received for U.S. Appl. No. 12/012,270, dated May 16, 2013, 9 pages.
Response to Final Office Action Filed for U.S. Appl. No. 12/012,270, dated Jul. 11, 2013, 13 pages.
Notice of Allowance received for U.S. Appl. No. 12/012,270, dated Aug. 2, 2013, 17 pages.
Response to Office Action received for Canadian Patent Application No. 2,705,609, filed Jul. 24, 2013, 4 pages.
Response to Office Action received for Canadian Patent Application No. 2,705,609, filed on Sep. 26, 2014, 13 pages.
Office Action Received for Canadian Patent Application No. 2,705,609, dated Feb. 9, 2015, 5 pages.
Notice of Allowance received for Canadian Patent Application No. 2,495,666, dated Oct. 3, 2013, 2 pages.
European Search report for EP Patent Application No. 05025122, dated Sep. 29, 2006, 7 pages.
Office Action received for Japanese Patent Application No. 2009-203174, dated Jul. 9, 2013, 3 Pages. (Official Copy Only).
Response to Final Office Action for JP Application No. 2009-203174, filed Nov. 7, 2013, 15 pages. (Official Copy Only).
Office Action received for Japanese Patent Application No. 2009-203174, dated Dec. 12, 2013, 4 Pages. (Official Copy Only).
Office Action received for Japanese Patent Application No. 2009-203174, dated Jun. 24, 2013, 32 pages. (12 pages Official copy + 20 pages English translation.
Response to Final Office Action for JP Application No. 2009-203174, filed on Sep. 22, 2014, 13 pages. (9 pages Official copy + 4 pages Amended Claims).
Notice of Allowance received for Japanese Patent Application No. 2009-203174, dated Nov. 5, 2014, 2 pages. (Official Copy Only).
Bayer et al., "A New Approach to Primary Strengthening of Colostomy With Marlex Mesh to Prevent Paracolostomy Hernia", Surgery, Gynecology and Obstetrics, vol. 163, 1986, pp. 579-580.
Benderev, Theodore V., "A New Endoscopic Bladder Neck Suspension for the Outpatient Treatment of Stress Urinary Incontinence", (video v-40), Journal of Urology, 149:197A, 1993.
Benderev, Theodore V., "A Modified Percutaneos Outpatient Bladder Neck Suspension System", Journal of Urology, vol. 152, Dec. 1994, pp. 2316-2320.
Benderev, Theodore V., "Anchor Fixation and Other Modifications of Endoscopic Bladder Neck Suspension", Journal of Urology, vol. 40, Nov. 1992, pp. 409-418.
Delorme, Emmanuel, "LLa Bandelette Trans-Obturatrice: Un Procede Mini-Invasif Pour Traiter L'incontinence Urinaire D'effort De La Femme", Progrés en Urologie, vol. 11, 2001, pp. 1306-1313.
Giesy et al, "Ureteral Instrumentation: A New System for Continued Access Via A Safety Guidewire", Journal of Urology, No. 4, Part 2, 1988, pp. 282A.
Gittes et al., "No-Incision Pubovaginal Suspension for Stress Incontinence", vol. 138, No. 3, Sep. 1987, pp. 568-570.
Haab et al., "Feasibility of Outpatient Percutaneous Bladder Neck Suspension Under Local Anesthesia", Urology, vol. 50, No. 4, Oct. 1997, pp. 585-587.
Jacquetin, B., "Utilisation du TVT dans la chirurgie de l'incontinence urinaire feminine", J. Gynecol. Obstet Biol Reprod. vol. 29, 2000, pp. 242-247.
Kovac et al., "Pubic Bone Suburethral Stabilization Sling for Recurrent Urinary Incontinence", Obstetrics & Gynecology, vol. 89, No. 4, Apr. 1997, pp. 624-627.
Leach et al., "Modified Pereyra Bladder Neck Suspension After Previously Failed anti-Incontinence Surgery: Surgical Technique and Results with Long-Term Follow-Up", Urology, vol. 23, No. 4, Apr. 1984, pp. 359-362.
Mattox et al., "Modification of the Miya Hook in Vaginal Colpopexy", The Journal Reproductive Medicine, vol. 40, No. 10, Oct. 1995, pp. 681-683.
Mitchell, J. P., "Hook Needle and Retractor for Posterior Urethroplasty", Journal of Urology, vol. 42, No. 5, Oct. 1970, pp. 599-600.
Nativ et al., "Bladder Neck Suspension in Bone Anchors for the Treatment of Female Stress Incontinence", ASAIO Journal, vol. 43, No. 3, May-Jun. 1997, pp. 204-208.
Norris et al., "Use of Synthetic Material in Sling Surgery: A Minimally Invasive Approach", Journal of Endourology, vol. 10, Issue 3, Jun. 1996, pp. 227-230.
Pereyra, Armand J., "A Simplified Surgical Procedure for the Correction of Stress Incontinence in Women", West. J. Surg. Obstetrics and Gynecology, 1959, pp. 223-226.
Petros et al., "Ambulatory Surgery for Urinary Incontinence and Vaginal Prolapse", The Medical Journal of Australia, vol. 161, Jul. 18, 1994, pp. 171-172.
Petros et al., "An Integral Theory and Its Method for the Diagnosis and Management of Female Urinary Incontinence", Scandinavian Journal of Urology and Nephrology, 1993, pp. 1-93.
Petros et al., "Urethral Pressure Increase on Effort Originates from Within the Urethra, and Continence From Musculovaginal Closure", Neurourology and Urodynamics vol. 14, No. 4, 1995, pp. 337-346.
Petros et al., "An Integral Theory of Bladder Neck Opening, Closure and Urinary incontinence in the Female", International Journal of Gynecology & Obstetrics, 1991.

(56) References Cited

OTHER PUBLICATIONS

Petros, P.P., "The Intravaginal Slingplasty Operation, a Minimally Invasive Technique for Cure of Urinary Incontinence in the Female", Australian and New Zealand Journal of Obstetrics and Gynaecology vol. 36, Issue 4, Nov. 1996, pp. 453-461.

Petros, P.P., "Medium-term Follow-up of the Intravaginal Slingplasty Operation Indicates Minimal Deterioration of Urinary Continence with Time", Australian and New Zealand Journal of Obstetrics and Gynaecology, vol. 39 No. 3, Aug. 1999, pp. 354-356.

Raz et al., "Vaginal Wall Sling", The Journal of Urology, vol. 141, 1989, pp. 43-46.

Raz, S., "Modified Bladder Neck Suspension for Female Stress Incontinence", Urology vol. 17 No. 1, Jan. 1981, pp. 82-85.

Raz et al., "Fascial Sling to Correct Male Neurogenic Sphincter Incompetence: The McGuire/Raz Approach", Journal of Urology vol. 139, No. 3, Mar. 1988, pp. 528-531.

Schaeffer et al., "Endoscopic Suspension of Vesical Neck for Urinary Incontinence", Urology vol. 23, No. 5, May 1984, pp. 484-494.

Stamey, Thomas A., "Endoscopic Suspension of the Vesical Neck for Urinary Incontinence", Surgery, Gynecology and Obstetrics, 136, 1973, pp. 547-554.

Stamey, Thomas A., "Endoscopic Suspension of the Vesical Neck", Surgery of Female Incontinence, 1986, pp. 115-132.

Stamey, Thomas A., "Endoscopic Suspension of the Vesical Neck for Urinary Incontinence in Females", Annals of Surgery, vol. 192, No. 4, Oct. 1980, pp. 465-471.

Staskin, D.R., "Sling Surgery for the Treatment of Female", Stress Incontinence vol. 5 No. 1, 1991, pp. 106-122.

Staskin et al., "The Gore-Tex Sling Procedure for Female Sphincteric Incontinence: Indications, Technique, and Results", World J of Urology, vol. 15, No. 5, 1997, pp. 295-299.

Sussman et al., "The Raz Bladder Neck Suspension: Five-Year Experience", The Journal of Urology, vol. 145, 1993, pp. 223A.

Ulmsten et al., "A Multicenter Study of Tension-Free Vaginal Tape (TVT) for Surgical Treatment of Stress Urinary Incontinence", Int Urogynecol J., vol. 9, No. 4, 1998, pp. 210-213.

Ulmsten et al., "A Three-Year Follow Up of Tension Free Vaginal Tape for Surgical Treatment of Female Stress Urinary Incontinence", British Journal of Obstetrics and Gynaecology, vol. 106, 1999, pp. 345-350.

Ulmsten et al., "Intravaginal Slingplasty", Zentralbl Gynakol, vol. 116, 1994, pp. 398-404.

Ulmsten et al., "Surgery for Female Urinary Incontinence", Current Opinion in Obstetrics & Gynecology, vol. 4, No. 3, 1992, pp. 456-462.

Ulmsten, U., "An Introduction to Tension-Free Vaginal Tape (TVT)—A New Surgical Procedure for Treatment of Female Urinary Incontinence", Int Urogynecol J. Pelvic Floor Dysfunct. (Suppl 2), 2001, pp. S3-S4.

Ulmsten, U., "Connective Tissue Factors in the Aeticology of Female Pelvic Disorders", Ann. Med., vol. 22, No. 6, Dec. 1990, pp. 403.

Ulmsten, U., "The Basic Understanding and Clinical Results of Tension-Free Vaginal Tape for Stress Urinary Incontinence", Urologe A., Jul. 2001, pp. 269-273.

Ulmsten et al., "An Ambulatory Surgical Procedure Under Local Anesthesia for Treatment of Female Urinary Incontinence", International Urogynecology Journal, vol. 7, No. 2, 1996, pp. 81-86.

Ulmsten et al., "Intravaginal Slingplasty (IVS): An Ambulatory Surgical Procedure for Treatment of Female Urinary Incontinence", Scand J Urol Nephrol, vol. 29, No. 1, Mar. 1995, pp. 75-82.

Notice of Allowance for CA Application No. CA2,705,609, dated Apr. 11, 2016, 1 page.

* cited by examiner

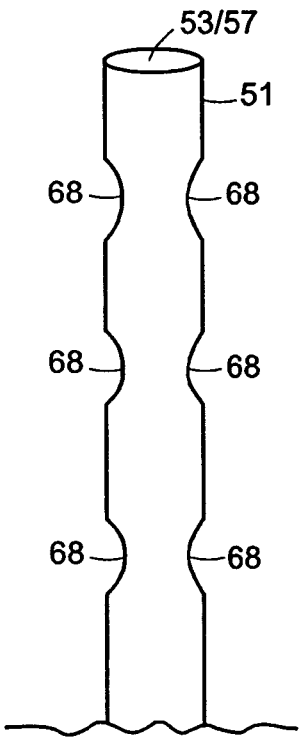 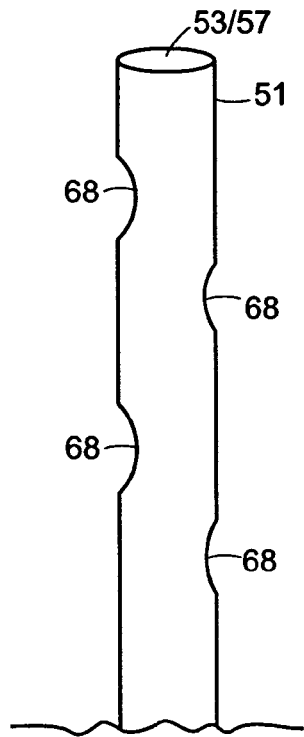
FIG. 10B        FIG. 11
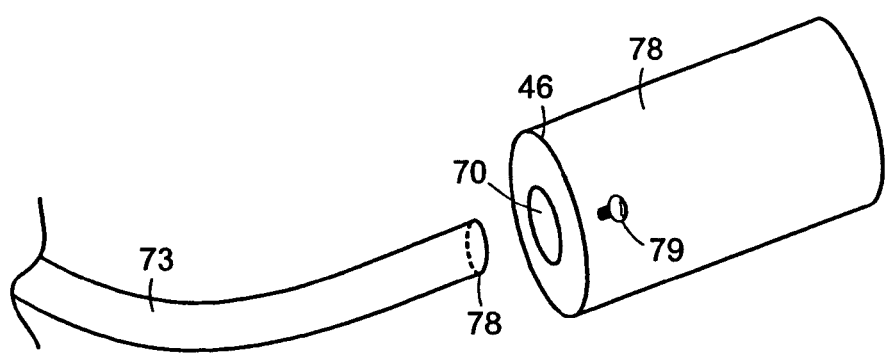
FIG. 12

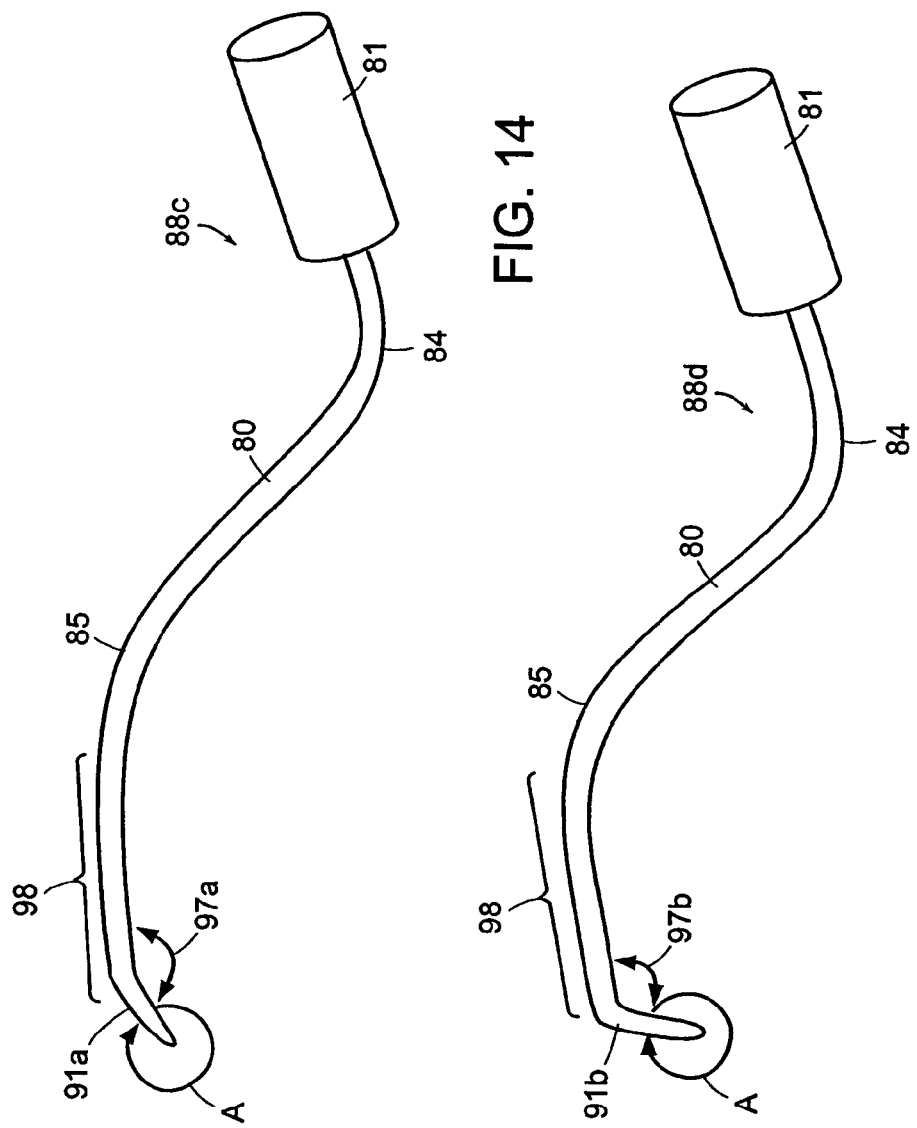

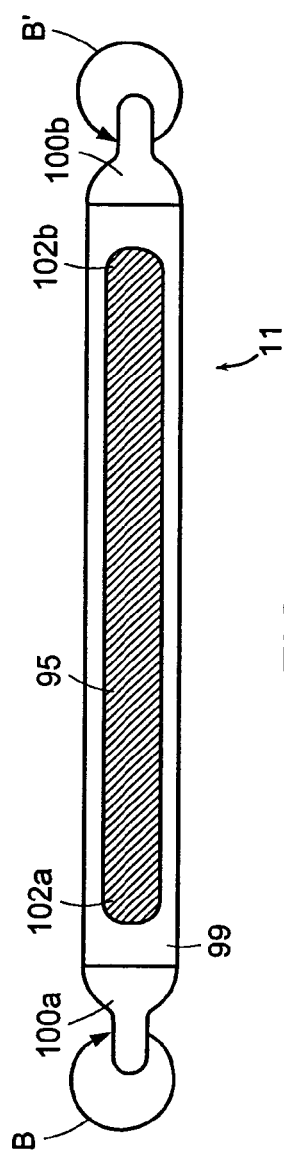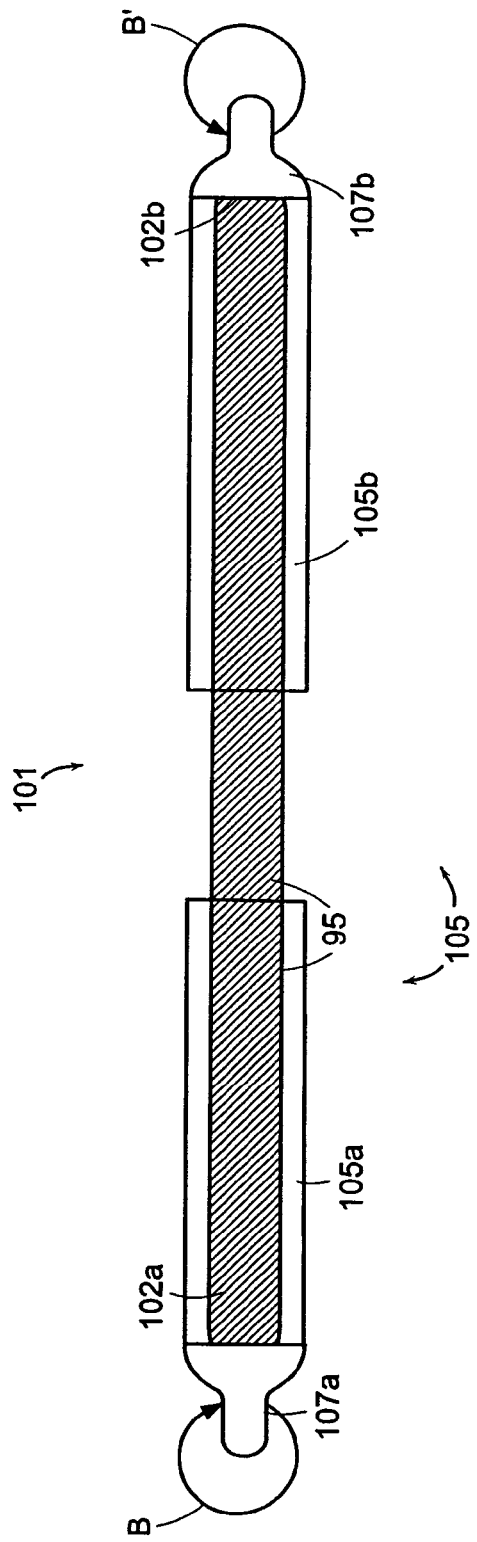
FIG. 19
FIG. 20

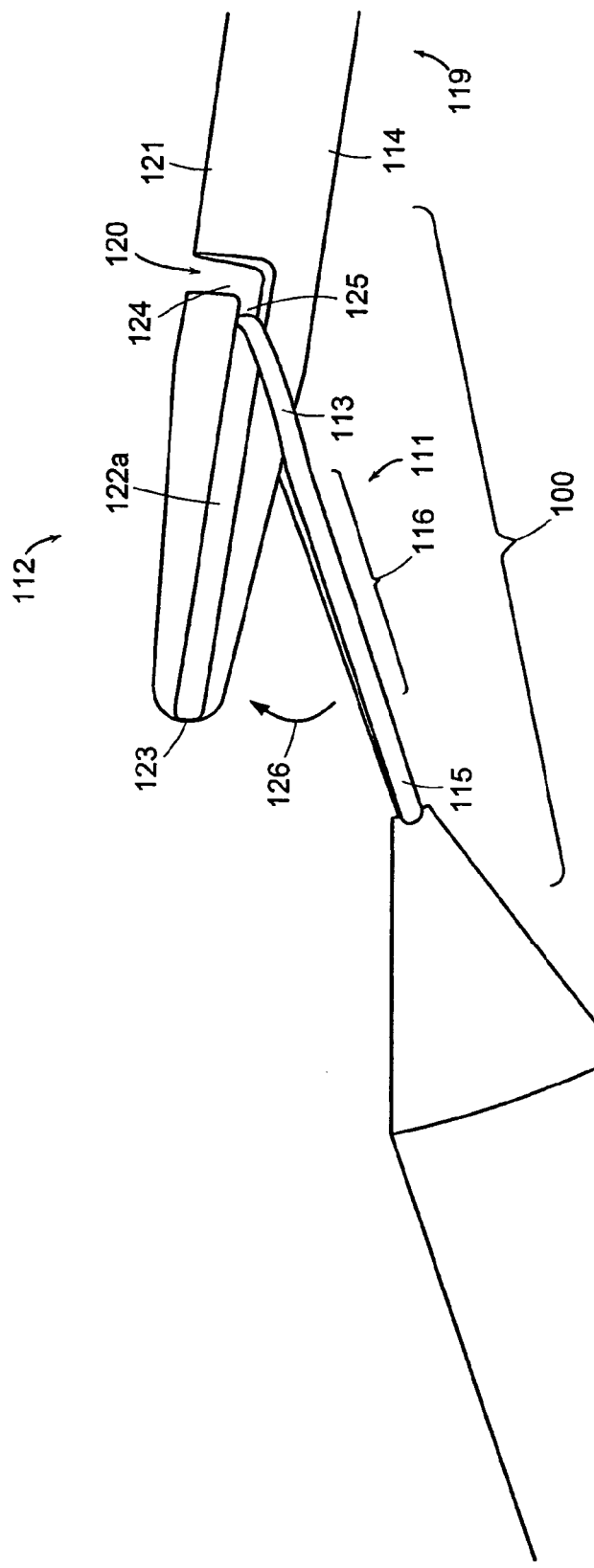

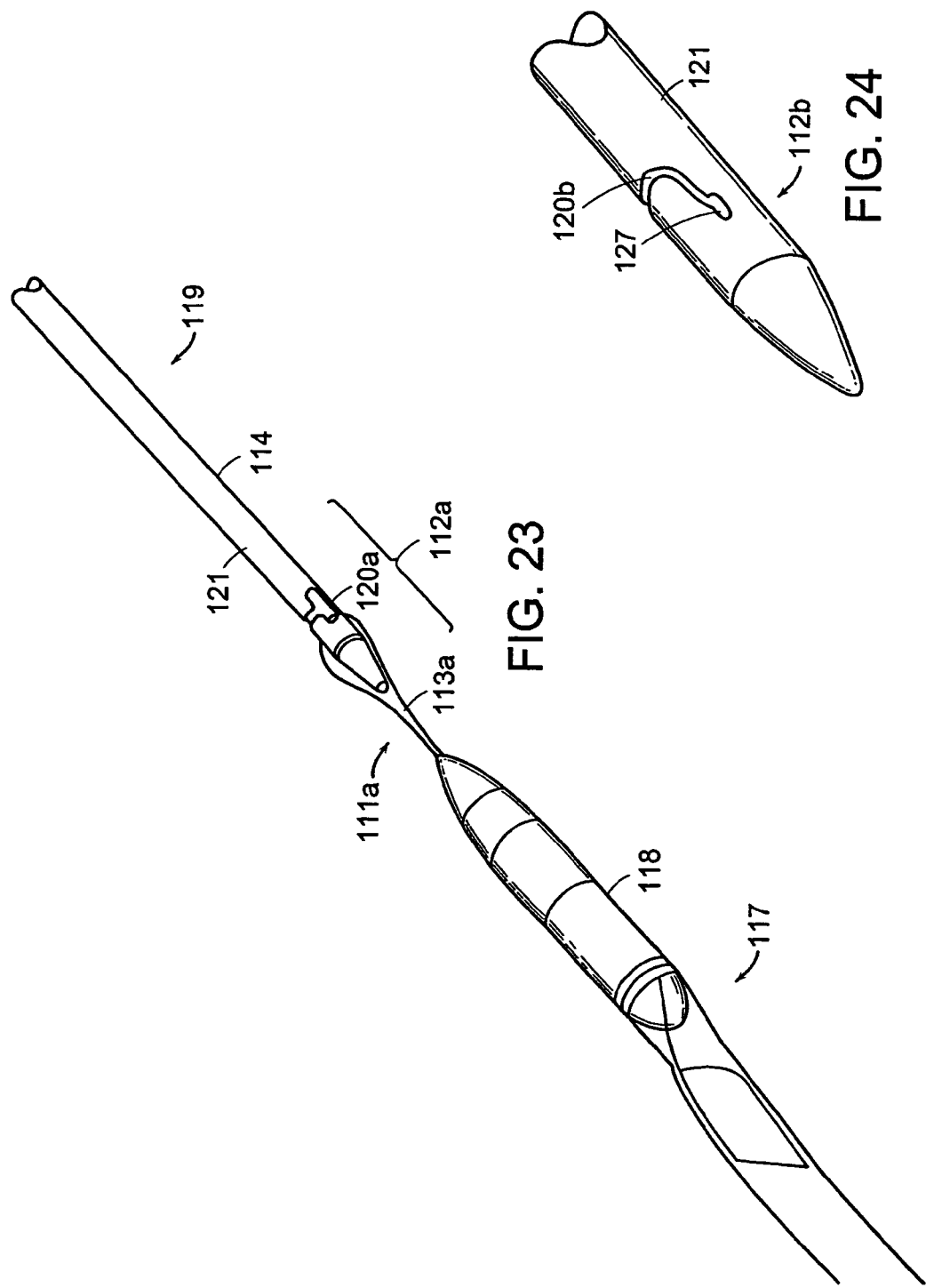

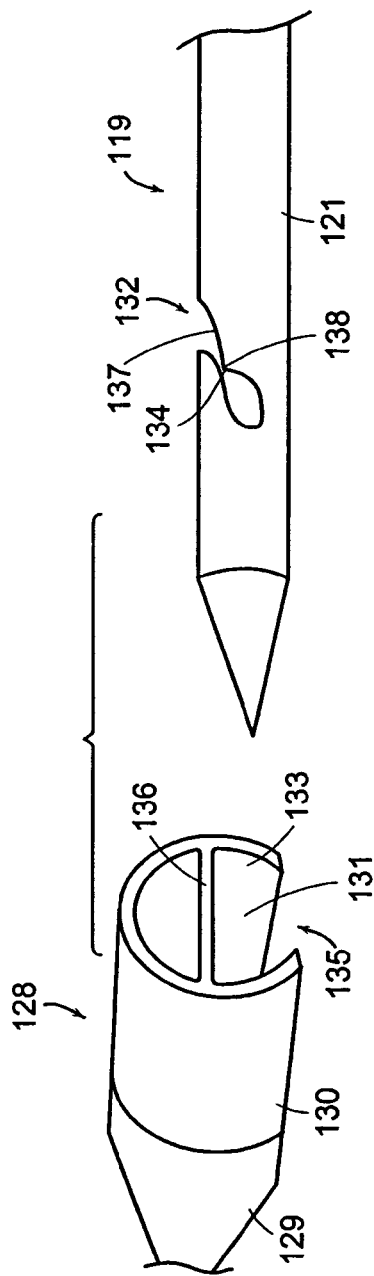
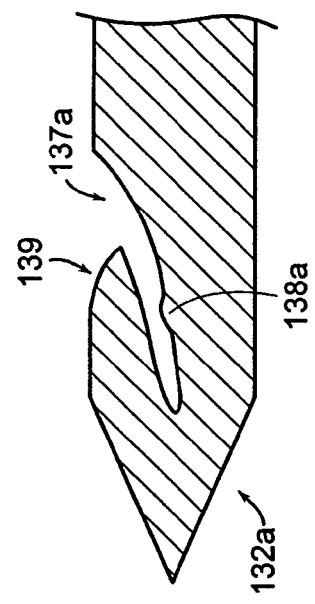
FIG. 25
FIG. 26

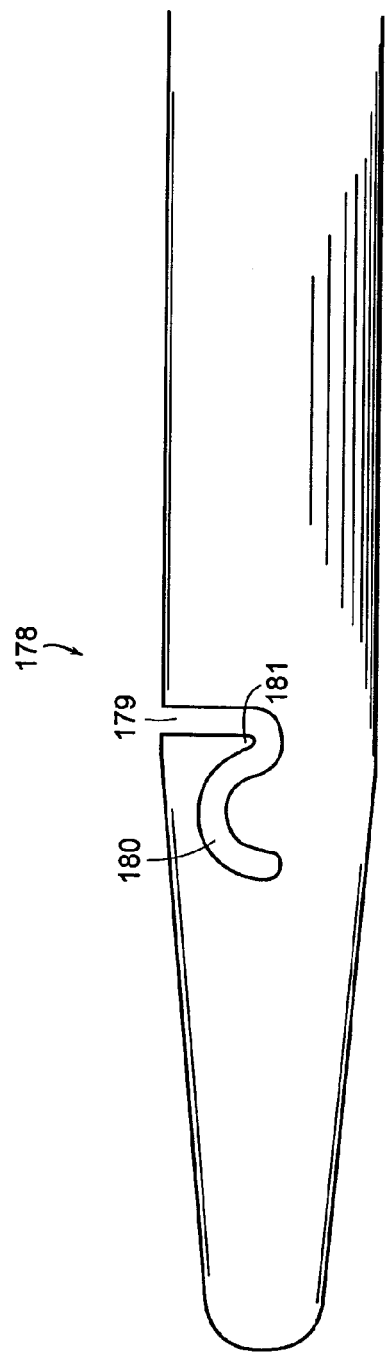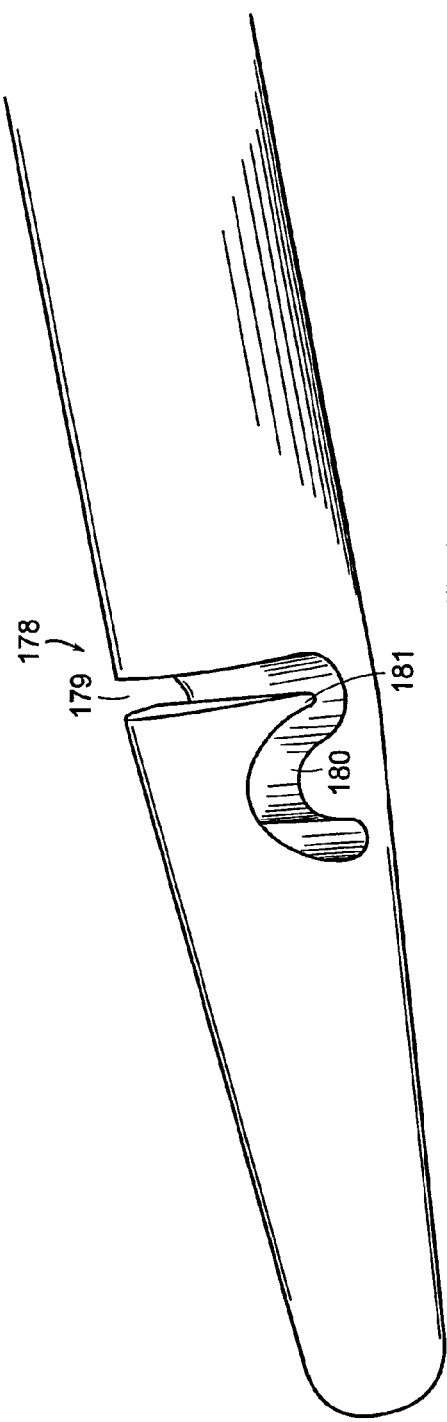

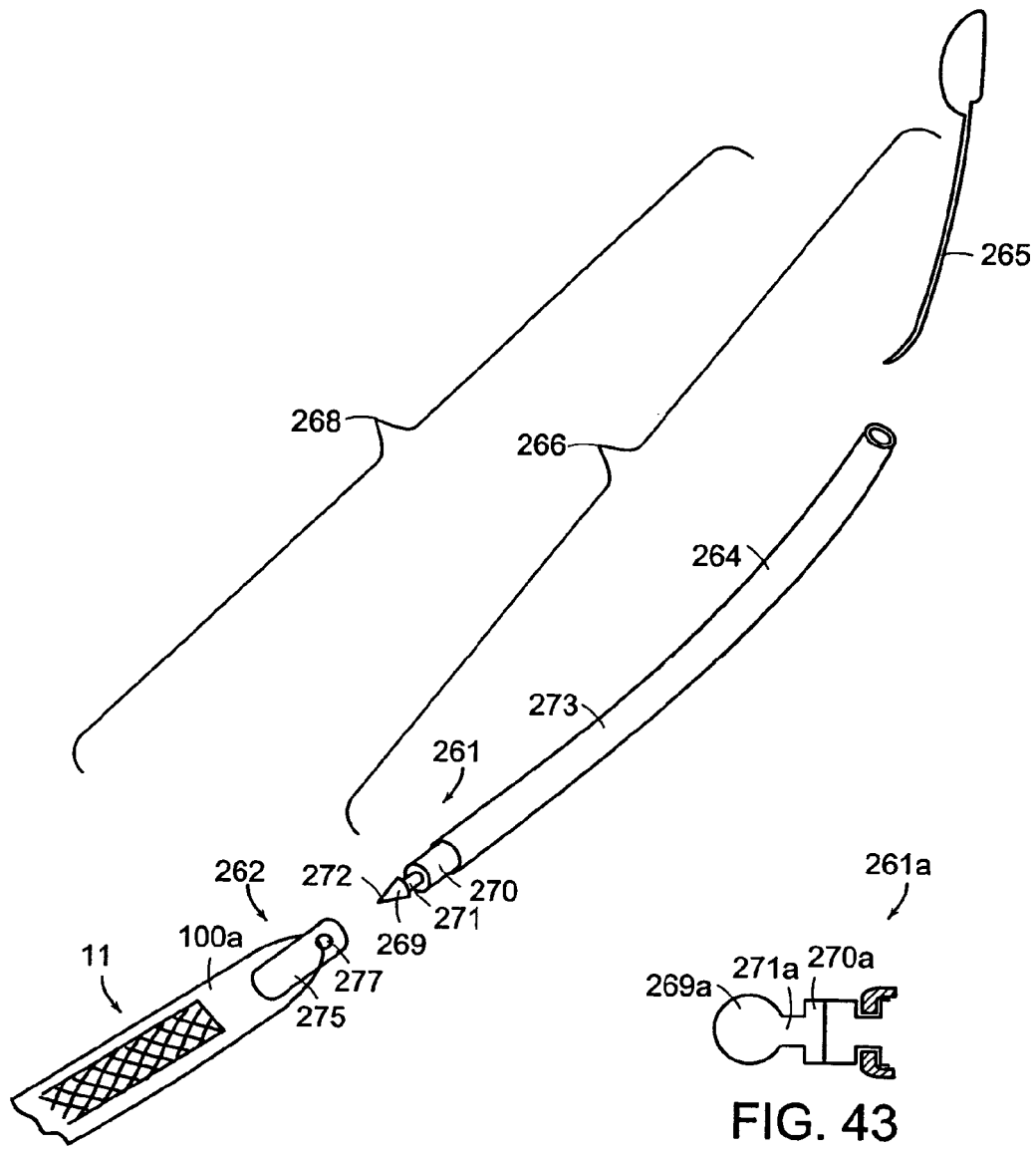
FIG. 42A
FIG. 43
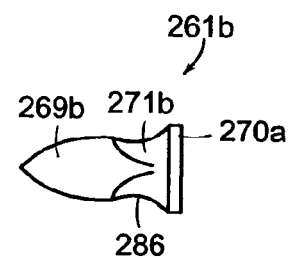
FIG. 44

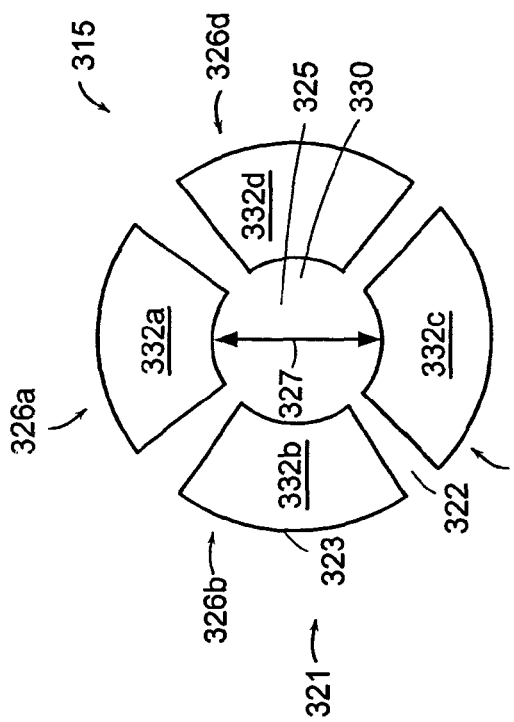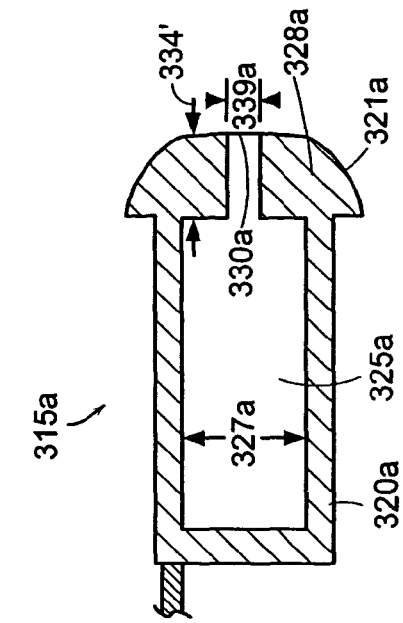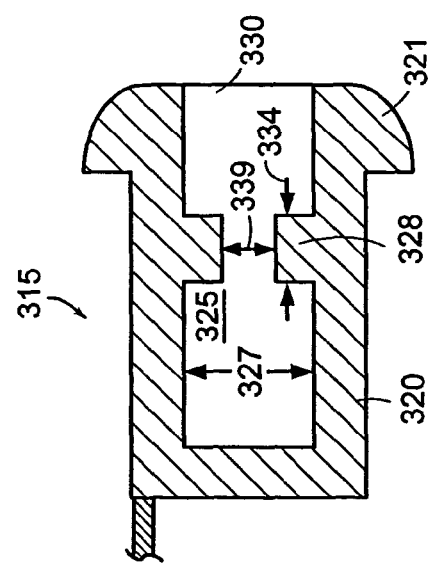

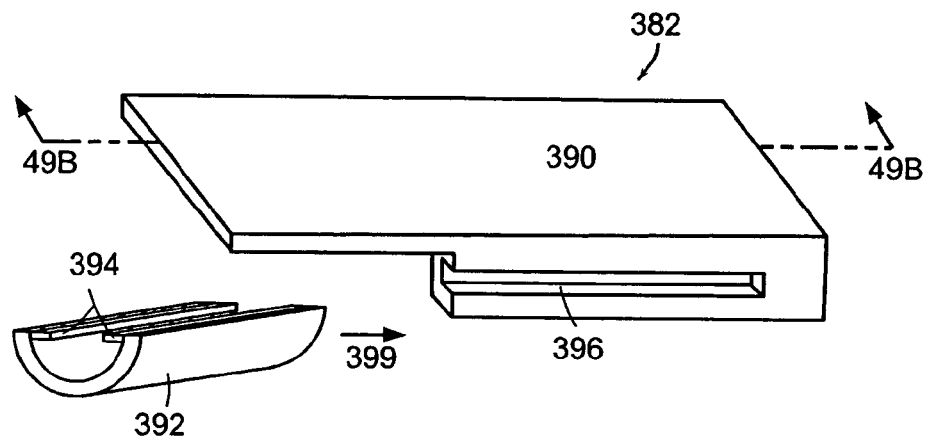
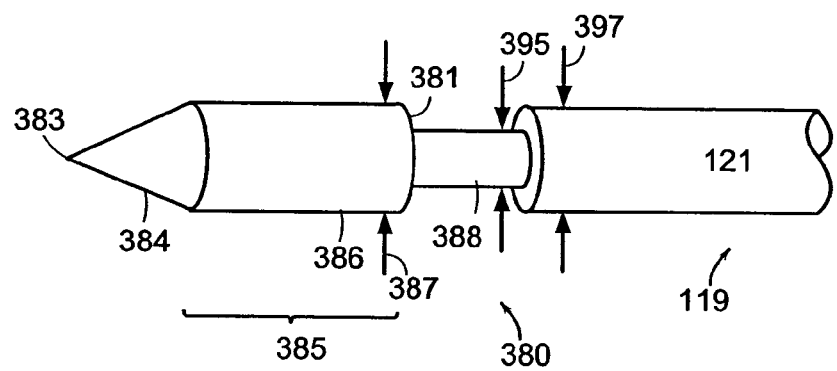
FIG. 49A
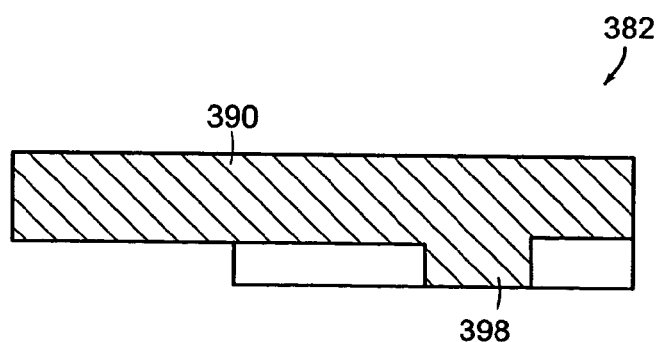
FIG. 49B

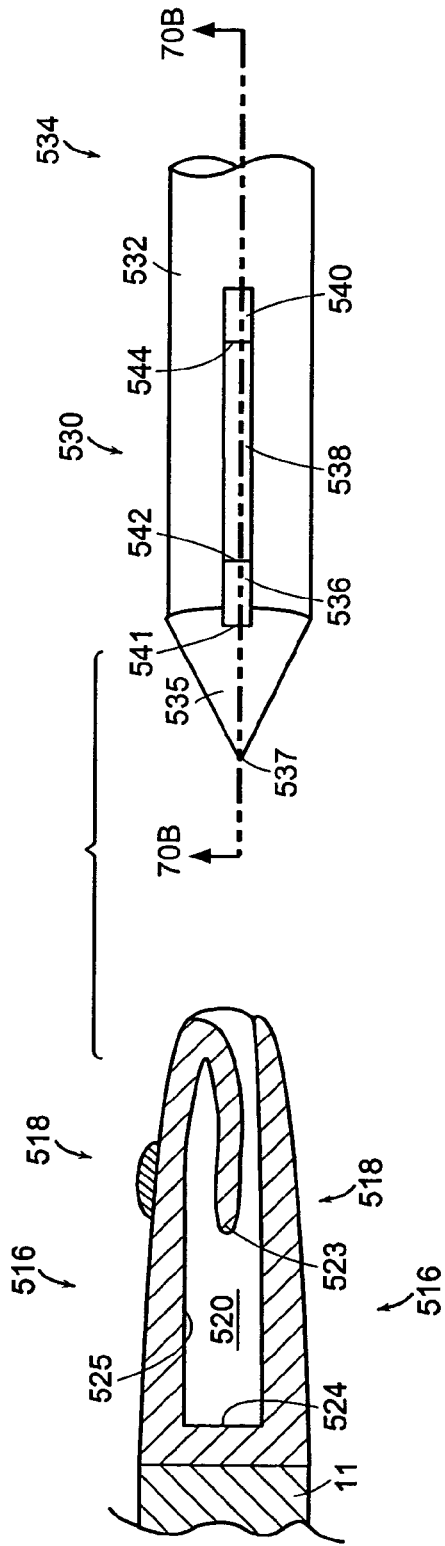
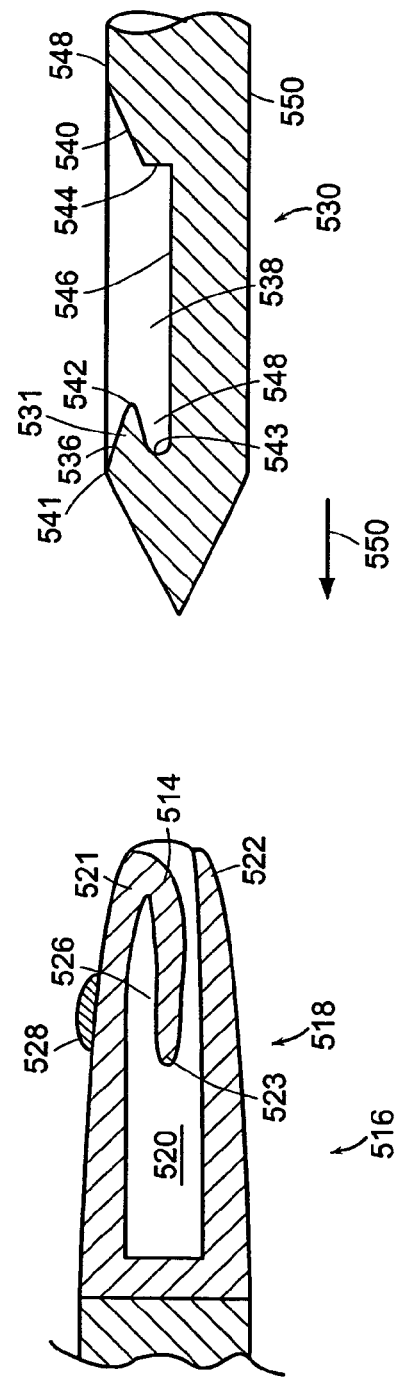
FIG. 61A
FIG. 61B

SYSTEMS, METHODS AND DEVICES RELATING TO DELIVERY OF MEDICAL IMPLANTS

CROSS-REFERENCE TO RELATED APPLICATIONS

This application is a continuation of, and claims priority to, U.S. application Ser. No. 10/642,365, filed on Aug. 14, 2003, entitled "SYSTEMS, METHODS AND DEVICES RELATING TO DELIVERY OF MEDICAL IMPLANTS", which, in turn, is a continuation-in-part application of U.S. patent application Ser. Nos. 10/093,371, 10/093,398, 10/093,424, 10/093,450, 10/093,498, and 10/094,352 filed in the United States Patent Office on Mar. 7, 2002, which claim benefit of and priority to provisional patent application Ser. No. 60/274,843 filed in the United States Patent Office on Mar. 9, 2001 and provisional patent application Ser. No. 60/286,863 filed in the United States Patent Office on Apr. 26, 2001. The entire contents of these six nonprovisional applications are incorporated by reference herein. This application is also based on and claims priority to certain provisional U.S. patent applications, namely, Ser. No. 60/403,555 filed on Aug. 14, 2002, Ser. No. 60/418,827 filed on Oct. 15, 2002, Ser. No. 60/418,642, filed on Oct. 15, 2002, Ser. No. 60/434,167 filed on Dec. 17, 2002, Ser. No. 60/449,465 filed on Feb. 24, 2003, Ser. No. 60/465,722 filed on Apr. 25, 2003, and Ser. No. 60/483,534 filed on Jun. 27, 2003, the entire contents of all of which are incorporated herein by reference

TECHNICAL FIELD

The invention relates generally to systems, methods and devices for delivering a medical implant, to an anatomical site in the body of a patient.

BACKGROUND INFORMATION

Urinary incontinence occurs in both men and women. Various types of incontinence are caused by different conditions and call for different treatments. For example, stress urinary incontinence (SUI) is known to be caused by at least two conditions, intrinsic sphincter deficiency (ISD) and hypermobility. In women, these conditions may occur independently or in combination. In ISD, the urinary sphincter valve, located within the urethra, fails to close properly (coapt), causing urine to leak out of the urethra during stressful activity. Hypermobility is a condition in which the pelvis floor is distended, weakened or damaged, causing the bladder neck and proximal urethra to rotate and descend in response to increases in intra-abdominal pressure (for example, due to sneezing, coughing, straining, etc.). As a result, the patient's response time becomes insufficient to promote urethral closure and, consequently, the patient suffers from urine leakage and/or flow.

One way to treat incontinence, both in men and women, is to place a surgical sling or suture in the periurethral tissue such as under the bladder neck or the urethra to provide a urethral platform. Placement of the sling limits the endopelvis fascia drop while providing compression to the urethral sphincter to improve coaptation. The sling may be affixed using a bone anchoring method. Alternatively, a medical professional can use an anchorless approach to stabilize the urethra with a sling by placing the sling in the periurethral tissue and relying on tissue compression and eventual tissue in-growth to secure the sling in position.

SUMMARY OF THE INVENTION

The invention addresses deficiencies of the prior art by providing devices, systems and methods for facilitating delivery of an implant to an anatomical site. According to a preferred embodiment, the device can be used to deliver an implant, such as a sling for treating urinary incontinence, to a mid-urethral location of a patient. The methods and systems of the invention simplify the delivery of the implant by using a slot-loop connector pair for attaching a medical implant to a delivery device. In particular, the medical implant includes a closed loop connector which interfits with a slotted connector located at the distal end of the shaft of the delivery device. In a preferred configuration of the slotted connector, the slot extends distally towards the tip of the shaft so as to allow the implant to be pulled to the desired anatomical site within the body. The invention further features protuberances for engaging the loop once it is placed in the slotted connector and these protuberances prevent the loop from prematurely disengaging with the slot. The invention also provides a free sliding tube that can be placed over the interconnection area once the loop and slot have been connected. The tube provides a smooth surface such that when the medical operator, for example, withdraws the delivery device from the body of the patient minimal damage is caused to the surrounding tissues. The advantage of the invention is that it provides an effective and simple means for connecting an implant to a delivery device.

Accordingly, in one aspect, the invention features a connector pair for attaching a medical implant to a delivery device. The connector pair includes a closed loop connector located at an end of a medical implant, and a slotted connector formed in a distal end of a shaft of a delivery device for interfitting with the closed loop connector of the medical implant, the slotted connector including first and second legs, the first leg extending radially into the shaft and the second leg extending axially in a distal direction along the shaft.

The slotted connector can be configured to interfit with the closed loop connector. Alternatively, the closed loop connector can be configured to interfit into the first and/or second leg of the slotted connector. In one embodiment, the closed loop connector and the slotted connector are sized for end to end interconnection between the medical implant and the shaft of the delivery device.

The closed loop connector is preferably substantially rigid and can be formed from various materials such as a suturing material or semi-flexible, shape retaining material. Generally it is shaped to track the distal end of the shaft. In one embodiment, the closed loop connector includes a base portion, a tapered portion and a loop portion, the base portion extending from the end of the medical implant to the tapered portion, the tapered portion tapering radially outward and extending axially from the based portion to the loop portion, the loop portion being curved. In this embodiment, the distal end of the shaft is tapered for interfitting with the tapered portion of the closed loop connector.

In another embodiment, the slotted connector can include first and second channels located substantially diametrically opposite each other in the distal end of the shaft and extending distally from the second leg of the slotted connector. The tapered portion of the closed loop connector can be sized to snap fit into and track the first and second channels in the distal end of the shaft.

The first and second legs of the slotted connector can have various configurations. In one embodiment, the second leg of the slotted connector is longer than the first leg of the slotted connector. In another embodiment, the second leg of the slotted connector extends distally at about a 90 degree angle relative to the first leg of the slotted connector. In yet another embodiment, the second leg includes a narrowing for locking the looped connector into the second leg. The narrowing can be formed where the second leg initially extends from the first leg. The width of the second leg at the narrowing can be less than that of the loop portion of the closed loop connector. In another embodiment, the narrowing includes a protuberance in a wall of the second leg for preventing the loop from moving once it is in the second leg. The protuberance can form a substantially flat shoulder facing a distal most end of the shaft.

The second leg of the slotted connector can have a defined shape. In one example, the second leg is substantially spherical in shape having an opening for accepting the looped connector at an intersection with the first leg. The width of the opening in the second leg has a width of less than that of the loop portion of the closed loop connector. In another example, the second leg includes a curved portion and can further include a narrowing for locking the looped connector into the second leg. The narrowing can be formed where the second leg initially extends from the first leg.

In another embodiment, the invention features a slidable tubular sleeve on the shaft for sliding over and covering the slotted connector subsequent to interfitting the closed loop connector with the slotted connector. In some embodiments, the tubular sleeve is freely slidable. However, in other embodiments, the sleeve is operably coupled to and actuatable from the handle of the delivery device. The sleeve provides a smooth surface over the connected slotted connector and closed loop connector. The slidable tubular sleeve can extend past the base portion of the closed loop connector onto the end of the medical implant. In one embodiment, the slidable tubular sleeve includes an aperture for aligning with the first leg of the slotted connector during interfitting of with the closed loop connector. Preferably, the slidable tubular sleeve is sized relative to the shaft so that it slides over the slotted connector in response to the shaft being withdrawn from a body of a patient.

In another aspect, the invention features a connector pair for attaching a medical implant to a delivery device. The connector pair includes a closed loop connector located at an end of a medical implant, and a slotted connector formed in a distal end of a shaft of a delivery device for interfitting with the closed loop connector of the medical implant, the slotted connector extending into the shaft from a first location to a second location, the second location being least as distal along the shaft as the first location, the slotted connector including a narrowing.

The slotted connector is narrowed so as to ensure that the loop is securely held and does not release prematurely. In one example, the narrowing has a width of less than that of the loop portion of the closed loop connector and can include a first or second protuberance in a first and/or second wall of the slotted connector. The first and second protuberances can be axially aligned relative to each other or can be axially offset relative to each other. In one embodiment, the narrowing forms an inward facing shoulder, for example, an inward facing shoulder that is flat, in the slotted connector.

The closed loop connector or slotted connector can have various shapes. For example, the closed loop can be substantially triangular in shape and the slotted connector can be curved.

In another aspect, the invention features a connector pair including an adjustable size closed loop connector located at an end of a medical implant, and a slotted connector formed in a distal end of a shaft of a delivery device for interfitting with the closed loop connector of the medical implant, the slotted connector extending into the shaft from a first location to a second location, the second location being least as distal along the shaft as the first location. In one embodiment, the closed loop connector includes a filament for forming the closed loop, and a housing through which the closed loop extends in a first direction and first and second ends of the filament extend in a second direction.

In another embodiment, at least of one of the first and second ends, or both of the ends, of the filaments slidably interfit with the closed loop connector housing such that it may be actuated to constrict the size of closed loop. The housing can include a locking mechanism, such as teeth, for locking the filament in place to control the size of the closed loop. The housing can also includes an unlocking mechanism for enabling at least one of expansion and constriction of the closed loop.

BRIEF DESCRIPTION OF THE DRAWINGS

In the drawings, like reference characters generally refer to the same parts throughout the different views. The drawings are not necessarily to scale and emphasis instead is generally placed upon illustrating the principles of the invention.

FIG. 10B depicts a side view of a portion of the guide tube of FIG. 10A according to an illustrative embodiment of the invention.

FIG. 11 depicts a side view of an alternative illustrative embodiment of a portion of a guide tube of the general type depicted in FIG. 10A.

FIG. 12 depicts a perspective side view of a portion of a delivery device including a handle and a shaft according to another illustrative embodiment of the invention.

FIGS. 14-16 depict perspective side views of illustrative delivery devices, each having a variously angled distal end according to the invention.

FIG. 19 depicts a top view of an exemplary sling assembly that may be employed with the various illustrative delivery devices of the invention.

FIG. 20 depicts a top view of another exemplary sling assembly that may be employed with the various illustrative delivery devices of the invention.

FIG. 22C depicts a side view of the connectors of FIG. 22A partially interconnected according to an illustrative embodiment of the invention.

FIG. 23 depicts a perspective top view of interconnected loop and receptacle connectors according to another illustrative embodiment of the invention.

FIG. 24 depicts a perspective side view of a receptacle connector of the type that may be employed with the loop connector of FIG. 23.

FIG. 25 depicts a perspective side view of a receptacle connector and a mating loop connector according to an illustrative embodiment of the invention.

FIG. 26 depicts a cross-sectional side view of an alternative receptacle connector of the type that may be employed with the loop connectors of FIGS. 23 and 25.

FIG. 32A depicts a side view of another receptacle connector of the type that may be employed with the loop connectors of FIGS. 23 and 25.

FIG. 32B depicts a side perspective view of the receptacle connector of FIG. 32A.

FIG. 42A depicts a side perspective view of a plug and receptacle connector pair along with components of an implant delivery system including a shaft, a guide tube and a sling assembly, according to another illustrative embodiment of the invention.

FIGS. 43 and 44 depict side views of alternative embodiments of plug connectors of the type depicted in FIGS. 42A and 42B.

FIG. 46B depicts a cross-sectional end view of the distal end of the receptacle connector shown in FIG. 46A, along the line "46B-46B."

FIGS. 46C and 46D depict longitudinal cross-sectional views of alternative embodiments of the receptacle connector shown in FIG. 46A along the line "46C/46D-46C/46D."

FIG. 49A depicts an exploded view in perspective of a portion of a plug and receptacle connector pair according to another illustrative embodiment of the invention.

FIG. 49B depicts a cross-sectional view of a portion of the receptacle connector of FIG. 49A, along the line "49B-49B."

FIG. 61A depicts a longitudinal cross-sectional view of a receptacle connector, and a side view of its mating plug connector, according to another illustrative embodiment of the invention.

FIG. 61B depicts a longitudinal cross-sectional view of the connector pair of FIG. 61A.

DESCRIPTION

The invention relates to delivering and placing an implant, such as a sling, mesh, or suture, for the treatment of urinary incontinence, at an anatomical site (such as the periurethral tissue) in the body of a mammal. The patient may be either a female patient or a male patient.

The following description is divided into five sections. The first section, describes various illustrative delivery devices. The second section describes implants (such as sling assemblies) that may be delivered by, without limitation, any of the illustrative delivery devices. The third section describes connectors that may be used to interconnect two or more parts in an implant delivery system, such as, for example, interconnecting a sling assembly with a delivery device. The fourth section describes various illustrative methods for treatment of urinary incontinence, including illustrative embodiments that utilize components and systems described in this and the incorporated patents and patent applications. The fifth section describes guide members that may be interconnected with the sling assembly and their related methods of use. A delivery device, an implant, and optionally one or more guide members and/or connectors together generally form an implant delivery system.

It should be noted that, any of the described components (in any described variations) can be operatively combined with one or more of any of the other described components (in any described variations), and such operative combinations are intended to fall within the scope of the invention and are included herein even if not expressly called out.

I. Delivery Devices

Without limitation, exemplary delivery systems, slings, sling attachments and methodologies that may be employed in combination with the spacers of the invention can be found in U.S. patent application Ser. No. 10/093,498; U.S. patent application Ser. No. 10/093,398; U.S. patent application Ser. No. 10/093,450; U.S. patent application Ser. No. 10/094,371; U.S. patent application Ser. No. 10/094,352; U.S. patent application Ser. No. 10/093,424; U.S. provisional patent application Ser. No. 60/403,555; U.S. patent application Ser. No. 09/916,983; U.S. provisional patent application Ser. No. 60/465,722; U.S. provisional patent application Ser. No. 60/418,827; U.S. provisional patent application Ser. No. 60/418,642; U.S. provisional patent application Ser. No. 60/274,843; U.S. provisional patent application Ser. No. 60/286,863; and U.S. provisional patent application Ser. No. 60/434,167, the disclosures of which are incorporated herein by reference.

Figure 1:
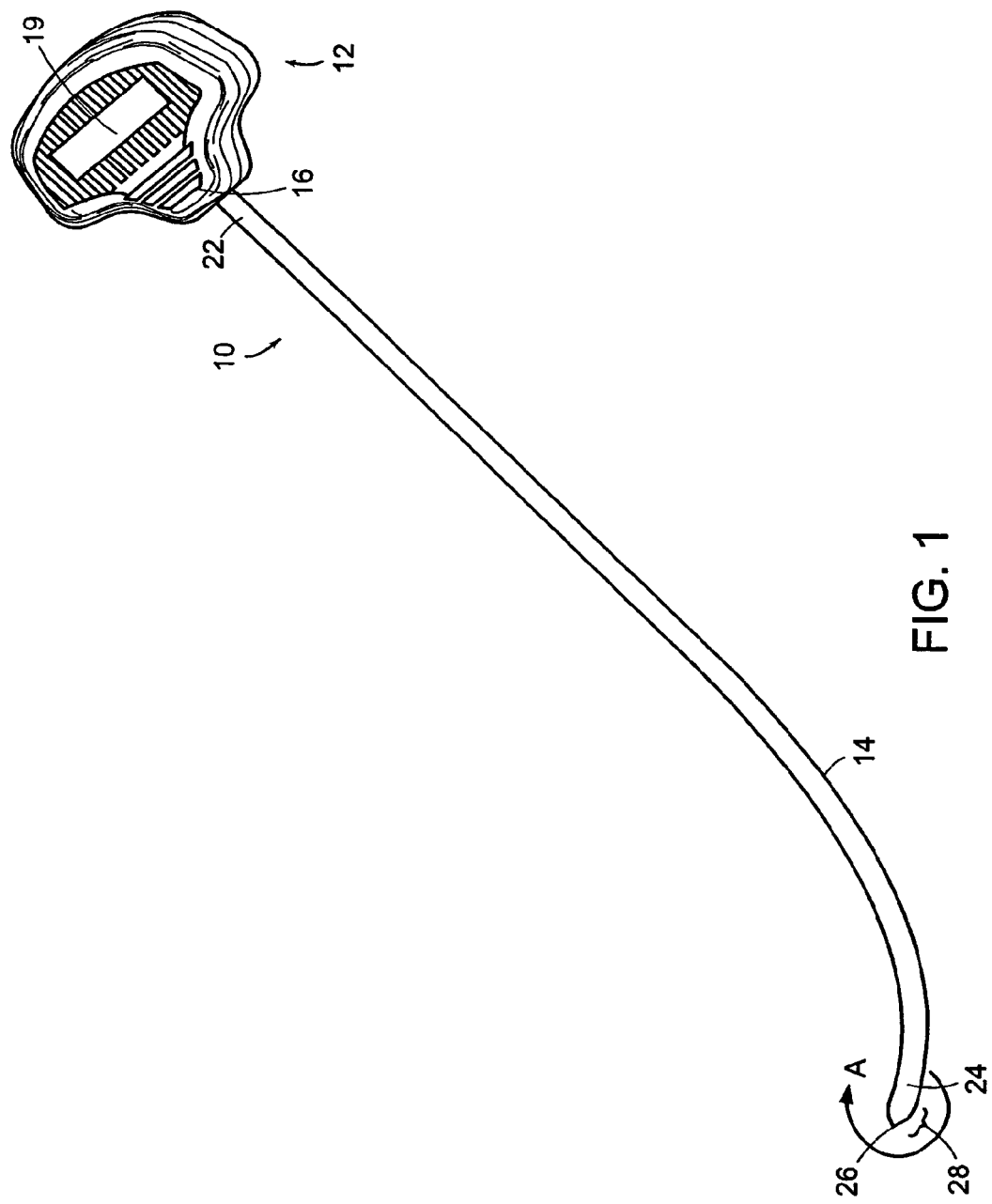
FIG. 1 depicts a perspective side view of a delivery device including a handle and needle according to an illustrative embodiment of the invention.

Referring to FIG. 1, an illustrative delivery device 10 includes a handle 12 associated with a curved shaft 14. The shaft 14 may be, for example, any suitable needle, cannula, tubular member, tunneler, dilator or the like. The delivery device 10 may also include other components, such as connectors, sheaths, guide tubes and actuating assemblies, described in further detail below. A distal end 24 of the curved shaft 14 is marked by circle "A" to indicate that it may include one or more connectors such as the ones described below.

In one illustrative embodiment, the curved shaft 14 is formed from a rigid material, for example, a metal or a polymeric material. Examples of suitable metals include, but are not limited to, stainless steel, titanium, and alloys such as nitinol. Suitable polymers, which can be used as a coating on a metal to form the shaft 14, include but are not limited to, plastics such as polytetrafluoroethylene (PTFE). In one embodiment, the shaft 14 is rigid. In another embodiment, the shaft 14 has some flexibility, and can be described as semi-rigid. The shaft 14 has a proximal end 22, i.e., the end that is closest to an origin of attachment, typically the operator, and the distal end 24. The shaft 14 generally has a pointed tip 26 at the distal end 24 that is designed for percutaneous punctuation and/or advances through the tissue. However, the tip 26 may be blunt or sharp. In some configurations, the tip 26 is conical. A blunt tip 26 may provide some resistance to unintended penetration through tissue or organ, such as the bladder. The distal end 24 of the shaft 14 may include a tapered section 28 that leads to the distal tip 26. The tapered section 28 aids dilation and tunneling through the tissue.

The shaft 14 may be solid or hollow. If the shaft 14 is at least partly hollow, it may include a lumen (not shown) that has one or more openings on the shaft 14, for example, at the distal tip 26 or along the side of the shaft 14. The cross-section of the shaft 14 may have a constant shape and size, or its shape and size may vary along the length of the shaft 14. The cross-section of the shaft 14 may assume any shape, for example, circular, semi-circular, oval, triangular or rectangular. In other embodiments, the distal end 24 may include an enlarged, flared portion to dilate tissue beyond the typical diameter of the shaft 14.

Part or the entire shaft 14 may assume a curved, angled, a helical shape or any other suitable shape including substantially straight. Different shapes of the shaft 14 have advantages in different procedures, which is discussed in more detail below.

In one embodiment, the surface of the shaft 14 is smooth. However, the surface of the shaft 14 may be coated with one or more drugs such as anesthetic, anti-inflammatory, coagulating, anticoagulating, antibiotic or antimicrobial agents. The drug may be delivered to the patient's tissue while the shaft 14 is in contact with the tissue. The surface of the shaft 14 may be coated with a light-absorbing coating to reduce glare, for example, under a cystoscope. The coating may be a polymer, such as Teflon, or other suitable material, and may be colored to aid in detection. The surface of the shaft 14 may be painted so that one can easily tell it apart from surrounding tissue and fluid under a cystoscope to make it easier to detect under the cystoscope. In other illustrative embodiments, the shaft 14 is textured, for example, by stippling, to provide increased traction relative to a gloved hand of a medical operator. In another illustrative embodiment, the shaft 14 is fitted with a colored sheath, such as a blue plastic sheath or guide tube.

The handle disposed at the proximal end of the device for the various devices illustrated herein is depicted with particular configurations, but may be manufactured from rigid or flexible plastic, or a combination thereof, and may assume any suitable shape (such as a substantially cylindrical or T-shape) to fit a particular application with which it is used, for example, such applications described in detail below. Advantageously, the handle is of an ergonomic design and construction that reduces operator fatigue and discomfort, provides needed leverage and gripping surface for the user, orients the user as to the direction of the needle, and/or provides fingertip or palm control over the needle. For example, in FIG. 2, the handle 12 is substantially D-shaped or kidney-shaped, and has a proximal end 15, a distal end 16, a first face 18, and a second, opposite face 19 (shown in FIGS. 1 and 3). The proximal end 15 of the handle 12 is relatively flat with a slight curve, and rests comfortably against the operator's palm. The operator's fingers stabilize the distal end 16 of the handle 12 by gripping the two cut-off sections 20a and 20b that flank the distal end 16. The handle 12 may also include external ribs 21a and 21b on one or both sides of the handle 12. The external ribs 21a, 21b provide tactile orientation of the handle 12 for the operator. Optionally, the handle 12 includes ribs or grooves 17 on one or both faces 18 and 19 of the handle 12, which may also assist gripping and inhibit slippage. This design is advantageous for both a pulling and pushing motion through the handle 12.

Figure 2:
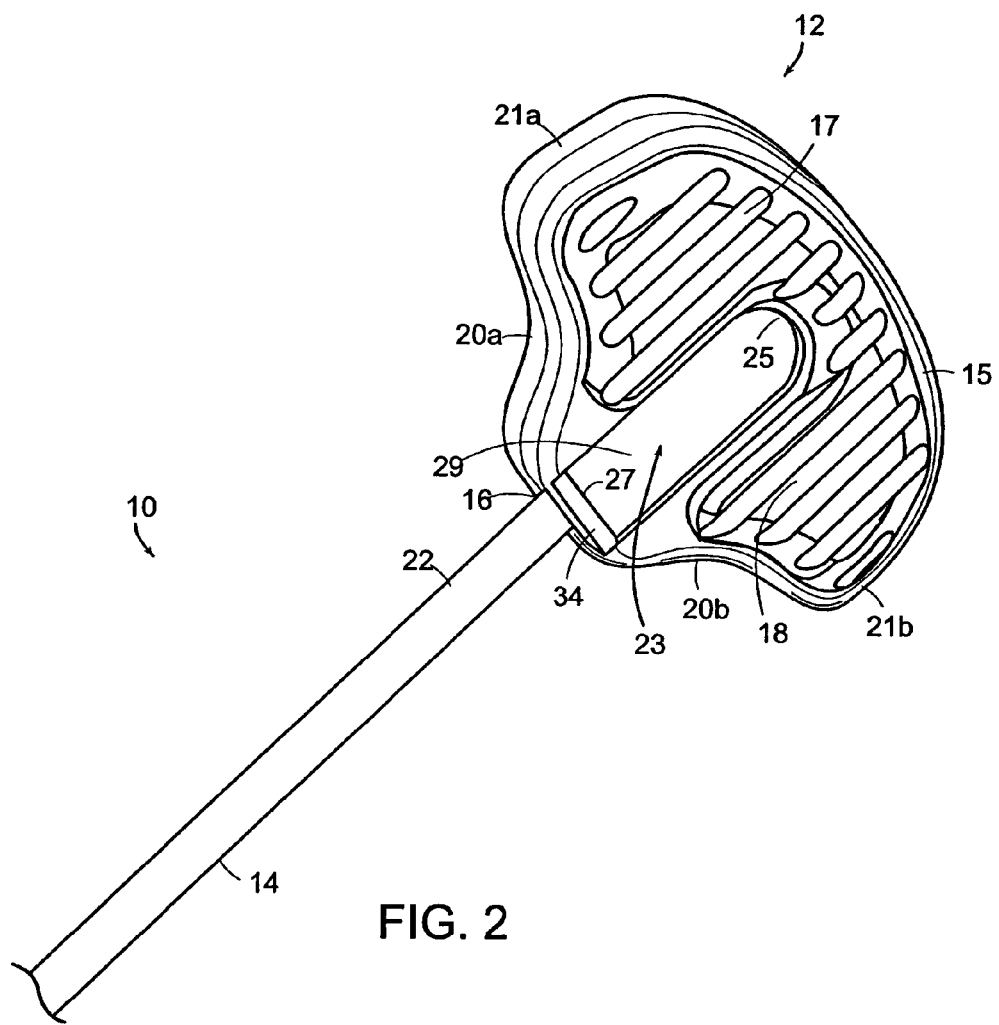
FIG. 2 depicts an enlarged perspective side view of the handle and a portion of the needle of the device of FIG. 1.

Still referring to FIG. 2, the handle 12 includes on the first face 18 a recess 23, such as a slot. The recess 23 has a proximal end 25, a distal end 27, and a floor 29. A raised stop 34 is located at the distal end 27 of the recess 23 and projects away from the floor 29 of the recess 23. The recess 23 may be used to fit an accessory part such as a pusher assembly, which will be discussed in more detail later in connection with FIGS. 5 and 6.

The connection between the proximal end 22 of the shaft 14 and the distal end 16 of the handle 12 may be permanent or reversible, i.e., removable and reusable. Such a connection may be accomplished through any suitable means, such as threading, chemical bonding, heat molding, gluing, tight-fitting, fastening, an O-ring fitting, and the like. In one embodiment, the material for the handle 12 and the shaft 14 is the same or compatible enough that the two are manufactured as one integral piece. In other words, the delivery device 10 can include a shaft 14 with an enlarged proximal end that serves as the handle 12.

The illustrative handle 12 may be attached to the shaft 14 in a particular manner to select a desired orientation of the shaft 14. In FIG. 1, the shaft 14 is attached to the handle 12 such that the shaft 14 curves toward the second face 19 of the handle 12. A particular orientation between the shaft 14 and the handle 12 allows an operator to control the orientation of various parts of the shaft 14 inside a patient even when visualization is difficult or impossible.

Figure 3:
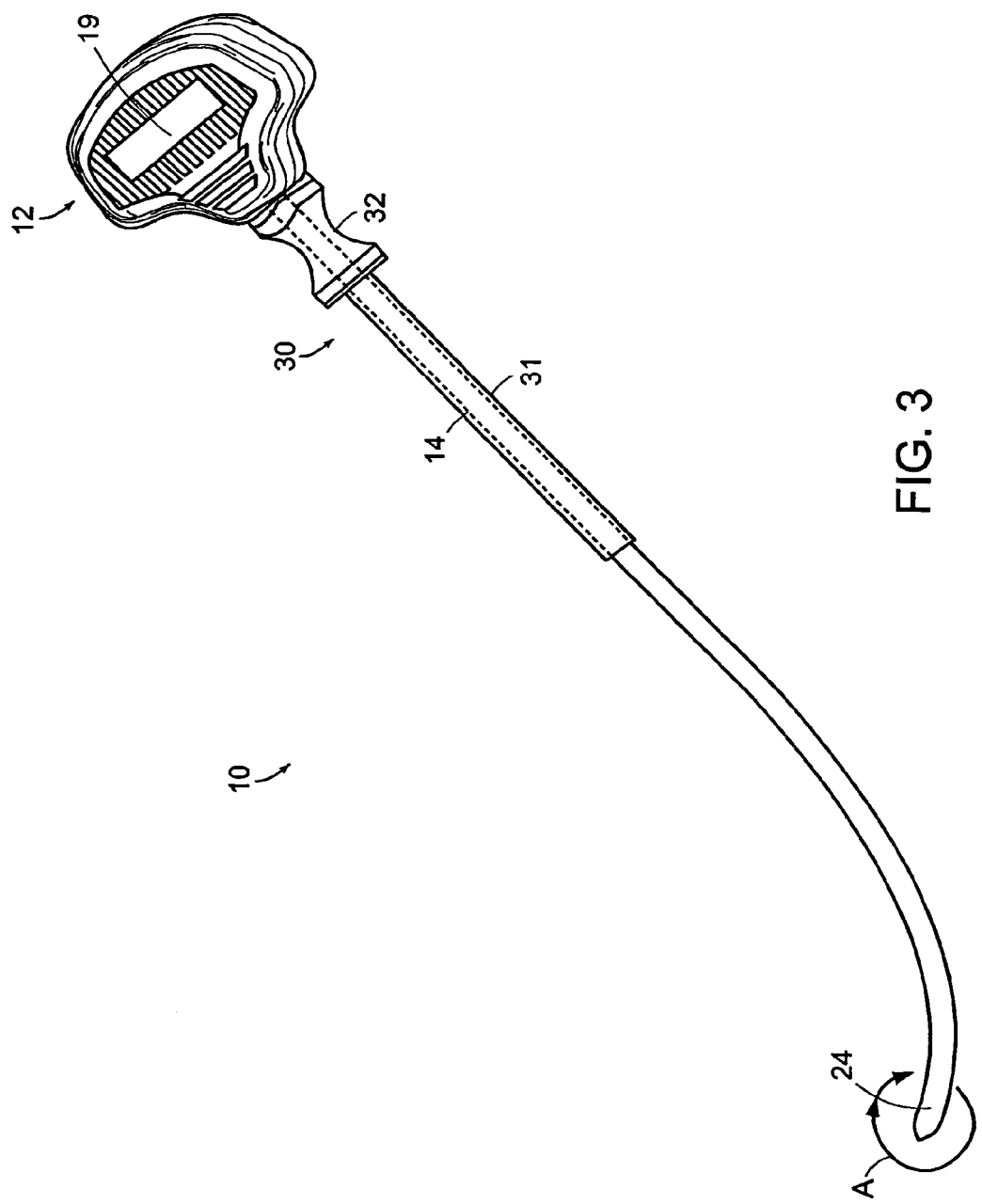
FIG. 3 depicts a perspective side view of the delivery device of FIG. 1 with a pusher assembly incorporated into the device according to an illustrative embodiment of the invention.

Referring now to FIG. 3, a pusher assembly 30 can be incorporated into the delivery device 10. The distal end 24 of the shaft 14 is marked by a circle "A" to indicate that it may include one or more connectors such as the ones described below. In the illustrative embodiment of FIG. 3, the pusher assembly 30 includes a pusher tube 31, a pusher button 32, and a tongue 33 (shown in FIGS. 4 and 5). In the assembled state, the pusher tube 31 and the pusher button 32 are slidably moveable over the shaft 14. The pusher assembly 30 is interconnected with the handle 12, as explained below in connection with FIG. 5, through the tongue 33. The pusher assembly 30 may be used, for example, to assist slidable removal or extension of a component slidably interlined over at least part of the shaft 14.

Figure 4:
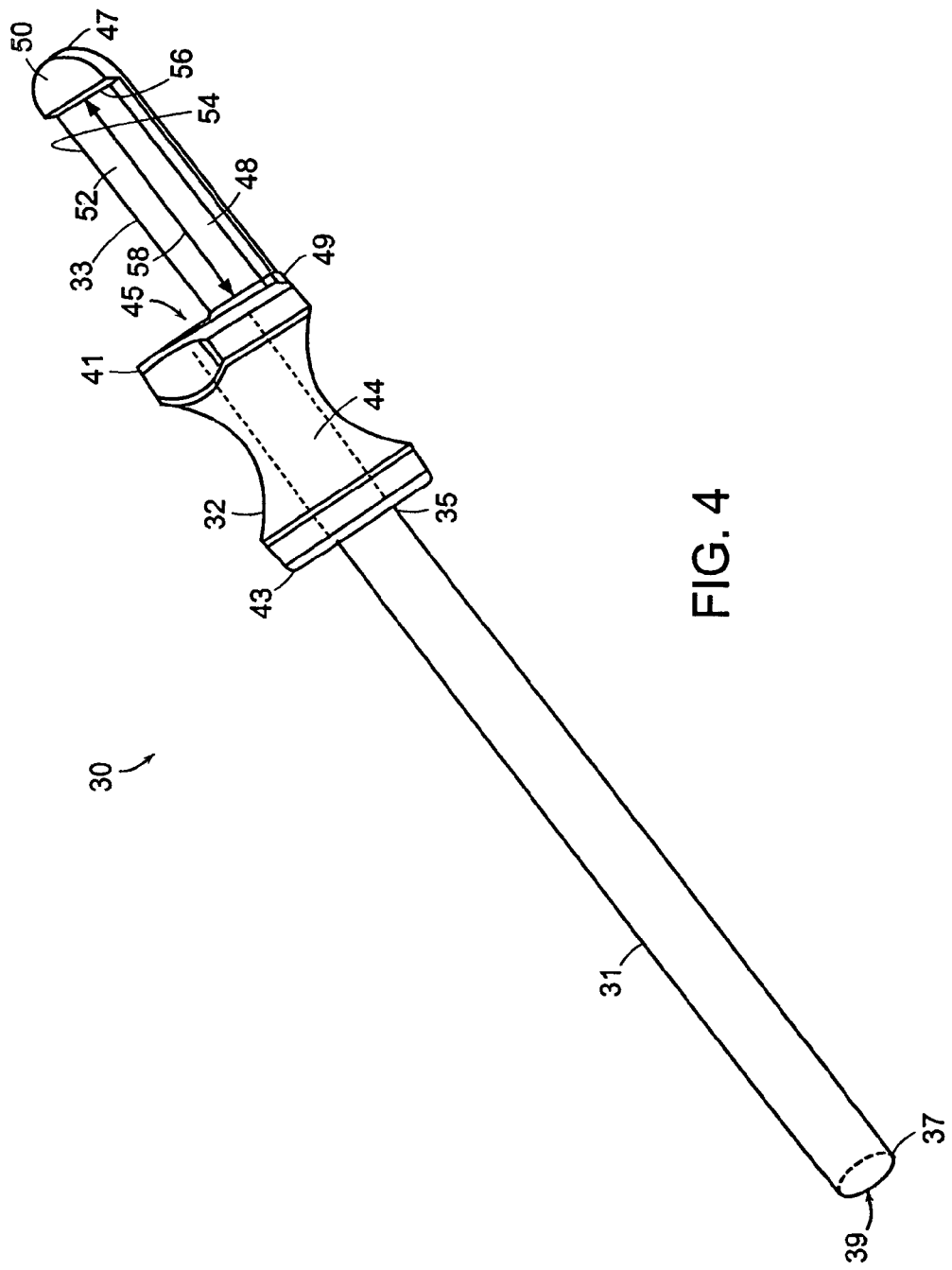
FIG. 4 depicts a perspective side view of the pusher assembly shown in FIG. 3.
Figure 5:
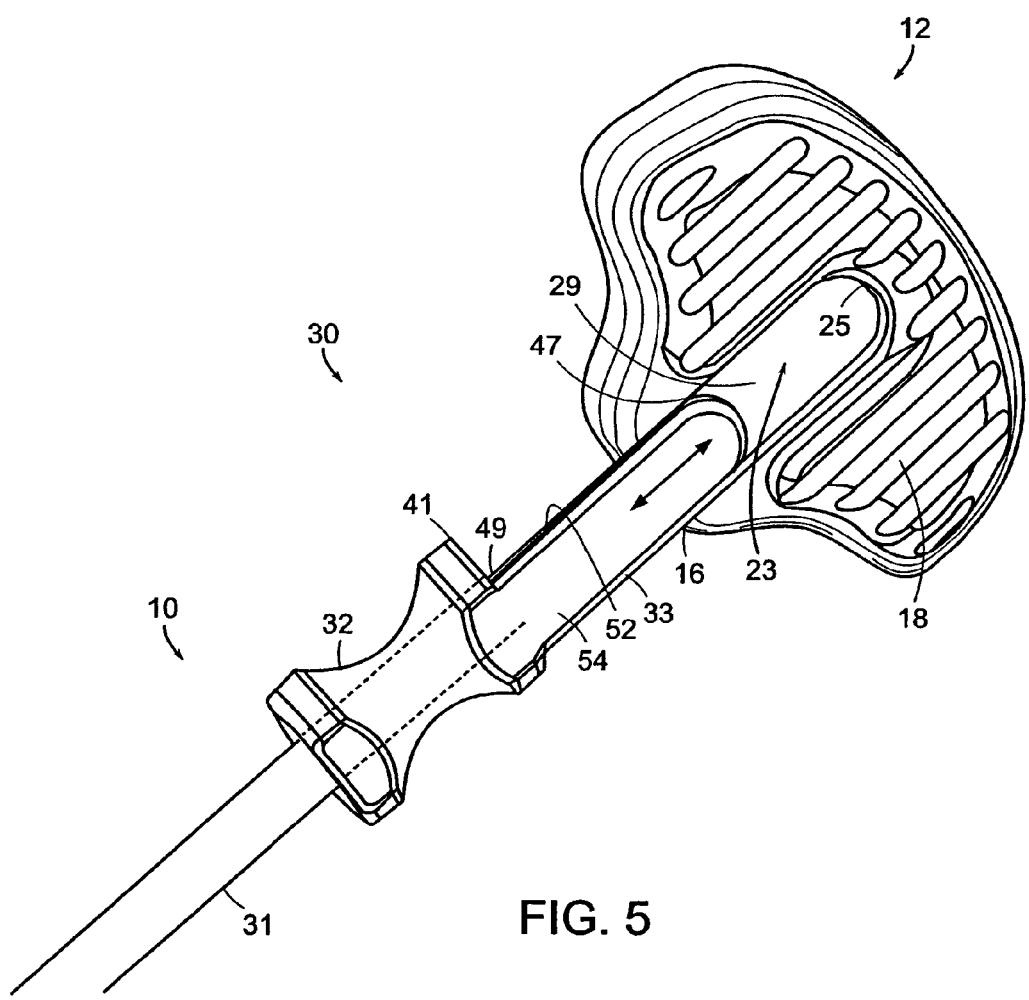
FIG. 5 depicts an enlarged perspective side view of the handle and pusher assembly portion of the device shown in FIG. 3.

Referring to FIGS. 4 and 5, the illustrative pusher assembly 30 includes a pusher tube 31, a pusher button 32, and a tongue 33. The pusher tube 31 has a proximal end 35, a distal end 37, and a lumen 39, which extends from the proximal end 35 to the distal end 37. The pusher button 32 has a proximal end 41, a distal end 43, and a lumen 45, which extends from the proximal end 41 to the distal end 43 and which is in fluid communication with the lumen 39 of the pusher tube 31 when assembled.

The pusher tube 31 attaches at its proximal end 35 to the distal end 43 of the pusher button 32. The pusher tube 31 and the pusher button 32 may form one integral component. Alternatively, the proximal end 35 of the pusher tube 31 may be placed within the lumen 45 of the pusher button 32 and be fixed by, for example, an adhesive to the surface of the lumen 45 of the pusher button 32.

Specifically referring to FIG. 4, the pusher tube 31 may be manufactured from a metal, for example, stainless steel, or from suitable polymer, plastic or other materials that have sufficient durometer hardness to function as a pusher. In one embodiment, the lumen 39 of the pusher tube 31 has a size and shape that substantially matches the cross section of the shaft 14 such that the pusher 31 fits closely around the shaft 14 (shown in FIG. 3). The outer surface and/or the inner surface of the pusher tube 31 may be coated or implanted with a hydrophilic agent, and/or other coating, to reduce surface friction. Similarly, the lumen 45 of the pusher button 32 may also be coated or implanted with a hydrophilic agent, and/or other coating or implantation, to reduce surface friction. Part or the entire outer surface and/or the inner surface of the pusher tube 31 and/or the inner surface of the pusher button 32 may, in some embodiments, be coated or implanted with one or more pharmaceuticals, for example, with anesthetic, anti-inflammatory, coagulating, anticoagulating, antibiotic or antimicrobial agents.

The pusher button 32 may assume any shape conducive to effecting motion to the pusher assembly 30. In the illustrative embodiment, parts of the pusher button 32, such as its proximal 41 and distal 43 ends are larger in cross-section than the pusher tube 31. And there is a reduced diameter area 44 in between the two ends 41 and 43. The reduced diameter area 44 is tapered and curved to allow easy identification and grasping (such as between two adjacent fingers on one hand, so that the pusher can be actuated while grasping the device with the same hand). In the particular illustrative embodiment of FIG. 4, the proximal end 41 of the pusher button 32 has a substantially rectangular or square perimeter. One side of the rectangular perimeter of the proximal end 41 is attached to the tongue 33.

The tongue 33 of the pusher assembly 30 has a proximal end 47, a distal end 49, and a body 48 extending therebetween. The body 48 has two opposite surfaces: an inner surface 52 and an outer surface 54 (better shown in FIG. 5), with the inner surface 52 facing the lumen 45 of the pusher button 32. The illustrative tongue 33 includes, at its proximal end 47, a projection 50, which has a baseline 56. The distance 58 between the distal end 49 of the tongue 33 and the baseline 56 can be varied through the manufacturing process.

Referring now to FIG. 5, the tongue 33 of the pusher assembly 30 is sized and shaped to be slidably moveable inside the recess 23 on the first face 18 of the handle 12 with the inner surface 52 of the tongue 33 facing the floor 29 of the recess 23. At least the proximal end 47 of the tongue 33 can slide back and forth in the directions indicated by arrows 55. Thus, an operator may slide the pusher assembly 30 a limited distance distally and proximally over the delivery shaft 14 (FIG. 3) by advancing the pusher button 32 distally or withdrawing the pusher button 32 proximally, respectively. The limit for distal advance of the pusher assembly 30 is set when the projection 50 of the tongue 33 is stopped by the raised stop 34 on the handle 12 (see FIGS. 2 and 4).

Similarly, the limit for proximal withdrawal of the pusher assembly 30 is set when the proximal end 47 of the tongue 33 is stopped within the recess 23 by the proximal end 25 of the recess 23. Thus, the pusher assembly 30 is limited to a fixed travel distance, i.e., the distance 58 between the distal end 49 of the tongue 33 and the baseline 56 of the projection 50 of the tongue 33 (see FIG. 4). The distance 58 may vary to suit a particular clinical application of the delivery device 10. In one embodiment, the distance 58 that the pusher assembly 30 can travel is approximately one (1) inch (about 2.54 cm).

Another advantage of the illustrative pusher assembly embodiment illustrated here is that through the interaction between the projection 50 of the tongue 33, the stop 34 of the handle 12, and the proximal end 25 of the recess 23, as described above, the tongue 33 of the pusher assembly 30 remains in constant contact with the handle 12. As a result, the pusher button 32 is also prevented from rotating about the delivery shaft 14.

Figure 6:
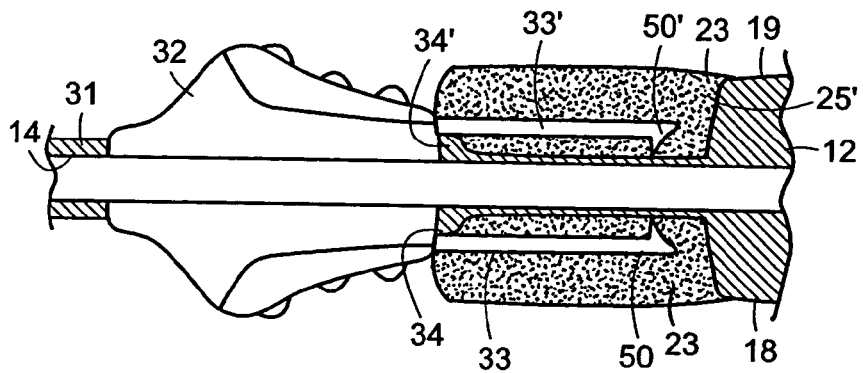
FIG. 6 depicts a longitudinal cross-sectional view of a pusher assembly on a delivery device according to an alternative embodiment of the invention.

Referring to FIG. 6, a recess 23' similar to the described recess 23 on the face 18 of the handle 12 is made on the other face 19 of the handle 12. The recess 23' also has a raised stop 34' similar to the stop 34 in the recess 23. And the tongue 33 is duplicated on the opposite side of the pusher assembly 30 as a second tongue 33', i.e., the tongue 33' also has a projection 50' similar to the projection 50 on the tongue 33. As a result, the projection 50' of the second tongue 33' slides between stop 34' and the proximal end 25' of the recess 23', simultaneously with the projection 50 of the first tongue 33. The two-tongue configuration makes it even easier to operate the pusher assembly 30.

Referring now to FIGS. 7A, 7B, 8A and 8B, according to alternative embodiments of the invention, a delivery device 57 includes a shaft 59 (which may be a needle or non-needle element), a guide tube 60, and a handle 61. In this particular embodiment, both the shaft 59 and the guide tube 60 are attached to the handle 61. The guide tube 60 has a proximal end 62 and a distal end 64, and can also function as a dilator tube. A tubular member or wall of the guide tube 60 forms a lumen that allows the shaft 59 to slidably move inside the guide tube 60. The guide tube 60 may be made of a metal such as stainless steel or a plastic. In one embodiment, the guide tube 60 is made of the same material as the shaft 59. The distal end 63 of the shaft 59 (FIGS. 7B and 8A), and the distal end 64 of the guide tube 60 (FIGS. 7A and 8B) are both marked by circles "A" to indicate that they may both include one or more connectors such as the ones described and illustrated in more detail below.

Figure 7A:
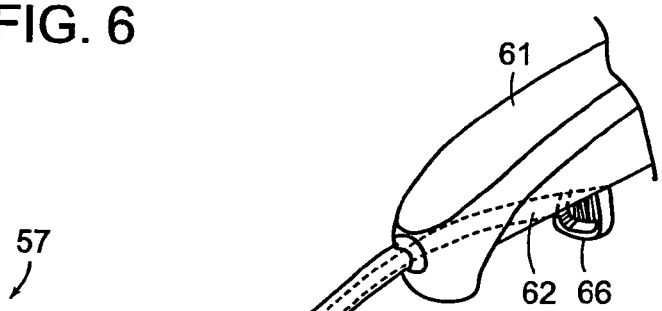
FIG. 7A depicts a perspective side view of a delivery device that includes a guide tube and a shaft, with the guide tube actuated to be in a first position relative to the shaft according to an embodiment of the invention.
Figure 7B:
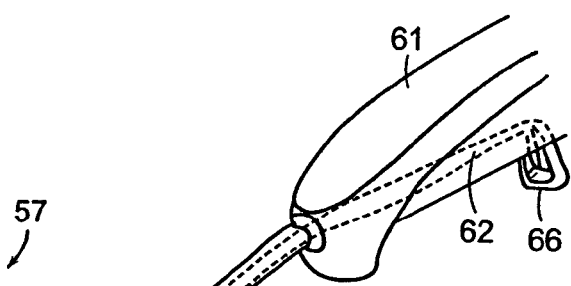
FIG. 7B depicts a perspective side view of the delivery device of FIG. 7A where the guide tube is actuated to be a second position relative to the shaft.

Specifically referring to FIGS. 7A and 7B, the handle 61 includes an actuator 66 operatively connected to the proximal end 62 of the guide tube 60. The connection between the actuator 66 and the proximal end 62 of the guide tube 60 may be permanent or reversible (removable and reusable). The illustrative actuator 66 operates through a mechanical interconnection. However, in alternative embodiments, it may operate through electrical, chemical, magnetic, mechanical, or other suitable mechanism, separately or in combination. In one embodiment, the actuator 66 includes a first set of threads (not shown) that interfits with a second set of threads (not shown) in the guide tube 60. In the illustrative embodiment, the actuator 66 includes a mechanical slider that has at least two positions. In FIG. 7A, the actuator 66 is at its distal position, and the distal end 64 of the guide tube 60 is positioned distal to the tip 67 of the shaft 59, for example, by about 0.5 to about 2 inches. In FIG. 7B, the actuator 66 is at a proximal position and resultantly withdraws the distal end 64 of the guide tube 60 to be proximal to the tip 67 of the shaft 59. Through manipulating the actuator 66, the operator can choose to either shield or expose the tip 67 of the shaft 59 at different stages in an operation. The illustrative guide tube 60 is longer than the shaft 59. However, in other embodiments, the guide tube 60 may be of the same or shorter length than the shaft 59. In one embodiment, the guide tube 60 is separate from, i.e., not attached to or connected with, the handle 61.

Figure 8A:
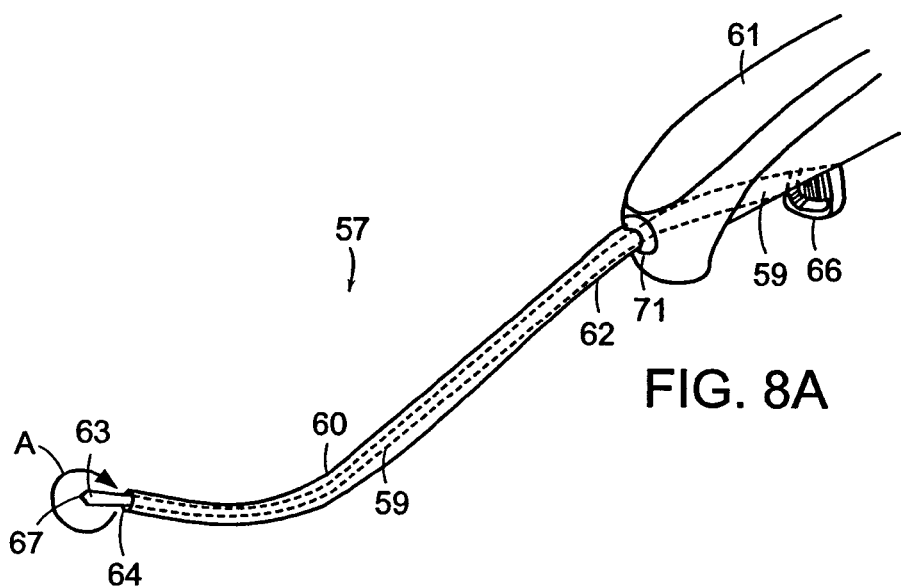
FIG. 8A depicts a perspective side view of a delivery device that includes a guide tube and a shaft, with the shaft actuated to be in a first position relative to the guide tube, according to an alternative embodiment of the invention.
Figure 8B:
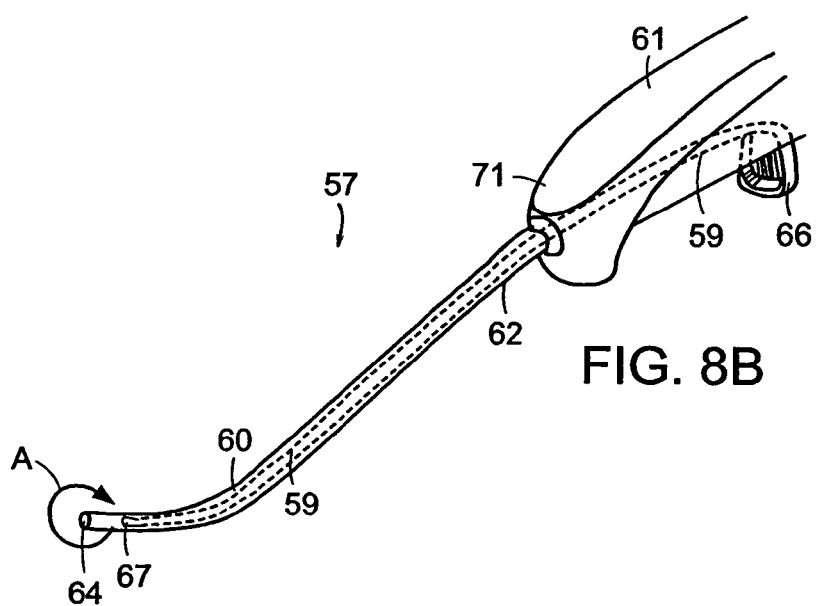
FIG. 8B depicts a perspective side view of the delivery device of FIG. 8A with the shaft actuated to be in a second position relative to the guide tube.

Specifically referring to FIGS. 8A and 8B, the actuator, for example, the slider 66, is instead operatively connected to the proximal end 46 of the shaft 59. The proximal end 62 of the guide tube 60 may be connected to the distal end 71 of the handle 61, for example, through frictional fitting, adhesive, threading, or the like. In FIG. 8A, the slider 66 is at its distal position. As a result, the tip 67 of the shaft 59 is exposed and at a position distal to the distal end 64 of the guide tube 60. In FIG. 8B, the actuator 66 is at a proximal position. As a result, the tip 67 of the shaft 59 is withdrawn proximal to the distal end 64 of the guide tube 60 and shielded by the guide tube 60. Through manipulating the actuator 66, the operator can, similar to using the embodiment depicted in FIGS. 7A and 7B, choose to either expose or shield the tip 67 of the shaft 59 at different stages in an operation.

Figure 9A:
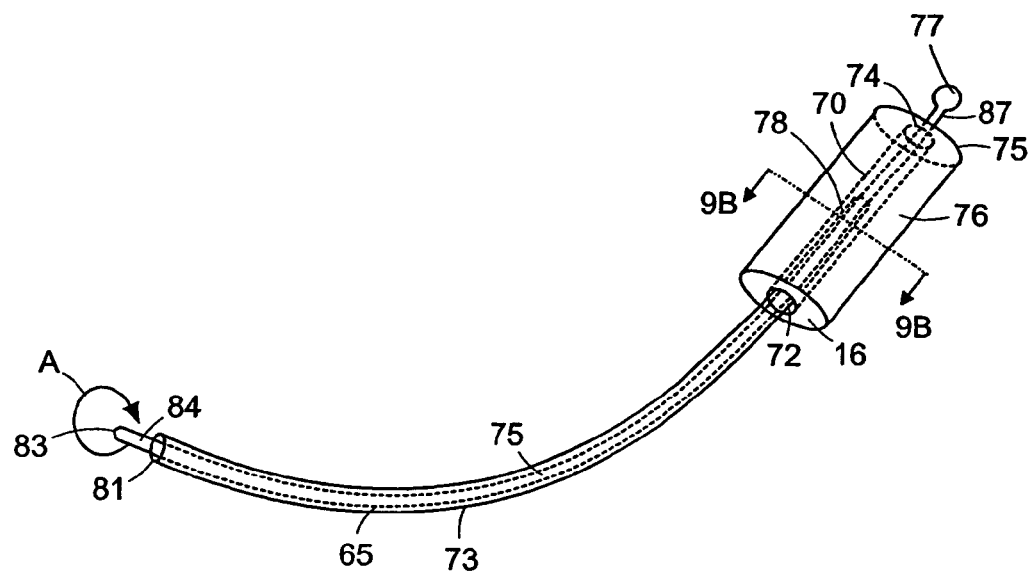
FIG. 9A depicts a perspective side view of a delivery device according to another illustrative embodiment of the invention.
Figure 9B:
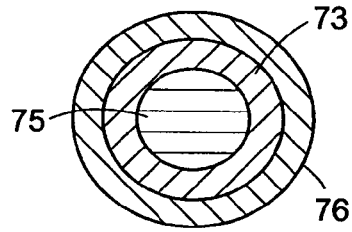
FIG. 9B depicts a cross-sectional view of the device shown in FIG. 9A along the line "9B-9B."

Referring now to FIGS. 9A and 9B, according to another illustrative embodiment of the invention, the delivery device includes a guide tube 73, a shaft 75 (which may be a needle or non-needle element), and a handle 76. The handle 76 includes an axial lumen 70 extending between a distal opening 72 at the distal end of the handle 76 and with a proximal opening 74 at the proximal end of the handle 76. The axial lumen 70 of the handle 76 is sized and shaped so that at least the proximal end 78 of the guide tube 73 is slidably moveable within at least part of the axial lumen 70. In one embodiment, a proximal end 78 of the guide tube 73 can slide through the proximal opening 74 of the handle 76. In an alternative embodiment, the proximal end 78 of the guide tube 73 does not exit the proximal opening 74 of the handle 76 as a proximal part of the lumen 70 of the handle can be narrower or completely blocked towards the proximal end of the handle 76. In one embodiment, the handle 76 can be pulled off the proximal end 78 of the guide tube 73.

The guide tube 73 has the proximal end 78, the distal end 64, and defines a lumen 65 that allows the shaft 75 to slidably move inside the tube 73. The guide tube 73 may be made of a metal such as stainless steel, a polymer, plastic or other suitable material. In one embodiment, the guide tube 73 is made of the same material as the shaft 75. The guide tube 73 may assume a shape substantially similar to that of the shaft 75. Additionally, it may be substantially rigid, semi-rigid, semi-flexible or flexible. The guide tube 73 may include one or more curves.

The shaft 75 is slidably moveable inside the guide tube 73. At one position, the tip 83 of the shaft 75 is distal to the guide tube 73 and thus exposed. The distal end 84 of the shaft 75 is marked by a circle "A" to indicate that it may include one or more connectors such as the ones described below. In one embodiment, the proximal end 87 of the shaft 75 includes a graspable structure, for example, a knob 77 or an enlarged end. By grasping the knob 77, the operator can insert or withdraw the shaft 75 from the lumen 65 of the guide tube 73, through the proximal opening 74 of the handle 76. FIG. 9B illustrates the relative position between the shaft 75, the guide tube 73, and the handle 76 through a cross-sectional view. There can be clearance (not shown) between any of the three structures.

Figure 10A:
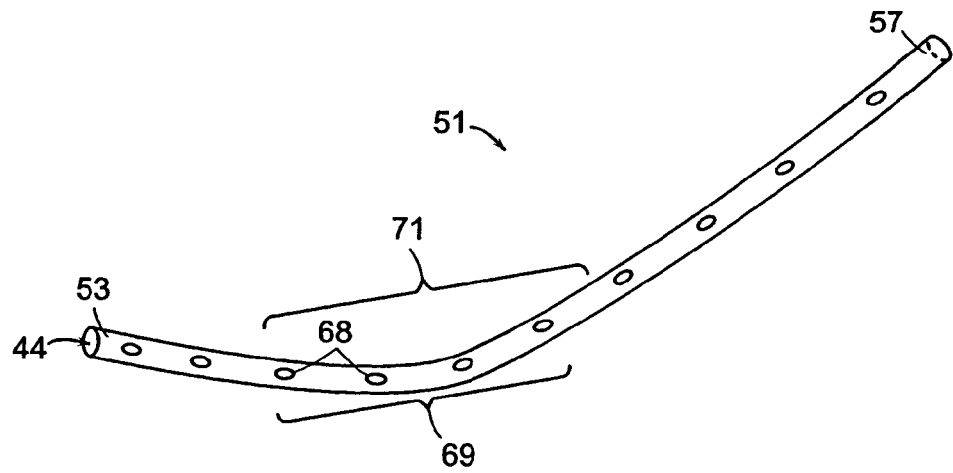
FIG. 10A depicts a perspective side view of an exemplary guide tube according to one illustrative embodiment of the invention

Referring now to FIG. 10A, an illustrative guide tube 51 has openings on both its distal end 53 and its proximal end 57. A lumen 44 is in fluid communication with both the ends 53, 57 of the guide tube 51. One or more apertures 68 penetrate the wall of the guide tube 51 and are in fluid communication with the lumen 44. In one embodiment, the apertures 68 penetrate the wall of the guide tube 51 between the convex 69 and the concave 71 regions defined by the curve of the guide tube 51. Because of the apertures 68, if the distal end 53 of the guide tube 51 inadvertently punctures an organ, such as the bladder, during the operation, the operator would be alerted when he sees fluid from the punctured organ, such as urine or blood, flowing out of the apertures 68. Both the distal end 53 and the proximal end 57 of the guide tube 51, marked by circles "A", may include a connector or one member of a connector pair, to be described and illustrated in more detail below.

Referring to FIG. 10B, in one illustrative embodiment, the apertures 68 are distributed along a longitudinal axis of the guide tube 51 such that at least two complementary apertures 68 are equidistant from one end 53 or 57 of the guide tube 51. Referring to FIG. 11, alternatively, the apertures 68 may be distributed in an alternating pattern along the longitudinal axis of the guide tube 51. The apertures 68 can be any shape, such as circular, elliptical, and slotted, for example. The edges of the apertures 68 may be beveled or rounded to prevent abrasion of surrounding tissue during use of the delivery system inside a patient.

FIG. 12 illustrates one way to associate the guide tube 73 and the handle 76. A setscrew 79 is positioned at the distal end 46 of the handle 76 and extends into the axial lumen 70 of the handle 76. The lumen 70 slidably receives the proximal end 78 of the guide tube 73. The setscrew 79 can be tightened to hold the guide tube 73 stationary, and loosened to remove the handle 76 from the guide tube 73. Alternatively, the guide tube 73 is associated with the handle 76 by any other detachable junction known in the art, such as a snap junction, threading, interference fit, for example. In other embodiments, the guide tube 73 is not detachable from the handle 76.

Figure 13A:
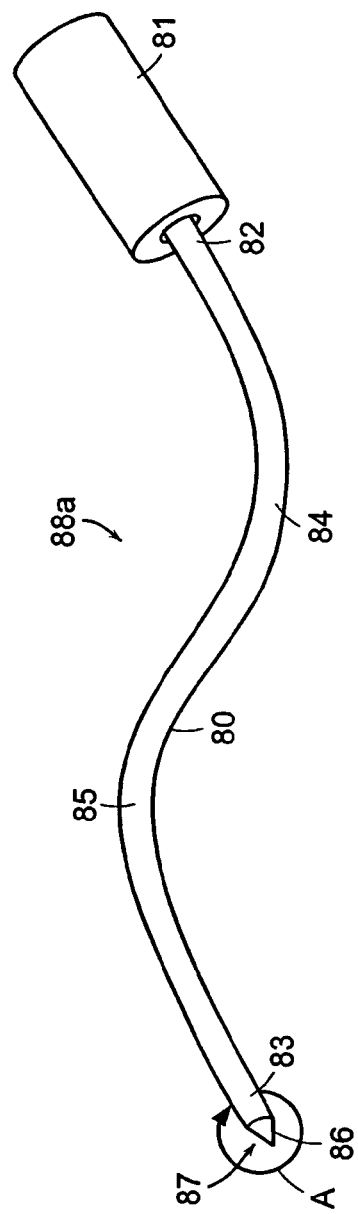
FIGS. 13A and 13B depict perspective side views of delivery devices with multiple bends according to illustrative embodiments of the invention.

Referring to FIG. 13A, the delivery device 88a includes a shaft 80 and a handle 81. In addition to the features and properties described above, the shaft 80, according to this embodiment of the invention, includes a plurality of curves, bends, or arcs distributed between its proximal end 82 and the distal end 83. For example, the shaft 80 may describe two, three, four arcs or more. In one embodiment, for example, the shaft 80 describes a first arc 84 next to the proximal end 82 and a second arc 85 next to the distal end 83. The two arcs 84 and 85 can be adjacent each other and form a continuous curvature resembling a wave with a peak and a valley, for example. Alternatively, the two arcs may not be adjacent each other. In one embodiment, the multiple arcs 84 and 85 are substantially located in the same common plane.

The shaft 80, in one embodiment, tapers from its proximal end 82 to its distal end 83, with its widest part at its proximal end 82. In another embodiment, the shaft 80 is not tapered and maintains a substantially uniform outer diameter. In one particular embodiment, the shaft 80 is not tapered and has an outer diameter of about 0.125 inches. The distal end 83 of the shaft 80 may include a tapered, for example, a conical, section 86 that leads to the tip 87. The tip 87 may be sharp, pointed, or blunt. In the depicted embodiment, the shaft 80 is a solid shaft, but may be hollow or have a hollow portion.

Figure 13B:
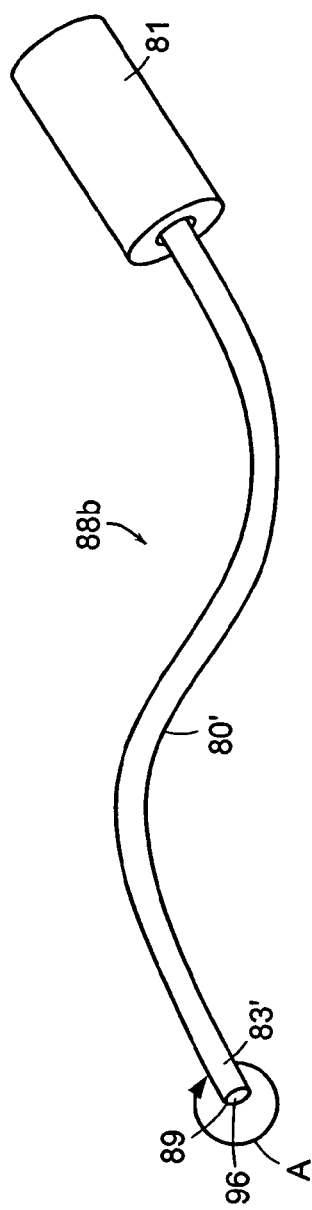

FIG. 13B depicts a delivery device 88b including a shaft 80' attached to a handle 81. The shaft 80' includes a tubular member with an opening 89 at its distal end 83'. The opening 89 is in fluid communication with a lumen 96. The distal ends 83 and 83' of the shafts 80 and 80' are marked by circles "A" to indicate that they may include various different types of connectors. Illustrative connectors are described in more detail below. Additionally, as with previously described delivery devices, the handles 81 and the shafts 80 and 80' may be permanently, or removably and reusably attached to each other.

Figure 16:
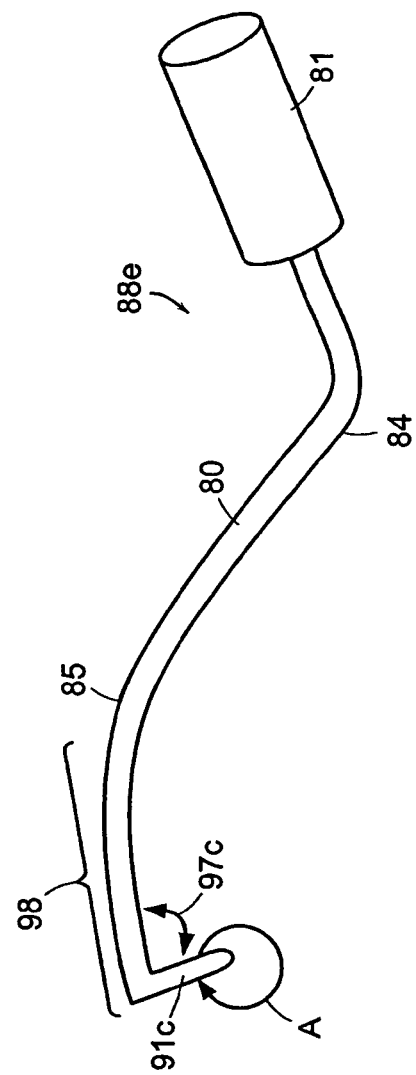

Referring now to FIGS. 14-16, in alternative embodiments of delivery devices 88c, 88d, and 88e, in addition to describing multiple arcs 84 and 85 along its length, the shaft 80 may further include an angled or further curved distal end 91a, 91b, or 91c that is at an angle 97a, 97b, or 97c relative to an adjacent portion 98 of the shaft 80, according to the invention. In one embodiment, the angled distal end 91a, 91b or 91c is substantially straight. The adjacent portion 98 may include part or all of one of the arcs, for example, arc 85 which forms a concave region relative to the angled distal end 91a, 91b or 91c. Alternatively, the adjacent portion 98 may be substantially straight. The degree and flexibility of the angle 97a, 97b, or 97c, and the length of the angled distal end 91a, 91b, or 91c of the shaft 80, may be selected according to the surgical application so that the distal end 91a, 91b, or 91c of the shaft 80 and its adjacent portion 98 follow or accommodate the contour of part of the patient's anatomy, for example, the pubic bone. In one illustrative embodiment, the angle 97a, 97b, or 97c and the length of the angled distal end 91a, 91b, or 91c are pre-selected to conform to the front contour of the female pubic bones. For example, as illustrated in FIG. 14, the angle 97a between the distal end 91a and its adjacent portion 98 of the shaft 80 is obtuse. Alternatively, as illustrated in FIG. 15, the angle 97b is about 90°, and as illustrated in FIG. 16, the angle 97c is acute, for example, about 60°. In other embodiments, the angle of the bent by the distal end 97a, 97b, or 97c can be greater than about 45°, or greater than about 60°. These angle embodiments may have advantages for accommodating particular body anatomy, such as the outline of the public bone. In one embodiment, the multiple arcs 84, 85, and the angled distal end 91a, 91b, or 91c are all substantially located in the same common plane. Preferably, the length of the angled distal end 91a, 91b, or 91c constitutes no more than about 10%, 20% or 25% of the entire length of the shaft 80 that is outside the handle 81.

In one embodiment, the angled distal end 91a, 91b, or 91c is employed to deflect the shaft 80 over the patient's pubic bone. According to both the suprapubic-to-vaginal approach and the pre-pubic-to-vaginal approach, the angled distal end 91a, 91b, or 91c of the shaft 80 is preferably pointed toward the pubic bone and away from internal organs.

Figure 17:
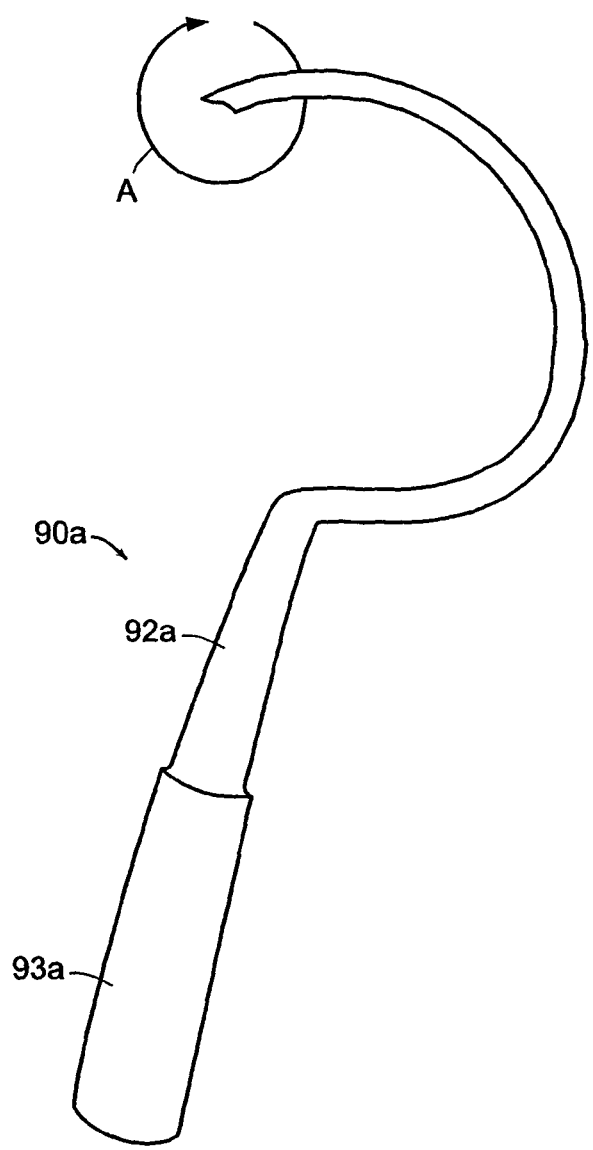
FIG. 17 depicts a perspective side view of a particularly curved delivery device according to an illustrative embodiment of the invention.

FIG. 17 depicts an alternative illustrative delivery device 90a including a shaft 92a and a handle 93a. The shaft 92a, at least in part, describes an arc of a substantial degree, for example, no less than about 45, about 60, or about 90 degrees in various embodiments. In one embodiment, the curve in the shaft 92a forms a "C" configuration.

Figure 18:
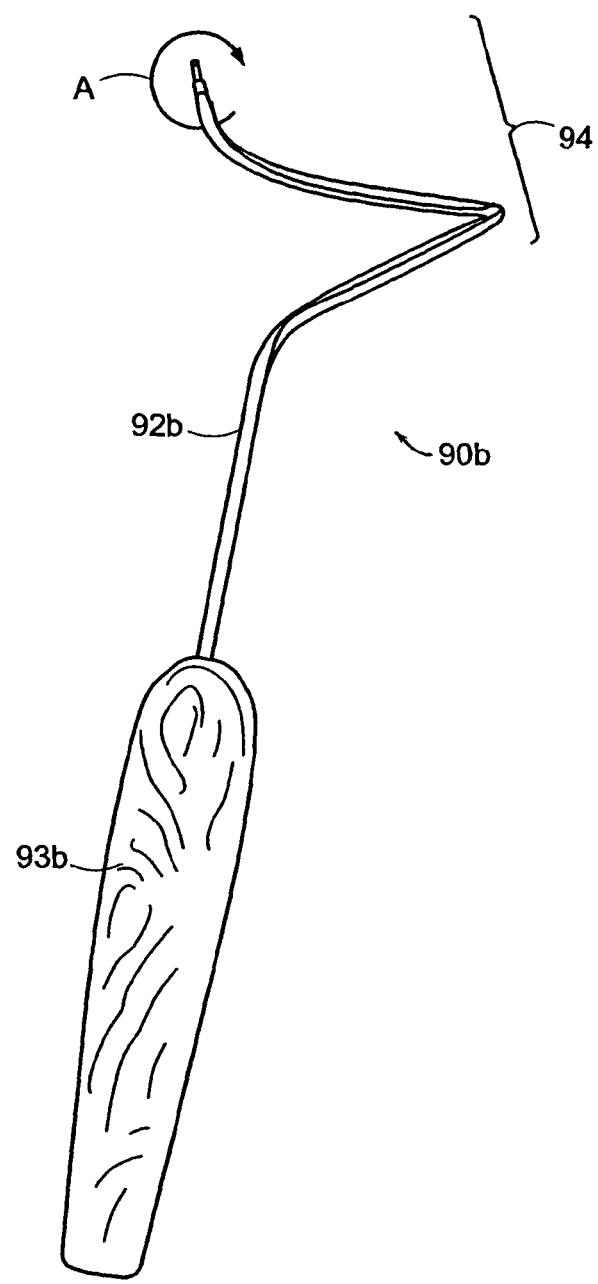
FIG. 18 depicts a perspective side view of alternatively curved delivery devices according to another illustrative embodiment of the invention.

FIG. 18 depicts another alternative delivery device 90b, including a shaft 92b attached to a handle 93b. The shaft 92b describes a helical curve 94 of between one and two turns. However, the helical curve 94 may include any suitable number of turns. The delivery devices 90a and 90b may be used to perform a trans-obturator procedure to place an implant such as a sling for treating urinary incontinence as described in more detail below.

II. Implants

The delivery devices described above may be used to deliver and place any suitable implant, such as a sling assembly, at an anatomical site in a patient's body.

Without limitation, exemplary sling/sleeve configurations that may be operable with illustrative embodiments of the invention may be found in U.S. patent application Ser. No. 10/641,170, entitled Medical Slings, to Rao et al, filed on Aug. 14, 2003; U.S. patent application Ser. No. 10/641,192, entitled Medical Slings, to Chu, filed on Aug. 14, 2003; U.S. provisional patent application no. 60/495,439, entitled Surgical Slings, to Li et al, filed on Aug. 14, 2003, U.S. patent application Ser. No. 10/640,838, entitled Medical Implant, to Chu et al., filed, on Aug. 24, 2003, U.S. provisional patent application Ser. No. 60/403,555; U.S. provisional patent application Ser. No. 60/465,722; U.S. patent application Ser. No. 10/460,112; and U.S. patent application Ser. No. 09/096,983, the entire contents of which are incorporated herein by reference.

FIG. 19 depicts an illustrative sling assembly 11 including a sling 95 and a sleeve 99 suitable for use with the previously described delivery devices. The sling 95 may be formed, for example, from a strip of mesh, a network of fabric, a suture, a permeable, non-permeable, porous, non-porous, or any other material constructed for support or constriction. Non-limiting examples of materials that can be employed to manufacture the sling 95 include polypropylene, polyesters, polyolefins, polytetrafluoroethylene, polyethylene, polyurethanes, nylons, and co-polymers thereof as described in U.S. Pat. No. 6,042,592, the disclosure of which is incorporated herein by reference. The sling 95 may be formed natural tissues (such as human cadaveric, bovine, porcine, equine, etc.), or the sling may be formed from a hybrid of synthetic materials and natural tissues; and may contain features described in co-owned patent applications U.S. Ser. No. 09/916,983 and U.S. Ser. No. 10/460,112, the entire disclosures of both are incorporated by reference. The sling 95 may be coated, for example, with a pharmaceutical.

Optionally, the sling 95 may include rough edges containing projections called tangs. The sling 95 may also have a partly de-tanged edge that is free of any tangs. These and other optional features of the sling 95 are described in co-owned U.S. patent application Ser. No. 10/092,872 and Ser. No. 10/093,498, the entire disclosures of both are incorporated herein by reference.

Still referring to FIG. 19, in certain embodiments, the sling 95 is at least partly enclosed in a sheath envelope or envelope-like structure, such as the sleeve 99. In the illustrative embodiment, the sleeve 99 fully encloses the sling 95, and the sling 95 is substantially free floating in the sleeve 99. The sleeve 99 surrounding the sling 95 reduces the likelihood that the sling 95 will become contaminated with foreign matter, such as bacteria, during the delivery and placement procedure at an anatomical site. Additionally, the sleeve 99 provides added structural integrity to the sling 95 so that the sling 95 does not get twisted, or over-stretched during the delivery process. The sleeve 99 can also assist the operator in adjusting the position and tension in the sling 95 during placement or implantation.

The sleeve 99 may be coated, for example, with a pharmaceutical on its outer surface and/or its inner surface. Non-limiting examples of materials that can be employed to manufacture the sleeve 99 include polypropylene, polyethylene, polyester, polytetrafluoroethylene, or co-polymers thereof. The sleeve 99 may include tear features such as apertures to assist the operator in removing the sleeve 99 from the sling 95 after delivery. The sleeve may associate with other structures such as spacers, scaffolds, fasteners, tongues, and tabs that assist in the delivery and placement of the sling assembly 11. These and other optional features of the sleeve 99 or other parts of the sling assembly 11, including the sling 95, are described in co-owned U.S. patent applications, namely appication Ser. No. 10/640,838 and application Ser. No. 10/641,376 "Systems, Methods and Devices Relating to Delivery of Medical Implants," both of which filed on even date herewith, and the entire content of which is incorporated herein by reference.

The two ends 100a and 100b of the sleeve 99 may include structures such as tabs or dilators. Such structures can be made of the same material or a material different from the sleeve 99. In some embodiments, such material is selected to have more structural rigidity than the sleeve 99. The two ends 100a and 100b of the sleeve 99 are marked by circles "B" and "B'" to indicate that may include one or more connectors for connecting to the shafts, guides tubes, guide members, dilators and/or dilator tubes of delivery devices. Such connectors are described in detail below. In embodiments where the sling assembly 11 does not include the optional sleeve 99, the two ends 102a and 102b of the sling 95 may include structures such as tabs, dilators, and connectors (also described below in detail).

FIG. 20 depicts an alternative sling assembly 101, including a sleeve 105, formed from two sleeve portions 105a and 105b and only partly enclosing the sling 95. In this embodiment, the sleeve portions 105a and 105b are separated and distinct and provide for an interment portion of the sling 95 to be sleeveless. The two ends 102a and 102b of the sling 95 are fixedly attached to parts of the sleeve portions 105a and 105b, for example, through heat bonding, a suture or any other suitable mechanism. The two ends 107a and 107b of the sleeve 105 are marked by circle "B" and "B'" to indicate that they may include one or more connectors as described in detail below.

Figure 21:
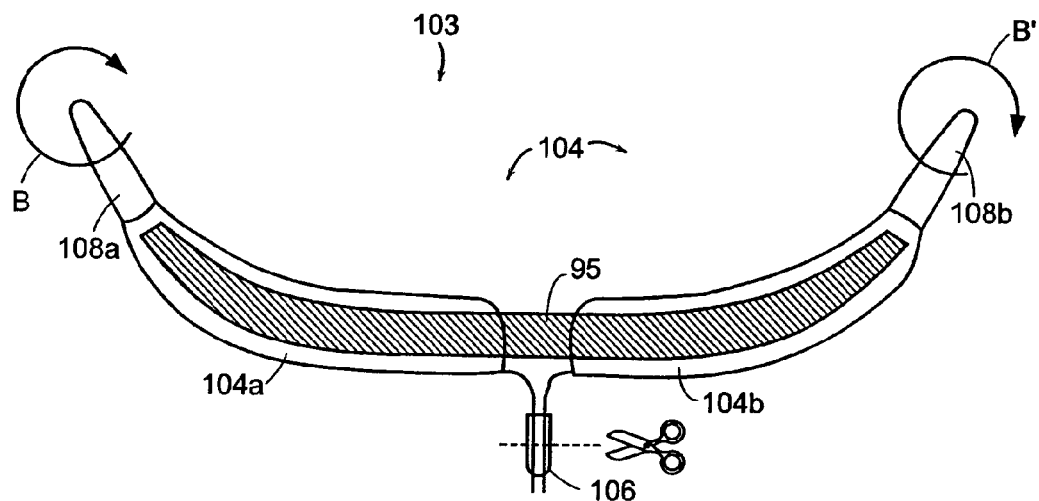
FIG. 21 depicts a top view of another exemplary sling assembly that may be employed with the various illustrative delivery devices of the invention.

Referring now to FIG. 21, in another alternative embodiment, a sling assembly 103 includes a sleeve 104 that also partly encloses the sling 95. The sling 95 is free floating inside the sleeve 104. The sleeve 104 includes two separate portions 104a and 104b. However, the sleeve portions 104a and 104b are fastened to each other on one side through a fastener 106, for example, a tab. Alternatively, the one side of the sleeve portions 104a and 104b is one integral piece that can be formed into a loop that is oriented within or around a fastener or spacer. Cutting across the fastener 106 allows the operator to remove the fastener 106 and the two sleeve portions 104a and 104b become separate from each other. Then, the operator can remove the sleeve portions 104a and 104b from the patient's body by pulling on two ends 108a and 108b of the sleeve portions 104a and 104b. A more detailed description of the fastener 106 and other means of fastening the sleeve portions 104a and 104b are provided in the co-pending U.S. patent application Ser. No. 10/641,376, filed on Aug. 14, 2003 "Systems, Methods and Devices Relating to Delivery of Medical Implants." The two sleeve ends 108a and 108b, also marked by circle "B" and "B'" and to be shown in detail in subsequent figures, may include one or more connectors described below.

III. Connectors

Connectors can be used to interlock and/or attach various parts in a delivery system permanently or reversibly (i.e. removably and reusably). For example, connectors can be used to attach and/or interlock two or more of the following: an implant or implant assembly (for example, a sling assembly), a delivery device, or a guide member. Alternatively, connectors can be used to attach and/or interlock parts within the sling assembly, or within the delivery device, or within the guide member. Connectors may also serve additional functions besides the above, such as dilation or tunneling.

Some exemplary sling/sleeve termination configurations and connectors are disclosed in U.S. patent application Ser. No. 10/325,125; U.S. provisional patent application Ser. No. 60/418,827; U.S. provisional patent application Ser. No. 60/418,642; U.S. provisional patent application Ser. No. 60/434,167; and U.S. provisional patent application Ser. No. 60/403,555; the disclosures of which are incorporated herein by reference.

Each pair of connectors typically includes two connector members; each may be located on a part of the delivery system, for example, the sling assembly, the delivery device, or the guide member. For ease of reference, the part of the delivery system on which a connector is located is referred to as the "base part." A connector can be integral with its base part, for example, the connector may be a slot, a reduced-diameter section, or an aperture in the base part or may be attached to its base part. Additionally, the connector may be made out of the same material as the base part, for example, through thermal extrusion or molding.

A connector and its base part may be attached in a permanent, or reversible, (i.e., removable and reusable) fashion. Any suitable mechanism may be used to attach a connector with its base part, for example, use of an O-ring or other fasteners, or use of heat bonding or an adhesive. For convenience of illustration, one member of each connector pair may be shown in the drawings as located on a particular structure, for example, a sling assembly, but it should be understood that each member of a connector pair can be interchangeably located with the other member of the pair.

FIGS. 22A-22D depict a connector pair 110 including a loop connector 111, and a mating slotted receptacle connector 112. The illustrated loop connector 111 includes a loop portion 113 at its distal end and a base portion 115 at an opposite end, bridged by a neck portion 116, which tapers inward from the loop portion 113 to the base portion 115.

In this illustrative embodiment, the loop connector 111 is located at the sling assembly end 117. More particularly, the illustrated base portion 115 of the loop connector 111 is attached to a dilator 118 located at the sling assembly end 117. The base portion 115 may be, for example, insert molded to the dilator 118 or bonded by any suitable means.

The loop connector 111 may be formed from any filament such as wire, cable or suture, which may be made, for example, of plastic, steel or any other suitable material, including a shape memory material. In one embodiment, the loop connector 111 is rigid. In an alternative embodiment, the loop connector 111 is not rigid, but has sufficient durometer hardness to maintain a pre-selected shape. In a further embodiment, the loop connector 111 is malleable to fit the outline of a slot 120 after the connector 111 hooks onto the receptacle connector 102. In yet another embodiment, the loop connector 111 is flexible. The loop connector 111 may be of a variety of shapes, for example, circular, semi-circular, oval, triangular or rectangular. The entire loop connector 111 can be made of a unitary material, or in sections.

The receptacle connector 112, in this illustrative embodiment, is located at a shaft distal end 121 of a shaft 114 in a delivery device 119. As shown, the connector 112 includes an L-shaped slot 120 formed in the distal end 121. The connector 112 also includes two lateral grooves 122a and 122b extending axially in a distal direction from the L-shaped slot 120 to the tip 123 of the distal end 121. The L-shaped slot 120 includes an entry slot 124 extending from a peripheral side of the shaft distal end 121 radially inwards. The L-shaped slot 120 also includes a retention slot 125 extending axially in distal direction.

Figure 22A:
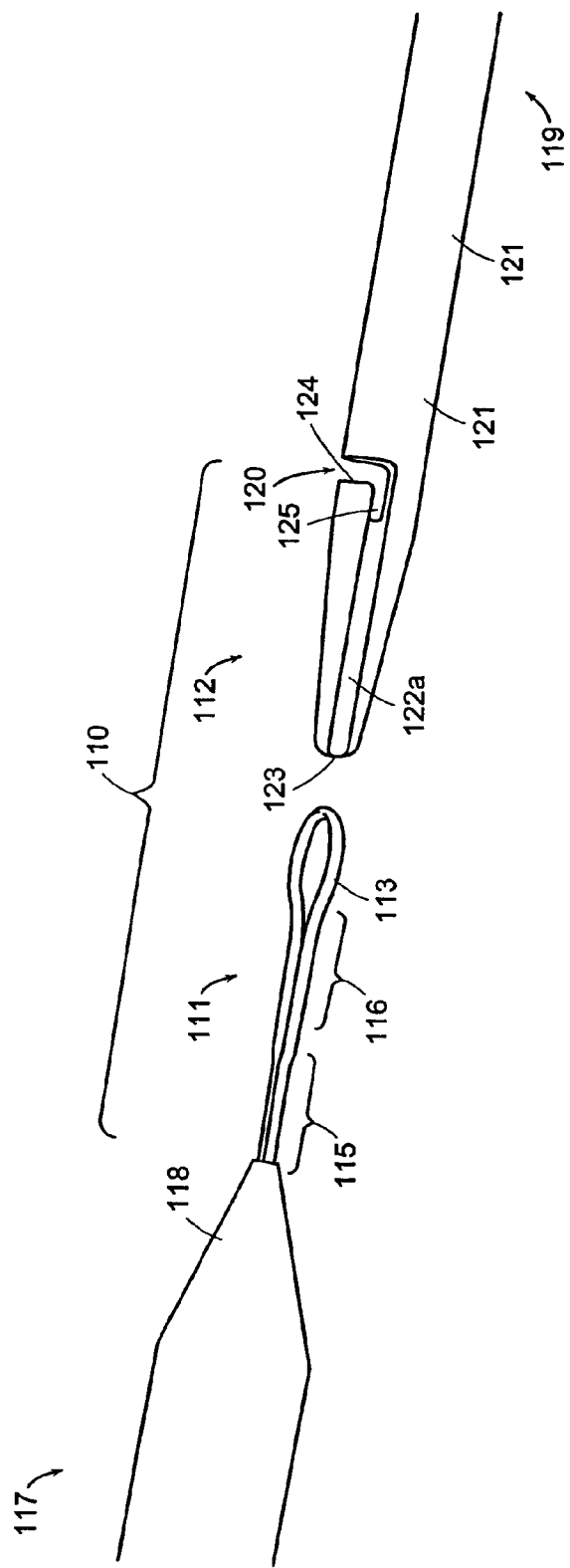
FIG. 22A depicts a side perspective view of a loop connector and mating receptacle connector prior to interconnection, according to an illustrative embodiment of the invention.
Figure 22B:
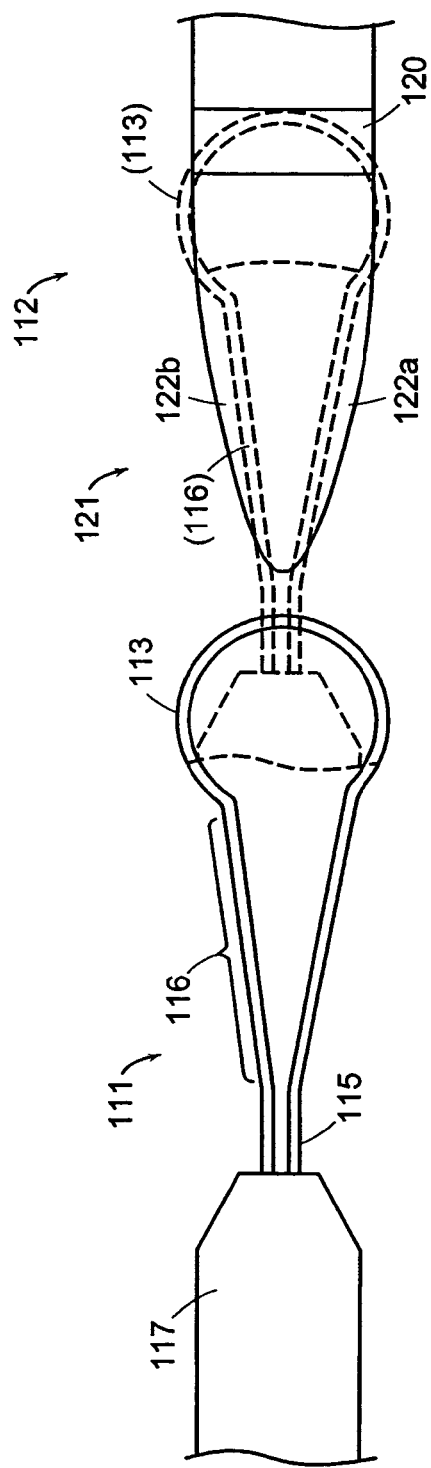
FIG. 22B depicts a top view of the connectors of FIG. 22A, with an interconnected state shown in phantom.

Referring specifically to FIG. 22B, the loop portion 113 of the loop connector 111 fits into the slot 120 and the tapered neck portion 116 interfits into the lateral grooves 122a and 122b. Preferably, the tapering of the neck portion 116 is shaped to match the tapering of the shaft distal end 121. This is illustrated in FIG. 22B where parts of the loop connector 111 are depicted in phantom lines. The tapered neck portion 116 is also sized to fit snugly in and interlock with the groves 122a and 122b when the loop connector 111 and the slotted, receptacle connector 112 are mated.

FIG. 22C is illustrative the mating process between the loop connector 111 the receptacle connector 112. As depicted, the loop portion 113, which may be semi-rigid, is first hooked into the entry slot 124. Then, the shaft distal end 112 and/or the loop connector 111 are moved in axially opposite directions, continuing into the retention slot 125. The loop connector 111 is rotated in the direction shown by the arrow 126 toward the lateral grooves 122a and 122b (FIG. 22B). Because the neck portion 116 of the loop connector 111 is shaped and sized to fit snugly in the grooves 122a and 122b, the operator needs to force the neck portion 116 against the periphery of the shaft distal end 121 as he rotates the loop connector 111.

Figure 22D:
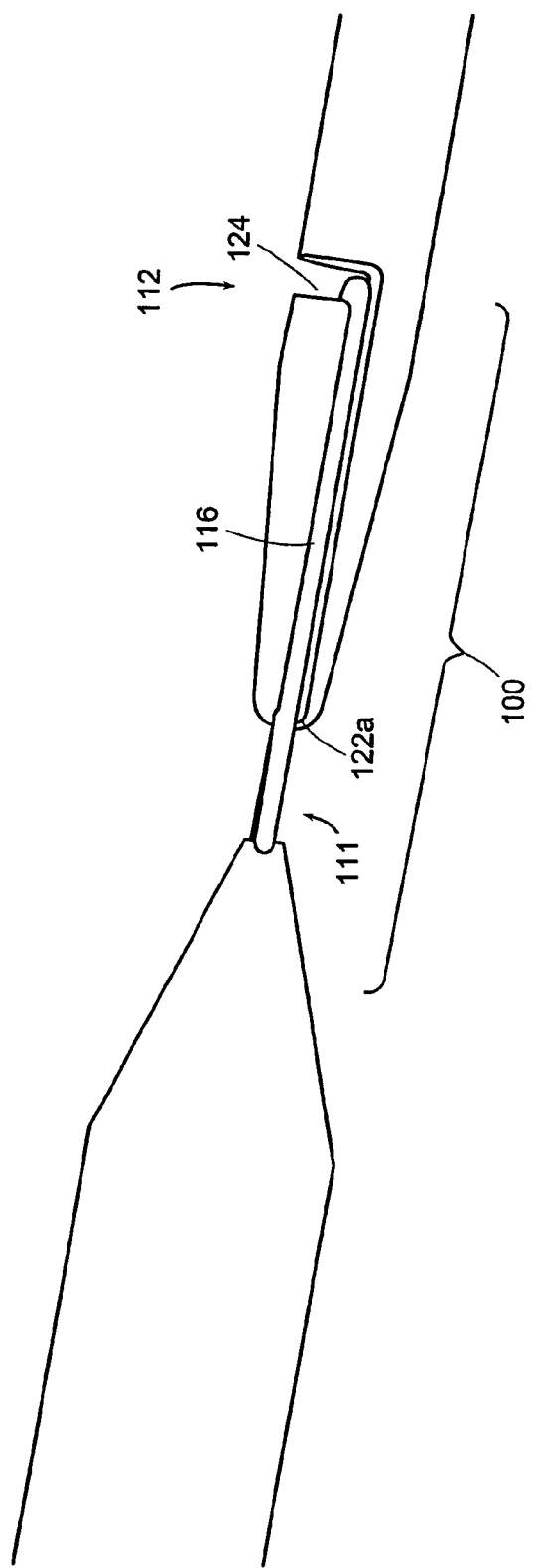
FIG. 22D depicts a side view of the connectors of FIG. 22A fully interconnected.

FIG. 22D shows the neck portion 116 fitted into the grooves 122a and 122b (not shown) of the receptacle connector 112. The neck portion 116 can be made, for example, of a material with some elasticity, for example, a metal or a polymer, such that the neck portion 116 returns to its original size after having been expanded temporarily to enter the lateral grooves 122a and 122b. As a result, the neck portion 116 stays locked inside the grooves 122a and 122b of the receptacle connector 112. This orientation provides for a smooth transition from shaft to sling assembly, in an end-to-end interconnection, which minimizes edges that could produce tissue trauma. To disconnect the two connectors, the procedure is simply reversed, i.e., the neck section 116 is forced against the periphery of the shaft distal end 121 to expand temporarily so that it can come out of the lateral grooves 122a and 122b (FIG. 22B).

FIG. 23 depicts a loop connector 111a interconnected with a receptable connector 112a, according to another illustrative embodiment of the invention. The loop connector 111a includes a loop 113a that may be a flexible wire, suture, or cable, and may be made of, for example, a polymeric material or metal. The loop 113a may be of single strand, multiple strands, or coated. In one embodiment, the filament that makes up the loop 113a is between about 0.006 inch and about 0.016 inch in diameter.

In the illustrative embodiment, the loop connector 111a is bonded to the sling assembly end 117, specifically, a dilator 118. The receptacle connector 102a is illustrated as located on the shaft distal end 121 of the delivery device 119. In this illustrative embodiment, the receptacle connector 112a includes an axially extending indentation, channel or slot 120a for retaining the loop 113a.

FIG. 24 depicts a receptacle connector 112b located on the shaft distal end 121 of a delivery device 119 according to another illustrative embodiment of the invention. The receptacle connector 112b includes slot 120b, extending radially into the distal end of 121 axially in a distal direction. As depicted, the slot 120b is curved. Optionally, the receptacle connector 112b also includes a section 127, which extends axially both distally and proximally.

FIG. 25 depicts a perspective view of a loop connector 128 that can be interconnected with a slotted receptacle connector 132 according to an alternative embodiment of the invention. In this illustrative embodiment, the loop connector 128 attaches to a sling assembly end 129 and the receptacle connector 132 is disposed on the shaft distal end 121. The loop connector 128 includes a tubular member 130 with an axial lumen 131 extending from a distal opening 133. In one embodiment, the tubular member includes an optional axial opening 135 along the axial lumen 131. The tubular member 130 includes an internal loop 136, for example, a bar across the lumen 131, that interconnect with a receptacle connector.

The illustrative receptacle connector 132 includes a slot 137, for example, an oblique notch, which may further include a protuberance 138. The protuberance 138 helps to prevent premature release of a captured loop, for example, the internal loop 136 of the loop connector 128, as the protuberance 138 serves as a barrier for the filament's exit. The protuberance 138 can be of any size or shape as long as it effectively restricts the captured loop from exiting the slot 137, for example, by creating a narrowing, a choke-point, or pinch-point 134, having a narrower width than that of the loop filament.

To interconnect the connectors 128 and 132, the operator slides the slotted receptacle connector 132 into the axial lumen 131 of the loop connector 128, either through the distal opening 133 or the axial opening 135. Then the operator orients the connectors such that the slot 137 on the connector 132 faces the internal loop 136 of the connector 128. The operator slides the internal loop 136 into the slot 137, and forces the internal loop 136 past the protuberance 138 in the slot 137. The protuberance 138 then locks the internal loop 136 inside the slot 137. Because the tubular member 130 of the loop connector 128 has a smooth cylindrical outer surface, having the internal loop 136 provides a smooth joint between parts of the delivery system that is advantageous for dilation and tunneling through patient tissue.

FIG. 26 depicts an optional recessed or rounded edge 139 in a receptacle connector 132a. This feature tends to smooth the entrance to the receptacle connector 132a and reduce the likelihood of it catching on tissue. Additionally, the rounded edge 139 also increases the ease with which the receptacle connector 132a captures a loop such as the loop 113a of the loop connector 111a (described above in FIG. 23), into the slot 137a. The slot 137a may also include a locking mechanism, such as a protuberance 138a.

Figure 27:
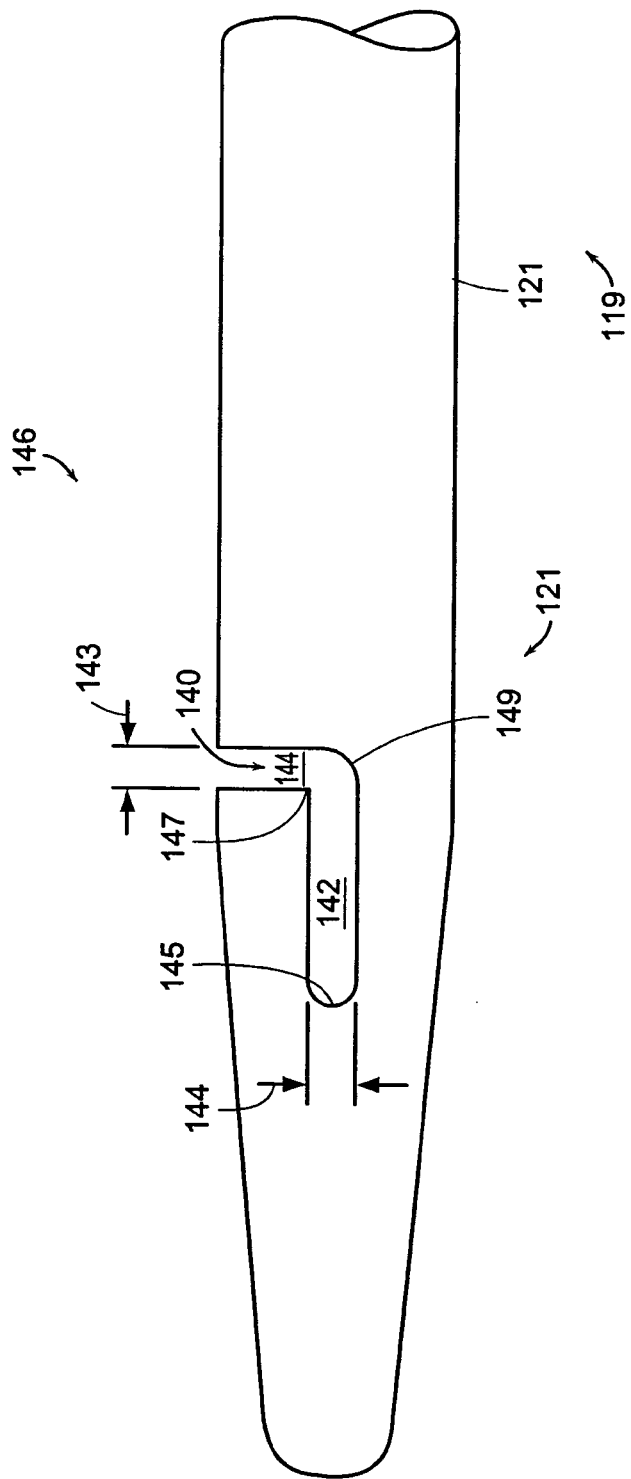
FIGS. 27-31 depict side views of various additional receptacle connectors of the type that may be employed with the loop connectors of FIGS. 23 and 25, according to various embodiments of the invention.

FIG. 27 depicts a receptacle connector 146 including a slot 140 that is L-shaped. While the connector 146 may be attached to or disposed on any part of a delivery system, in the illustrative embodiment, it is formed in the shaft distal end 121 of the delivery device 119. The slot 140 includes two legs: an entry notch 141, and a retention slot 142. In the illustrative embodiment, the entry notch 141 is a cutout substantially normal to a longitudinal axis of the distal shaft end 121. In one exemplary embodiment, the retention slot 142 is substantially perpendicular to the entry notch 106, and extends distally away from the entry slot 141. Further, the illustrative retention slot 142 is longer than the illustrative entry slot 141, with advantages in retaining a captured loop filament.

Both the entry slot 141 and the retention slot 142 can be of any dimension suitable to capturing a particular mating connector. In one embodiment, the retention slot 142 is narrower than the entry slot 141, for example, to substantially match the outer diameter of the loop filament in a mating loop connector such as the loop connector 111a (FIG. 23). For example, if the outer diameter of the loop filament is about 0.016 inches, the entry slot 141 may have a width 143 that is slightly wider, for example, about 0.018 inches, while the retention slot 142 may have a uniform width 144 that is about 0.016 inches. Alternatively, the retention slot 142 may be tapered to become narrower towards its distal end 145. For example, the retention slot 142 may be tapered from 0.018 inches to about 0.016 inches towards its distal end 145. A width 144 in the retention slot 142 that substantially matches or is less than that of the captured filament, for example, the loop portion 113a of the loop connector 111a (FIG. 23), is advantageous in retaining the filament after capture.

The retention slot 142 meets the entry slot 141 at an inside corner 147 and outside corner 149. Both the inside corner 147 and the outside corner 149 can assume a variety of shapes, for example, they can be smooth, (e.g., rounded), or sharp (e.g., angled). In FIG. 27, the illustrative inside corner 147 is sharp while the outside corner 149 is smooth. A smooth corner is advantageous in capturing a filament while a sharp corner may be advantageous in retaining the filament.

Figure 28:
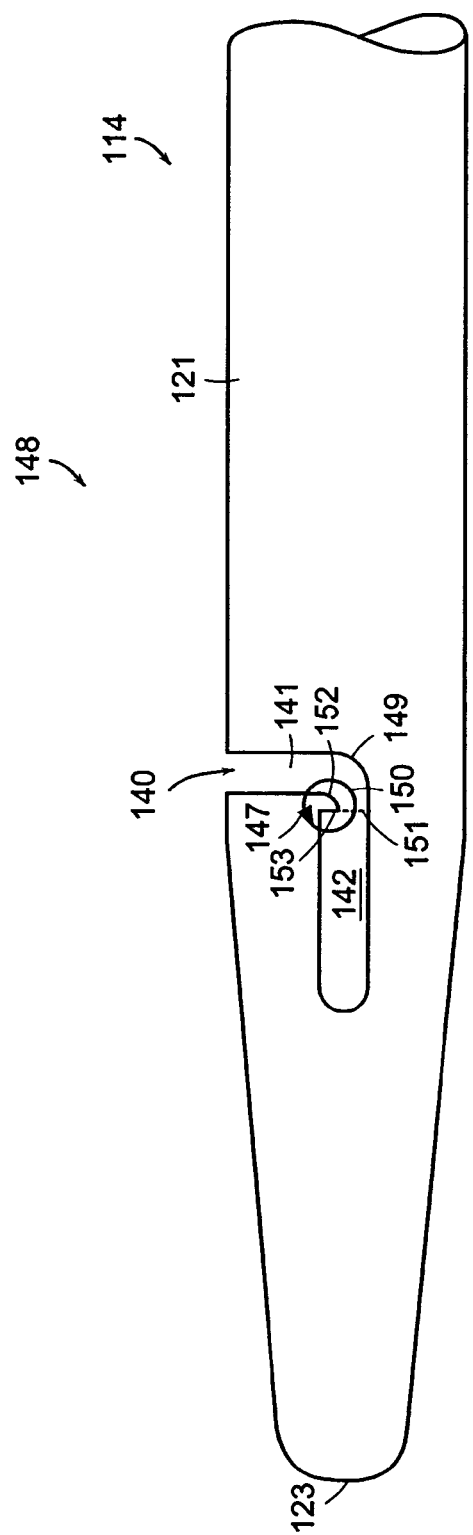

FIG. 28 depicts the slot 140 in an alternative receptacle connector 148 having retention features in addition to the features described in connection with the receptacle connector embodiment in FIG. 27. Specifically, the receptacle connector 148 has one or more protuberances 150. The protuberance 150 may assume a variety of shapes. For example, the protuberance 150 may be hooked or straight, and may have flat or rounded edges, with flat or rounded transitions between edges. In the illustrative embodiment, the protuberance 150 is located on the inside corner 147 and extends into the retention slot 142. However, in other embodiments, it may be alternatively or additionally located at the outside corner 149. Additionally, one or more protuberances 150 may alternatively or additionally project into the entry slot 141. In one embodiment, the protuberance 150 effectively imposes a choke point 151, which is the narrowest point in the slot 140, and is substantially the same or narrower than the diameter of a loop filament of a mating loop connector, for example, the loop portion 113a of the loop connector 111a (FIG. 23). For example, if the loop filament is about 0.016 inches, the choke point 151 may provide about 0.014 inches of clearance. As a result, after the loop filament is forced into the retention, slot 142 past the protuberance 150, it is prevented from exiting the retention section 142 absent a force directing it past the protuberance 150 in the other direction.

The protuberance 150 may be manufactured to make it easier to enter the retention slot 142 while also making harder to exit the retention slot 142. For example, the illustrative protuberance 150 has a rounded entry corner 152 which an entering filament encounters. The rounded entry corner 152 facilitates the capture of the filament by facilitating the filament in its sliding into the retention slot 142. On the other side of the protuberance 150, however, an exit corner 153 which an exiting filament encounters, provides a sharp corner to make it harder for the filament to escape. To further hinder exit, the protuberance 150 has a substantially flat shoulder 154 facing the distal tip 123 of the shaft 114.

The protuberance 150 can also be configured such that it effectively retains a captured connector permanently. For example, the choke point 151 can be so narrow that to free a captured filament, the protuberance 150 has to be broken off for the filament to exit the slot 140. Such permanent retention can also be effected through the geometry of the protuberance 150.

Figure 29:
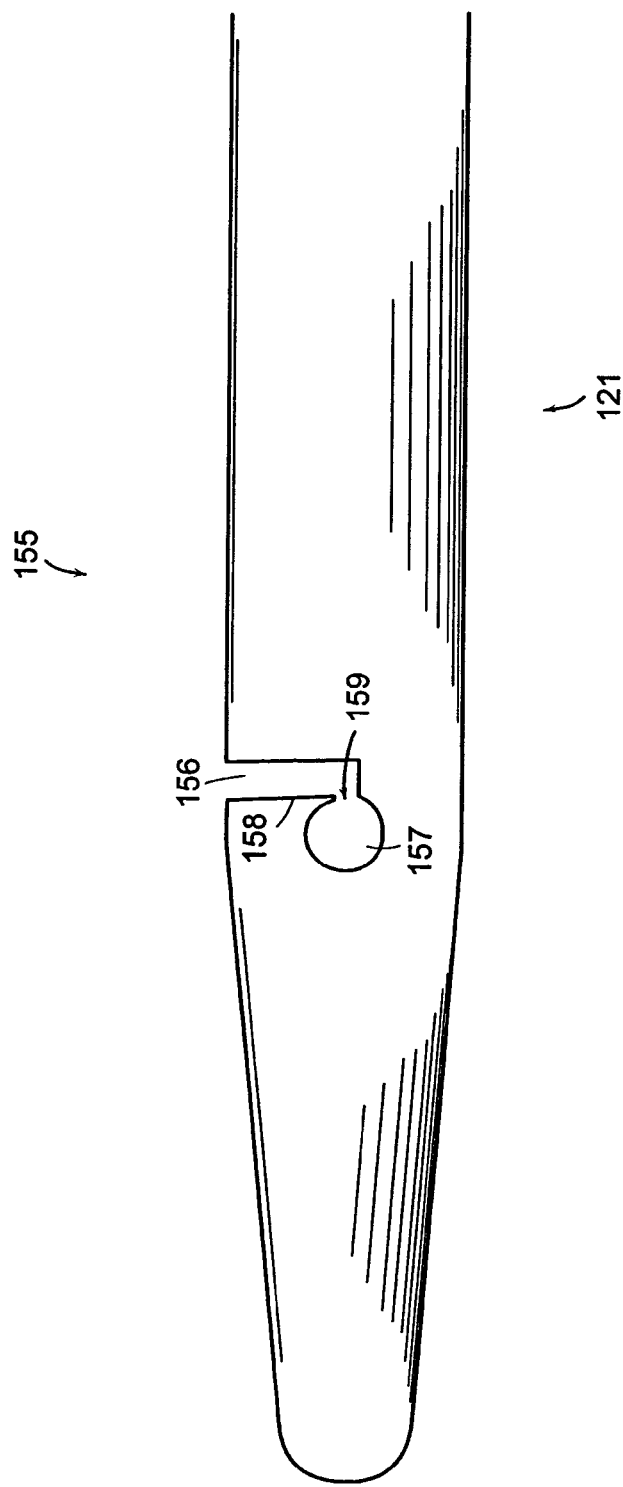

FIG. 29 depicts a receptacle connector 155 including an entry slot 158 and a substantially cylindrical retention section 157. According to another alternative illustrative embodiment. In the illustrative embodiment, receptacle connector 155 is disposed on the distal shaft end 121. In a similar fashion to, previously discussed embodiments, the entry slot 156 extends radially into the distal shaft end 121. The substantially cylindrical retention section extends axially through the distal shaft end 121 and is located distally adjacent to the entry slot 156. The retention 157 and entry 156 slots intersect at a reduced width passage 159 formed by the shoulder 158. The retention cylinder has a diameter or width that is larger than the diameter of a captured filament, for example, the loop 113a of a loop connector 111a, so that a section of the loop 113a can reside in it. The shoulder 158 projects into the passage 159 between the reservoir 157 to impose a choke point that restricts the passage of a captured filament. The shoulder 158 may be configured such that it effectively retains a captured connector permanently. Alternatively, the retention imposed by the shoulder 158 may be temporary and can be overcome.

Figure 30:
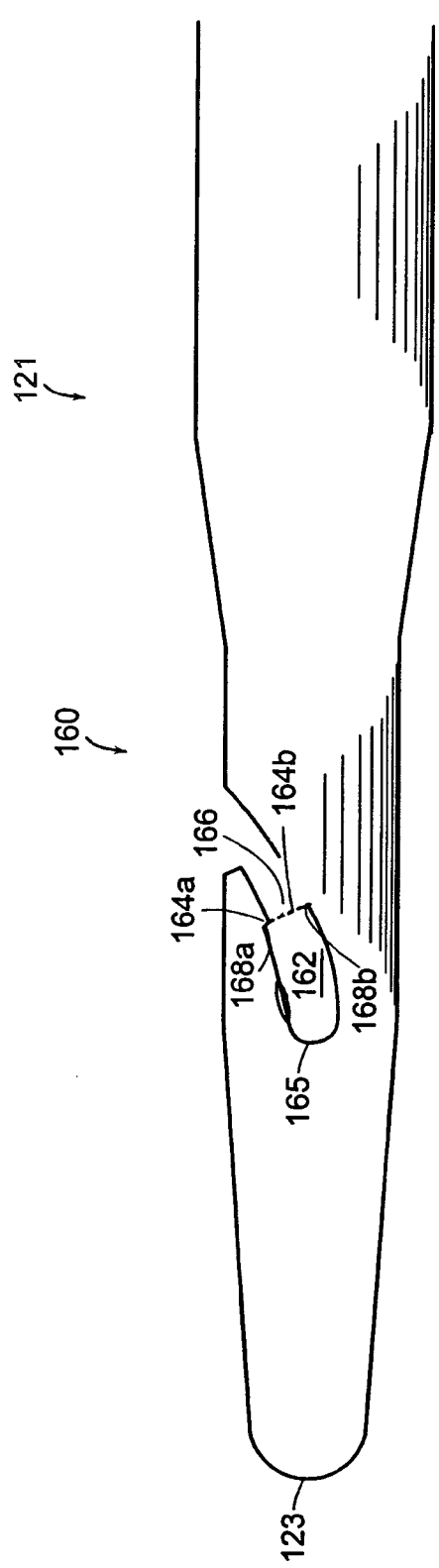

FIG. 30 depicts a receptacle connector 160 including a slot 162 for receiving and retaining a filament, for example, the loop 113a of the loop connector 111a (FIG. 23). The illustrative receptacle connector 160 is disposed on the shaft distal end 121. The optionally curved slot 162 extends toward the distal tip 123 of the shaft distal end 121 has one or more protuberances 164a and 164b in between. In the specific embodiment depicted, the protuberances 164a and 164b are each disposed on one side of the slot 162 and roughly equidistant from a distal end 165 of the slot 162. Therefore, the illustrative protuberances 164a and 164b are axially aligned relative to each other. The protuberances 164a and 164b impose a choke point 166 in between them. The choke point 166 serves to restrict loop filament movement within the slot 162. In the illustrative embodiment, the protuberances 164a and 164b are stepped shoulder portions. The protuberance 164a and 164b may each have a sharp exit corner (168a, 168b) to discourage filament exit. An example of the loop filament that can be employed is the loop 113a of the loop connector 111a (FIG. 23).

Figure 31:
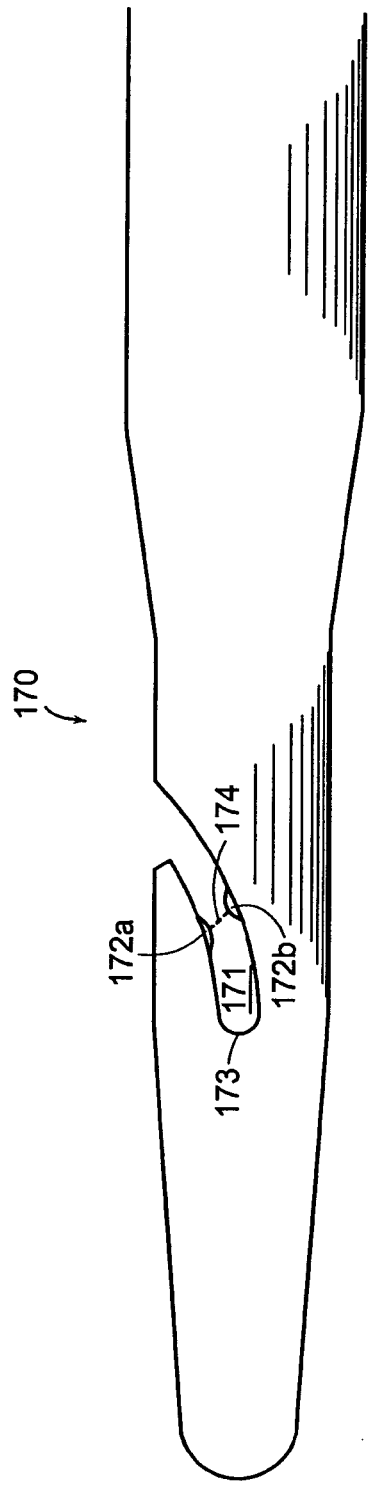

FIG. 31 depicts a receptacle connector 170 including a slot 171 where two protuberances 172a and 172b are not equidistant to a distal end 173 of the slot 171. Therefore, the illustrative protuberances 172a and 172b are axially offset relative to each other. In the illustrative embodiment, the two protuberances 172a and 172b are disposed in such proximity that a choke point 174, the narrowest point in the slot 171, is the space or clearance between the two protuberances 172a and 172b. In the illustrated embodiment, each of the protuberances 172a and 172b, are formed as a curved bump.

FIGS. 32A and 32B depict, respectively, a side view and a side perspective view of a receptacle connector 178 including an entry notch 179 joined to a retention slot 180. In the illustrated embodiment, the entry notch 179 is substantially straight, and the retention slot 180 is curved. On one hand, a curved retention slot 180 may be advantageous in retaining a captured filament and preventing premature release because the curvature requires changes in direction as the captured filament maneuvers to escape. On the other hand, intended release of the captured filament may be accomplished with relative ease because an operator can manually direct the movement of the captured filament through the curvature of the slot 180. In the particular embodiment illustrated, the retention slot 180 comprises a half-circular arc that resembles a hook.

In one embodiment, the retention slot 180, as described earlier in other embodiments, may have a width that is substantially the same or less than the diameter of the captured filament, such that movement of the filament is restricted in the retention slot 180. In one embodiment, the filament is immobilized as it is stuck in the narrow passage of the retention slot 180. Optionally, there may be one or more protuberances along the length of the retention slot 180, for example, at the inside corner 181 where the retention slot 180 meets the entry notch 179. As described above, a protuberance assists in the retention of a captured filament.

Figure 33:
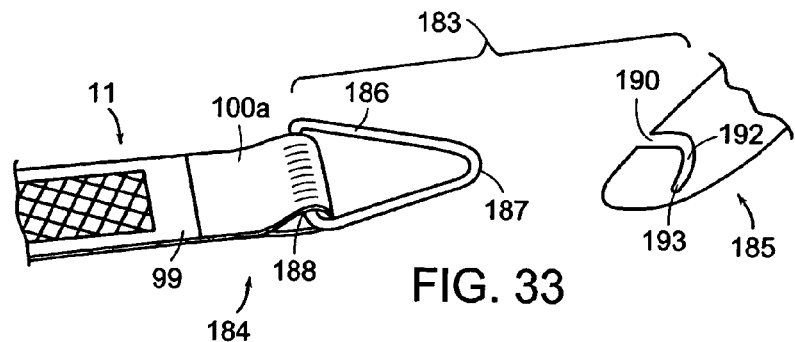
FIG. 33 depicts a side perspective view of a loop and mating receptacle connector pair according to another illustrative embodiment of the invention.

FIG. 33 depicts a connector pair 183 including a loop connector 184 and a receptacle connector 185 before they become interconnected with each other, according to one illustrative embodiment of the invention. The loop connector 184 includes a loop 186 that is substantially of a triangular shape with an apex 187 and a base side 188. While the loop connector 184 can be attached to any part of the delivery system, it is shown in this exemplary embodiment to be attached to an end 100a of a sleeve 99 of a sling assembly 11. For example, one end 100a of the sleeve 99 is looped around the loop base side 188 and adhered to the sleeve end 100a itself to effect the attachment. The ends of the filament for the loop 186 may remain separated inside the sleeve end 100a, or they may be joined by welding or through a connector, such as a hypo-tube (not shown). The hypo-tube may be crimped to secure the filament in place.

The loop filament 186 may be rigid or malleable. The substantially triangular shape of the loop 186 is advantageous for dilating tissue while passing through the body of a patient. According to a further advantage, flatness of the loop 186 causes the resultant tunnel to be relatively two-dimensional, which helps to keep the sling assembly 11 in its flat configuration instead of getting folded or twisted while passing through the tunnel. A relatively flat dilator or tunneler may also be advantageous in aligning or orienting parts of the delivery system.

Still referring to FIG. 33, the receptacle connector 185 includes a curved slot 190. To interconnect the loop connector 184 with the receptacle connector 185, the loop apex 187 of the loop connector 184 first approaches the slot 190 in the receptacle connector 185. After entry into the slot 190, the loop 186 slides into a retention section 192 and eventually resides close to the distal end 193 of the retention section 192.

Figure 34:
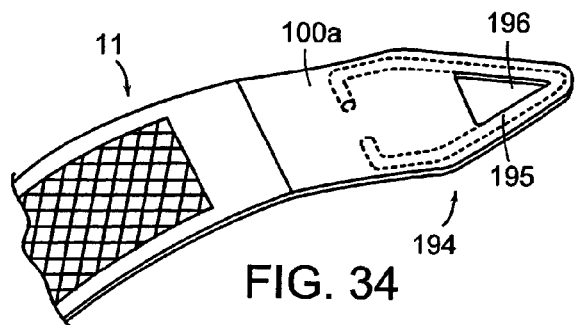
FIG. 34 depicts a side perspective view of an alternative embodiment of the loop connector of FIG. 33.

FIG. 34 depicts a loop connector 194 including a loop filament 195 that is at least partly embedded in the sleeve end 100a of the sling assembly 11. An aperture 196 is defined at least partly by the embedded loop filament 195. The aperture 196 can be of a variety of shapes, for example, a triangular shape. The loop connector 194 shown in this embodiment can interconnect with various embodiments of the receptacle connectors, including the ones shown in all the previous figures, for example, FIGS. 22A-33, in a manner similar to the embodiment described in connection with FIG. 33.

Figure 35A:
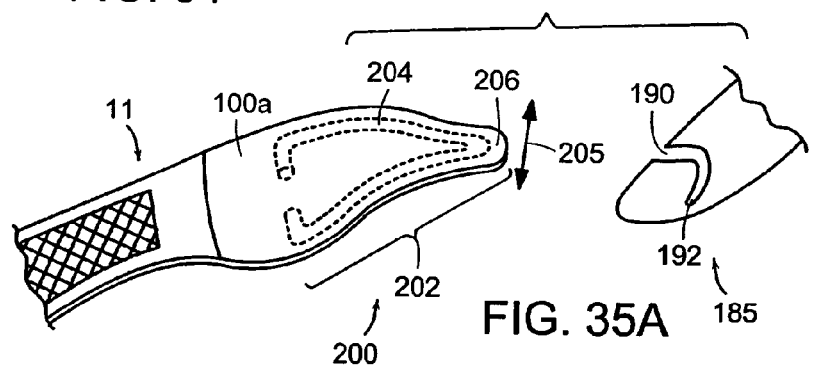
FIG. 35A depicts a side perspective view of a connector pair prior to interconnection.
Figure 35B:
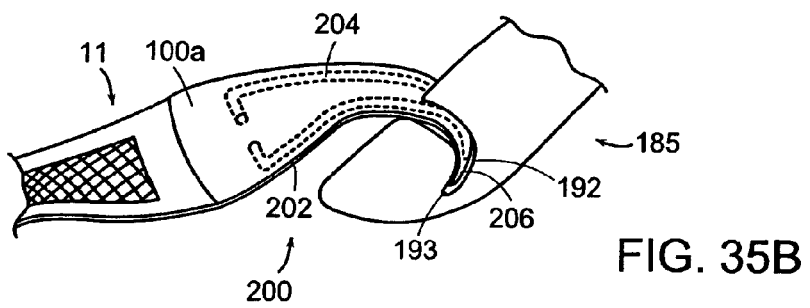
FIG. 35B depicts a side perspective view of the connector pair of FIG. 35A subsequent to interconnection.

FIGS. 35A and 35B, depict a connector 200 including a malleable portion 202 that can be inserted into the slotted receptacle connector 185, and preferably be retained after the malleable portion 202 changes its shape or form. In the illustrated example where the connector 200 is attached to the sleeve end 100a of the sling assembly 11, the malleable portion 202 includes part of the sleeve end 100a that envelopes a loop filament 204. The sleeve end 100a is typically made of a soft, flexible plastic, and therefore, the shape and form of the connector 200 is largely determined by the shape and form of the loop filament 204. For example, the loop filament 204 may bend in a normal direction to the plane, in which the sleeve end 100a resides, as indicated by the arrows 205.

During interconnections the malleable portion 202 enters the slot 190 with its distal end 206 first. As the malleable portion 202 passes through the slot 190 into the retention section 192, the malleable portion 202 bends to conform to the curvature of the slot 190 until the distal end 206 of the malleable portion 202 reaches the distal end 193 of the retention section 192. The connector 185 can also be used to interconnect with other slotted receptacle connectors described herein.

Figure 36A:
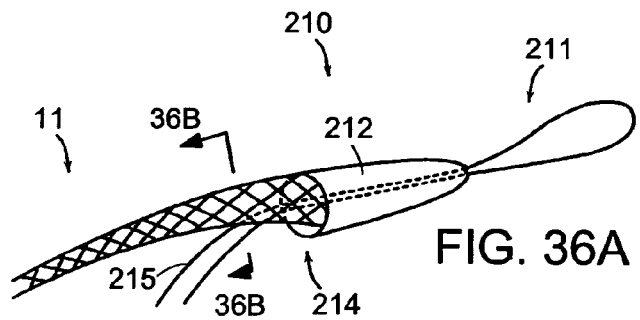
FIG. 36A depicts a side perspective view of a loop connector with an adjustable loop according to an embodiment of the invention.
Figure 36B:
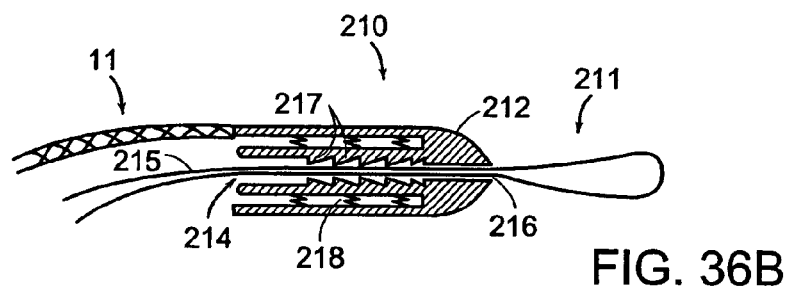
FIG. 36B depicts a cross-sectional view, along the line "36B-36B," of the loop connector shown in FIG. 36A.

FIGS. 36A and 36B, depict, through a side perspective view and a cross-sectional view, a loop connector 210 with an adjustable loop 211. The loop connector 210 is illustrated as attached to a base part, for example, the sling assembly 11. In one embodiment, the loop connector 210 includes a housing 212 that at least partly encloses a locking mechanism 214. A filament 215 that makes up the loop 211 is threaded inside the housing 212, for example, through a lumen 216, so that the locking mechanism 214 can lock the loop 211 at a particular size as its filament 215 moves through the housing 212. Numerous structures can be used as the locking mechanism 214.

For example, in FIG. 36B, the illustrative locking mechanism 214 includes a clip where one or more teeth 217 can engage each other to lock the positions of the loop filament 215. Engagement of the teeth 217 may be prompted by compression of a spring-loaded housing 212. Disengagement of the teeth 217, hence, release of the filament positions, may be prompted by a second action of compressing the housing 212 where one or more springs 218 act to deactivate the locking mechanism 214, for example, by disengaging the teeth 217. Another example of the locking mechanism is a ratchet in which a pawl engages the sloping teeth of a wheel or bar, permitting motion in one direction only.

Figure 37A:
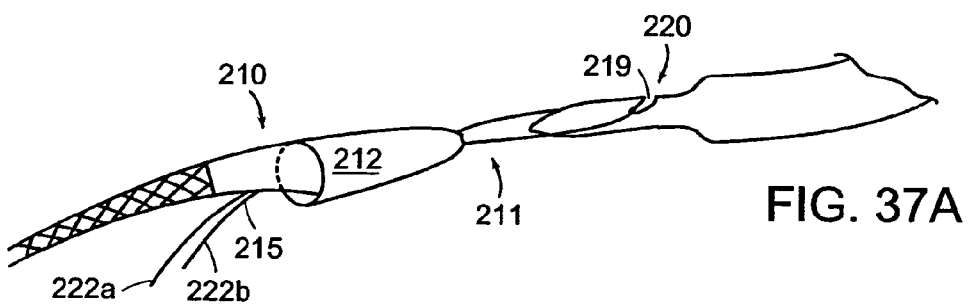
FIG. 37A depicts a side perspective view of the loop connector of FIG. 36A interconnected with a mating receptacle connector with the loop connector in an extended state.
Figure 37B:
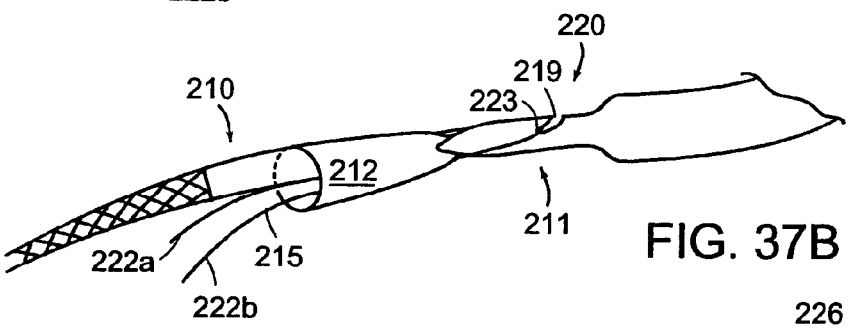
FIG. 37B depicts a side perspective view of the connector pair of FIG. 37A with the loop connector in a retracted state.

FIGS. 37A and 37B depict the extended state and the retracted state, respectively, of the adjustable loop 211 of the loop connector 210 for interconnection purpose. Referring specifically to FIG. 37A, the loop 211 is typically at an extended state when a receptacle connector 220 captures the loop 211 in a slot 219. To adjust the loop 211 to its retracted state, the operator can pull both ends 222a and 222b of the loop filament 215. Alternatively, the operator can hold one filament end (222a or 222b) fast while pulling on the other filament end (222b or 222a). Further alternatively, the operator can hold both filament ends 222a and 222b fast and push the housing 212 towards the receptacle connector 220. The size of the loop 211 can be reduced until the housing 212 is in contact with the receptacle connector 220 as shown in FIG. 37B. The locking mechanism 214 can be activated during this process to lock the loop 211 at a particular size. In the illustrative embodiment in FIG. 37B, the loop 211 is retracted until it wraps snugly around portions of the receptacle connector 220, including the distal end 223 of the slot 219. At this point, the locking mechanism 214 (FIG. 36B) can be activated to lock in the loop size such that the loop connector 210 and the receptacle connector 220 form a snug joint so that they move as one piece.

To enlarge the size of the loop 211, the operator deactivate the locking mechanism 214, then pulls the housing 212 away from the receptacle connector 220 while holding the latter fast.

Figure 38:
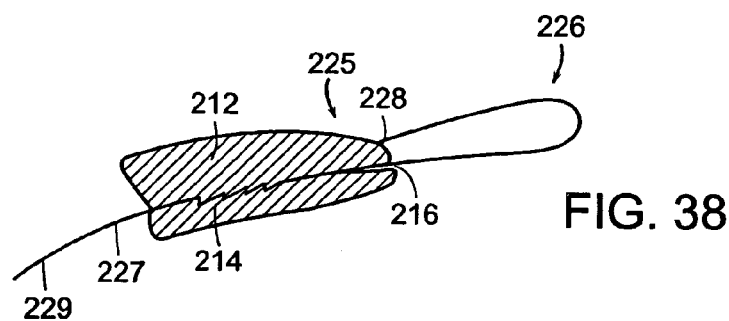
FIG. 38 depicts a cross-sectional view of an adjustable loop connector according to another illustrative embodiment of the invention.

FIG. 38 depicts an alternative loop connector 225 including an adjustable loop 226 made from a filament 227 threaded through the housing 212. One end 228 of the loop filament 227 is fixedly attached to the housing 212 such that only the other filament end 229 is threaded through the lumen 216 and affected by the locking mechanism 214. Adjusting the size of the loop 226 is similar to the procedure described in connection with FIGS. 37A and 37B, except that only one filament end 229 is needed and available for manipulation.

Figure 39A:
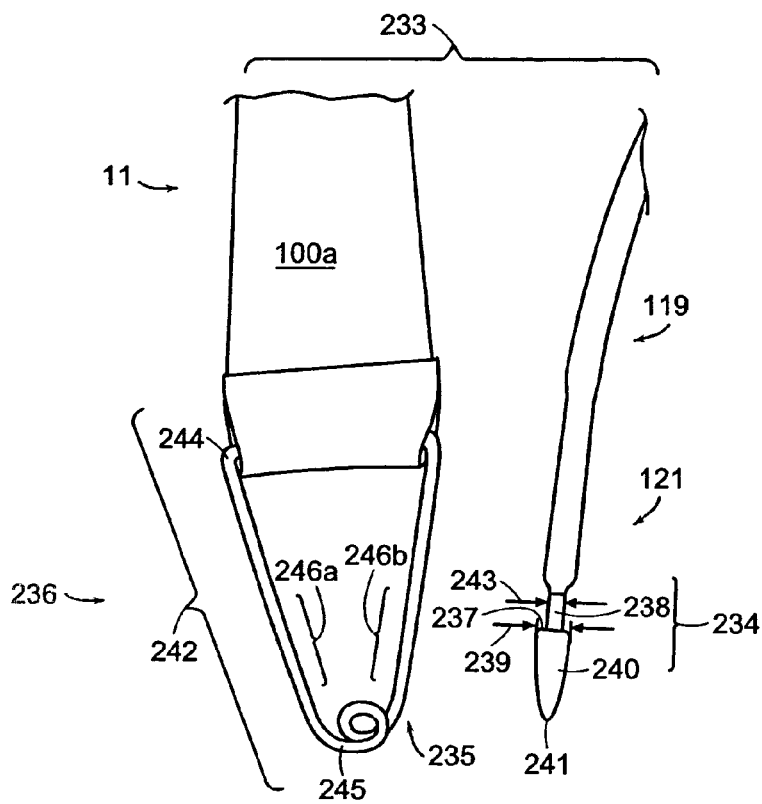
FIG. 39A depicts a top perspective view of a plug and receptacle connector pair according to an illustrative embodiment of the invention.
Figure 39B:
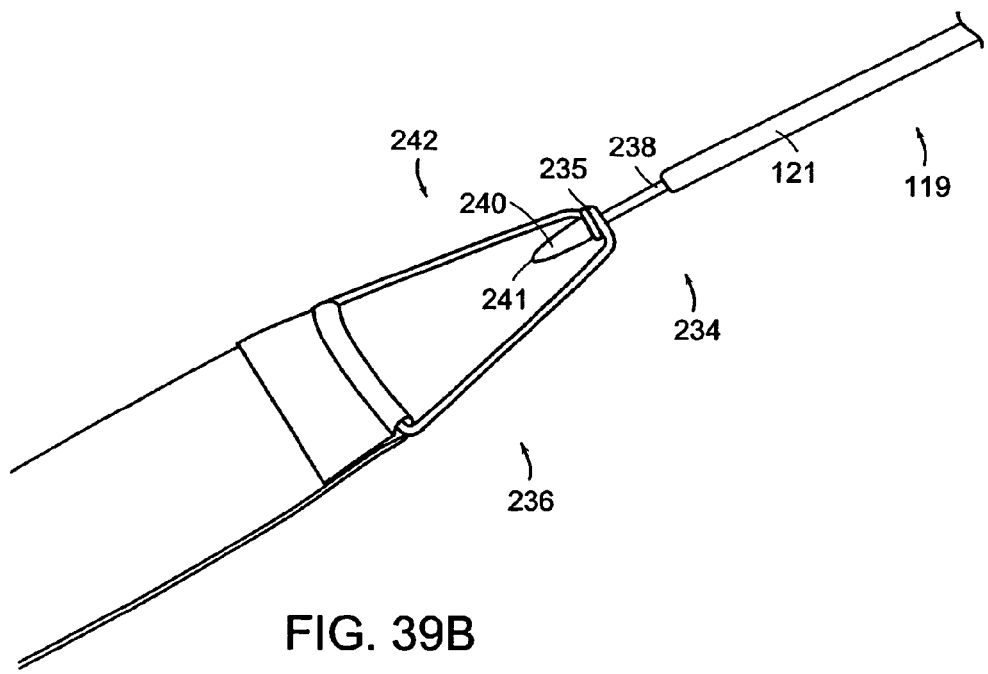
FIG. 39B depicts a top perspective view of the connector pair of FIG. 39A interconnected in an in-line configuration.
Figure 39C:
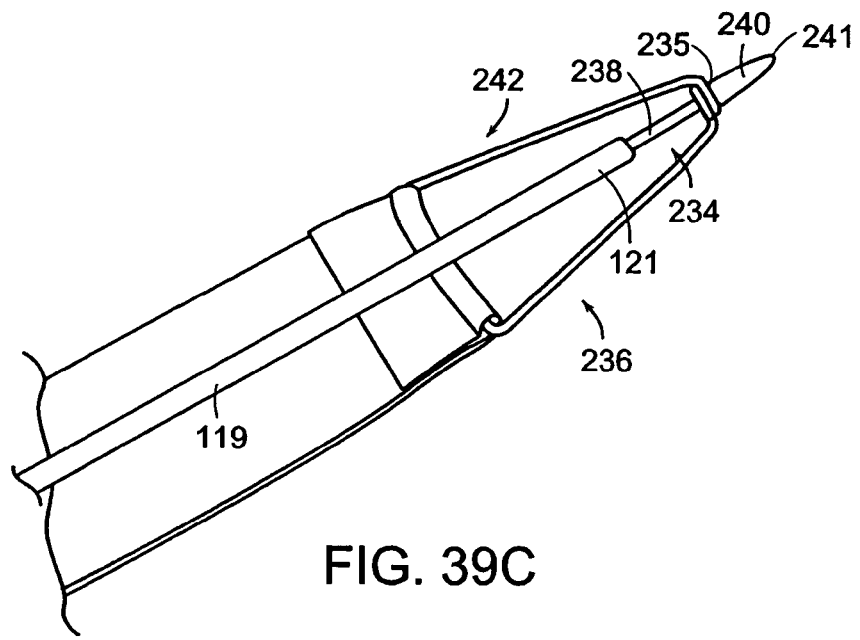
FIG. 39C depicts a top perspective view of the connector pair of FIG. 39A interconnected in an alternative configuration.

FIGS. 39A-39C depict an illustrative connector pair 233 including a plug connector 234 and a receptacle connector 236, which interconnect with each other through a receptacle loop 235 in the receptacle connector 236. The illustrative plug connector 234 is attached to the shaft distal end 121 of the delivery device 119. The illustrative plug connector 234 has a reduced-diameter section 238 proximal to a conical, tapered distal section 240. In the illustrative embodiment, the tapered distal section 240 tapers towards a tip 241. The tip 241 may be blunt or sharp. The tapered distal section 240 has its thickest point at its proximal base 237 which is adjacent the reduced-diameter section 238. A diameter 239 at the base 237 is larger than a diameter 243 of the reduced diameter section 238. The plug connector 234 may have a variety of shapes in cross-sections along its length, for example, circular, oval, triangular, or rectangular.

The receptacle connector 236 is characterized by the receptacle loop 235, which receives and retains the plug connector 234. The illustrative receptacle connector 236 is attached to the sleeve end 100a of the sling assembly 11. In other embodiments, the receptacle connector 236 is attached to other types of medical implants (not shown). In an exemplary embodiment, the receptacle connector 236 includes an optional support loop 242, which may be of a substantially triangular shape or of any other suitable shapes. For purpose of attaching the receptacle connector 236 with the sling assembly 11, the sleeve end 100a may simply wrap around a base side 244 of the support loop 242, and be heat-bonded to the sleeve end 100a itself. The two ends of the support loop 242, which may therefore be embedded in the sleeve end 100a, can remain separate, or joined by welding or through a hypo-tube (not shown). The hypo-tube may add structural support when the support loop 242 is used in dilation or tunneling.

The helical receptacle loop 235 may be disposed at any location in the receptacle connector 236, with any orientation. In the illustrative embodiment, the helical receptacle loop 235 is located at the apex 245 of the triangular support loop 242. Further, the illustrative helical receptacle loop 235 is oriented substantially normal to the plane where the support loop 242 resides. Such an orientation helps to facilitate end-to-end alignment between the distal shaft end 119 and the sling assembly 11. As discussed above, such alignment makes it easier to tunnel the implant, such as the sling assembly 11, through patient tissue without twisting or king the sling assembly 11, and causes less trauma for the patient.

Since the receptacle loop 235 only needs a structure to support it, the first loop 242 can be replaced with any suitable support structure, without, deviating from the scope of the invention. For example, a rod or a solid, flat substrate with or without any aperture in it can easily replace the support loop 242. However, a loop structure, while can be used for support purpose, as described in previous embodiments, can also be used, much as a loop connector, to hook into a slot in a slotted receptacle connector. Advantages from having a relatively flat dilator like the support loop 242, which is triangular is also described above.

In FIG. 39A, the illustrative receptacle loop 235 is formed, for example, in a spiral or helical structure, by a filament, for example, the same filament that forms the triangular support loop 242. In one preferred embodiment, the filament is a stainless steel wire with about a 0.028 inch diameter. The receptacle loop 235 may include less than one complete loop, one loop, or more than one loop. In one preferred embodiment, the receptacle loop 235 is about 1.5 loops. The loop 235 may assume any suitable shape, for example, circular, oval, rectangular or a horseshoe shape. In one embodiment, the filament that makes up both the first support loop 242 and the second receptacle loop 235 has certain flexibility and elasticity. As a result, the operator, by pressing or squeezing both sides of the triangular support loop 242, for example, at "release regions" 246a and 246b, which are regions adjacent the apex 245 of the triangular loop 242, can enlarge the size of the receptacle loop 235 where the filament crosses over to form the receptacle loop 235, such as in the illustrated embodiment. Once the operator stops squeezing the release regions 246a and 246b, its elasticity in the filament causes the receptacle loop 235 to return to its original size. Such a feature is useful for initial mating and subsequent releasing of a connector.

FIGS. 39B and 39C depict at least two ways to interconnect the plug connector 234 with the receptacle connector 236. Specifically referring to FIG. 39B, in a head-on approach, the two distal ends of the connectors 234 and 236 start the interconnecting process by facing each other. Then, the distal tapered section 240 of the plug connector 234, with the tip 241 first, enters the receptacle loop 235 and into the space above the support loop 242. In one embodiment, the receptacle loop 235, in its relaxed state, has an inner diameter smaller than the diameter of the thickest point in the tapered distal section 240 of the plug connector 234. As described earlier, however, the tapered section 240 can ply and expand the receptacle loop 235 where allowed by the flexibility of the loop filament. Once the entire distal section 240 passes the receptacle loop 235, the receptacle loop 235 drops into the reduced-diameter section 238. As dictated by the elasticity in its filament, the receptacle loop 235 returns to much of its original size and therefore is retained in the reduced-diameter section 238.

An advantage of this embodiment of the connector pair is that, one connector can easily rotate about its longitudinal axis while remaining interconnected with the other connector but without rotating the other connector. This allows an operator to unwind twisted base parts, for example, the sling assembly 11. This type of head-on interconnection can be useful in implanting a urinary sling using the so-called "top-down," supra-pubic, pre-pubic, or trans-obturator approach.

Specifically referring to FIG. 39C, in an alternative "back-end" approach, the interconnecting process starts with the distal tip 241 of the plug connector 234 behind the receptacle loop 235 and above the support loop 242. Then, with the tip 241 first, the distal tapered section 240 of the plug connector 234 enters the receptacle loop 235 from the space above the triangular support loop 242. Similar to the head-on approach, once the distal section 240 of the plug connector 234 passes the receptacle loop 235 of the receptacle connector 236, the reduced-diameter section 240 in the plug connector 234 engages the receptacle loop 235. As a result, the plug connector 234 remains interconnected with the receptacle connector 236. This type of backend connection can be useful in implanting a urinary sling using the so-called "bottom-up," trans-vaginal, or trans-obturator approach.

To disconnect the connectors, as described in connection with FIG. 39A, the operator can squeeze both sides of the triangular support loop 242 of the receptacle connector 236, for example, at the release regions 246a and 246b, to temporarily expand the receptacle loop 235 for releasing the plug connector 234.

FIGS. 40A-41C depict receptacle connectors 247 and 248, both including receptacle loops 249 and 250 that resemble U-shaped horseshoes. Both the illustrative receptacle connectors 247 and 248 can employ the plug connector 234 of the type previously described with respect to FIG.

39A. Specifically referring to FIG. 40A, a support loop 252 supports the receptacle loop 249 of the receptacle connector 247. Further, the illustrative receptacle connector 247 including the support loop 252 and the receptacle loop 249 is made of a single filament.

Figure 40B:
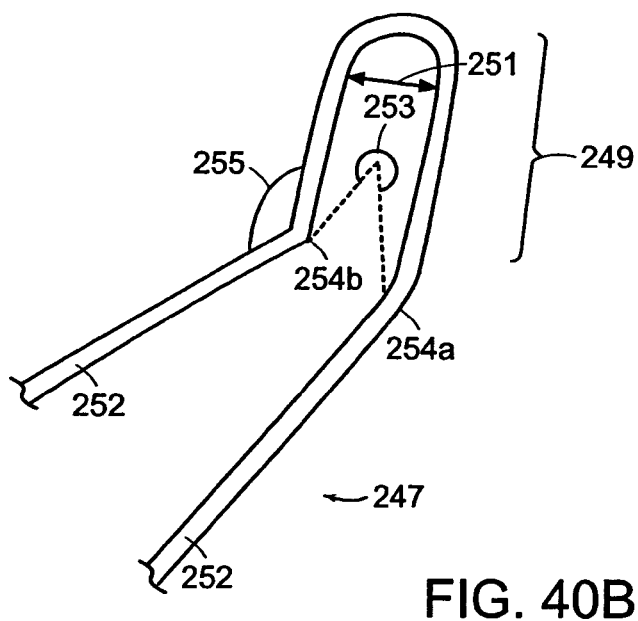
FIG. 40B depicts an enlarged top view of a portion of the loop connector of FIG. 40A.
Figure 40A:
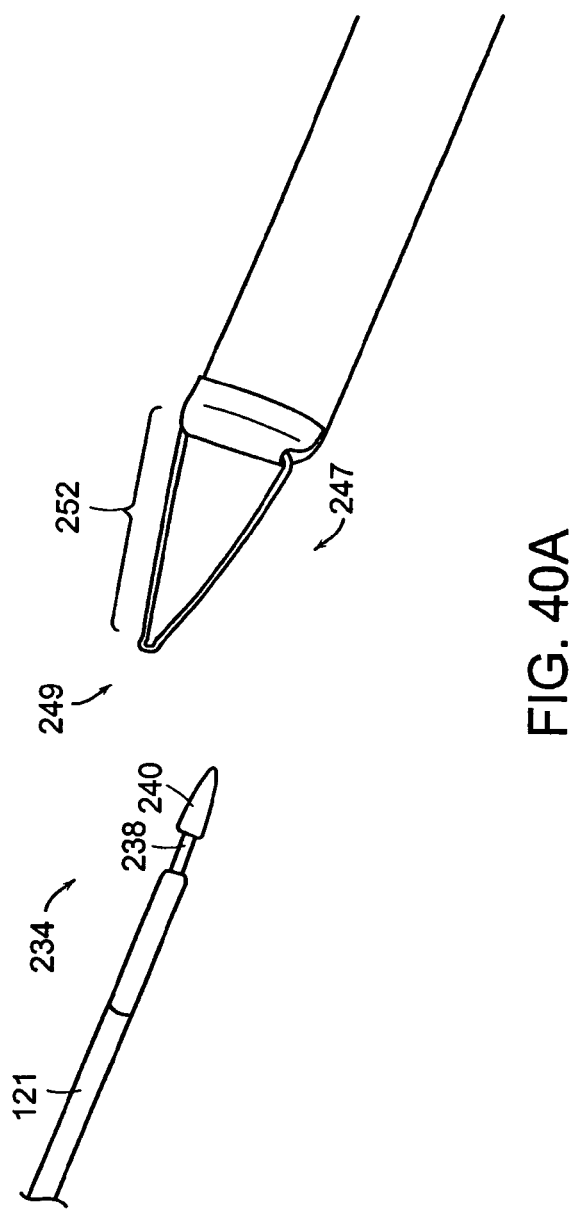
FIG. 40A depicts a top perspective view of a plug and loop connector pair according to another illustrative embodiment of the invention.

FIG. 40B depicts an enlarged top view of the distal portion of the receptacle connector 247. In the illustrative embodiment, the width 251 of the loop 249 can be measured as the curvature 253 from the center of the loop to two unconnected ends 254a and 254b. The curvature 253 is preferably between about 270 and about 360 degrees. Additionally, the receptacle loop 249 resides in a plane that is at an angle 255 to the plane of the support loop 252. The angle 255 is preferably about 90 degrees, but may be anywhere between 0 and 180 degrees. Both the curvature 253 and the angle 255 of the horseshoe receptacle connector 247 can be varied to accommodate a wide range of shapes of mating plug connectors, and to accommodate variations in operative procedures.

Figure 41A:
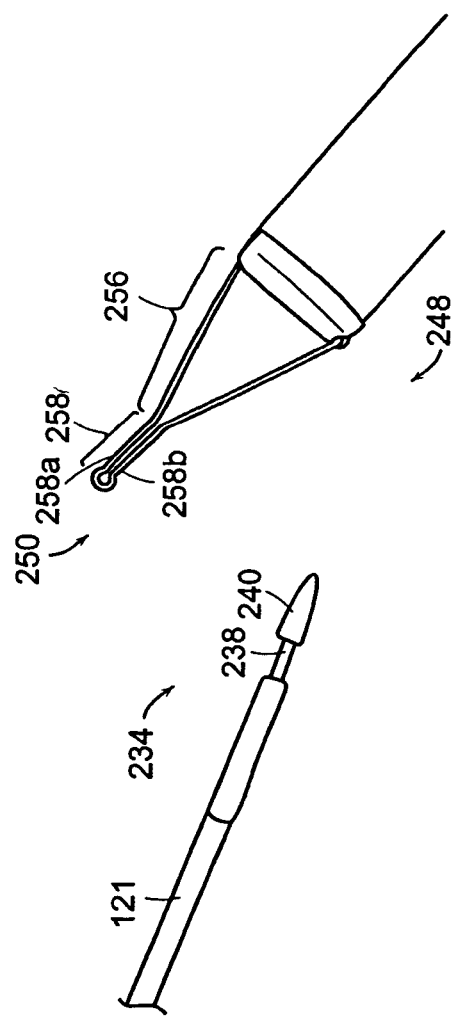
FIG. 41A depicts a top perspective view of the plug connector of FIG. 40A and an alternative configuration of the loop connector of FIG. 40A.

FIG. 41A depicts an alternative embodiment 248 of the horseshoe receptacle connector 247. In the embodiment of FIG. 41A, the support structure of the receptacle loop 250 includes a narrowed neck portion 258 extending between the receptacle loop 250 and the triangular support loop 256. Again, the entire illustrative receptacle connector 248 is made from a single filament. In the narrowed neck portion 258, the two opposite sides 258a and 258b are arranged substantially in parallel and are closer together than the diameter of the receptacle loop 250.

The narrowed neck portion 258 reduces the likelihood of premature release of a captured plug connector such as the plug connector 234. More specifically, the narrowed neck portion 258 helps to prevent unintended expansion in the receptacle loop 250 because its length serves to dissipate any expansive force transferred from the support loop 256, for example, when the sides of the support loop 256 are squeezed during dilation. This advantage of the narrowed neck portion 258 is especially apparent when the receptacle loop includes a filament cross-over such as the 1.5-turn helical structure depicted in receptacle loop 235 (for example, FIG. 39A). This is because the filament cross-over, much like the pivot in a pair of scissors, causes one side to open up when the other side closes. Accordingly, the feature of a narrowed neck portion in combination with other receptacle loop structures, such as the one depicted in FIG. 39A is specifically contemplated by this invention.

Figure 41B:
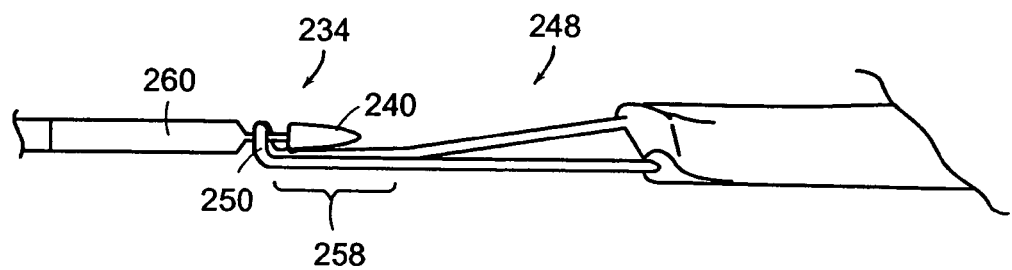
FIG. 41B depicts a perspective side view of the connector pair of FIG. 41A in an interconnected state with an in-line configuration.
Figure 41C:
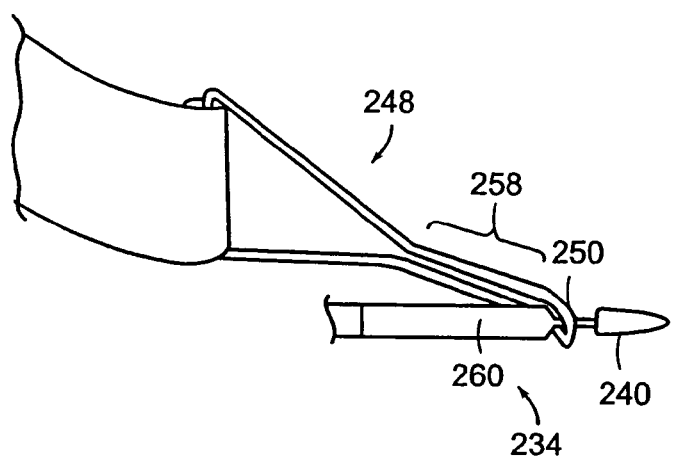
FIG. 41C depicts a perspective side view of the connector pair of FIG. 41A in an interconnected state with an alternative configuration.

A second advantage of having the neck portion 258 is illustrated through FIGS. 41B and 41C, which show the plug connector 234 and the receptacle connector 248 interconnected in a head-on (or in-line) approach and a backend approach, respectively. Interconnection between a plug connector and horseshoe receptacle connector under either approach is similar to what is described in connection with FIGS. 39B and 39C except that the circular receptacle loop 235 has been replaced with a horseshoe-shaped receptacle loop, for example, 249 or 250. As shown by FIGS. 41B and 41C, because there is little space within the narrowed neck portion 258, it serves as a physical barrier against the plying of the tapered distal section 240 (FIG. 41B) or a base section 260 (FIG. 41C) of a captured plug connector 234. As a result, the narrowed neck section 258 serves as a locking mechanism.

FIG. 42A depicts a further embodiment of a plug connector 261 and a receptacle connector 262. In the illustrated embodiment, the receptacle connector 262 is attached to the sleeve end 100a of the sling assembly 11. The plug connector 261 is attached to a guide tube 264. The guide tube 264 slidably interfits over a handled shaft 265.

The plug connector 261 includes a tapered distal section 269 and a base section 270, bridged by a circular notch 271. The distal section 269 of the plug connector 261 tapers towards a distal tip 272, which may be sharp or blunt. In the illustrative embodiment, the distal section 269 is of a conical shape. The illustrative base section 270 is over molded to a distal end 273 of the guide tube 264. In another embodiment, the base section 270 is attached to a distal end of the shaft 265. The base section 270 and other parts of the plug connector 261 may be made of a variety of materials, for example, polymers such as acrylonitrile butadiene styrene (ABS).

The receptacle connector 262 includes a relatively flat substrate 275. The substrate 275 is preferably of a thickness that is less than or equals the length of the circular notch 271 in the plug connector 261. The sleeve end 100a may be heat bonded, molded or otherwise attached to the substrate 275. The substrate 275 has an eyelet or aperture 277. The aperture 277 may have a rim (not shown) around it. In a preferred embodiment, the aperture 277 is of a size slightly smaller than the cross-section of the thickest point in the distal section 269 of the plug connector 261.

To interconnect the plug connector 261 with the receptacle connector 262, the plug tip 272 enters the aperture 277 first. The rest of the plug distal section 269 is then forced through the aperture 277 until the substrate 275 drops into the plug connector 261's circular notch 271 in a "snap-on" action. The interconnection can take either the head-on approach or the backend approach as described above. In the particular application where the plug connector 261 is attached to a guide tube 264, the shaft 265 may first be inserted into the guide tube 264 to give support for the interconnection.

Figure 42B:
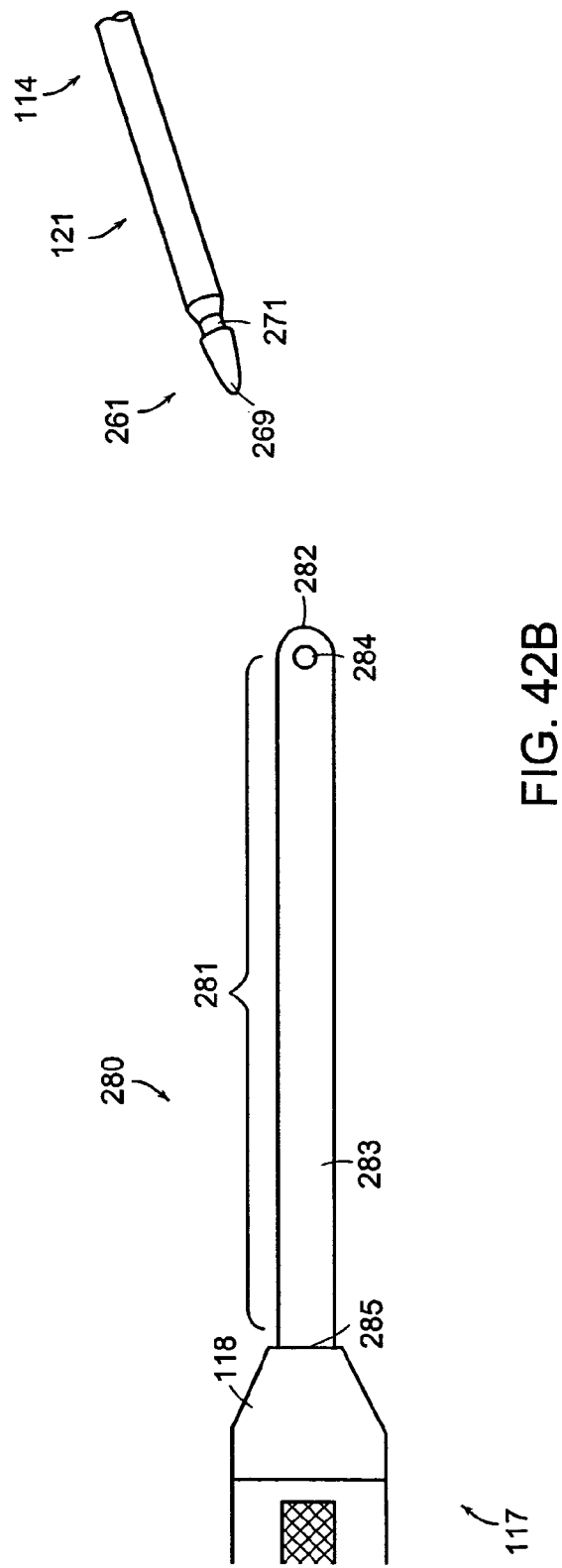
FIG. 42B depicts a side perspective view of an alternative embodiment to the plug and receptacle connector pair of FIG. 42A.

FIG. 42B depicts an alternative embodiment of a plug and receptacle connector pair including the plug connector 261 and an alternative receptacle connector 280. The illustrative plug connector 261 is disposed at the distal end 121 of the shaft 114. The receptacle connector 280 includes an elongated substrate 281 extending from a first distal end 282 to a second proximal end 283. A lateral aperture through 284 is located in the substrate end 282. The substrate end 283 attaches to the dilator 118 of the sling assembly end 117. In one embodiment, the elongated substrate 281 is strap-like (i.e., narrow, flat, and elongated) and is bendable, but has sufficient tensile strength to be pulled through the patient's tissues. The elongated substrate 281 has a length that is substantially greater than conventional embodiments of receptacle connectors used to interconnect the delivery device and the sling assembly. In one embodiment, the elongated substrate 281 is at least about 8 inches, which is longer than the typical length between a lower abdominal incision and the anterior vaginal wall (not shown) of a patient. In one embodiment, the elongated substrate 281 is made of a flexible plastic. In another embodiment, the elongated substrate 281 is made of a malleable metal.

The plug connector 261 can be interconnected with the receptacle connector 280 in a way similar to the method described in connection with FIG. 42A, e.g., by forcing the plug distal section 269 into the aperture 284 until the substrate 281 advances into the reduced diameter section 271. In an exemplary procedure, a percutaneous passage between the anterior vaginal wall and a lower abdomen incision is required for delivery of a sling assembly. In an embodiment where the elongated substrate 281 spans the length of that percutaneous passage, the shaft 114 and an interconnected receptacle connector 280 can travel the entire length of the percutaneous passage before the dilator 118 has to enter the patient's tissue. As a result, less drag is created in the patient's tissue and the stress or tension at the connection point between the receptacle connector 280 and the plug connector 261 is reduced by the stress otherwise created by dilation. Once the shaft 114 passes through the patient's tissue, the operator may then separate the receptacle connector 280 from the plug connector 261. The operator can pull the remaining portions of the receptacle connector 280, together with the dilator 118 and the rest of the sling assembly, through the patient's tissues. At this time, the dilation takes place and the resultant tension on connector pairs falls on an attachment site 285 between the proximal connector end 283 and the dilator 118. Because a permanent or otherwise more durable attachment can be manufactured with respect to the attachment site 285 beforehand, the attachment site 285 is more likely to withstand the tension brought by the dilation process than the interconnection between connectors 280 and 261, especially if that interconnection is reversible. Accordingly, the elongated substrate 281 reduces the risk of separation between two interconnected parts during a trans-percutaneous procedure.

FIGS. 43 and 44 depict alternative embodiments 261a and 261b to the plug connector 261. Each of the alternative embodiments (261a, 261b) has a distal section (269a, 269b) that is separated from a base section (270a, 270b) by an reduced-diameter section (271a, 271b). The reduced-diameter section (271a, 271b) functions much like the reduced diameter section 271 of the plug connector 261 described in FIGS. 42A and 42B, and they can substitute each other for purpose of this invention. In FIG. 43, the illustrative distal section 269a includes a bulbous head and the illustrative reduced-diameter section 271a is a circular notch or a stepped-down portion. In FIG. 44, the illustrative distal section 269b includes a spearhead and the illustrative reduced-diameter section 271b includes multiple valleys 286.

Figure 45:
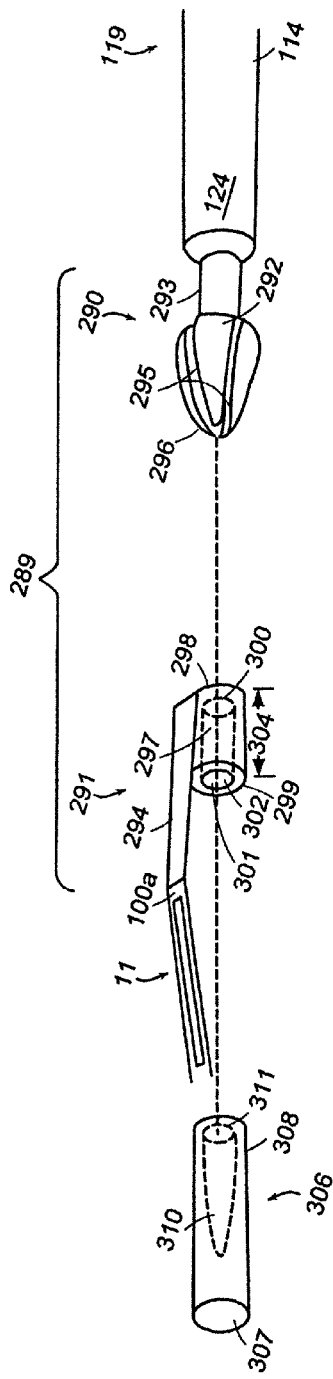
FIG. 45 depicts a side perspective view of a plug and receptacle connector pair where the plug connector alternately contracts and expands to interlock with the receptacle connector, and a release tool, according to an illustrative embodiment of the invention.

FIG. 45 depicts a connector pair 289 including a plug connector 290 and a receptacle connector 291 where the plug connector 290 alternately contracts and expands to interlock with the receptacle connector 291. The illustrative plug connector 290 is attached to the distal end 121 of the shaft 114 of the delivery device 119. The illustrative receptacle connector 291 is attached to the sleeve end 100a of the sling assembly 11. The plug connector 290 includes a distal section 292 and an reduced-diameter section 293, for example, a circular notch, which is disposed between the distal section 292 and the rest of the shaft 114. In one illustrative embodiment, the reduced-diameter section 293 is a stepped-down portion of the shaft 114, and the plug connector 290 is made out of the same material as and formed integrally with the rest of the shaft 114. However, in other embodiments these components may be made from different materials and attached together using any suitable approach. Optionally, one or more slits 295 are disposed along at least part of the distal section 292 of the plug connector 290, substantially parallel to a long axis of the shaft 114. In the illustrative embodiment, the slits 295 extend to the tip 296 of the plug connector 290 and therefore, the tip 296 of the plug connector 290 is hallowed. Although the illustrative embodiment employs four slits 295, any number may be used. There may be any number of slits 295, for example, four. The slits 295 allow the distal section 292 to compress inwardly. If the material that makes up the distal section 292 has sufficient elasticity, for example, as is the case with many metals and plastics, the distal section 292 will return to its relaxed and more expanded configuration once the compressive force disappears.

The illustrative receptacle connector 291 attaches to the sleeve end 100a through an extension tongue 294. The illustrative tongue 294 is elongated and spaces the receptacle 297 away from the sleeve end 100a. This makes it easier for the operator to interfit the plug connector 290 with the receptacle connector 291 using the head-on approach or the backend approach. In one embodiment, the tongue 294 is between about 0.5 inch to about one inch long.

The receptacle connector 291 includes a receptacle 297 for receiving and retaining the plug connector 290. In one embodiment, the receptacle 297 is tubular and includes a lumen 301 extending between first 300 and second 302 axially spaced apertures. The receptacle 297 has a length 304 that is preferably less than or equal to the length of the reduced-diameter section 293 of the plug connector 290.

In one embodiment, the lumen 301 in the receptacle connector 291 has a smaller diameter than the thickest point in the distal section 292 of the plug connector 290 and/or the thickest point on the shaft 114. To interconnect the two connectors, the tip 296 of the plug connector 290 enters the receptor lumen 301 through either the distal opening 300 (head-on approach) or the proximal opening 302 (backend approach) of the receptacle 297. The slits 295 constrict and compress as the thicker portion of the distal section 292 of the plug connector 290 as it squeezes into the receptor lumen 301. However, when the plug distal section 292 passes through the receptacle 297 to radially align the receptacle 297 with the reduced-diameter section 293 of the plug connector 290, the plug distal section 292 expands and returns to its relaxed configuration, acting as a barrier for separation from the receptacle connector 291.

FIG. 45 also depicts a release tool 306, for separating and releasing the receptacle connector 291 from the plug connector 290. The release tool 306 includes a first end 307, a second end 308, a lumen 310, and an opening 311 on the second end 308 in fluid communication with the lumen 310. Optionally, the release tool 306 may also have a second opening (not shown) in fluid communication with the lumen 310, however, for the purpose of this invention, the lumen 310 only needs one opening 311. The diameter of the illustrative lumen 310 in the release tool 306 is substantially similar to the diameter of the lumen 301 of the receptacle 297. Preferably, the length of the lumen 310 is greater than or equal to the length of the plug distal section 292. In a preferred embodiment, the lumen 310 in the release tool 306 is of a conical shape with the opening 311 being the base of the cone.

To separate the receptacle connector 291 from the plug connector 290, the operator slides the release tool 306, through its opening 311, first over the tip 296 and then over the distal section 292 of the plug connector 290. The lumen 310 of the release tool 306 contracts and compresses the plug distal section 292 as the release tool 306 advances over it. Once the plug distal section 292 is substantially inside the lumen 310, the receptacle 297 can slide over the now compressed distal section 292 towards the tip 296 of the plug connector 290. This motion replaces the receptacle connector 291 with the release tool 306. Accordingly, the release tool 306 and the receptacle connector 291 are removed, in tandem, from the distal section 292 of the plug connector 290. This disconnection procedure works for interconnected connectors whether they were interconnected through a head-on or backend approach.

Figure 46A:
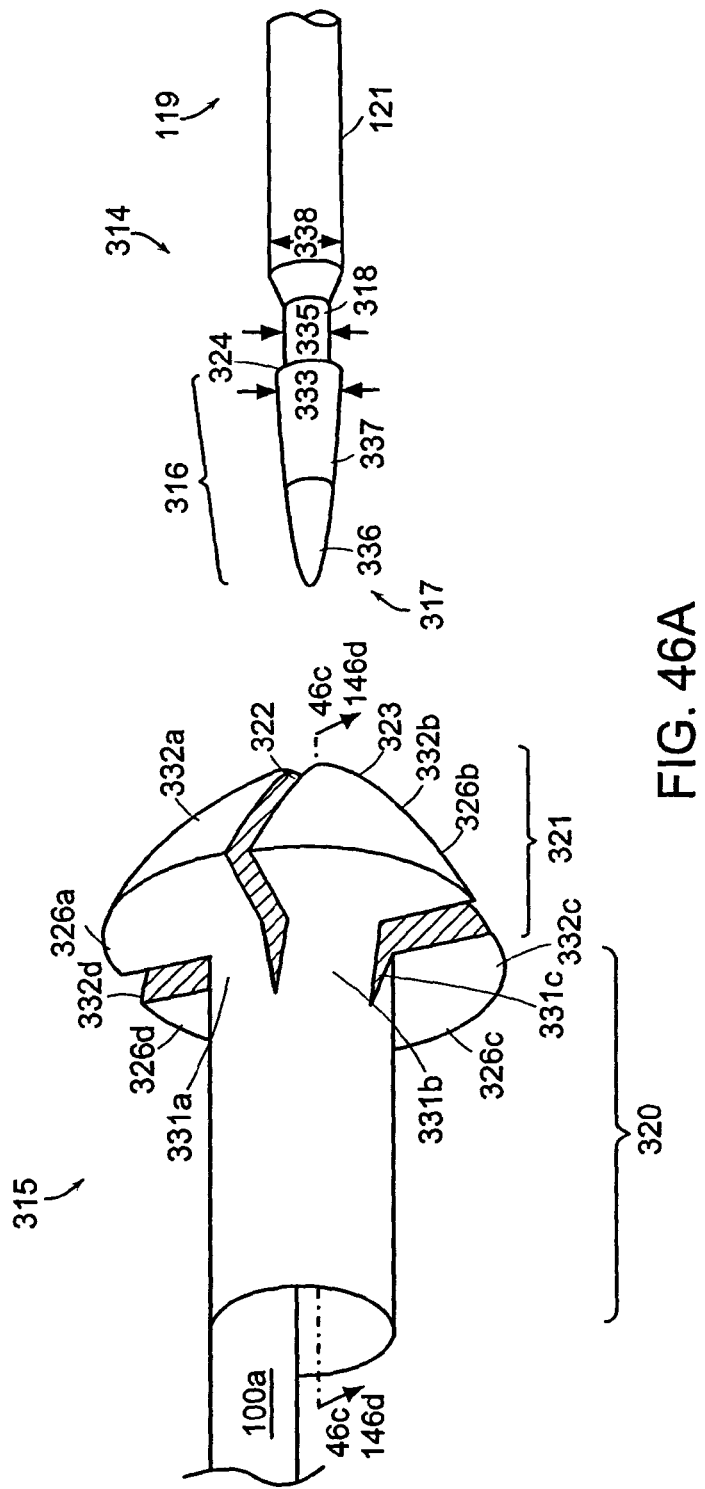
FIG. 46A depicts a side perspective view of a plug and receptacle connector pair where the receptacle connector alternately expands and contracts to interlock with the plug connector.

FIG. 46A depicts a plug connector 314 and a receptacle connector 315 where the receptacle connector 315 alternately expands and contracts to interlock with the plug connector 314. The illustrative plug connector 314 is disposed at the shaft distal end 121 of the delivery device 119. The plug connector 314 includes a distal section 316 that tapers to a tip 317 and an reduced-diameter section 318, for example, a circular notch, which is disposed between the distal section 316 and the rest of the shaft 114. The tapered distal section 316 has a proximal base 324 adjacent the reduced-diameter section 318. The tapered distal section 316 reaches its maximum diameter 333 at the proximal base 324. The maximum diameter 333 in the tapered distal section 316 is larger than the diameter 335 of the reduced-diameter section 318. The diameter 338 for the shaft distal section 121 is also larger than the diameter 335 of the reduced-diameter section 318. The illustrative distal section 316 of the plug connector 314 is conical in shape and includes telescoped sections 336 and 337.

The illustrative receptacle connector 315 is attached to the sleeve end 100a of a sling assembly. The receptacle connector 315 has a tubular portion 320 with a free and enlarged head portion 321. The illustrative head portion 321 is substantially conical. One or more slits 322 are disposed along the head portion 321 and optionally, part of the tubular portion 320, substantially parallel to a long axis of the receptacle connector 315. In one embodiment, the slits 322 extend to the very distal end 323 of the receptacle connector 315. There may be any number of slits 322. In the illustrative embodiment, four slits 322 results in four axial projections 326a, 326b, 326c, and 326d. For example, the axial projections 326a, 326b, and 326c extend from their respective base portions 331a, 331b, and 331c to their respective enlarged head 332a, 332b, and 332c. The base portions 331a, 331b and 331c, and the base portion (not shown) of the projection 326d, together form part of the radial structure of the receptacle tubular portion 320. The enlarged heads 332a, 332b, 332c, and 332d (of the projection 326d), which extend radially outward from the receptacle connector 315, together form the substantially conical head portion 321 of the receptacle connector 315.

FIG. 46B depicts a cross-sectional end view of the distal end 323 of the receptacle connector 315. Each of the slits 322 extends radially from the periphery of the head portion 321 to an axial channel 325. The channel 325 radially circumscribed by the enlarged heads 332a-332d and the axial projections 326a-326d. When the enlarged heads 332a-332d expand radially outward, the channel 325 expands as well, and the channel diameter 327 increases. Although the channel 325 is depicted as being generally cylindrical in shape, any suitable shape for mating with the plug connector 314 may be employed. Once the expansive force is removed, the head portion 321 returns to its relaxed and less expansive state, and the channel diameter 327 returns to its smaller, default value.

FIGS. 46C and 46D depict two exemplary embodiments of receptacle connectors 315 and 315a, where the channels 325 and 325a extend from openings 330 and 330a at the head portions 321 and 321a into the tubular portions 320 and 320a respectively. One or more protuberances 328 or 328a are disposed inside the channel 325 or 325a, for example, in the tubular portion 320 (FIG. 46C), or in the head portion 321a (FIG. 46D). In the illustrative embodiments, the protuberance 328 or 328a is an annular ring with an axial length 334 or 334a that is less or the same as the reduced diameter section 318 (FIG. 46A) of the plug connector 314. The channel diameter 339 or 339a between the annular protuberance 328 or 328a is less than the maximum diameter 333 of the plug distal section 316 (FIG. 46A) and/or the diameter 338 of the shaft distal end 121 (FIG. 46A). Preferably, the diameter 339 or 339a is greater than or equal to the diameter 335 of the reduced-diameter section 318 of the plug connector 314 (FIG. 46A). The channel diameter 327 or 327a in the rest of the channel 325 or 325a is substantially the same or larger than both the diameter 333 of the plug distal section 316 and the diameter 338 of the shaft distal end 121.

To interconnect the plug connector 314 with the receptacle connector 315, for example, the operator slides the distal opening 330 of the receptacle connector 315 over the tip 317 and then the distal section 316 of the plug connector 314. The plug distal section 316 travels further into the receptacle channel 325 until stopped by the protuberances 328. However, because of the slits 322, which preferably extend to the protuberance 328, the channel 325 expands further to allow the distal section 316 of the plug connection 314 to pass the protuberance 328 so as to engage the protuberance 328 with the reduced-diameter section 318. Because the diameter 339 at the protuberance 328 is selected to be less than the diameter 333 of the plug distal section 316 or the diameter 338 of the shaft distal end 121, the protuberance 328 locks the plug connector 314 inside the receptacle connector 315.

Figure 47:
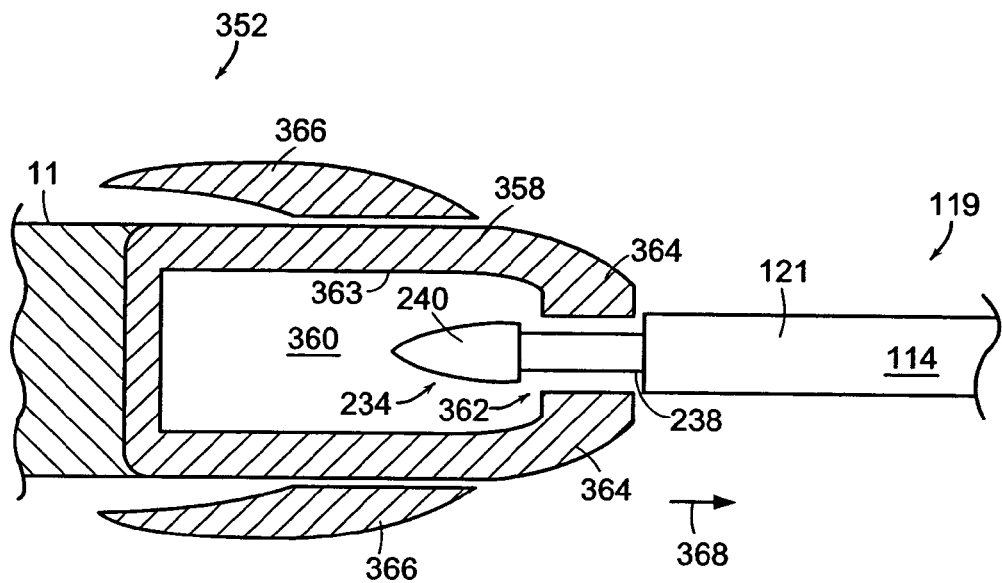
FIGS. 47 and 48 depict longitudinal cross-sectional views of receptacle and plug connector pairs at different stage of interconnection according to an illustrative embodiment of the invention.

FIG. 47 depicts a cross-sectional view of the connector pair according to another illustrative embodiment of the invention. The connector pair if FIG. 47 includes a plug connector 234 of the type previously described with respect to FIG. 39A. The connector pair also includes a receptacle connector 352. The receptacle connector 352 includes a tubular member 358 and a tightening collar 366. The tubular member 358 includes an inner wall 363 which defines a receptacle 360. The inner wall 363 includes an annular shoulder 364 which protrudes radially inward from and extends around the inner wall 363 to define a housing opening 362. The tightening collar 366 interfits concentrically around the tubular member 358. In some embodiments, the tubular member 358 includes axially extending slits (not shown) disposed around its circumference to enhance its ability to expand and contract.

In some embodiments, the tubular member 358 is made from a semi-rigid or flexible material and the tightening collar 366 is made from a substantially rigid material.

Figure 48:
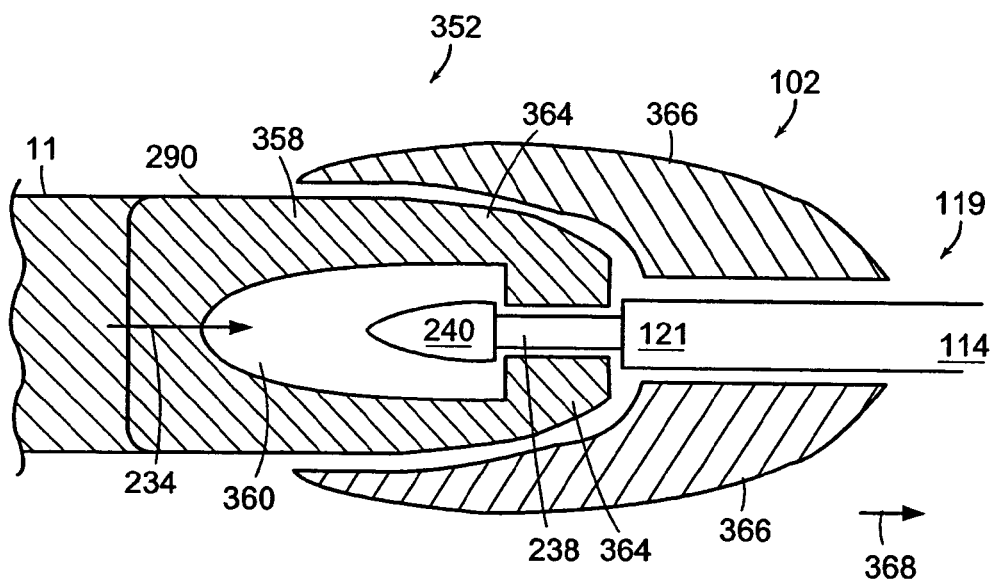

To interconnect the plug connector 234 with the receptacle connector 352, with the tightening collar 366 in the unlocked state of FIG. 47, inserts the plug connector 234 into the opening 362 until the annular shoulder aligns with 364 the reduced-diameter section 238. Then, the operator slides the tightening collar 366 in the proximal direction indicated by arrow 368 to compress the tubular member 358 around the plug connector 234. Referring now to FIG. 48, once the tightening collar 366 is slid over the tubular member 358 and a portion of the distal end 121 of the shaft 114, the lumenal diameter in the tubular member 358 is reduced such that the shoulder 364 engages the reduced diameter section 238 and locks the tapered distal section 240 of the plug connector 234 in place. To release the plug connector 234 from receptacle 360, the above procedure is reversed: the second collar 366 is slide in the distal direction opposite the arrow 368.

FIG. 49A depicts an exploded view of portions of the plug connector 380 and a receptacle connector 382. The plug connector 380 attaches to or is an integral part, for example, of the shaft distal end 121 of the delivery device 119. The plug connector 380 includes, from its distal tip 383, a conical distal section 384, a cylindrical section 386, and a reduced-diameter section 388. The cylindrical section 386 includes proximal base 381 adjacent the reduced-diameter section 388. The conical distal section 384 and the cylindrical section 386 constitute a tip section 385. The tip section 385 reaches its maximum diameter 387 at the proximal base 381, which is larger than the diameter 395 of the reduced-diameter section 388. Accordingly the maximum diameter 387, in this illustrative embodiment, is also the maximum diameter of the plug connector 380. The diameter 395 of the reduced-diameter section 388 is also smaller than the diameter 397 of the shaft distal end 121.

The receptacle connector 382 includes a first portion 390 and a second portion 392. In one embodiment, the second portion 392 includes one or more rails 394. The rails 394 may extend along the full length of the second portion 392, or, alternatively, only partially along the length of the second portion 392. The first portion 390 includes grooves or slots 396 complementary to the rails 394 on the second portion 392. Portions 390 and 392 can assume a variety of shapes. For example, as illustrated, the first portion 390 may resemble part of a box, while the second portion 392 may resemble part of a tube. The two portions can, of course, assume similar shapes.

Referring now to FIG. 49B, the first portion 390 of the receptacle connector 382 includes a protuberance 398 that complements or conforms to at least a substantial part of the reduced-diameter section 388 in the plug connector 380, illustratively about half of the reduced-diameter section 388. Accordingly, the protuberance 398 may be, for example, semi-annular in shape.

To interconnect the receptacle connector 382 with the plug connector 380, the operator, in one embodiment, places the first portion 390 of the receptacle connector 382 on the plug connector 380. The protuberance 398 mates with the reduced-diameter section 388 of the plug connector 380. Then, the operator, matching the rails 394 with the slots 396, slides the second portion 392 onto the first portion 390, in the direction indicated by arrow 399. The first portion 390 and the second portion 392 should be sized such that when they are slid together, with the help of the protuberance 398 inside the first portion 390, they effectively prevent the captured plug connector 380 from exiting. To release the plug connector 380 from the receptacle connector 382, the operator slides the second portion 392 of the receptacle connector 382 in the direction opposite the arrow 399 and separates the second portion 392 from the first portion 390. Then, the first portion 390 and the plug connector 380 are free to separate from each other.

In an alternative embodiment, to interfit the first portion 390 with the second portion 392, rather than sliding the rails 394 of the second portion 392 into the complementary slots 396 of the first portion 390, the operator snaps the rails 394 into the complementary slots 396 to force-fit the second portion 392 onto the first portion 390.

Figure 50A:
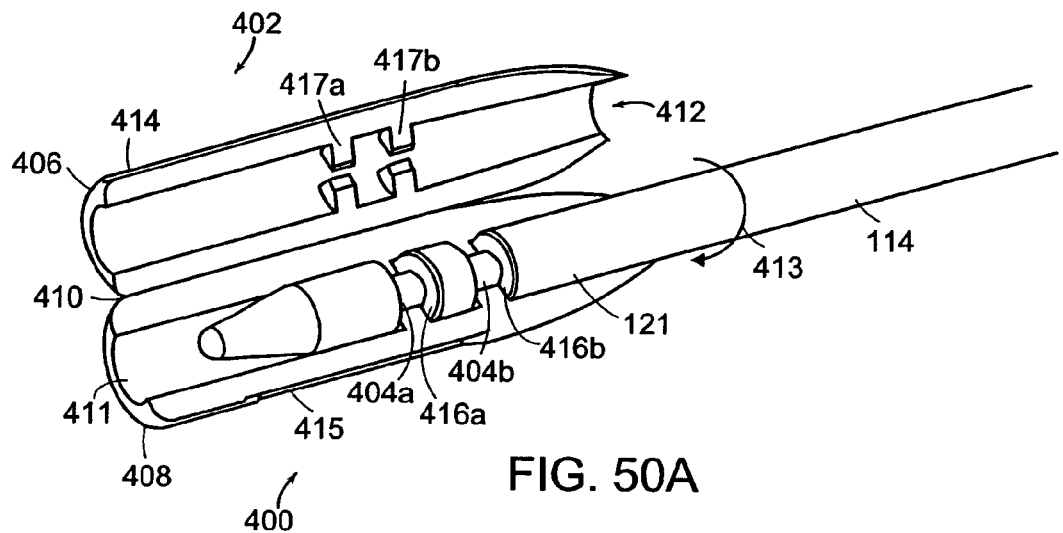
FIG. 50A depicts a side perspective view of a plug and receptacle connector pair where the receptacle opens and closes to facilitate interconnection, according to an illustrative embodiment of the invention.

FIG. 50A depicts a plug connector 400 and an opened receptacle connector 402 where the receptacle connector 402 locks the plug connector 400 inside when a lid portion 406 of the receptacle connector 402 closes. The plug connector 400 is attached to, for example, the shaft distal end 121 of the delivery device 119. The plug connector 400 includes one or more reduced-diameter sections 404A and 404B.

The receptacle connector 402 includes a lid portion 406 and a body portion 408 linked by, for example, a longitudinal hinge 410 that enables the lid portion 408 to open and close in a radial direction. In its closed configuration (not shown), the receptacle connector 402 may substantially match the shape of the plug connector 400. For example, if the plug connector 400 is substantially cylindrical, the receptacle connector 402, in its closed configuration, may be substantially tubular with at least one opening 412 through which the shaft distal end 121 can extend. The receptacle connector 402 may further include a snapping member 414 positioned on the lid portion 406 and a locking member 415 positioned on the body portion 408. The body portion 408 of the receptacle connector 402 includes one or more projections or protuberances 416a and 416b that complements or conforms to a substantial part of the reduced-diameter sections 404a and 404b, for example, half of the reduced-diameter sections 404a and 404b. Accordingly, the protuberances 416a and 416b may each be, for example, semi-annular in shape. Optionally, the lid portion 406 may include similar protuberances 417a and 417b to complement its half of the reduced-diameter sections 404a and 404b. In one embodiment, the interior of the receptacle connector 402 is molded to mirror the entire contour of the plug connector 400, much like the box of a musical instrument would typically form-fit the instrument.

To interfit the receptacle connector 402 over the plug connector 400, the operator first opens the two portions 326, 328 of the receptacle connector 402 to the illustrated open configuration. The operator then places the plug connector 400 in the lumen 411 of the body portion 408 of the receptacle connector 402 such that the protuberances 416a and 416b of the body portion 408 mate with the reduced-diameter sections 404a and 404b. To lock the plug connector 400 inside the receptacle connector 402, the operator rotates the lid portion 406 in the direction indicated by arrow 413 onto the body portion 408 and snaps the snapping member 414 into the locking member 415. To release the plug connector 400, the operator reverses the aforementioned steps.

Figure 50B:
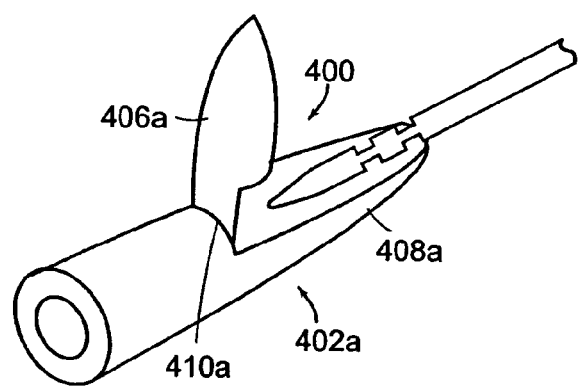
FIG. 50B depicts a side perspective view of an alternative embodiment of the connector pair of FIG. 50A.

FIG. 50B depicts an alternative receptacle connector 402a that can also lock the plug connector 400 (described above with respect to FIG. 50) by closing a lid portion 406a. The receptacle connector 402a includes features similar to those of the receptacle connector 402, described with respect to FIG. 50, except that a lateral hinge 410a replaces the longitudinal hinge 410. The lateral hinge 410a is located along a portion of the circumference of the receptacle connector 402a, links the lid portion 406a and the body portion 408a, and enables the lid portion 406a to open and close in an axial direction.

Figure 51A:
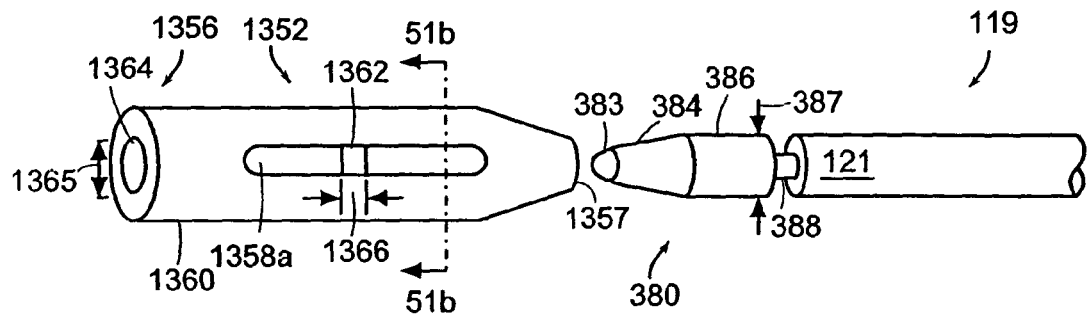
FIG. 51A depicts a side perspective view of a plug and receptacle connector pair with a protuberance to facilitate interlocking, according to an embodiment of the invention.
Figure 51B:
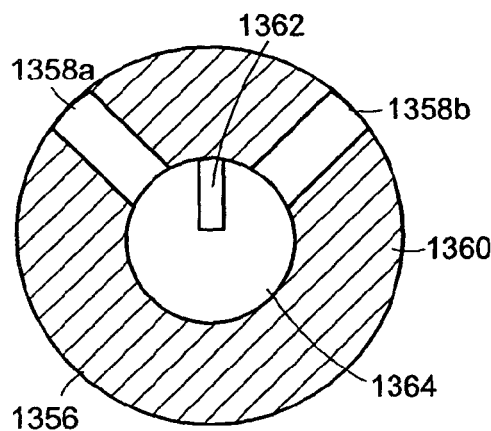
FIG. 51B depicts a cross-sectional view of the receptacle connector of FIG. 51A along the line "51B-51B."

FIGS. 51A and 51B depict, through a perspective side view and a cross-sectional view, a receptacle connector 1352 having a protuberance 1362 that facilitates interlocking with plug connector 380 of the type previously described with respect to FIG. 49A. The receptacle connector 1352 includes a substantially tubular housing 1356 open at least at one end 1357 for receiving the plug connector 380. The tubular housing 1356 includes one or more apertures 1358. In the illustrated embodiment, two apertures 1358a and 1358b extend axially along the tubular housing 1356. A protuberance 1362 extends radially into the housing 1356.

In one embodiment, the length 1366 of the protuberance 1362 is less than or equal to the depth of the reduced-diameter section 388 in the plug connector 380. In the illustrative embodiment, the protuberance 1362 is a retractable or spring-loaded pin. In an alternative embodiment, the protuberance 1362 is a flap made of a moldable material, such as, for example, rubber, and is capable of being bent or displaced upon insertion of the plug connector 380, as described in more detail below. In one embodiment, the flap is insert molded to the inner surface of the tubular wall 1360 of the receptacle connector 1352. In another embodiment, the flap is a cutout portion of the tubular wall 1360 that remain attached to the tubular housing 1356 through a hinge, which enables the operator to rotate the flap up and down, as explained below in connection with FIG. 52.

In one embodiment, the receptacle 1364 in the tubular housing 1356 has a diameter 1365 that is equal to or less than the maximum diameter 387 of the plug connector 380. However, because the locking function by the protuberance 1362 the receptacle 1364 may have a diameter larger than the maximum diameter 387 of the plug connector 380. In the latter embodiment, the tubular housing 1356 does not need to have any of the apertures 1358*a* or 1358*b*.

To interfit the receptacle connector 1352 over the plug connector 380, the operator inserts the tip 383 of the plug connector 380 into the opening at the end 1357 of the receptacle connector 1352. As the operator advances the plug connector 380 further into the receptacle 1364, the apertures 1358*a* and 1358*b* in the tubular housing 1356 allow the receptacle 1364 to expand and accommodate the tapered distal section 384 and the cylindrical section 386 of the plug connector 380. Alternatively, if no apertures 1358 are present on the receptacle connector 1352, the operator force fits the plug connector 380 into the receptacle 1364 of the receptacle connector 1352.

In an embodiment where the protuberance 1362 is a spring-loaded pin, the protuberance 1362 is initially biased to project radially into the receptacle 1364. As the operator advances the plug connector 380 into the receptacle 1364, the tapered distal section 384 of the plug connector 380 gradually deflects the protuberance 1362, either axially or radially. After the entire tapered distal section 384 and the cylindrical section 386 pass the protuberance 1362, the protuberance 1362 returns to its original untensioned position in the adjacent reduced-diameter section 388 in the plug connector 380. By engaging with the reduced diameter section 388, the protuberance 1362 locks the plug connector 380 inside the receptacle connector 1352.

In an embodiment where the protuberance 1362 is manually retractable, it can be initially retracted as the operator advances the plug connector 380 into the lumen 1364 of the receptacle connector 1352. When the reduced-diameter section 388 in the plug connector 380 reaches the protuberance 1362, the operator can let the protuberance 1362 extend or simply fall back into the receptacle 1364 to engage the reduced-diameter section 388, thereby locking the plug connector 380.

In an embodiment where the protuberance 1362 is a flap, for example, insert molded to the inner surface of the tubular housing 1356 of the receptacle connector 1352, the flap can be bent and displaced by the operator inserting the plug connector 1234 into the receptacle 1364. The flap rides along the surface of the plug connector 380 until it reaches the reduced-diameter section 388 of the plug connector 234, at which point it engages the reduced-diameter section 388, locking the plug connector 234.

Figure 52:
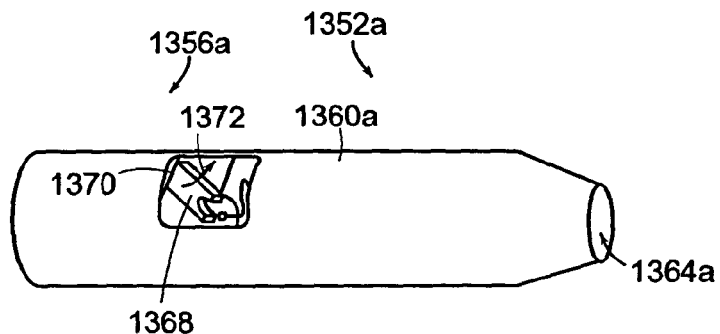
FIG. 52 depicts a side view partially in perspective of a receptacle connector similar to the receptacle connector of FIG. 51A, but including a flap, according to an illustrative embodiment of the invention.

FIG. 52 depicts an embodiment of the receptacle connector 1352, in which a receptacle connector 1352*a* includes a protuberance that is a flap 1368 attached to the tubular housing 1356*a* through a hinge 1370. In some embodiments, the flap 1368 may be formed as a cutout of the tubular hosing 1356*a*. The operator initially deflects the flap 1368 in the direction indicated by arrow 1372, and holds the flap 1368 coplanar with one side of the tubular housing 1356*a*. The operator then advances the plug connector 380 into the receptacle 1364*a*. When the reduced-diameter section 388 of the plug connector 380 is aligned with the flap 1368, the operator deflects the flap 1368 in the direction opposite the arrow 1372 to engage the reduced-diameter section 388, thereby locking the plug connector 380. The operator may use any suitable tool to accomplish the flap deflection.

Figure 53:
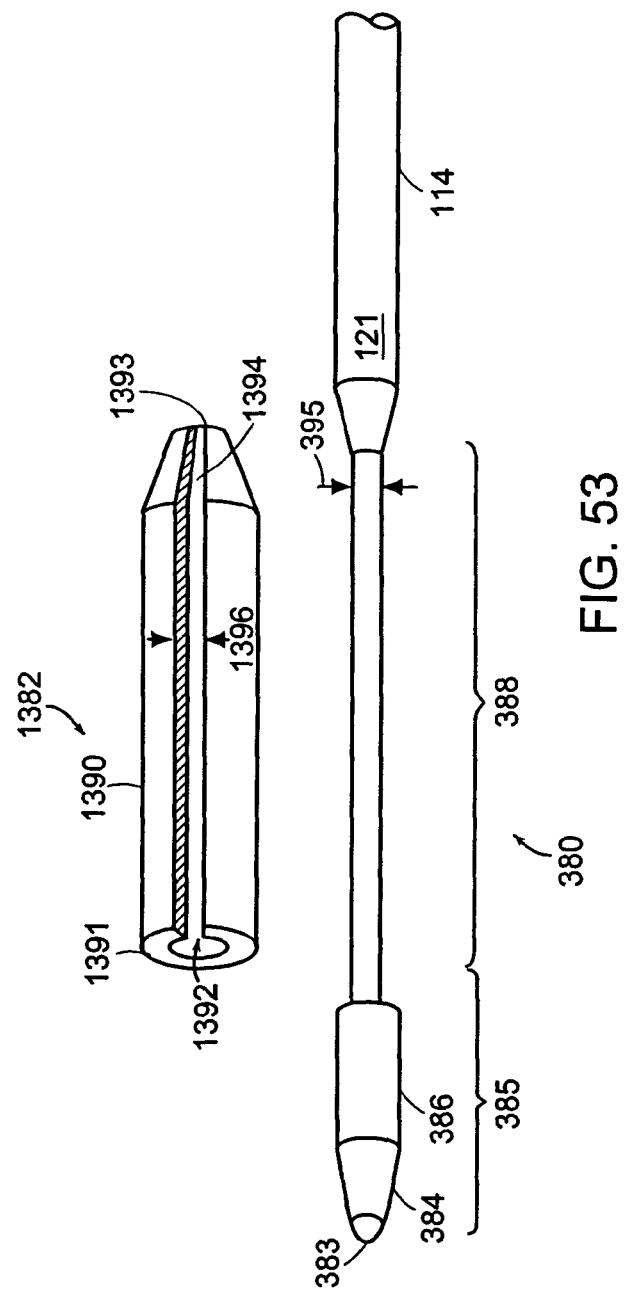
FIG. 53 depicts a side perspective view of a receptacle and plug connector pair, according to another illustrative embodiment of the invention.

FIG. 53 depicts a receptacle connector 1382 that can be side mounted onto the plug connector 380 of the type previously described with respect to FIG. 49A. The illustrative receptacle connector 1382 includes a cylindrical tubular member 1390 defining a channel 1392. The tubular member 1390 has a first end 1391 that can attach to a part of a delivery system, for example, a sling assembly end (not shown), and a second end 1393. A slot 1394 extends axially in the tubular member 1390 from the first end 1391 to the second end 1393. The illustrative slot 1394 exposes a channel 1392 and has a width 1396 that is less than or equal to the diameter 395 of the reduced-diameter section 388 of the plug connector 380. The illustrative slot 1394 has a length that is less than or equal to that of the reduced-diameter section 388. Optionally, in one embodiment, the channel 1392 has a diameter that is greater than or equal to that of the reduced-diameter section 388.

To interconnect the receptacle connector 1382 with the plug connector 380, the operator aligns the slot 1394 with the reduced-diameter plug section 388. The operator then interfits the reduced-diameter section 388 through the slot 1394 into the channel 1392. Then the tubular member 1390 snaps onto the reduced-diameter section 388 as the slot 394 returns to its normal width to lock the plug connector 380 into the receptacle connector 1382.

After the two connectors 1380 and 1382 have been interconnected, the operator can rotate either the connector 1380 or 1382 about a longitudinal axis without rotating the other connector and while maintaining the interconnection. This is advantageous where a base part, for example, the sling assembly, attached to either connector needs to be untwisted after getting twisted or wound during the delivery or placement.

Figure 54A:
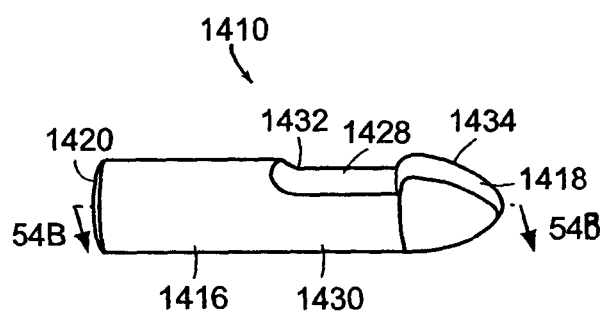
FIG. 54A depicts a side perspective view of a receptacle connector, according to another illustrative embodiment of the invention.
Figure 54B:
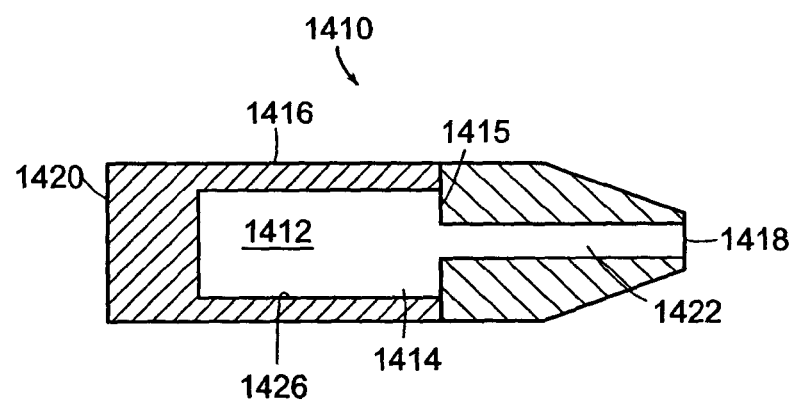
FIG. 54B depicts a cross-sectional view of the connector of FIG. 54A, along the line "54B-54B."

FIGS. 54A and 54B depict a receptacle connector 1410 where an axially extending receptacle 1412 includes a radially enlarged portion 1414 for accommodating the tip section 385 of the plug connector 380 previously described with respect to FIG. 49A.

The illustrative receptacle connector 1410 includes a substantially tubular housing 1416 with a distal opening 1418. The housing 1416 can attach to a component of a delivery system such as a sling assembly (not shown) through its proximal end 1420. The illustrative proximal housing end 1420 does not contain any proximal opening, but in an alternative embodiment, there can be such an opening. Better shown in FIG. 54B through a longitudinal view, the receptacle 1412 extends axially from a distal opening 1418 into the housing 1416. The receptacle 1412 includes an enlarged portion 1414 and a narrow portion 1422. A substantially annular ring 1424 with a shoulder 1415 projects from an inner wall 1426 and narrows the receptacle 1412 to its narrow portion 1422. The narrow portion 1422 is similar to the channel 1392 described with respect to FIG. 53 and for receiving the reduced diameter section 388 of the plug connector 380 (FIG. 49A). The enlarged portion 1414 is sized and shaped to receive the tip section 385 of the plug connector 380 (FIG. 49A).

Referring specifically to FIG. 54A, an axial slot 1428 extends radially from the housing outer surface 1430 into the receptacle 1412. Corresponding to and aligned with the enlarged receptacle portion 1412 and the narrow receptacle portion 1422, the illustrative axial slot 1428 includes an enlarged portion 1432 and a narrow portion 1434. The enlarged slot portion 1432 and the narrow slot portion 1434 are narrower than the tip section maximum diameter 387 and diameter 395 of the reduced-diameter section 388 of the plug connector 380 (FIG. 49A), respectively, for locking the plug connector 380. In an alternative embodiment, the slot 1428 has uniform width.

Side-mounting the receptacle connector 1410 onto the plug connector 380 is similar to the steps described above in connection with FIG. 53 except that at least part of the plug connector 380 is snapped into the enlarged receptacle portion 1412 through the enlarged slot portion 1432.

Figure 54C:
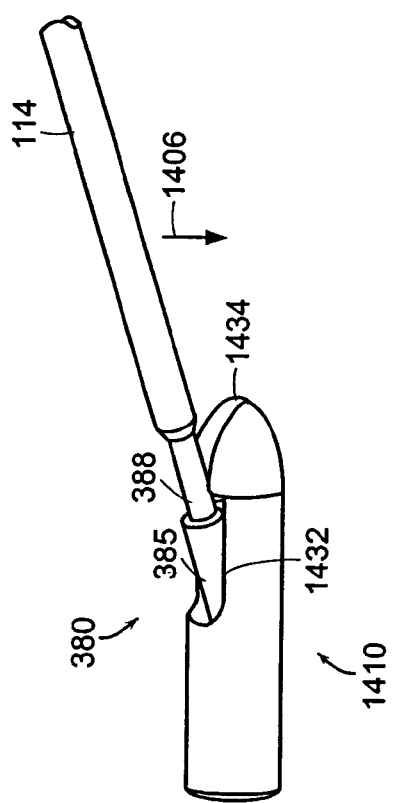
FIG. 54C depicts a side perspective view of the receptacle connector of FIG. 54A partially interconnected with the type of plug connector depicted in FIG. 53.

FIG. 54C depicts an additional method of interfitting the receptacle connector 1410 with the plug connector 380, as it may be advantageous to use this method during certain delivery procedures. The operator inserts a part of the tip section 385 of the plug connector 380 into the enlarged slot portion 1432 at an angle, with the reduced-diameter section 388 above the narrow slot portion 1434. The operator moves the shaft 114 in a clockwise direction indicated by the arrow 1406 towards the receptacle connector 1410. Through this motion, the operator snap fits the reduced-diameter section 388 of the plug connector 380 through the narrow slot portion 1434 into the narrow receptacle portion 1422 (FIG. 54B), and the tip section 385 through the enlarged slot portion 1432 into the enlarged receptacle portion 1414 (FIG. 54B).

Figure 55:
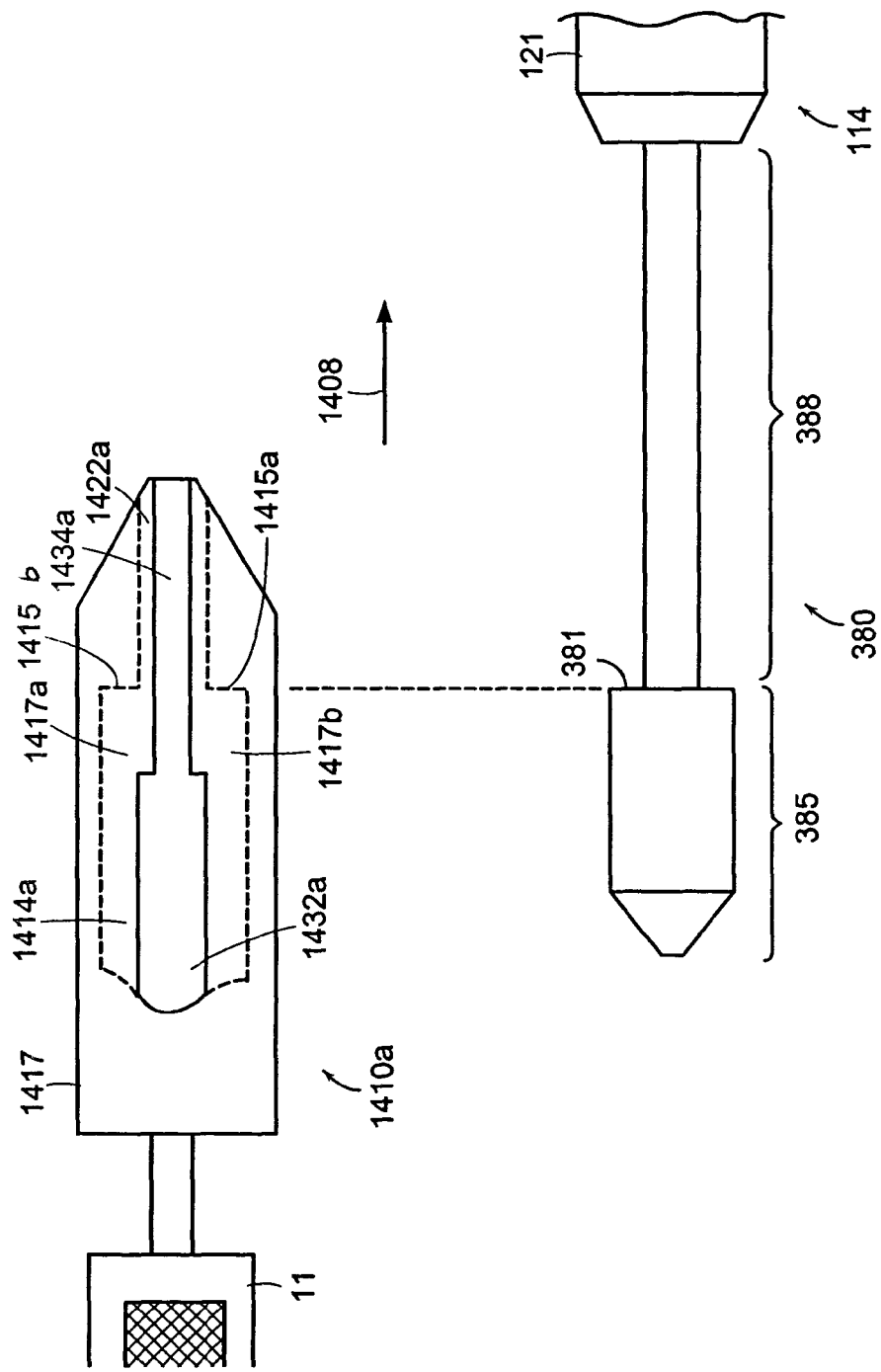
FIG. 55 depicts a top schematic view of a connector pair as an alternative embodiment to the connector pair of FIG. 54C.

FIG. 55 depicts a schematic view of a receptacle connector 1410a which is an alternative embodiment to the receptacle connector 1410. The receptacle connector 1410a includes a tubular housing 1416a formed from a substantially tubular wall 1417, and defines an enlarged receptacle portion 1414a and a narrow receptacle portion 1422a. The receptacle connector 1410a also includes an enlarged slot portion 1432a, aligned with the enlarged receptacle portion 1414a, and a narrow slot portion 1434a, aligned with the narrow receptacle portion 1422a. In this embodiment, the slot portion 1432a overhangs the enlarged receptacle portion 1414a, both axially and radically, and the slot portion 1434a overhangs the narrow receptacle portion 1422a axially. In some embodiments, the enlarged receptacle portions 1414a is sized to be axially longer than the plug connector tip section 385. In such embodiments, subsequent to mating and in response to exerting axially opposing forces on the plug 380 and receptacle 1410a connectors, the tip section 385 slides axially in the direction indicated by an arrow 1408 under the overhang 1417a and 1417b. The tip section 385 stops when its base 381 abuts shoulders 1415a and 1415b of the enlarged receptacle portion as indicated in phantom and becomes locked in place.

In other embodiments, the receptacle portions 1414a and 1422a are sized as are their counterparts 1414 and 1422 of FIG. 54B, and the overhangs of the slot portions 1432a and 1434a have reduced length and/or width relative to their counterparts 1432 and 1434 of FIG. 54B and/or relative to the receptacle portions 1414a and 1422a. In all the above embodiments, the overhangs provide further more secure interlocking between the plug connector 380 and the receptacle connector 1410a, and reduce the likelihood of inadvertent separation.

The receptacle connector 1410a further includes an enlarged slot portion 1432a and a narrow slot portion 1434a similar to the enlarged slot portion 1432 and the narrow slot portion 1434, respectively (FIG. 54B). However, the enlarged slot portion 1432a and the narrow slot portion 1434a are not aligned with but offset from their counterpart receptacle portions 1414a and 1422a. Portions 1417a and 1417b of the tubular wall 1417 narrows the slot space radially outside distal parts 1440a and 1440b of the enlarged receptacle portion 1414a such that the narrow slot portion 1434a is longer than its counterpart 1434 in connector 1410.

The receptacle connector 1410a is mounted on the plug connector 380 as with the receptacle connector 1410. However, the operator can move the shaft 114 in a direction indicated by an arrow 1408 to move the tip section 385 into the roofed distal parts 1440a and 1440b of the enlarged receptacle portion 1414a until the base 381 abuts shoulders 1415a as indicated by phantom line. As a result, the interconnection between the two connectors 380 and 1410a is more secure than between connectors 380 and 1410.

Figure 56D:
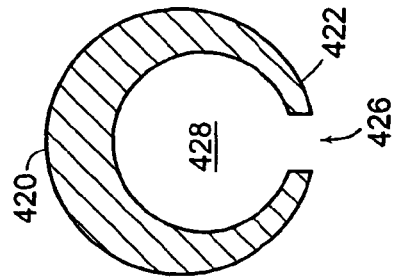
FIGS. 56B-56D depict cross-sectional views of the receptacle connector of FIG. 56B, at various locations along its length.
Figure 56A:
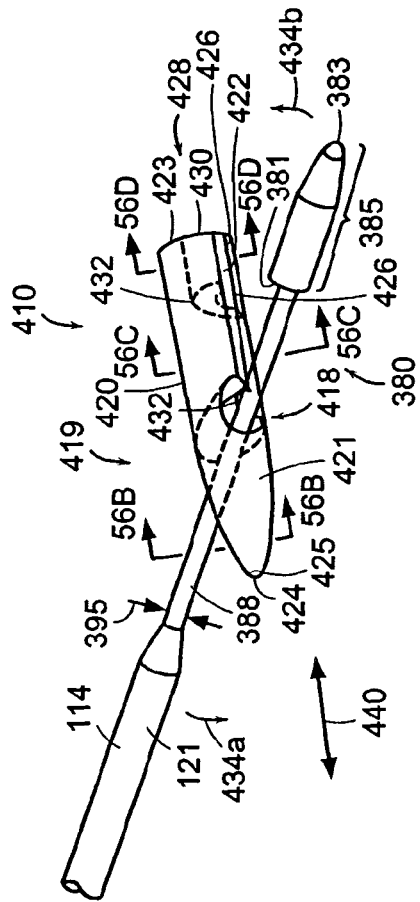
FIG. 56A is a perspective top view illustrating interconnection between a receptacle and plug connector pair, according to an embodiment of the invention.

FIG. 56A depicts another receptacle connector 419 which interfits, with the plug connector 380 described previously with respect to FIG. 49A. After they are interfitted, both connectors 419 and 380 can rotate independently while maintaining interfitted. In the illustrative embodiment of the plug connector 380, the reduced-diameter section 388 has substantially the same length as the receptacle connector 419.

The receptacle connector 419 includes a cylindrical housing 421 with a first 425 and second 423 ends. Preferably, the end 423 attaches to a part of a delivery system such as a medical implant. The housing 421 includes a transverse aperture 418 that extends from a top surface 420 of the connector 419 to a bottom surface 422. The receptacle connector 419 further includes a first channel 424 on the top surface 420 and a second channel 426 on the bottom surface 422. The first channel 424 extends from the transverse aperture 418 to the first housing end 425, and the second channel 426 extends from the transverse aperture 418 to the second housing end 423. The illustrative housing 421 includes an optional cavity 428 that extends from an opening 430 at the second housing end 423 axially toward the first end 425. The cavity 428 preferably is dimensioned and shaped to accommodate the tip section 385 of the plug connector 380. In the illustrative embodiment, the cavity 428 terminates at a back-wall 432.

Figure 56C:
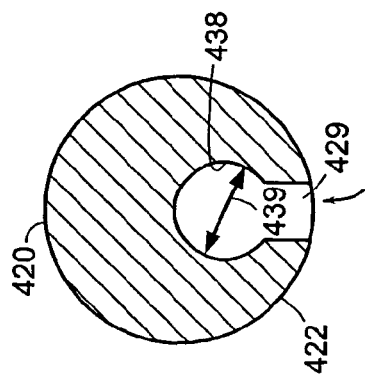
Figure 56B:
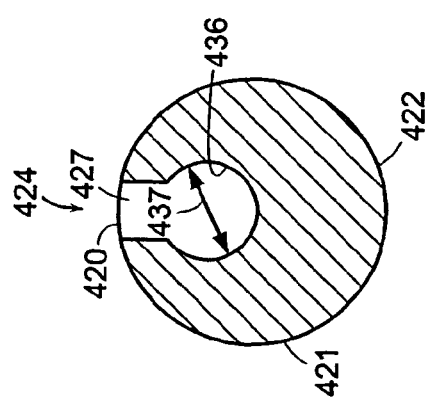

FIG. 56B depicts a cross-sectional view of the housing 421 of the receptacle connector 419, showing the first channel 424. FIG. 56C is a cross-sectional view of the housing 421 showing the second channel 426 at a point between the transverse aperture 418 and the back wall 432. FIG. 56D is a cross-sectional view of the housing 421 showing the second channel 426 and the cavity 428. As depicted in FIG. 56B-56D, the first channel 424 includes a first substantially cylindrical receptacle 436, and the second channel 426 includes a second substantially cylindrical receptacle 438. Both receptacles 436 and 438 are sized and shaped to accommodate the reduced-diameter section 388 of the plug connector 380. Specifically, the diameter 437 of the first receptacle 436 and the diameter 439 of the second receptacle 438 are both greater than or equal to the diameter 395 (FIG. 56A) of the reduced-diameter section 388. A first axial opening 427 in the housing top surface 420 provides access to the first channel receptacle 436. A second axial opening 429 in the housing bottom surface 422 provides access to the second channel receptacle 438. Both the first and second axial openings 427 and 429 are narrower than the diameter 395 of the reduced-diameter section 384 to lock the reduced-diameter section 388 within the receptacles 436 and 438.

Referring back to FIG. 56A, to interfit the plug connector 380 within the illustrative receptacle connector 419, the operator inserts the plug tip section 385 through the transverse aperture 418 from the top surface 420 to the bottom surface 422. After the reduced-diameter section 388 emerges from the bottom surface 422, the operator rotates the shaft 114 relative to the receptacle connector 419 in the direction indicated by arrows 434a and 434b. The reduced-diameter section 388 snap fits into the first and second receptacles 436 and 438, while the proximal base 381 of the tip section 385 fits into the cavity 428.

In response to axially opposing forces on the interfitted connectors 419 and 380, as indicated by the arrows 440, the plug tip section 385 backs into the housing cavity 428 until the base 381 of the tip section 385 abuts the back wall 432. This further locks the plug connector 380 inside of the receptacle connector 419.

Figure 57:
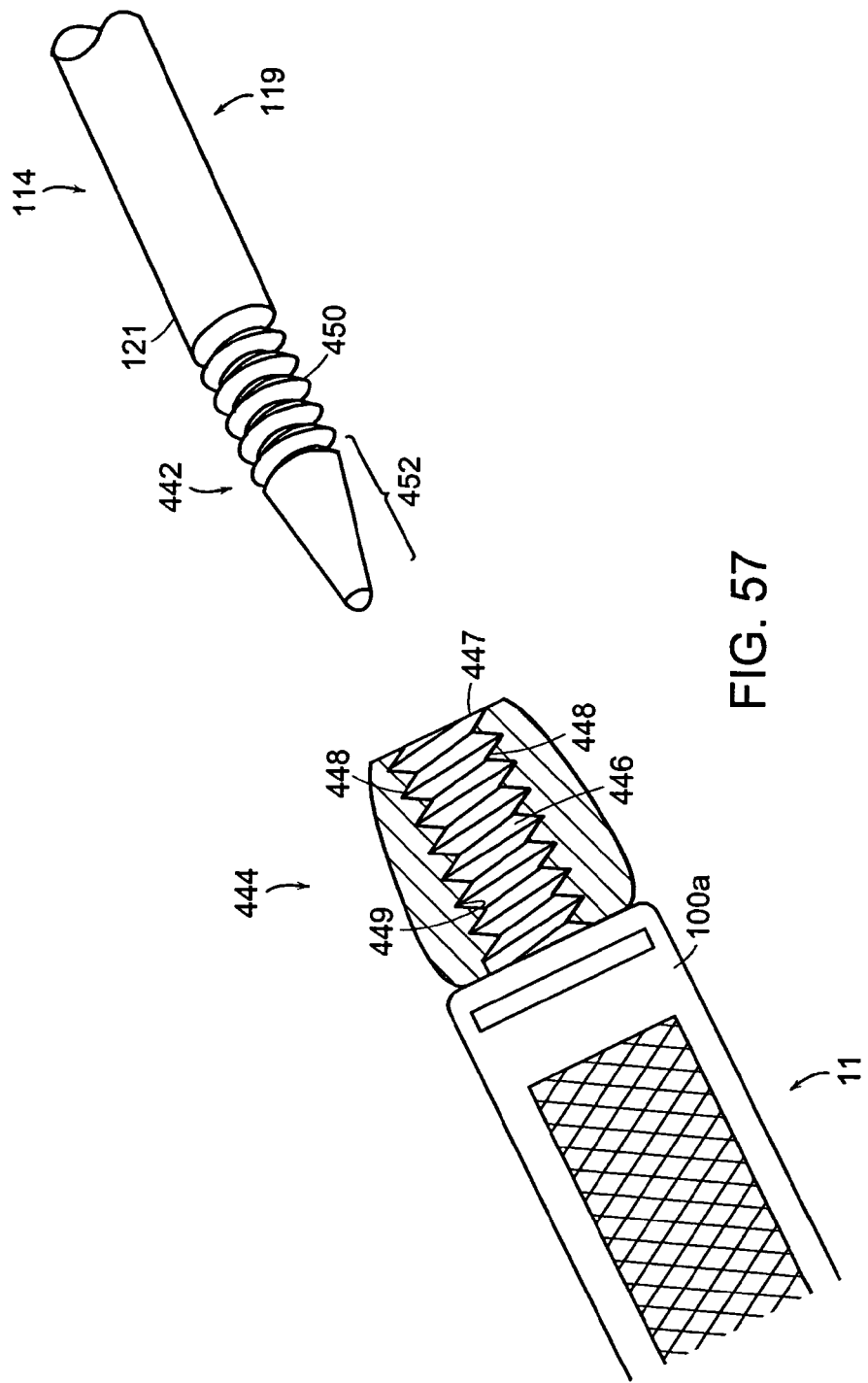
FIG. 57 depicts a perspective side view in partial cross-section of a threadable receptacle and plug connector pair.

FIG. 57 depicts a threaded plug 442 connector and receptacle 444 connector pair according to another illustrative embodiment of the invention. The illustrative plug connector 442 is depicted as being attached to or located at the distal end 121 of the shaft 114 in the delivery device 119, and the illustrative receptacle connector 444 is depicted as being attached to the sleeve end 100a of the sling assembly 11. However, as previously discussed the plug 442 and receptacle 444 connectors may be located on any delivery system component.

The receptacle connector 444 includes a threaded receptacle 446 having an opening 447. The receptacle 446 includes, on its inside wall 449, a first set of threads 448. The plug connector 442 includes a second set of corresponding threads 450 disposed around its periphery. The illustrative plug connector 442 optionally includes a conical distal section 452. To interfit the plug connector 442 with the receptacle connector 444, the operator positions the distal opening 447 over the plug distal section 452 and screws (i.e., rotates or threads), the first set of threads 448 onto the second set of threads 450. To separate the connectors 442 and 444, the operator rotates receptacle 444 and the plug 442 connectors in a counter clockwise direction relative to each other.

Figures 58A, 58B:
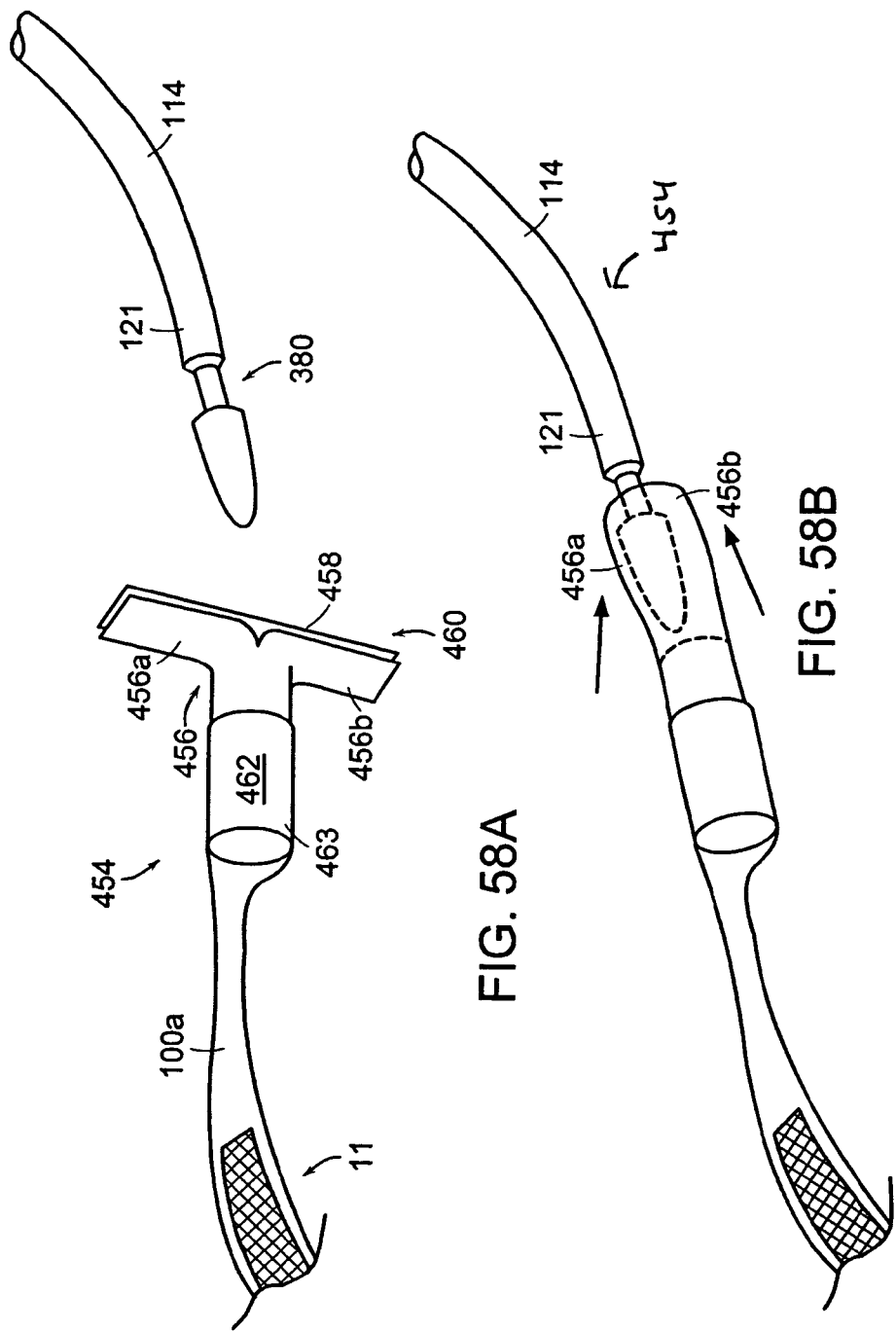
FIG. 58A depicts a side view perspective of a plug and receptacle connector pair in which the receptacle and plug connectors adhere to each other during interconnection.
FIG. 58B depicts a perspective side view of the connector pair of FIG. 58A subsequent to interconnection.

FIGS. 58A and 58B depict an illustrative plug 380 and receptacle 454 connector pair in which the receptacle connector 454 includes an adhesive surface 456. Preferably, illustrative adhesive surface 456 is sealed with a protective layer 458, which may be removed prior to use. The receptacle connector 454 further includes an optional support 462. While the illustrative support 462 is a substantially cylindrical, it can be of any other suitable shape. The illustrative support 462 attaches, through its proximal end 463, for example, to the sleeve end 100a. The adhesive surface 456 can be disposed anywhere on the support 462, for example, as in the illustrative embodiment, at its distal end 460. In the illustrative embodiment, the adhesive surface 456 include two adhesive flaps 456a and 456b that are diametrically opposed to each other, forming a pair of adhesive surfaces substantially normal to the support 462.

Referring now to FIG. 58B, to interconnect the receptacle connector 454 with the plug connector 380, the operator peels off the protective layer 458 or otherwise removes it to expose the adhesive surface 456. The operator then interfits the plug 380 and receptacle 454 connectors and folds down the two adhesive flaps 456a and 456b such that they wrap around the plug connector 380. A plug connector of any shape can be employed with the receptacle connector 454 and the same embodiment, extended onto and/or around the distal shaft end 121. In a preferred embodiment, the plug connector 380 and/or the shaft distal end 121 include a roughened surface or contours to facilitate bonding to the adhesive flaps 456a and 456b. The receptacle adhesive surface 456 can be used, for example, to form a non-detachable (e.g., non-reusable) connection between a medical implant and another delivery system component.

Figure 59A:
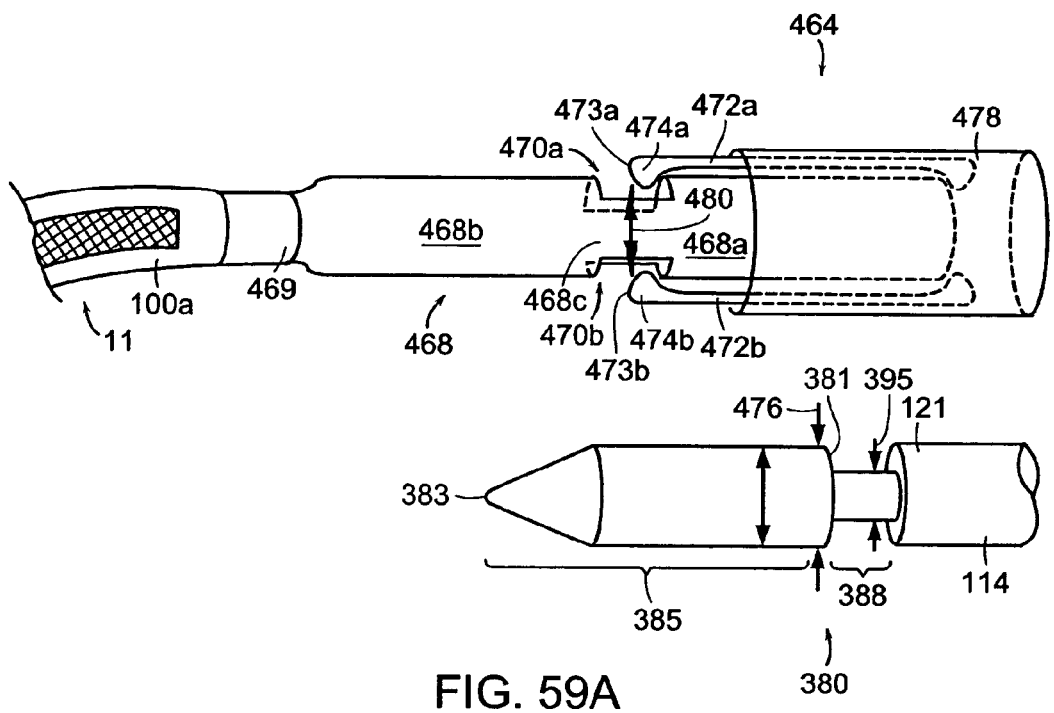
FIG. 59A depicts a perspective side view of a plug and receptacle connector pair that employs a spring-loaded locking device for interconnection, according to another illustrative embodiment of the invention.
Figure 59B:
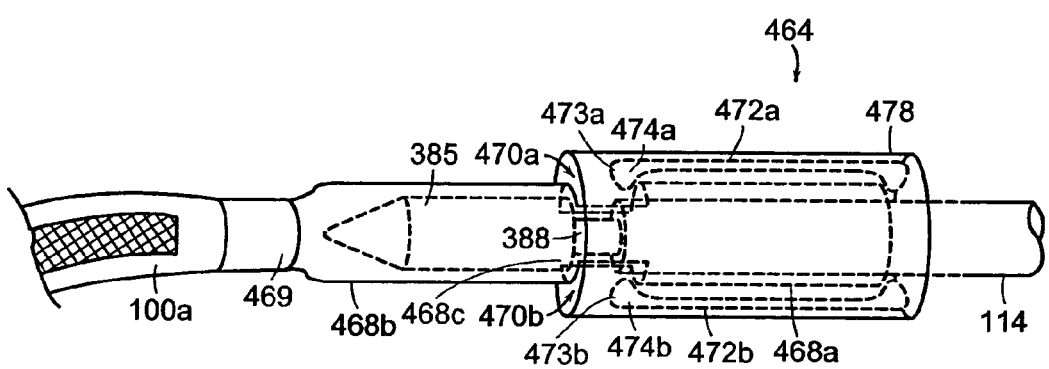
FIG. 59B depicts a perspective side view of the connector pair of FIG. 59A subsequent to interconnection.

FIGS. 59A and 59B depict a receptacle 464 and plug 380 connector pair that interfit through a spring-loaded mechanism. The receptacle connector 464 includes a substantially tubular housing 468 with three portions: a distal portion 468a and a proximal portion 468b, axially separated by an intermediary portion 468c. The intermediary portion 468c includes a wall portion 466 with one or more through apertures 470a and 470b. The illustrative receptacle connector 464 also includes two spring members 472a and 472b mounted on or formed integrally with the distal housing portion 468a. Each spring member 472a and 472b has on its respective proximal end 473a and 473b a protuberance 474a and 474b. In a rest state, the protuberance 474a extends into the aperture 470a and the protuberance 474b extends into the aperture 470b. A coaxial tube 478 slidably fits over the distal housing portion 468b and the two spring members 472a and 472b. The coaxial tube 478 provides an exemplary mechanism for securing the spring members 472a and 472b around the distal housing portion 468a.

The tubular member 468 has a tubular cavity 469 into which the protuberances 474a and 474b radically project. The tubular cavity 469 is sized and shaped to accommodate the plug connector 380. The distance 480 between the two spring protuberances 474a and 474b, when the spring members 472a and 472b are not tensioned, is less than the maximum diameter 387 of the plug tip section 385, but no less than the diameter 395 of the reduced-diameter section 388.

Referring now to FIG. 59B, to interfit the two connectors 464 and 380, the operator slides the distal housing portion 468a over the tip section 385 of the plug connector 380. In response to the distal section 385 of the plug connector 380 advancing into the intermediary portion 468c, the spring protuberances 474a and 474b are forced to expand radially outward via the apertures 470a and 470b. However, when the reduced-diameter section 388 aligns with the apertures 470a and 470b, the spring protuberances 474a and 474b spring back into the cavity 469 and engage the reduced-diameter section 388. With the reduced diameter section so engaged, the operator can slide the coaxial tube 478 over the proximal spring ends 473a and 473b to lock the spring members 472a and 472b in place.

Figure 60:
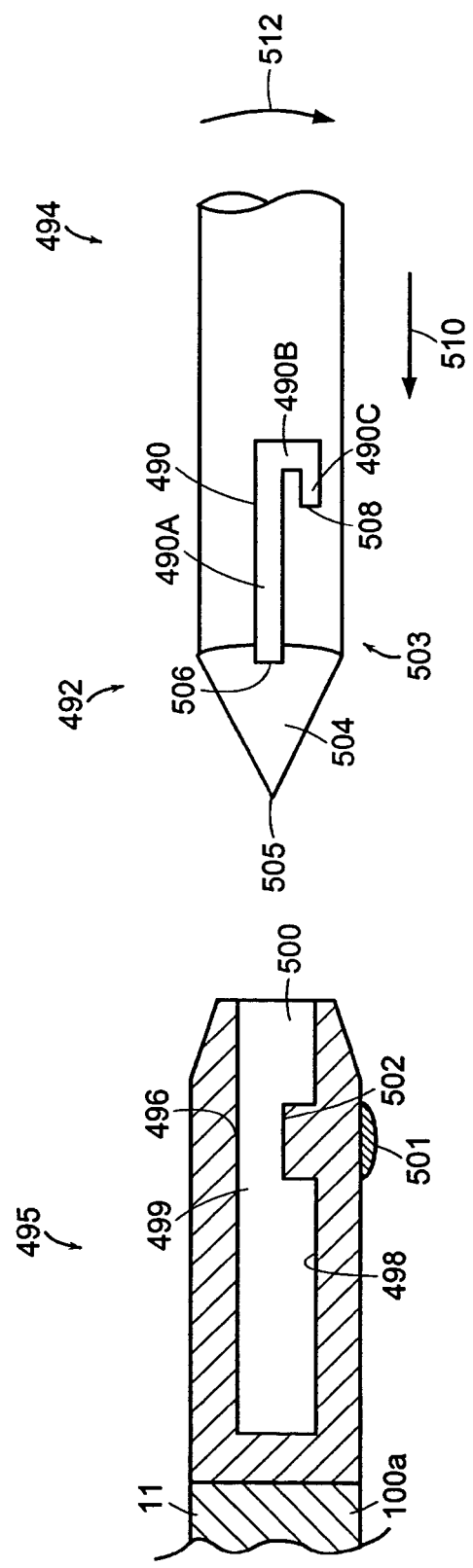
FIG. 60 depicts a side view in partial cross-section of a plug and receptacle connector pair, according to another illustrative embodiment of the invention.

FIG. 60 depicts a receptacle 495 connector and a plug 503 connector pair that mate through a keying feature according to another illustrative embodiment of the invention. The illustrative plug connector 503 is attached to or otherwise located, for example, at a distal end 492 of a delivery shaft 494. Shown in a cross-sectional view, the illustrative receptacle connector 495 is attached, for example, to an end of a sling assembly 11.

The illustrative receptacle connector 495 includes a substantially cylindrical receptacle 496 having a distal opening 500. A cavity 499 extends axially from the distal opening 500 into the receptacle 496. An inside wall 498 of the receptacle 496 includes a projection 502 that projects radially into the cavity 499. An internal projection, such as the projection 502, is advantageous in a surgical procedural including sling placement procedures because it will not catch tissue. Consequently, the internal protuberance 502 makes it easier to tunnel through tissue and reduces tissue trauma. The protuberance 502 may assume any shape and size that allows it to fit into a mating slot 490 in the plug connector 503. The illustrative protuberance 502 has a substantially rectangular longitudinal cross-section for ease of use, there may be a marking 501 on the outside of the receptacle 496 to indicate the location of the protuberance 502.

The plug connector 503 includes a slot 490 that extends axially towards a shaft distal tip 505. The slot 490 has an access terminal 506 in a conical tip section 504. The tapering of the conical tip section 504 allows a key element, such as the protuberance 502 in the receptacle connector 495, to enter or exit the slot 490. The illustrative slot 490 is substantially J-shaped and includes three distinct legs 490a, 490b, and 490c. While all three illustrative legs 490a, 490b, and 490c are substantially straight, any number of them may be curved. Each illustrative leg 490a, 490b, and 490c meets its adjacent leg at about a right angle, although other angles are contemplated by the invention as well. Traveling between the access terminal 506 and a locking terminal 508 of the slot 490 requires a substantially 180-degree reverse in travel direction. Optionally, other retention features described herein can be combined with the present feature. For example, the slot section 490c may narrow towards the locking terminal 508 such that the protuberance 502 is immobilized at the terminal 508. Alternatively, a locking protuberance such as those described in connection with FIG. 25, 28, 30, or 31 can be incorporated in the slot 490 for retaining a captured key element, such as the protuberance 502.

To interfit the receptacle-plug connector pair 495 and 503, the operator, with the visual aid of the marking 501 on the outside of the receptacle 496, aligns the internal protuberance 502 with the access terminal 506 of the slot 490. The operator then slides the receptacle opening 500 over the plug tip 505, and advances the plug distal section 504 into the receptacle cavity 499. The protuberance 502 slides into the access terminal 506 of the slot 490 and travels axially the length of the first leg 490a. Then, the operator rotates the receptacle connector 495 in the direction indicated by an arrow 512 to travel the length of the second slot leg 490b. Finally, the operator pulls back the receptacle connector 495 in the direction indicated by an arrow 510 to travel the length of the final leg 490c, and lock the protuberance 502, adjacent to the end 508 of the leg 490c. To unlock the connector 495 from the connector 503, the operator performs the above-described steps in reverse.

FIGS. 61A and 61B depict a connector pair 516 and 530 that mate through an internal clip-like protuberance 514 and a roofed slot 538 according to another illustrative embodiment of the invention. The illustrative receptacle connector 516 is attached, for example, to the sling assembly 11. The illustrative plug connector 530 is attached to or otherwise disposed at, for example, a distal end 532 of a delivery shaft 534.

An illustrative receptacle connector 516, depicted in longitudinal cross-section, includes a substantially cylindrical receptacle 518. A cavity 520 extends from an opening 522 axially into the receptacle 518. The internal protuberance 514 has a base 521 attached to or integrally formed with an inside wall 525 of the receptacle 518. The protuberance 514 may assume a variety of shapes and orientations. In the illustrative embodiment, the protuberance 514 resembles a clip with a clip tip 523 projecting towards an end 524 of the cavity 520. The illustrative protuberance 514 extends substantially axially resulting in an elongated space 526 between the protuberance 514 and the inside wall 525. The internal protuberance 514 may be made of an elastic material. There may be a marking 528, which may be a paint mark, on the outside of the receptacle 518 to indicate the location and orientation of the protuberance tip 523.

Referring to FIG. 61B, the mating plug connector 530 includes the slot 538 for capturing and retaining the internal protuberance 514. The illustrative slot 538 extends axially from a proximal end 544 to a distal end 543. The slot distal end 543 is under an overhang 531. The overhang 531, the slot distal end 543, and a slot floor 546 form a retention space 548 in the slot 538. An outer surface 536 of the overhang 531 is ramped downward toward the slot 538 and provides easy entrance into the slot 538. An outer surface 540 also ramps downward toward the slot 538 at the slot proximal end 544. The ramped surface 540 provides exit from the slot 538. Both ramped surfaces 536 and 540 can optionally include steps (not shown). The slot 538 is at least as long as the internal protuberance 514, so that the entire protuberance 514 can fit inside it. In an alternative embodiment, the slot 538 passes through from a first side 548 to a second side 550 of the connector 530.

To interfit the receptacle connector 516 with the plug connector 530, the operator, in one exemplary method and with the aid of the marking 528 on the outside of the receptacle connector 516, aligns the internal protuberance 521 with the distal end 541 of the ramped surface 536. The operator then slides the cavity opening 522 of the receptacle connector 516 over the conical section 535 of the plug connector 530, and advances the plug connector 530 into the receptacle cavity 520. During the advancement, the internal protuberance 514 starts to slide down the ramped surface 536 into the slot 538, until the protuberance base 521 is stopped by the proximal slot end 544. Then, the operator reverses his motion and pulls the receptacle connector 516 in the direction indicated by an arrow 550 so that the protuberance tip 523 slides into the retention space 548 in the slot 538. Meanwhile, the overhang 531 enters the elongated space 526 next to the protuberance 514. With the protuberance 514 and the overhang 531 projecting in the opposite directions, they interlock and thereby interlock the connectors 516 and 530.

Figure 62:
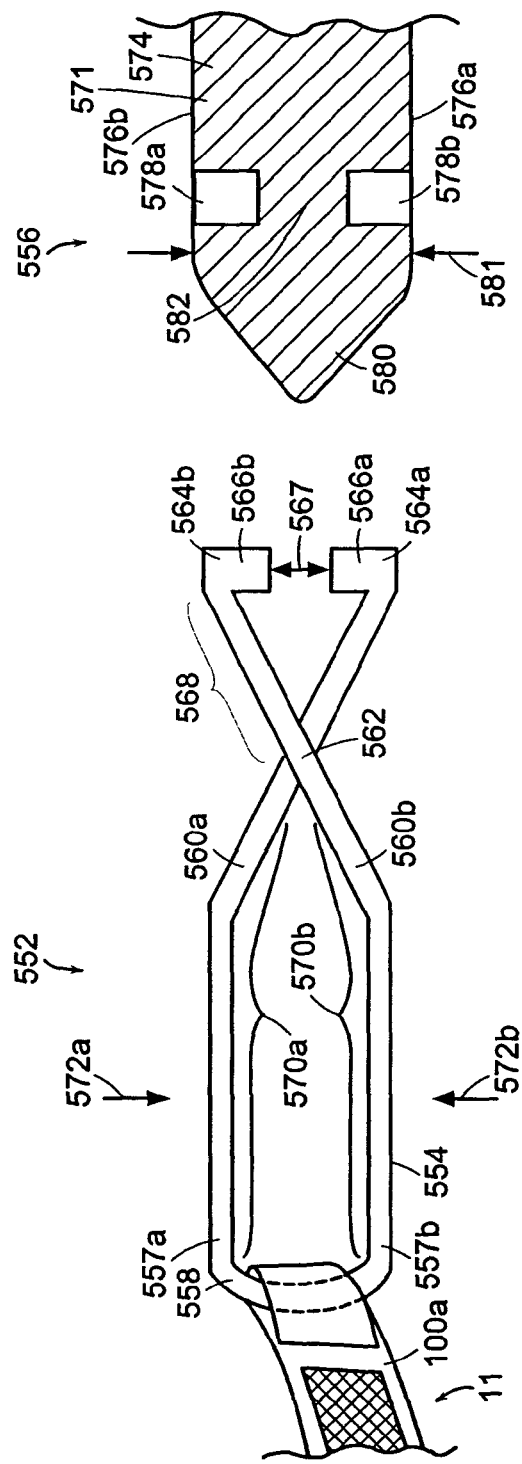
FIG. 62 depicts a perspective side view partially in cross-section of a connector pair, according to another illustrative embodiment of the invention.

FIG. 62 depicts an open loop 552 and a plug 556 connector pair according to another illustrative embodiment of the invention. The illustrative open loop connector 552 is attached, through a proximal bridge 558, for example, to the sling assembly 11. The illustrative plug connector 556 is attached to or otherwise located, for example, at a distal end 571 of a delivery shaft 574.

The illustrative loop connector 552 is formed from a single filament 554, and includes a first leg 560b and a second leg 560b. The two legs 560a and 560b are joined at their proximal ends 557a and 557b to form the C-shaped proximal bridge 558. Extending distally from the bridge 558, the two legs 560a and 560b cross, but do not couple to, each other at a crossing point 562, and terminate in ends 564a and 564b of the two legs 560a and 560a, respectively. Each of the ends 564a and 564b includes a hooks 566a, 566b, respectively. The hooks 566a and 566b, at a relaxed state, approach each other, with or without contacting each other. In the illustrative embodiment, there is a gap 567 between the two hooks 566a and 566b at the relaxed state.

Between the crossing point 562 and the bridge 558, the legs 560a and 560b provide a grip section 570a and 570b, respectively, which may be textured. The illustrative grip sections 570a and 570b run parallel to each other in a relaxed state. When the grip sections 570a and 570b are compressed towards each other, the first leg 560a moves in the direction indicated by an arrow 572a while the second leg 560b moves in the direction indicated by an arrow 572b. However, because the legs 560a and 560b cross over each other, the hooks 566A and 566B move away from each other to increase the gap 567. Where the entire or part of the filament 554 is elastic, such as a spring, the two legs 560a and 560*b* spring back to their relaxed state in response to the compressive force against the grip sections 570*a* and 570*b* is removed.

A first notch 578*a* is located on a first side 576*a* of the plug connector 556. A second notch 578*b* is located on a second, opposite side 576*b*. The diameter 581 of the plug connector is greater than the gap 567 between the two hooks 566*a* and 566*b* at a relaxed state. Therefore, after the hooks 566*a* and 566*b* engage the notches 578*b* and 578*a*, respectively and the operator removes the compressive force, they will be locked inside the plug connector 556. The illustrative notches 578*a* and 578*b* remain separated by a barrier 582 in between, but they can be joined to form a traverse opening (not shown). The illustrative plug connector 556 also includes a conical section 580 distal to the notches 578*a* and 578*b*.

To interconnect the two connectors 552 and 556, the operator compresses, manually or through an instrument, at least one of the grip sections 570*a* and 570*b* towards each other, causing the two distal hooks 566*a* and 566*b* to part and the open loop 568 to expand. Then the operator slides the two legs 560*a* and 560*b* onto the two sides 576*a* and 576*b* of the plug connector 556 until the hooks 566*a* and 566*b* enter the notches 578*b* and 578*a*, respectively. Then the operator releases the grip sections 570*a* and 570*b*, and the hooks 566*a* and 566*b* return from the compressed state to the relaxed state and converge to each other and project radically into respectively the notches 578*a* and 578*b*. To separate the two connectors 552 and 556, the operator reverses the above steps.

Figure 63A:
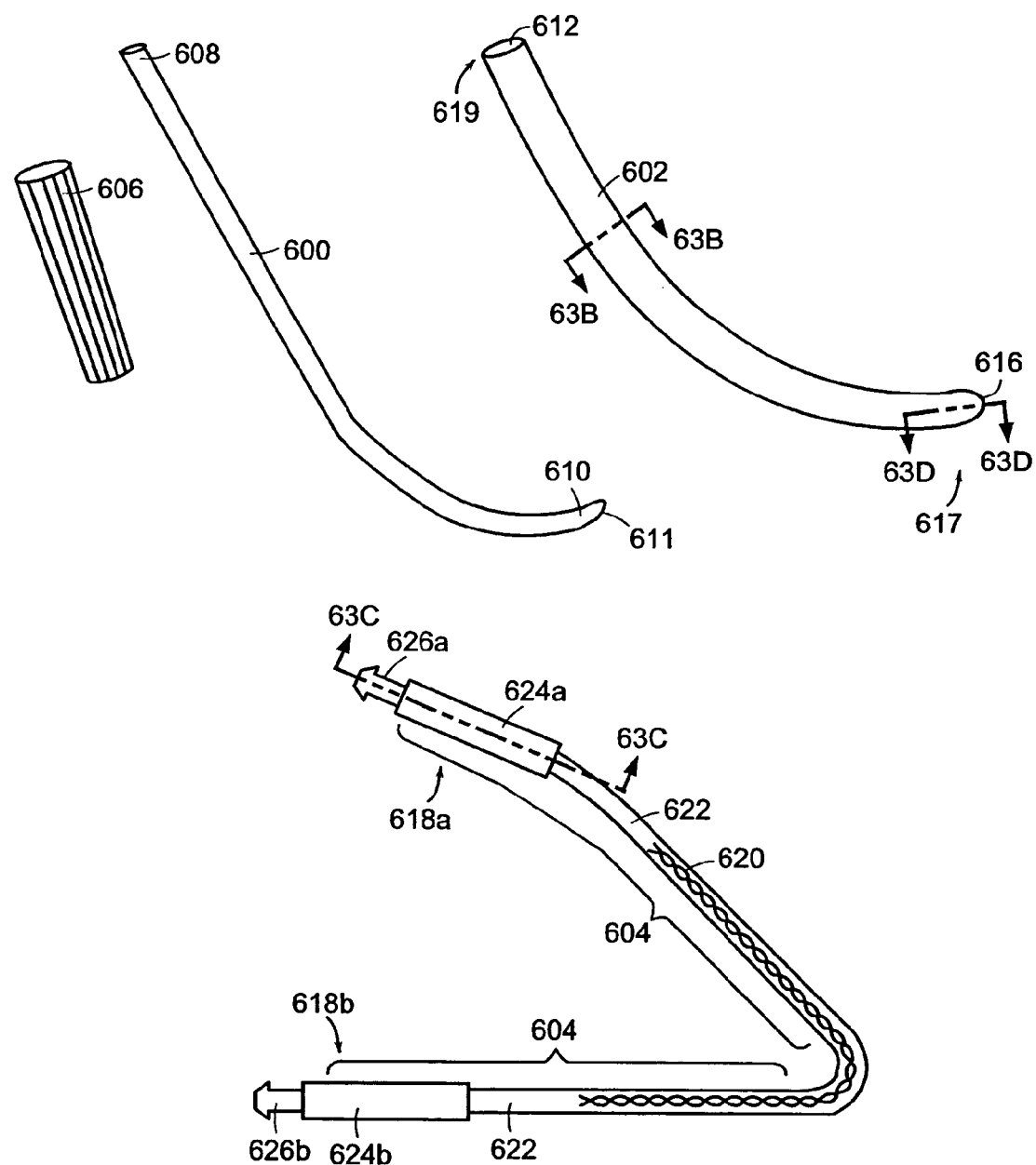
FIG. 63A depicts a delivery system that includes a handle, a shaft, a guide tube, a sling assembly and connectors according to an illustrative embodiment of the invention.

FIG. 63A depicts connectors that can potentially interconnect more than two parts of the delivery system, even if only temporarily, during use. This inventive aspect is illustrated with applications involving a guide tube, but are equally applicable to other parts of the delivery system.

In the illustrative embodiment, plug connectors 626*a* and 626*b* are provided to interconnect a shaft 600, a guide tube 602, and a sling assembly 604. The shaft 600 can optionally connect with a handle 606, for example, with a proximal shaft end 608 that slidably resides in an axial lumen in the handle 606. An opposite, distal end 610 of the shaft 600 slides into a proximal opening 612 of the guide tube 602 such that at least part of the shaft 600 slidably resides in an axial lumen 614 (FIG. 63B) of the guide tube 602. The illustrative shaft distal end 610 includes a tapered distal tip 611. The lumen 614 (FIG. 63B) of the guide tube 602 extends between a proximal opening 612 and a distal opening 616 of the guide tube 602 (not shown). The guide tube 602 includes a distal end 617 and a proximal end 619. In one embodiment, the proximal end 619 is flared, i.e., having an outer diameter larger than the rest of the guide tube 602. The sling assembly 604 includes two identical free ends: a first end 618*a* and a second end 618*b*, and a sling 620 at least partly enveloped in a sleeve member 622.

Optionally, the two ends 618*a* and 618*b* of the sling assembly 604 each include a dilator (624*a*, 624*b*). A first plug connector (626*a*, 626*b*) is attached to each of the free sling assembly ends 618*a* and 618*b*, for example, through pre-associating with the dilators 624*a* and 624*b*, respectively. The first connector (626*a*, 626*b*) can be manufactured as an integral piece with the dilator (624*a*, 624*b*).

Figure 63B:
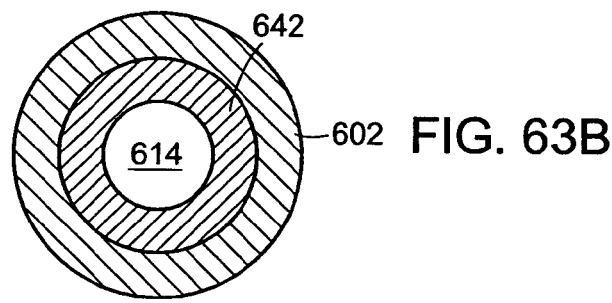
FIG. 63B depicts a radial cross-sectional view of the guide tube of FIG. 63A along the line "63B-63B."
Figure 63C:
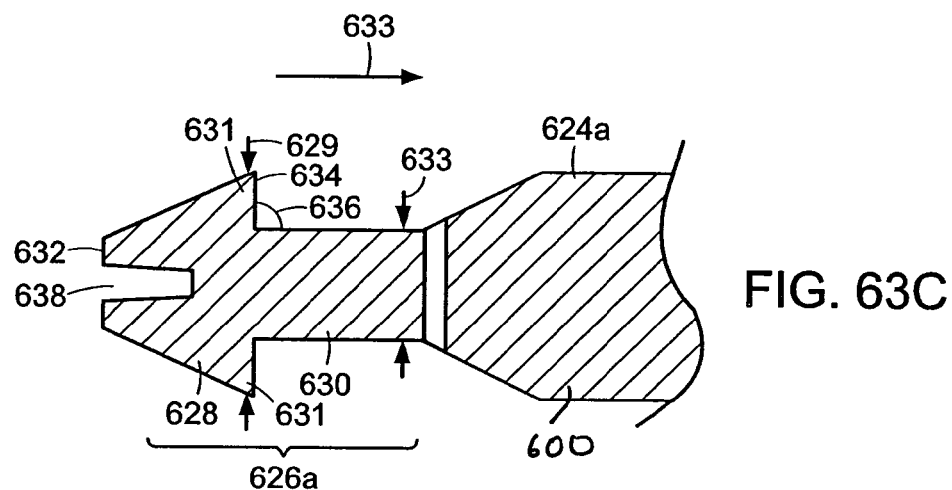
FIG. 63C depicts a longitudinal cross-sectional view of the plug connector of FIG. 63A along the line "63C-63C."

FIG. 63C depicts, in a cross-sectional view, the illustrative plug connector 626*a* including a "barbed" distal section 628 and a reduced-diameter section 630, for example, a circular notch. The distal section 628 has a maximum diameter 629 at its base 634. The maximum diameter 629 is greater than diameter 633 of the reduced-diameter section 630. The distal section 628 tapers radically inward towards a distal end 632 to facilitate insertion into a mating receptacle connector 640 and forms a shoulder 634 for hindering movement in the proximal direction as indicated by an arrow 633 by the distal section 628. The shoulder 634 may be formed at any angle 636 less than or equal to about 90° relative to a longitudinal axis of the connector 626*a*. Illustratively, the angle 636 is depicted as being 90°. The distal end 632 of the distal section 628 includes an opening 638 that is shaped and sized to fit at least a portion of the distal tip 611 of the shaft 600. The connector 626*a* may be made of any suitable material, for example, plastics, rubber, or a metal, through processes known in the art, for example, tip molding.

Figure 63D:
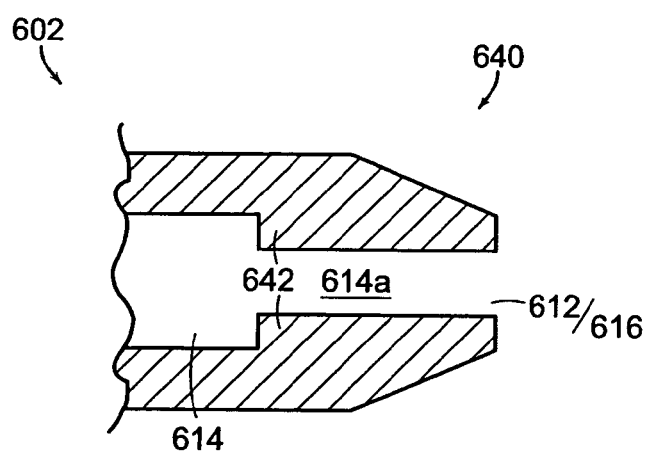
FIG. 63D depicts a longitudinal cross-sectional view of the receptacle connector of FIG. 63A along the line "63D-63D."

Referring back to FIG. 63A, the distal 617 and/or proximal 619 ends of the guide tube 602 can include a second receptacle connector 640. FIGS. 63B and 63D depict, in cross-sectional views, the second receptacle connector 640 including an optional annular stepped-up portion 642 narrowing the lumen 614. The resultant lumen space 614*a* between the protuberance 642 is narrower than the maximum diameter 629 in the distal section 628 of the first connector 626*a* (FIG. 63C). The illustrative stepped-up portion 642 is disposed at the opening 612 or 616 of the lumen 614. The internal protuberance 642 may be manufactured as an integral part of the receptacle connector 640 or the guide tube 602.

Figure 64:
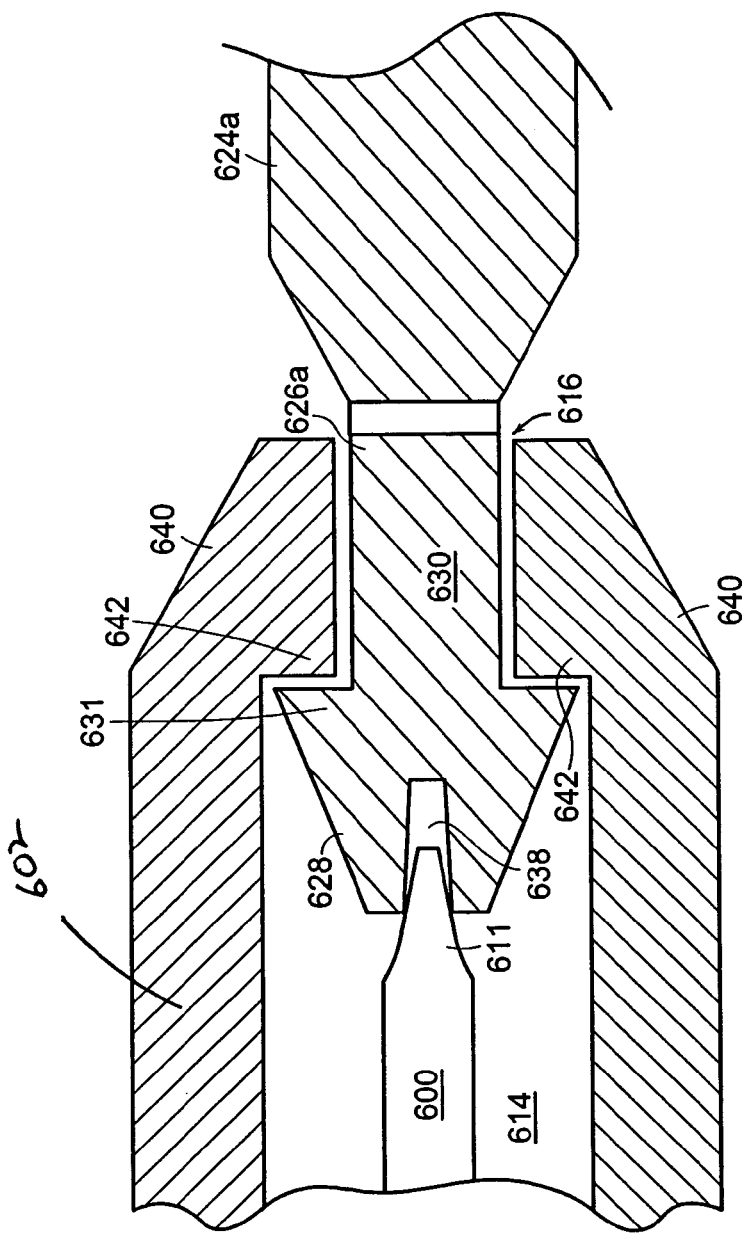
FIG. 64 depicts a longitudinal cross-sectional view of the interconnection between the shaft, receptacle and plug connectors of FIG. 63A.

FIG. 64 depicts the first plug connector 626*a* interconnecting with both the distal tip 611 of the shaft 600 and the second receptacle connector 640. There are a few ways to accomplish this connection. In a first example, the tip 611 of the shaft 600 is first inserted into the distal opening 638 in the first connector 626*a* when the tip 611 is extended outside the distal opening 616 of the guide tube 602. This insertion step can be accomplished by either moving the first connector 626*a* or the shaft 600 or both. Then, the operator can push the base part of the first connector 626*a*, for example, the dilator 624*a*, under the guidance of the interconnected shaft tip 611 into the distal opening 616 of the guide tube 602. Optionally, to facilitate the insertion of the first connector 626*a* past the internal protuberance 642, either or both the distal section 628 of the first connector 626*a* or the second connector 640 can include longitudinal slots as described in connection with FIGS. 45 and 46A. After the first connector 626*a* enters the distal opening 616 of the guide tube 602 and passes the protuberance 642, the protuberance 642 encircles the reduced-diameter section 630 of the first connector 626*a* and locks it in.

In a second example, the shaft tip 611 is inserted into and retained in the distal opening 638 of the first connector 626*a*, for example, if the distal opening 638's lumenal diameter is no larger than the thickest point on the shaft tip 611 such that the shaft tip 611 gets stuck once inserted into the distal opening 638. In alternative embodiments, any of the connector pairs or their associating features described in this specification can be utilized to retain or lock the connection between the shaft tip 611 and the distal opening 638 of the first connector 626*a* once the connection is made. Then, the operator withdraws the shaft tip 611 back into the lumen 614, guiding the first connector 626*a* into the distal opening 616 of the second connector 640. Of course, the operator can interconnect the first connector 626*a* with the second connector 640 by holding fast the second connector 640 in one hand and insert the first connector 626*a* through the distal opening 616 in the second connector 640. The rest of the steps are the same as described immediately above.

With the second connector 640 disposed in the proximal end 619 of the guide tube 602 and using one of the above described methods, the first connector 626a can be interconnected with the second connector 640 when the shaft 600 is withdrawn out of the guide tube 602. It is also contemplated by the invention that the shoulder 634 can form a barb 631 that is sufficient to interfit and retain itself inside the second connector 640 even if the second connector 640 does not have the internal protuberance 642, but instead a smooth inner wall. In that case, the shoulder 634 preferably has a cross-sectional dimension (for example, a diameter in a circular cross section) at least as large as the cross-sectional dimension of at least the narrowest part of the lumen 614 in the guide tube 602, so that the barb 631 engages the lumenal wall in the guide tube 602 to impede disconnection.

Figure 65A:
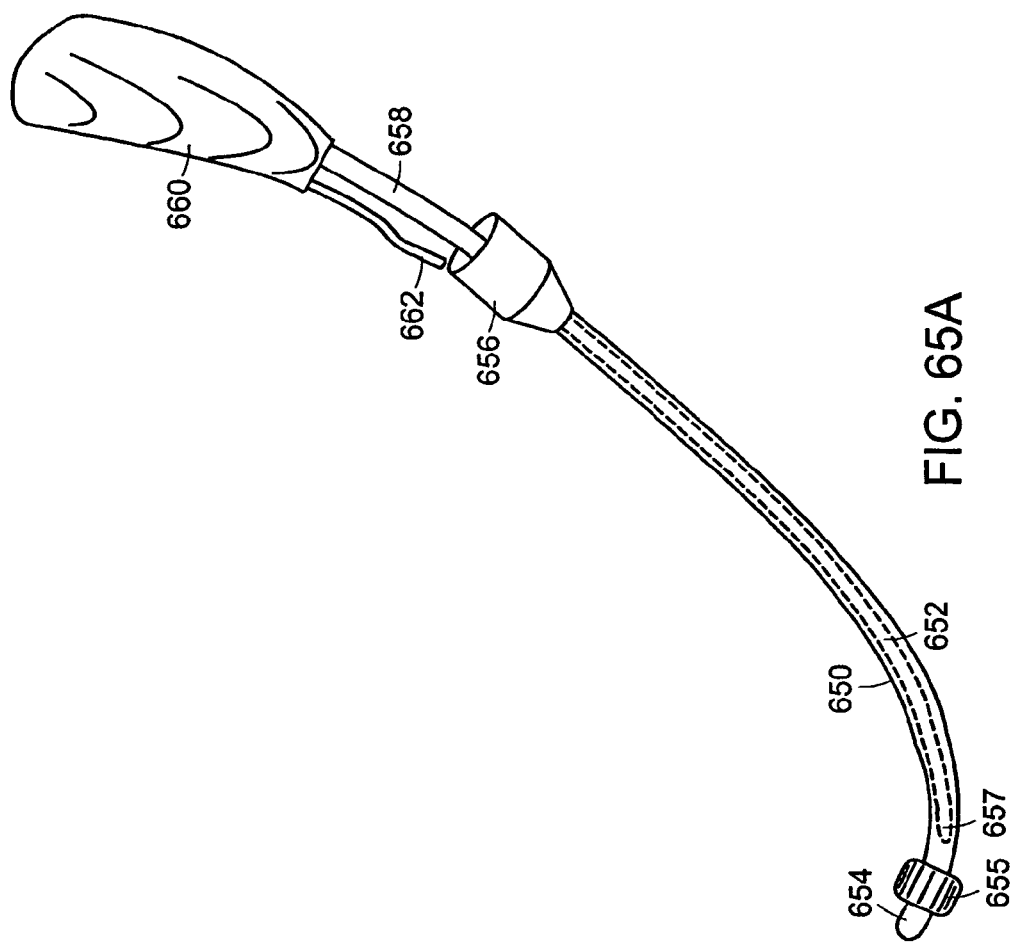
FIG. 65A depicts a perspective side view of a delivery device including a sheath at an advanced position, according to an illustrative embodiment of the invention.

FIG. 65A depicts a sheath 650 that can be used in combination with any connector pair, including the connectors described in this application. The sheath 650 slidably encloses a part in the delivery system, for example, at least a portion of a shaft 652. The sheath 650 can be disposed on other parts of the delivery system, such as the sling assembly. The sheath is preferably colored, for example, blue, so that a medical operator can distinguish it from surrounding tissue during a cystoscopy. The sheath 650 may be made, for example, of medical-grade plastics, silicone rubber, polymer or similar materials. In an alternative embodiment, the sheath 650 is made of a metal. The sheath 650 has a distal portion 654 and, optionally, a proximal "hub" 656 with an enlarged outer diameter. An annular collar 655 is, optionally, disposed in the distal portion 654 of the sheath 650. In one embodiment, the surface of the annular collar 655 is textured. The shaft 652 has a distal portion 657 and a proximal portion 658 that is associated with a handle 660. The sheath 650 may or may not be operatively connected to the handle 650 for slideable actuation along the shaft 652. Additionally, the length of the sheath 650 can range from less than about two inches to almost as long as the shaft 652.

In one embodiment, the stopper 662 extends from the handle 660 in the direction of the sheath 650. A stopper 662, when deployed, stops the sheath 650 from moving in the proximal direction, toward the handle 660 to maintain the distal portion 654 of the sheath 650 over the distal portion 657 of the shaft 652 (the "advanced position" of the sheath 650). When the stopper 662 is not deployed, the sheath 650 can slide in the proximal direction into a withdrawn position, for example, until the hub 656 meets the handle 660. An example of a suitable stopper 662 includes a spring lever that remains deployed unless compressed.

To advance the sheath 650 to its advanced position, the operator can manually push the proximal hub 656 in the distal direction. Alternatively, if there is a pusher assembly such as the one described in connection with FIGS. 3-6, the operator can actuate the pusher assembly to advance the sheath 650. Further, if the operator is pulling the sheathed shaft 652 in the proximal direction through a tunnel in the tissue, the surrounding tissue will push and squeeze the sheath or optionally the annular collar 655 at the distal portion 654 of the sheath 650 such that the sheath 650 advances in relation to the shaft 652.

Figure 65B:
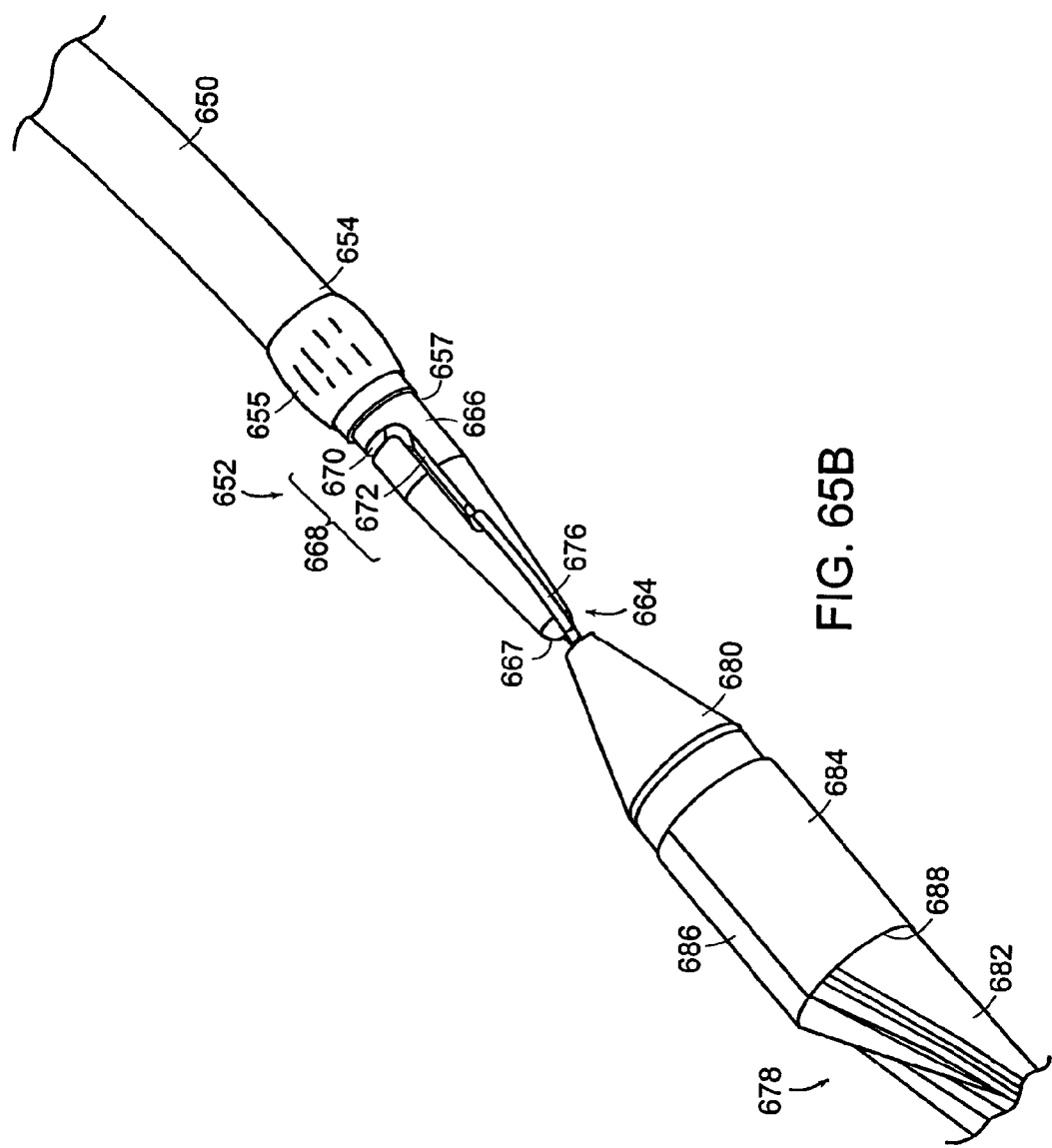
FIG. 65B depicts a perspective side view of a delivery device of the type depicted in FIG. 65A interconnected with a sleeve end through a loop connector and a slotted receptacle connector, where the sheath is in a retracted position.

Referring now to FIG. 65B, when the sheath 650 is at the retracted position. The retracted sheath 650 exposes a slotted connector at the distal shaft portion 657. In one embodiment, the connector is a receptacle connector 666 similar to receptacle connectors previously described in connection with FIGS. 22A-35. In the illustrative embodiment, the loop connector 664 is similar to loop connectors already described, such as those described in connection with FIGS. 22A-25, 33, 34, and 36A-38.

Once the loop 664 and receptacle 666 connectors are interfitted, the sheath 650 is axially actuated to the position shown in FIG. 65A to shield at least the receptacle connector 666. The stopper 662 is deployed to lock the sheath 650 at the advanced position. An otherwise exposed slot 668 shown in FIG. 65B can catch tissue during subsequent maneuver through patient tissue. In another embodiment, at the advanced position, the distal portion 654 of the sheath 650 abuts the dilator 680 to shield not only the receptacle connector 666 but also the interconnected loop connector 664 and a portion of the dilator 680. Accordingly, the interconnected shaft-dilator complex may have a smooth transition and a constant diameter, and the sheath 650 also serves a locking and retention function. To separate the connectors 664 and 666, the operator can deactivate the stopper 662 (FIG. 65A), and pull the proximal hub 656 towards the handle 660 to expose and separate the connectors.

Further, because the sleeve end 684 surrounds (e.g., through heat bonding) the proximal portion 686 of the dilator 680, the proximal portion 686, especially the back edge 688, will not be caught in the tissue during sling delivery or adjustment, for example, when the operator has to pull the sling assembly 678 back through a tunnel to reposition it. The sling assembly 678 needs to be repositioned when the bladder has been punctured during the delivery process. To aid the detection of bladder puncture under a cystoscope, the sleeve assembly 678, for example, the sleeve 682 or the mesh sling (not shown), may be colored (e.g., blue). In use, an operator can delay any cystoscopy until one or both sleeve ends of the sling assembly 678 are in one or two tissue tunnels to check for visual signs of the colored sling assembly and/or other colored components of the delivery system such as the shaft 652, the sheath 650, or a guide tube.

Figure 66A:
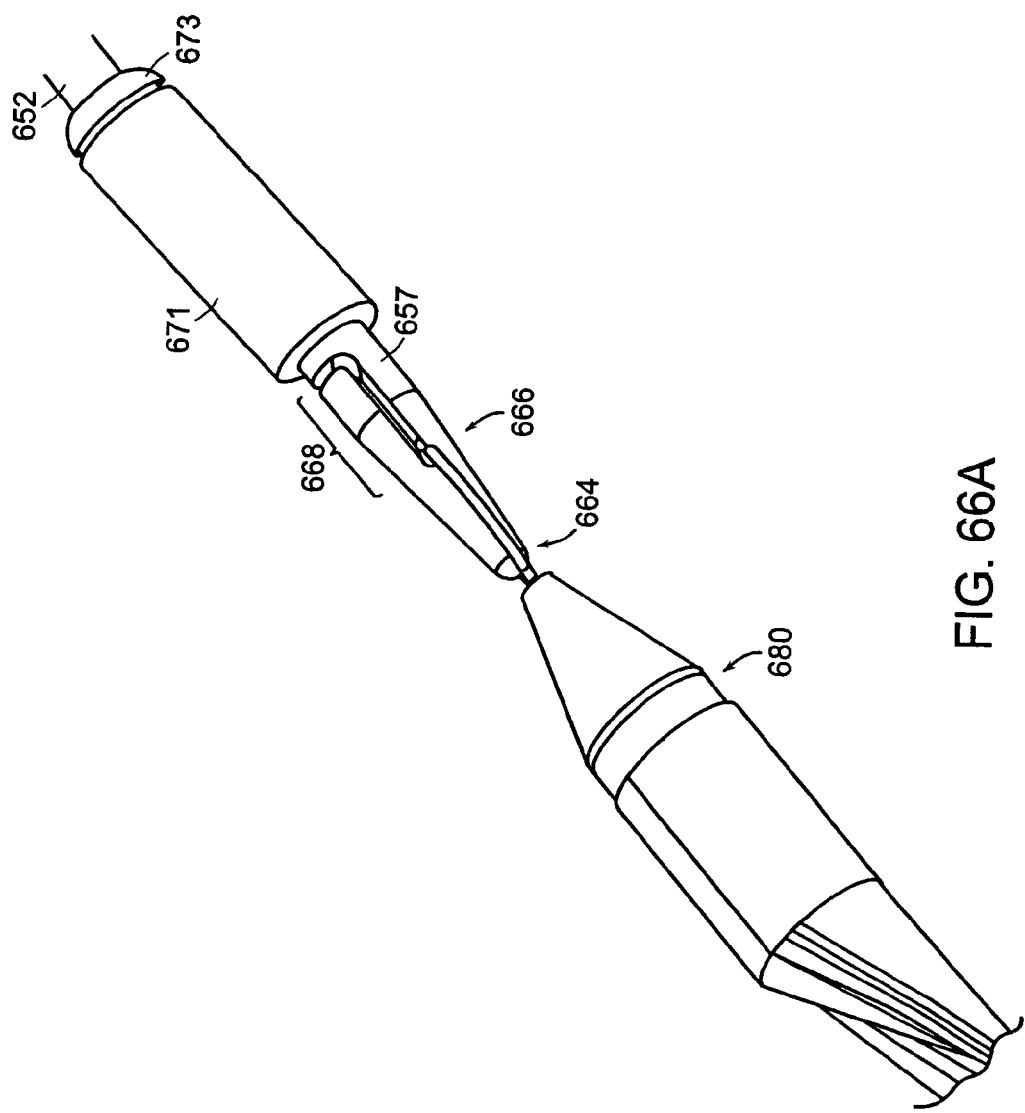
FIG. 66A depicts a perspective side view of interconnection between the delivery device and the sleeve end depicted in FIG. 65B with an alternative embodiment of the sheath.

FIG. 66A depicts a sheath 671 that can be used as an alternative to the sheath 650. In the illustrative embodiment, the sheath 671 slidably fits over the distal portion 657 of the shaft 652. The slotted receptacle connector 666 is disposed at the shaft distal portion 657 as previously described with respect to FIG. 65B. The loop connector 664 interconnects with the receptacle connector 666. An optional stopper 673 is disposed adjacent the shaft distal portion 657 to prevent the sheath 671 to travel past it over the shaft 652. The illustrated stopper 673 is an annular ring. In another embodiment, the stopper 673 is a stepped up portion of the shaft 652 that can extend proximally to any length. Alternatively, the sheath 671 can be friction fitted onto the shaft distal portion 657 such that no stopper is 673 needed and the sheath 671 will substantially maintain its position relative to the shaft 652. There are various ways to achieve a frictional fit. For example, the sheath 671 can have an inner diameter that matches or is slightly less than the outer diameter of the shaft distal portion 657. For example, the sheath 671 can have an axial opening and an inner diameter slightly less than the shaft outer diameter so that the sheath 671 can be snapped onto the shaft distal portion 657 through the opening. Alternatively, the sheath 671 can be heat shrunk over the shaft distal portion 657.

The illustrative sheath 671 is of a length that covers the joint length between the receptacle connector 666 and the loop connector 664 when the connectors are interconnected. In another embodiment, the sheath 671 is of a length that only covers the connector slot 668. In one embodiment, the sheath 671 is less than about one inch. The operator, after interconnecting the two connectors 664 and 666, can manually slide the sheath 671 over the connectors to lock the interconnection. In an alternative embodiment, the sheath 671 is located on the sleeve assembly, for example, the dilator 680, and can also be manually actuated to slidably shield the slotted receptacle connector 666, or both connectors 666 and 664.

Figure 66B:
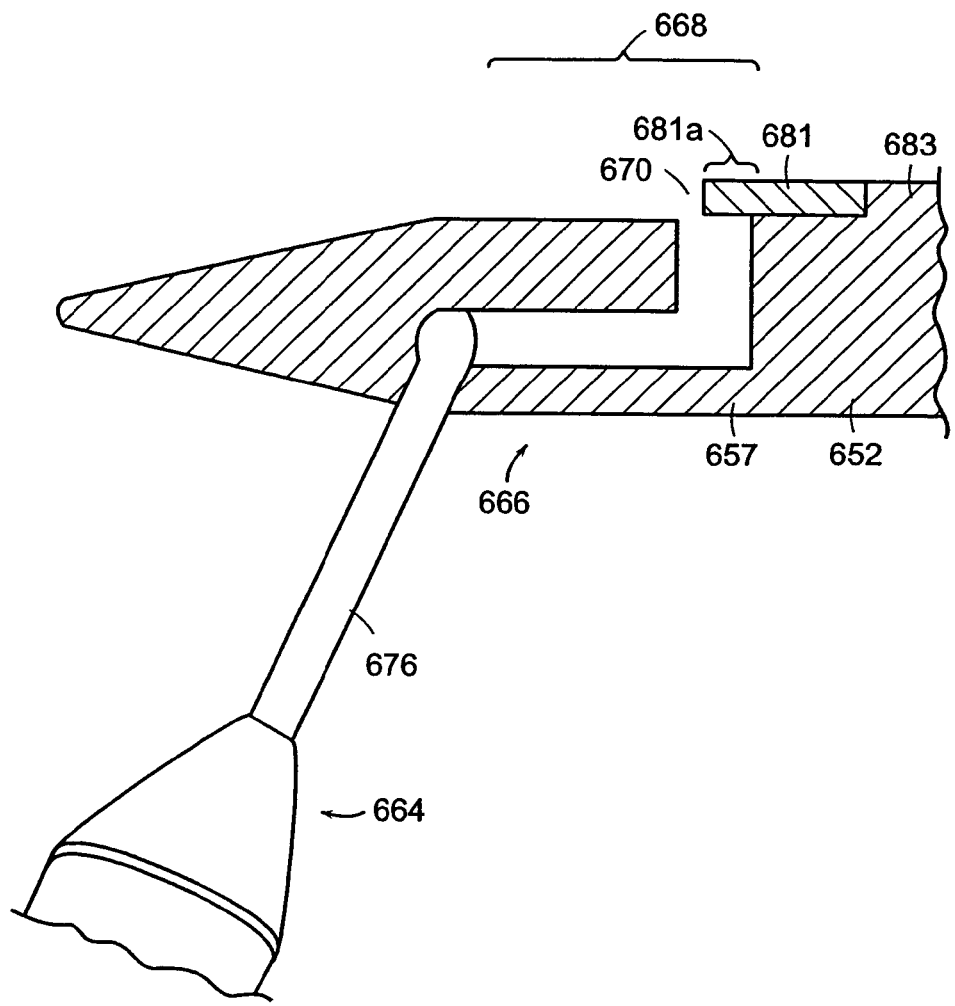
FIG. 66B depicts a partial cross-sectional view of the interconnection between a receptacle connector and a loop connector with a locking sheath embodiment.

FIG. 66B depicts a partial cross sectional view of another alternative sheath 681 that covers at least part of the slot 668 in the receptacle connector 666. The illustrative sheath 681 abuts a stepped-up portion 683 of the shaft 652. A distal portion 681a of the sheath 681 covers a portion of an entry notch 670 of the connector slot 668. In use, a loop 676 of a mating loop connector 664 has to deflect the sheath distal portion 681a to enter the entry notch 670. The illustrative sheath 681 is flexible and returns to the overlaying position afterwards and locks the mating loop 676 inside the receptacle slot 668. The illustrated sheath 681 can be deflected to release the mating loop 676. In one embodiment, the sheath 681 is heat shrunk plastics such as polytetrafluoroethylene (PTFE) or tetrafluoroethylene (TFE).

Figure 67A:
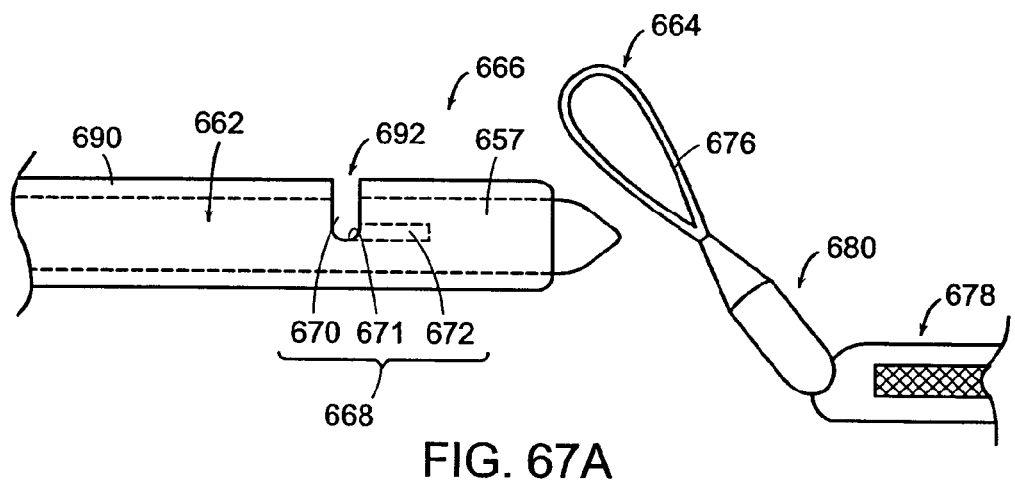
FIG. 67A depicts a side perspective view of an L-shaped receptacle connector and a mating loop connector, with a sheath located to enable interconnection according to an illustrative embodiment of the invention.
Figure 67B:
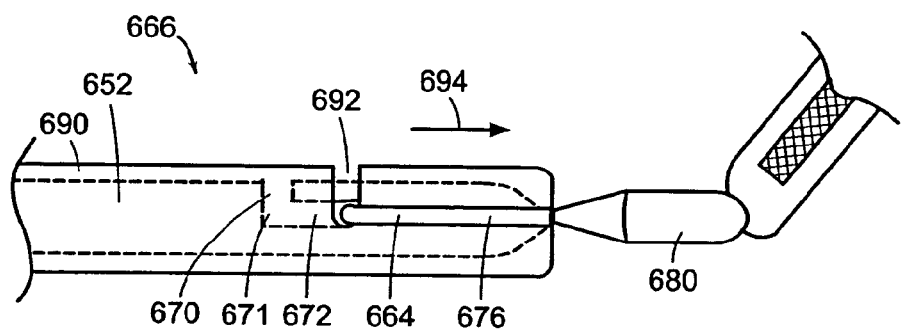
FIG. 67B depicts a side perspective view of the connector pair of FIG. 67A with the loop and L-shaped receptacle interfitted and the sheath located to facilitate locking.

FIGS. 67A and 67B depict an alternative sheath 690 that automatically locks in the connection between two connectors, even before the interconnected devices travel through the patient's tissue. The sheath 690 slidably encloses at least a portion of in the delivery system, for example, at least a portion of the shaft 652. The shaft 652 has the receptacle connector, for example, a receptacle connector 666, at the distal portion 657 of the shaft 652. The receptacle connector 666 includes a slot 668 that, in one embodiment, includes an entry notch 670 and a retention slot 672 connected at the bottom 671 of the entry notch 670, forming an "L."

The sheath 690 may share many features with the sheath embodiment 650 described immediately above. In addition, the sheath 690 has a slot 692 that extends from the periphery towards the long axis of the sheath 690. The slot 692 in the sheath 690 substantially matches, in size and shape, the entry notch 670 of the L-slot 668 in the receptacle connector 666.

The plug connector, for example, the loop connector 664 has a loop 676 and is attached to the dilator 680 of the sling assembly 678. The loop 676 may be formed from a suturing material. Alternatively, the loop 676 may be formed from a semi-flexible, shape-retaining material. To interconnect the loop connector 664 with the receptacle connector 666, the operator matches up the slot 692 in the sheath 690 with the entry notch 670 in the receptacle connector 666, and hooks the loop 676 of the loop connector 664 into the slot 692/entry notch 670. The operator then sinks the loop 676 into the bottom 671 of the entry notch 670 of the receptacle connector 666.

Specifically referring to FIG. 67B, after the loop 676 reaches the bottom 671 of the entry notch 670 of the receptacle connector 666, the operator can pull the dilator 680 in a direction indicated by an arrow 694 such that the loop 676 of the loop connector 664 slides down the retention slot 672 of the receptacle connector 666. Alternatively, if the loop 676 is an adjustable and lockable loop as described in connection with FIGS. 36A-38, the operator can tighten and lock the loop 676 against the distal portion 657 of the shaft 652, which would similarly cause the loop 676 of the loop connector 664 to slide down the retention slot 672 of the receptacle connector 666. Because the loop 676 is still hooked in the sheath slot 692, the sheath 690 advances in the direction indicated by the arrow 694 along with the loop 676 of the loop connector 664. Now that the sheath slot 692 is no longer matched up with the entry notch 670 in the receptacle connector 666, the sheath 690 locks the loop 676 inside the retention slot 672. To unlock the two connectors 664 and 666, the operator can pull the sheath 690 in the direction opposite to the arrow 694, or, in the case of a adjustable and lockable loop 676, unlocks and lengthens the loop 676, until the sheath slot 692 is matched up with the entry notch 670 in the receptacle connector 666.

Figure 68:
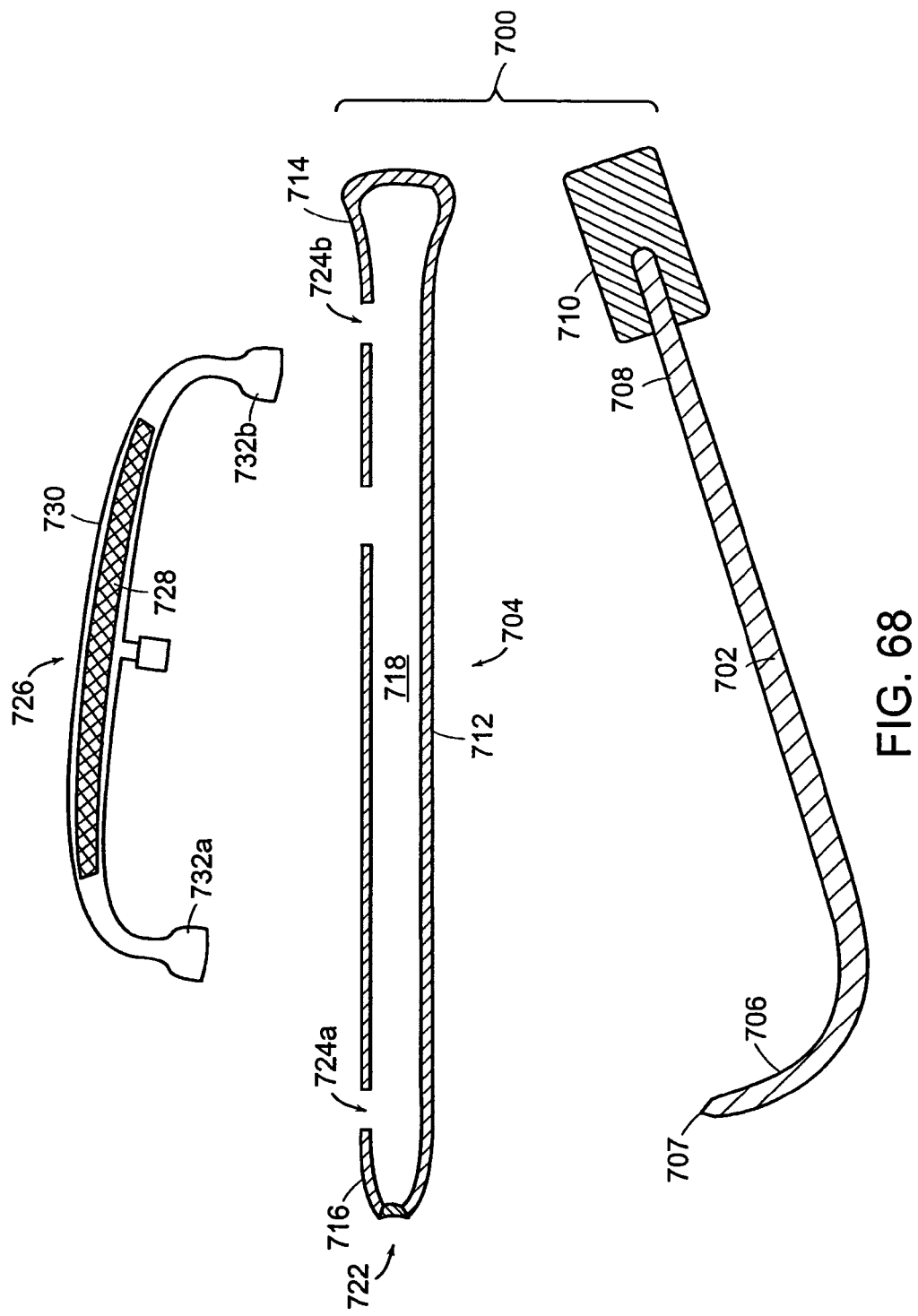
FIG. 68 depicts a cross-sectional view of a delivery device including a guide tube having connectors for mounting a sling assembly shown in perspective, according to an illustrative embodiment of the invention.

FIG. 68 illustrates, in a cross-sectional view, connectors with applications in associating an implant to the side of one or more guide tubes. A delivery device 700 includes a shaft 702 and a guide tube 704. The shaft 702 has a distal portion 706 and a proximal portion 708. The shaft 702 may be straight or curved, and may have features described elsewhere in this application. The proximal end 708 of the shaft 702 connects to the handle 710. The guide tube 704 may function as a dilator tube. In one embodiment, the guide tube 704 is separate from and not attached to, the handle 710. However other embodiments, the guide tube 704 attaches either reversibly or permanently the handle 710 through an actuator, such as those described in connection with FIGS. 7A and 7B.

The guide tube 704, according to an illustrative embodiment of the invention, is elongated and includes a wall 712. The wall 712 has a proximal end 714, a distal end 716. A lumen 718 axially extends between a distal opening 722 and a proximal opening 720. According to one feature of the illustrative embodiment, the lumen 718 slidably receives the shaft 702 through a proximal opening 720. In alternative embodiments, the guide tube 704 may instead include port 721 in the side of the wall 712 for receiving the shaft 702. The illustrative guide tube 704 is of a length such that when the shaft 702 resides inside the lumen 718, the distal tip 707 of the shaft 702 extends outside the distal opening 722. According to another feature, the proximal end 714 of the dilator tube 704 flares so that the outside diameter of the proximal end 714 is wider than the outside diameter of the remainder of the dilator tube 704. However, in alternative embodiments the outside diameter of the dilator tube 704 is substantially uniform from the proximal end 714 to the distal end 716.

According to one feature of the invention, the guide tube 704 has first 724a and second 724b connectors axially separated along it. Preferably the first connector 724a is located at the distal end 716 and the second connector 724b is located at the proximal end 714. In one embodiment, both the first and second connectors 724a and 724b include side openings or sockets and may extend into the lumen 718. In another embodiment, the first and second connectors 724a and 724b are depressions or indentations in the side of the guide tube 704 and do not extend into the lumen 718 of the guide tube 704. The first and second connectors 724a and 724b may be any suitable connectors, including those described elsewhere in this application. The first and second connectors 724a and 724b, in an optional feature, align with each other radically along guide tube 704. In another embodiments (not shown), the first connector 724a and second 724b may be radically offset from each others.

With continued reference to FIG. 68, an implant, for example, a sling assembly 726 is shown with a mesh sling 728 at least partly enveloped in an optional sleeve member 730. The sling assembly 726 attaches to the guide tube 704 via connectors 732a and 732b, which interfit with connectors 724a and 724b, respectively.

Figure 69:
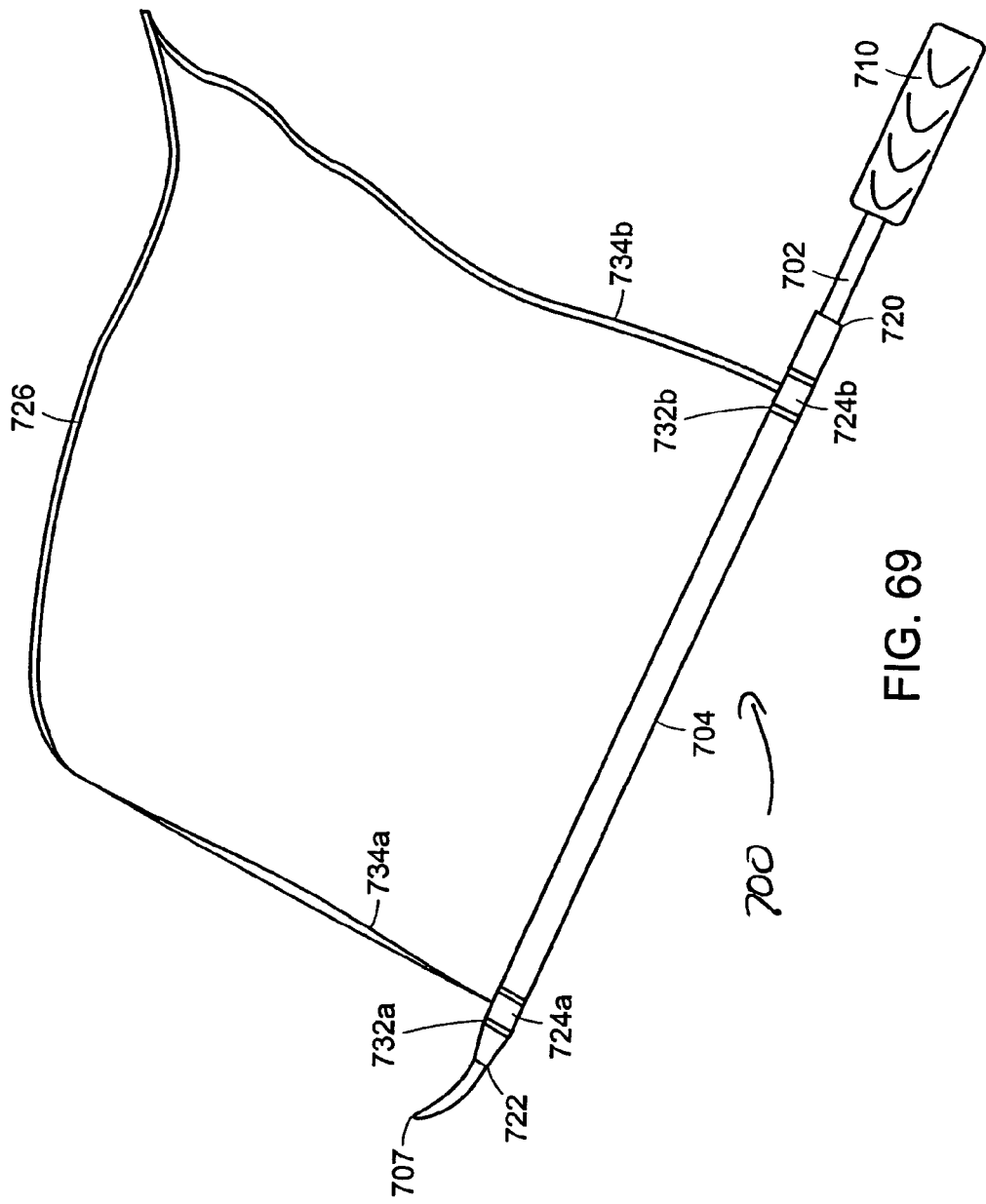
FIG. 69 depicts a perspective side view of the components shown in FIG. 68 assembled together, according to an illustrative embodiment of the invention.

Referring now FIG. 69, an assembled delivery system includes the delivery device 700 guide tube 704 and sling assembly 726. As shown, with the sling assembly 726 and guide tube 704 interconnected as described above, the guide tube 704 slidably interfitted proximal end 720 first over the shaft 702, to expose the distal tip 707 of the shaft 702. In an alternative embodiment (not shown), the guide tube 704 is longer than the shaft 702. In such an embodiment, the guide tube 704 can slidably retract to expose the distal tip 707 of the shaft 702 during a tissue piercing procedure. For example, the guide tube 704 can slidably retract into the handle 710. In another alternative embodiment, without regard to their comparative lengths, the shaft tip 707 is exposed by an actuator that is either operatively associated with the guide tube 704 or the shaft 702, an which can actuate the shaft 702 or the guide tube 704 axially, related to the other. Examples, of such embodiment are described in connection with FIGS. 7A-8B.

Figure 70:
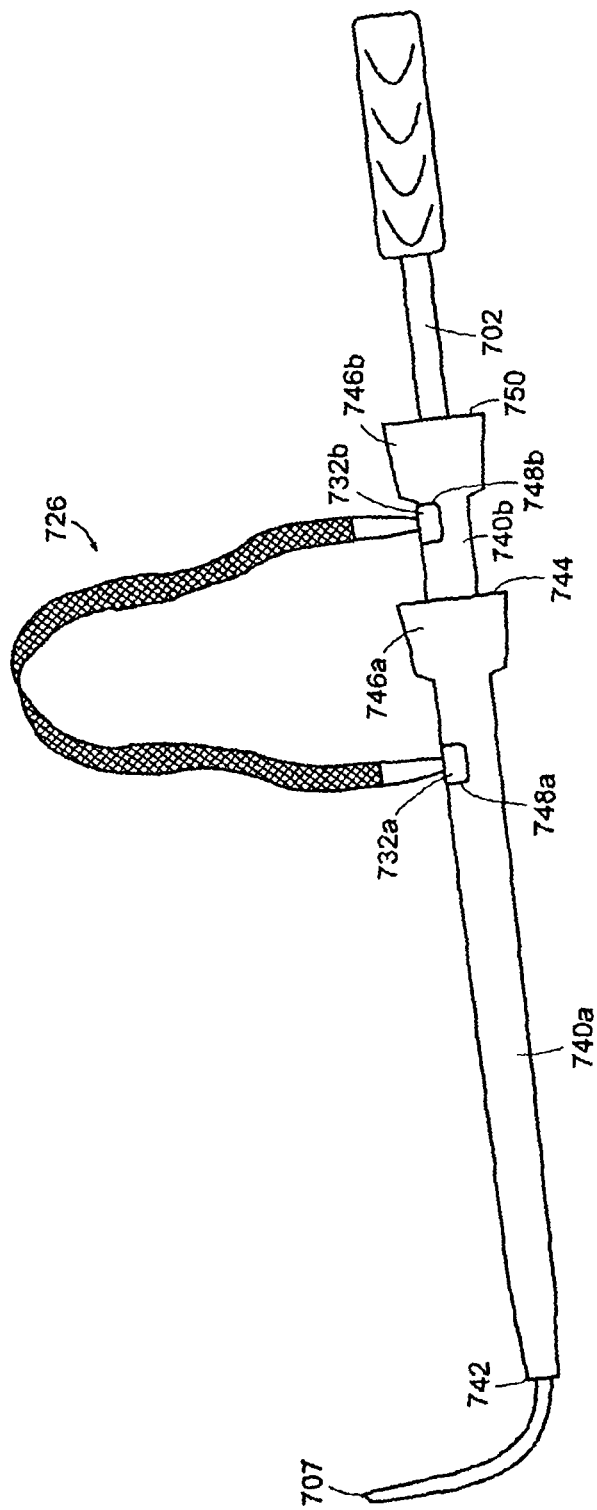
FIG. 70 depicts a perspective side view of an assembled delivery system with two guide tubes, a shaft with a handle, a sling assembly, and connectors, according to another illustrative embodiment of the invention.

FIG. 70 depicts a side view of a delivery system in which the sling assembly 726 is attached at the connector 732a to a proximal end 746a of the first guide tube 740a and at the connector 732b to a proximal end 746b of a second guide tube 740b. The second guide tube 740b slidably interfits over the shaft 702 via proximal opening 750. The first guide tube 740a slidably interfits over the second guide tube 740b via a proximal opening 744. The distal tip 707 of the shaft 702 extends through a distal opening 742 of the first guide tube 740a. Both illustrative proximal tube ends 746a and 746b are flared. Each of the guide tubes 740a and 740b has a connector 748a and 748b for mating interconnection with the sling assembly connectors 732a and 732b, respectively.

Figure 71:
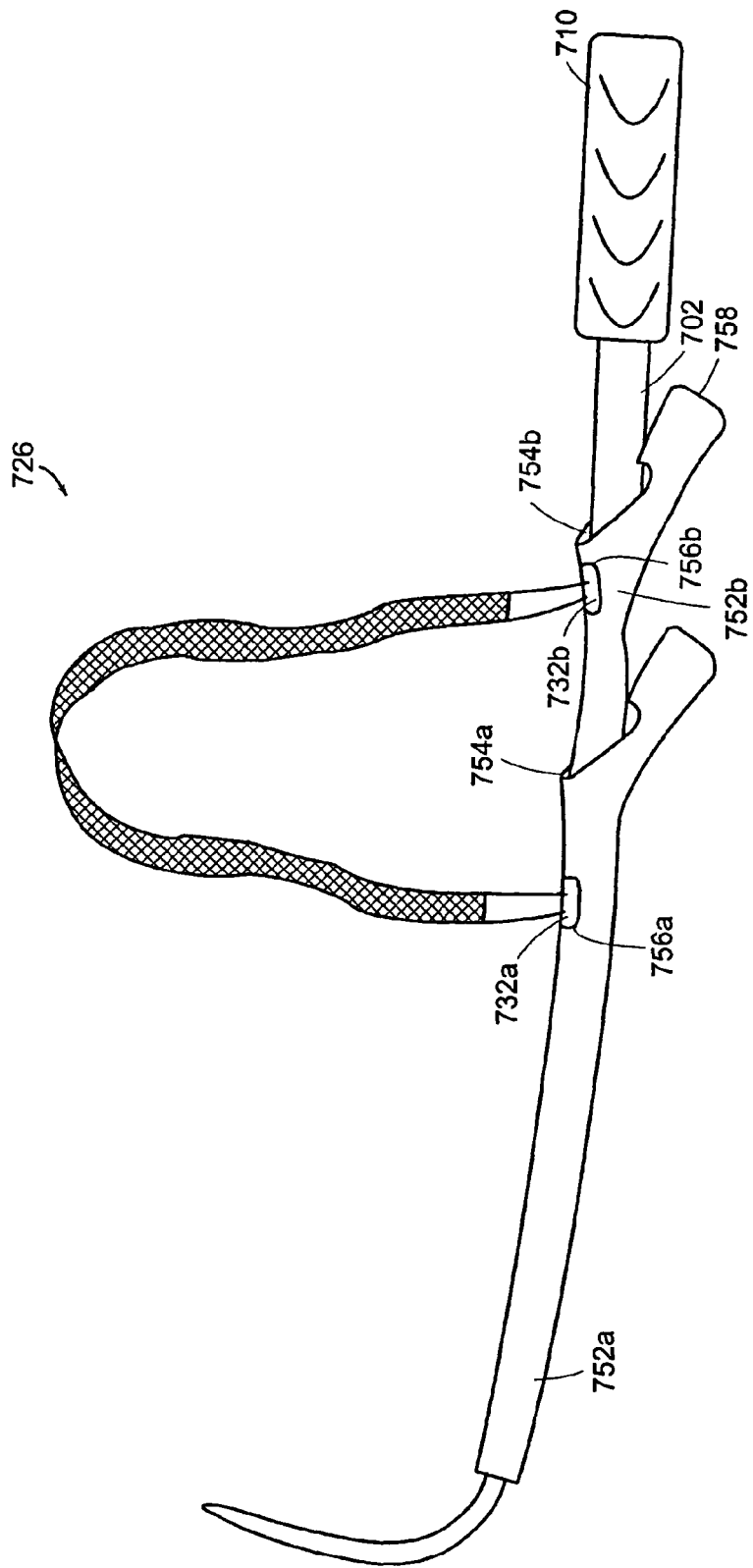
FIG. 71 depicts a perspective side view of an assembled delivery system with two guide tubes that are alternative embodiments of the ones shown in FIG. 70, a shaft with a handle, a sling assembly, and connectors, according to another illustrative embodiment of the invention.

FIG. 71 depicts an alternative embodiment where the sling assembly 726 is interconnected with guide tubes 752a and 752b having side ports 754a and 754b through which the shaft 702 is inserted. More particularly, the shaft 702 is passed through the guide tube 752b via the side port 754b, and the guide tube 752a slidably interfits over the guide tube 752b via the side port 754a. Similar to the guide tubes 740a and 740b depicted in FIG. 70, each of the guide tubes 752a and 752b has the connector 748a and 748b for mating interconnection with the sling assembly connectors 732a and 732b, respectively.

Figure 72:
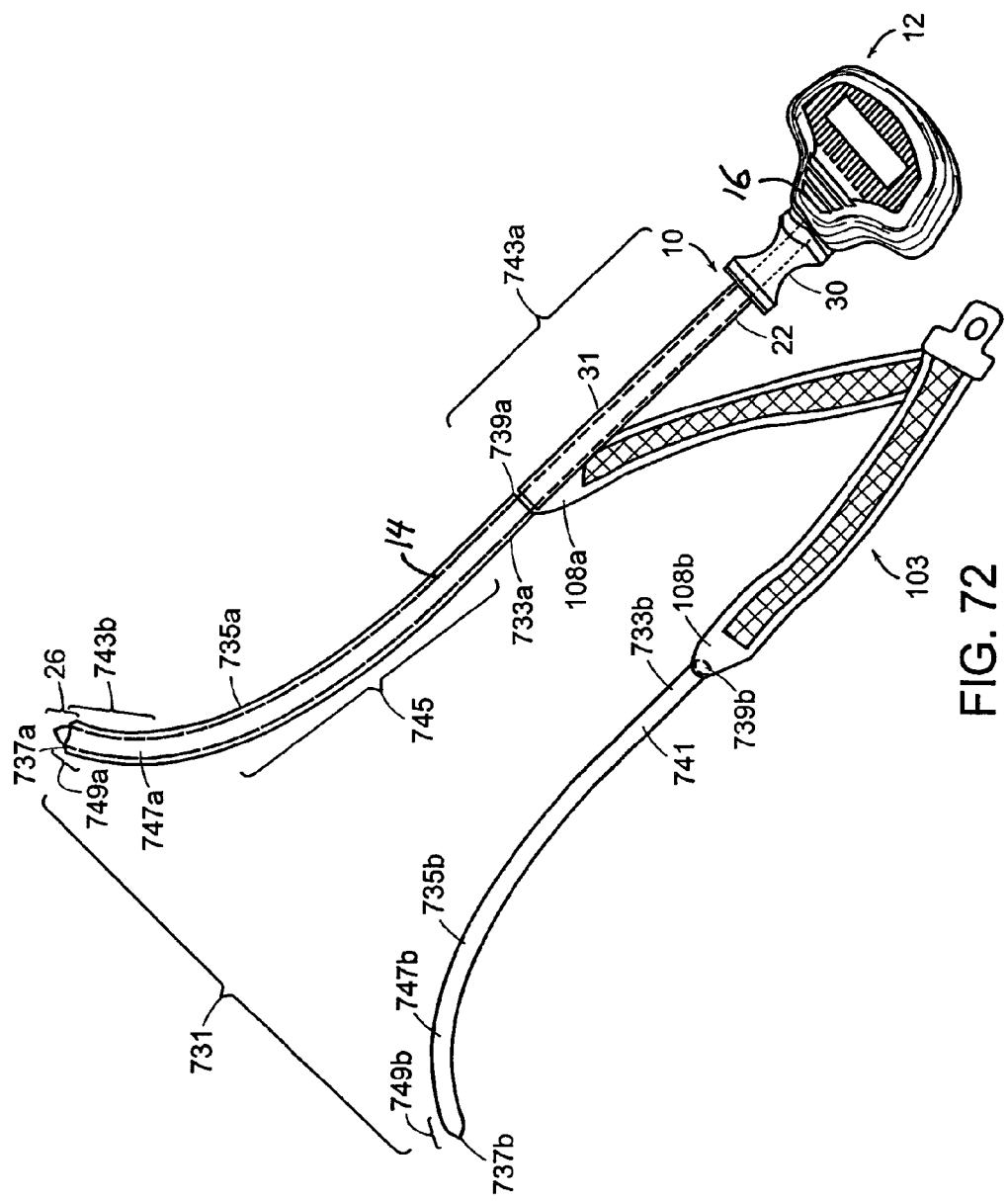
FIG. 72 depicts a perspective side view of an assembled delivery system with two ends of a sling assembly attached to two guide tubes where each guide tube slidably fits over a handled shaft next to a pusher assembly, according to one embodiment of the invention.

FIG. 72 depicts a sling delivery system 731 where the sling assembly 103 is attached to a guide tube 735a, the guide tube 735a slidably interfits over the shaft 14, and the pusher assembly 30 facilitates the removal of the guide tube 735a from the delivery shaft 14. The sling delivery system 731 includes at least one delivery device 10, the pusher assembly 30, the sling assembly 103, and two guide tubes 735a and 735b. The delivery device 10 is of the general type described above in FIGS. 1 and 2, and includes the handle 12, and the shaft 14 fixedly disposed at its proximal end 22 within the handle 12 and extending away from the handle 12.

The shaft 14 includes a first straight section 743a, a curved section 745, and a second straight section 743b. The first straight shaft section 743a attaches to and extends distally from a distal end 16 of the handle 12. The curved shaft section 745 extends distally from the first straight section 743a. The second straight section 743b extends distally from the curved section 745, and terminates at a conical distal tip 26.

The pusher assembly 30, described above with respect to FIGS. 3-6, includes the pusher tube 31 slideable fitted over a portion of the first straight shaft section 743. Both the illustrative shaft 14 and the illustrative pusher assembly 103 are formed of surgical grade stainless steel, and excluding the conical tip 26, have a constant diameter along their respective lengths.

The illustrative sling assembly 103 is of the type described above with respect to FIG. 21. The sleeve ends 108a and 108b connect to first ends 733a and 733b of guide tubes 735a and 735b, respectively. The illustrative sleeve ends 108a and 108b are heat bonded to the first tube ends 733a and 733b. The illustrative guide tubes 735a and 735b each include a first opening 737a or 737b, a second opening 739a or 739b and a lumen 741 extending there between. The second tube ends 747a or 747b includes a tapered section 749a or 749b, respectively, that substantially conforms to part of the conical shaft tip 26.

Each of the two guide tubes 735a and 735b slidably fits over the conical shaft tip 26 and along the length of the shaft 14, one at a time, to abut the pusher assembly 30. Each illustrative guide tube 735a or 735b is a blue, flexible polymer tube. When the pusher assembly 30 is retracted and the first tube end 733a abuts the pusher assembly 30, the conical shaft tip 26 extends beyond the distal tube end 747a or 747b, and can be used for tissue piercing or tunneling. When the operator pushes the pusher 30 into the advanced position, the second tube end 747a or 747b moves distal to the conical shaft tip 26 and becomes accessible for removal from the shaft 14. During removal, the medical operator grasps the tube end 747a or 747b, either by hand or using forceps and pulls in a proximal direction on the delivery device 10.

IV. Exemplary Procedures

Described below are various illustrative methods for delivering an implant, such as a sling or its assembly, to an anatomical site in the body of a mammalian patient. The illustrative methods include suprapubic, prepubic, transobtruator and transvaginal approaches.

FIGS. 73A-73E depict steps in an illustrative suprapubic-to-vaginal approach (the "suprapubic approach") to delivering a sling to a midurethral location or other suburethral tissue. Specifically referring to FIG. 73A, a delivery device 760 includes a shaft 762 attached at a proximal end 768 to a handle 764. A first optional guide tube 766 slidably interfits over a distal end 770 of the shaft 762 via a proximal opening 774. Interfitted as such, a conical tip 772 at a distal end 770 of the shaft 762 extends through a distal opening 776 in the guide tube 766. The shaft 762 may be curved or straight or include both curved and straight sections, and can be any of the various embodiments described in this application. The proximal end 775 of the guide tube 766 may or may not be operatively connected to the handle 764. The delivery device 760 may further include a pusher assembly, for example, as described in connection with FIGS. 3-6, for activating the guide tube 766 off the shaft 762. In the illustrated embodiment, the proximal end 775 of the guide tube 766 is depicted as being flared. However, this need not be the case. Either or both of the distal end 770 of the shaft 762 and a distal end 777 of the guide tube 766 include a first connector 779 marked in general with a circle, which can be any suitable connector, such as and without limitation, any of the connectors described herein or in a disclosure incorporated by reference.

Figure 73A:
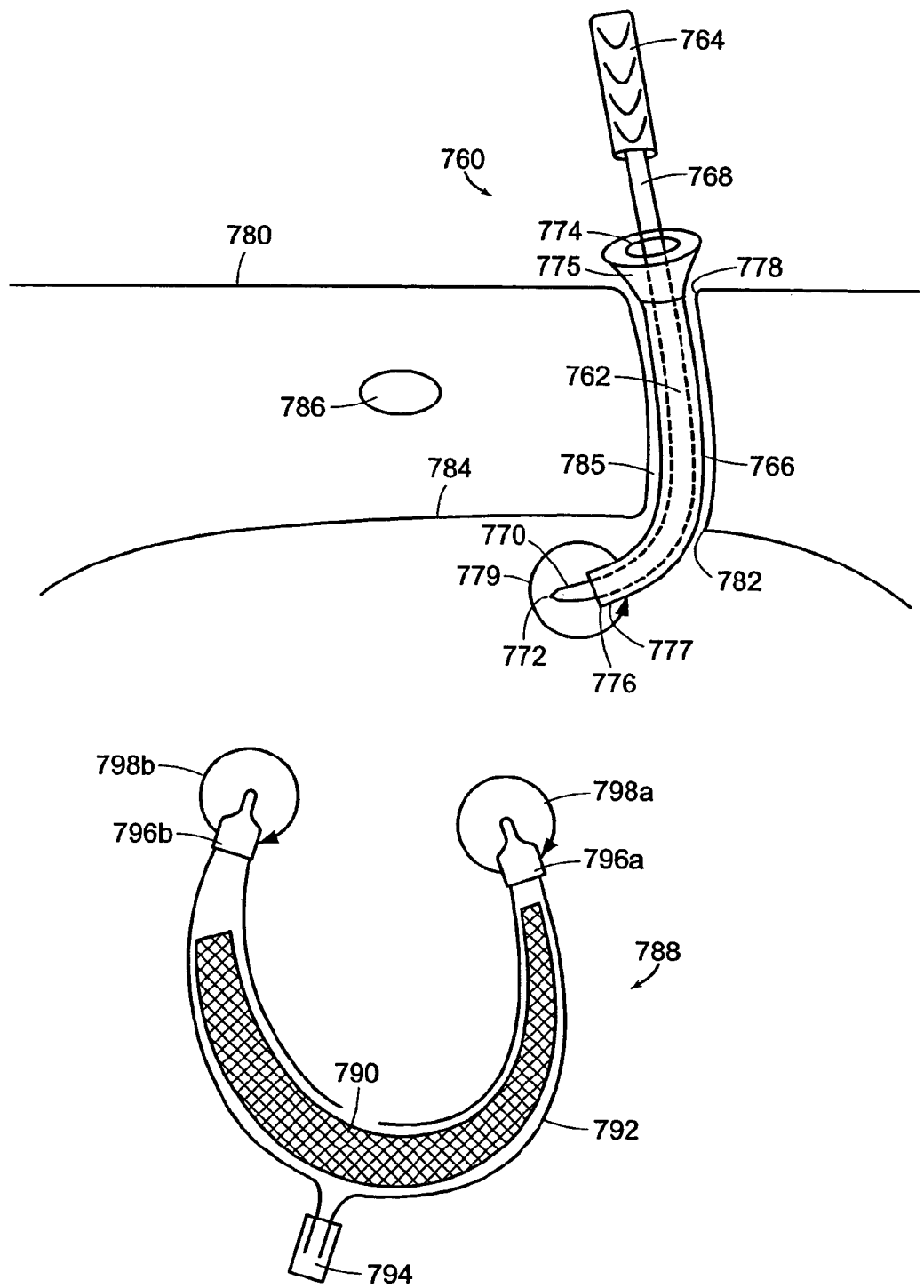
FIG. 73A depicts a schematic view of the tunneling step, using an optional guide tube, in a suprapubic approach to delivering a sling to an anatomical site, according to illustrative embodiments of the invention.
Figure 73B:
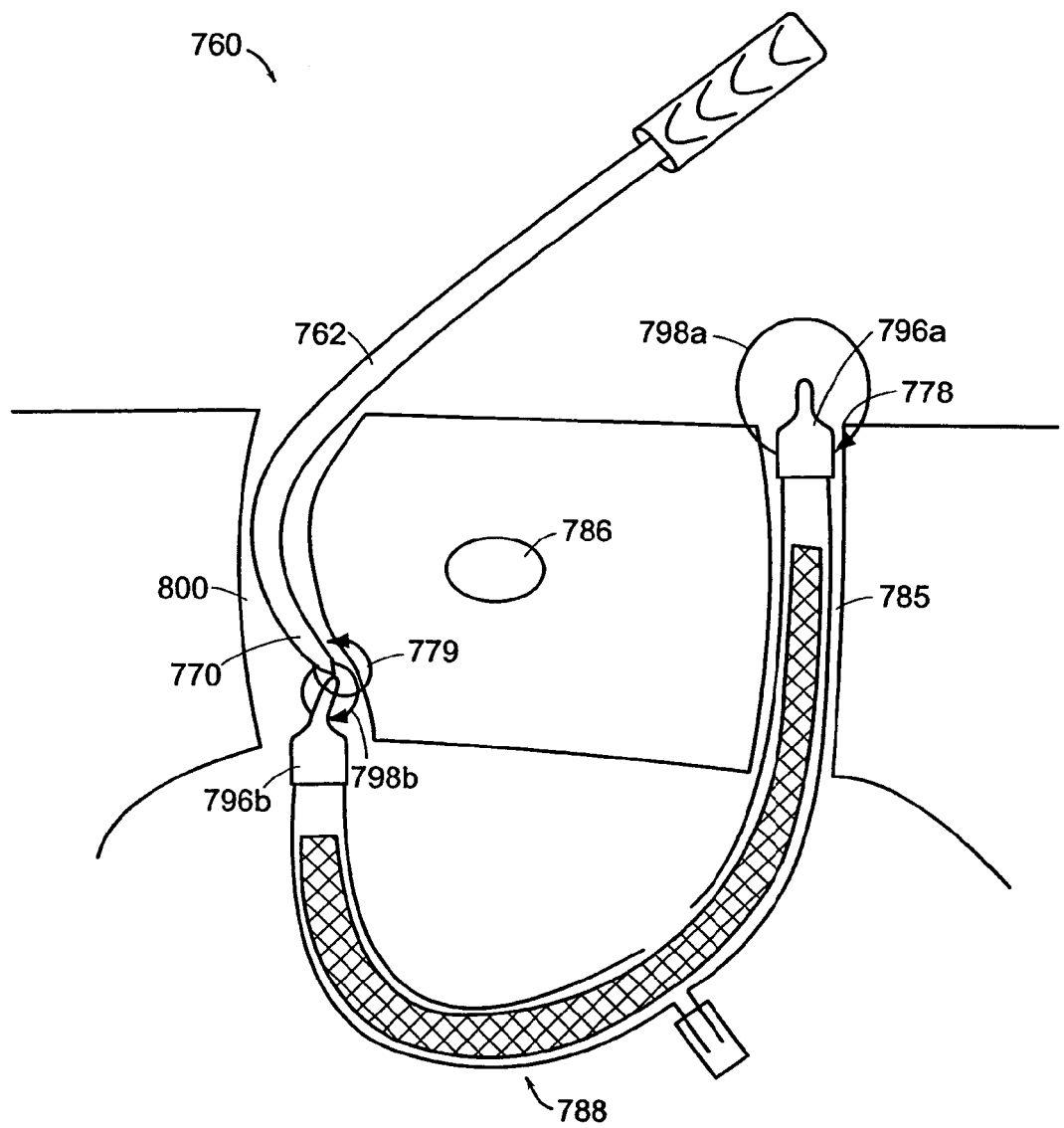
FIG. 73B depicts a schematic view of interconnection and other steps without using a guide tube subsequent to the step shown in FIG. 73A.
Figure 73C:
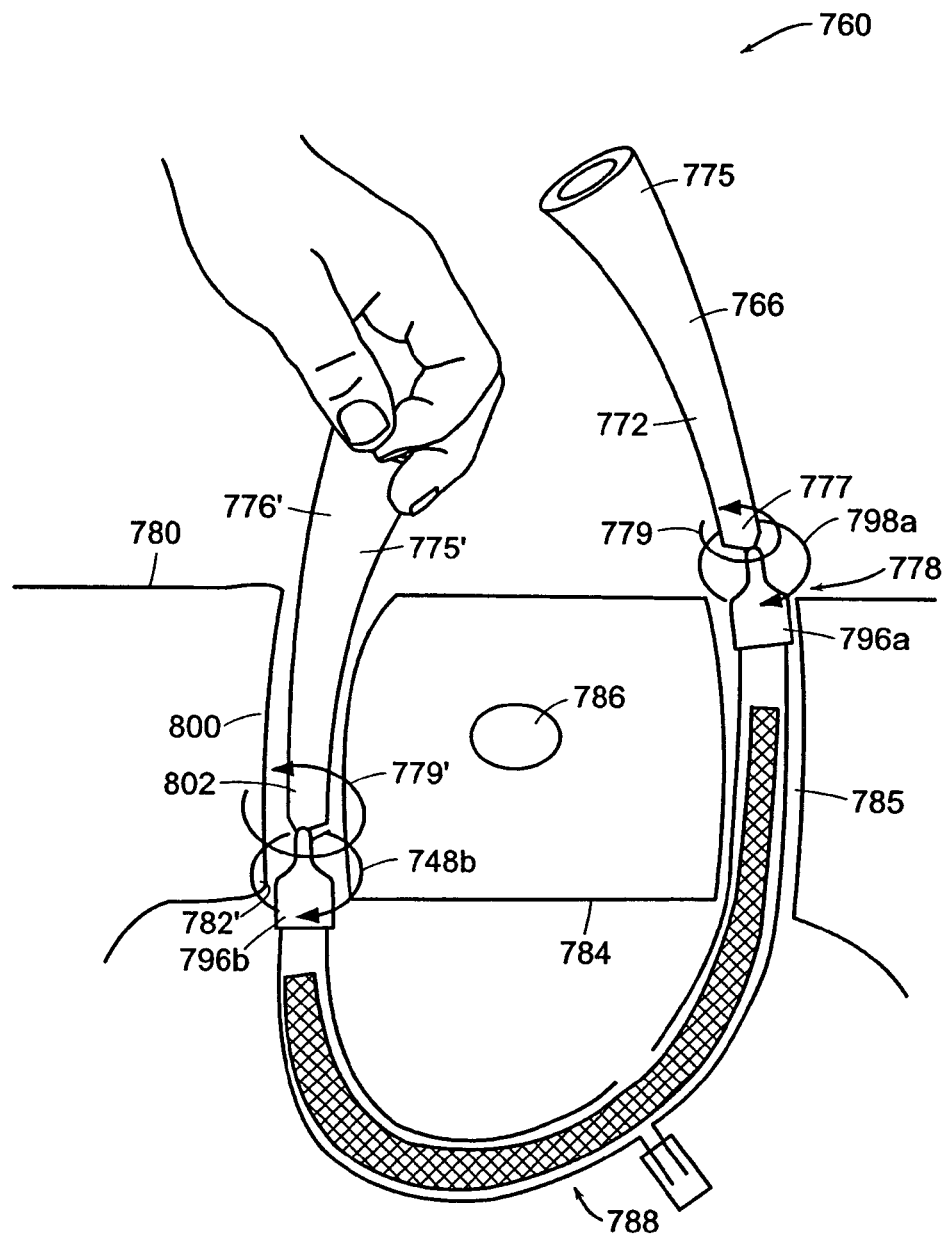
FIG. 73C depicts a schematic view of interconnection and other steps using guide tubes subsequent to the step shown in FIG. 73A.

The procedure of FIGS. 73A-73C employ a sling assembly 788. The sling assembly 788 may be any suitable sling assembly, such as and without limitation, any of the sling assemblies disclosed herein or in disclosures incorporated by reference. The particular sling assembly 788 includes a mesh sling 790, partially enclosed by a sleeve 792. A tab or fastener 794 attaches to the sleeve 792 at an intermediate location to aid in sling placement and in removal of the sleeve 792 from the body of the patient. The sling assembly 788 at end 796a includes or attaches to a connector 798a. Similarly, the sling assembly at end 796b attaches to or includes a connector 798b. The connectors 798a and 798b may be any suitable connector, such as and without limitation, any connector described herein or in a disclosure incorporated by reference.

In use, the medical operator grasps the proximal end 768 of the shaft 762 or the handle 764, and introduces the shaft 762, optionally sheathed in the guide tube 766, into a patient through a puncture 778 in the abdominal skin 780. The delivery device 760 tunnels through the abdominal wall, abdominal fascia, and rectus fascia until the shaft tip 772 emerges through a second puncture 782 in the vaginal wall 784, creating a first tunnel 785 between the abdominal puncture 778 and the vaginal puncture 782 on one side of the urethra 786.

To make sure that the bladder (not shown) is not accidentally punctured by the advance of the delivery device 760, a cystoscopy may be performed at any point during the surgical procedure to look inside the urethra 786 and the bladder. In a preferred embodiment, the guide tube 766 and/or the shaft 762 and/or the sleeve 792 and/or the sling 790 exhibits a visible or discernable optical property, for example, by being blue or green in color, to distinguish it from the tissue and fluid in the urethra and the bladder. In the embodiment where the guide tube 766 includes apertures as described in connection with FIGS. 10A, 10B and 11, the operator can skip the cystoscopy step and instead rely on being alerted by bodily fluid from the bladder, such as urine or blood, flowing out of one of the apertures, in case of inadvertent puncture of the bladder. Further, if the shaft 762 is sheathed by the guide tube 766, the guide tube 766 may be placed and cystoscopy delayed until another guide tube is placed on the contralateral side, and only one cystoscopy needs to be performed.

Referring also to FIG. 73B, in the embodiment where the delivery device 760 does not include a guide tube, the operator interconnects the shaft connector 779 with the sling assembly end connector 798a, and withdraws the shaft 762 back into the first tunnel 785 and out of the abdominal puncture 778 until the sling assembly end 796a emerges from the abdominal puncture 778. The operator then separates the connector 779 from the connector 798a.

The operator then repeats the above steps on the contralateral side of the urethra 786 and creates a second tunnel 800 with the same shaft 762 or a second shaft. As mentioned above, if a second shaft is used, the operator can leave the first shaft 762 in the first tunnel 785 and wait until this point to conduct a single cystoscopy to confirm that neither shaft has punctured the bladder. Assuming the operator is using the same shaft 762, however, the operator interconnects the shaft connector 779 to the sling assembly connector 798a. The operator then withdraws and pulls the shaft 762, along with the interconnected sling assembly end 796b, through the second tunnel 800 until the end 796b emerges on the contralateral side. The operator separates the connector 779 from the connector 798a or dissociates the connector 798b from the sling assembly 788, for example, by cutting.

Referring specifically to FIG. 73C, in the optional embodiment where the delivery device 760 includes a guide tube 766, after the distal end 777 of the guide tube 766 becomes interconnected with the sling assembly end 796a through the connector 779 and the connector 798, the operator withdraws the shaft back from the first tunnel 785 and out of the abdominal puncture 778, leaving the guide tube 766 inside the first tunnel 785. Subsequent to confirming through cystoscopy that the bladder has not been punctured or perforated, the operator pulls the guide tube 766 out of the abdominal puncture 778 through the first tunnel 785, along with the sling assembly end 796a. Alternatively, the operator can wait until a second guide tube is placed similarly on the contralateral side before pulling the first guide tube 766 out of the first tunnel 785, allowing a single cystoscopy to be performed. The proximal end 775 of the first guide tube 766 may be held in place, if necessary, with a hand or a medical instrument for example, a clamp. However, in the embodiment where the proximal end 775 of the first guide tube 766 is flared, i.e., has a larger outer diameter than rest of the guide tube 766, the flaring on the guide tube 766 helps to prevent the guide tube 766 from slipping into the first tunnel 785.

The operator repeats the above steps on the contralateral side of the urethra 786 and creates a second tunnel 800 with the delivery device 760, substituting the guide tube 766 with a guide tube 766' having a connector 779' at its distal end 802. The guide tube 766' is preferably identical to the guide tube 766. After the distal end 802 of the guide tube 766' emerges from a second vaginal puncture 782' in the vaginal wall 784, the operator interconnects the connector 779' attached to the guide tube 766' with the sling assembly connector 798b. The operator then pulls the guide tube 766' by its proximal end 775' through the second tunnel 800 until the end 796b of the sling assembly 788 emerges out of the abdominal incision through the second tunnel 800. After performing cystoscopy in series with the placement of each guide tube, or a single cystoscopy after both tubes are placed, to make sure that neither guide tube 766 or 766' has punctured the bladder, the operator separates the guide tube 766 from the sling end 796a and separates the guide tube 766' from the sling assembly end 796b. If a puncture is found in either the bladder or the urethra 786, the operator may remove either or both the guide tubes 766 and 766' and repeat the above steps to reinsert the guide tube(s).

Figure 73D:
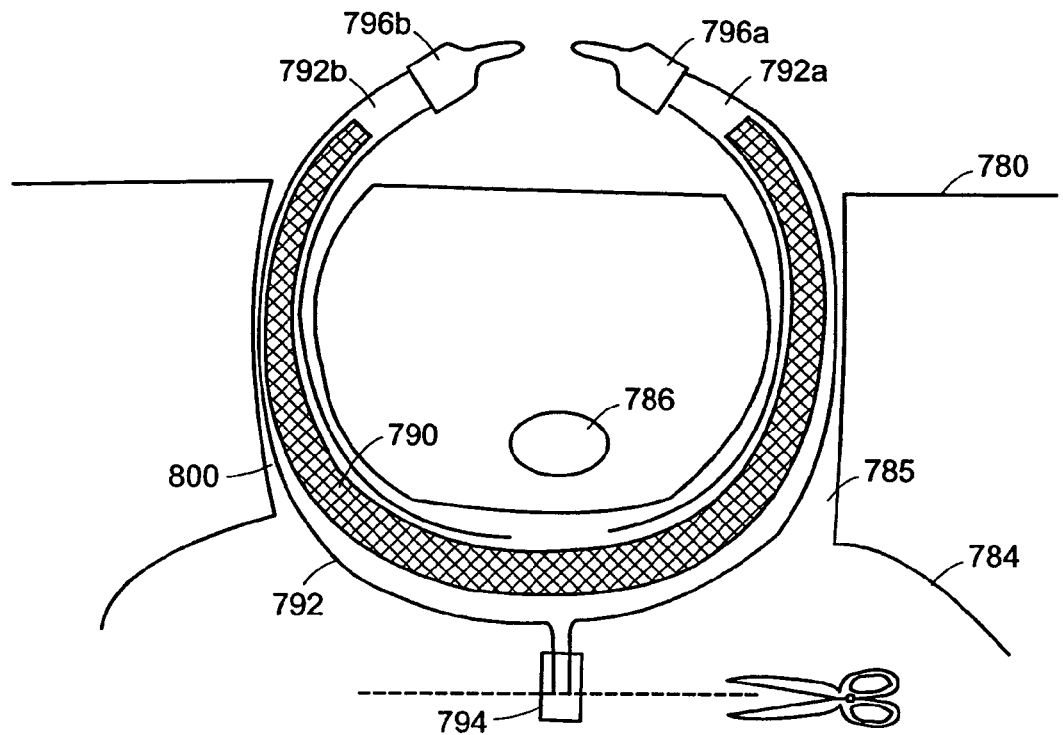
FIG. 73D depicts a schematic view of steps subsequent to those shown in either FIG. 73B or 73C.

Referring now to FIG. 73D, regardless of whether guide tubes (FIG. 73C) or only shafts (FIG. 73B) are used, the operator adjusts the position and tension in the sling assembly 788 to finish the delivery process. The operator may also use a medical instrument, for example, forceps, to adjust the sling assembly 788. Subsequently, the operator removes the sleeve 792, and other components of the sling assembly 788 such as the connectors 798a and 798b if still attached, from the patient. For example, the operator may cut the fastener tab 794 to separate the sleeve 792 into two sleeve segments 792a and 792b. Then the operator can pull the sleeve segments 792a and 792b by their ends 796a and 796b out the first 785 and second 800 tunnels, respectively. Only the mesh sling 790 is left within the patient body in the periurethral tissue, for example, underneath the midurethra 786 or the bladder neck, and may be trimmed at each end to just below the skin of the abdomen.

Figure 73E:
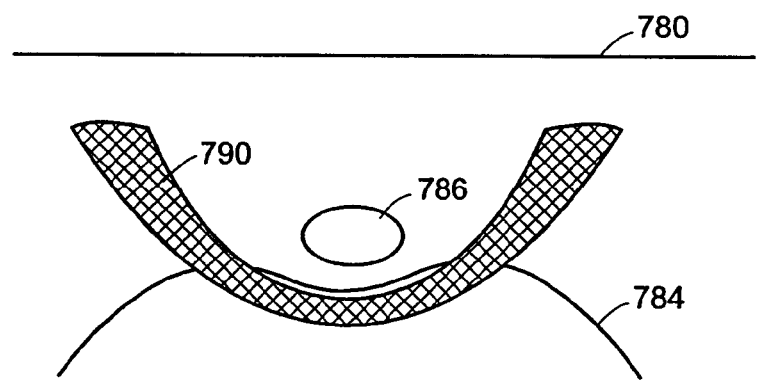
FIG. 73E depicts a schematic view of the final placement of a sling to treat urinary incontinence.

Referring now to FIG. 73E, after the mesh sling 790 has been delivered and placed in the periurethral tissue, the abdominal and vaginal wounds are sutured if needed. The implanted sling 790 elevates part of the vaginal wall 784 and its surrounding tissue, as a solution to treat urinary incontinence.

The above methodology may be employed for any abdominal entry approach, such as, for example, a prepubic approach.

In the above-described suprapubic and prepubic approaches, specific advantage may be achieved where a shaft 762 of the type described in connection with FIGS. 13A, 13B, and 14-16 is used. That advantage is now described in the context of tunneling from the abdominal puncture to the vaginal puncture using the shaft 80. The other steps in this embodiment of the approach are similar to the ones described in connection with the shaft 762 and will not be repeated.

Figure 74:
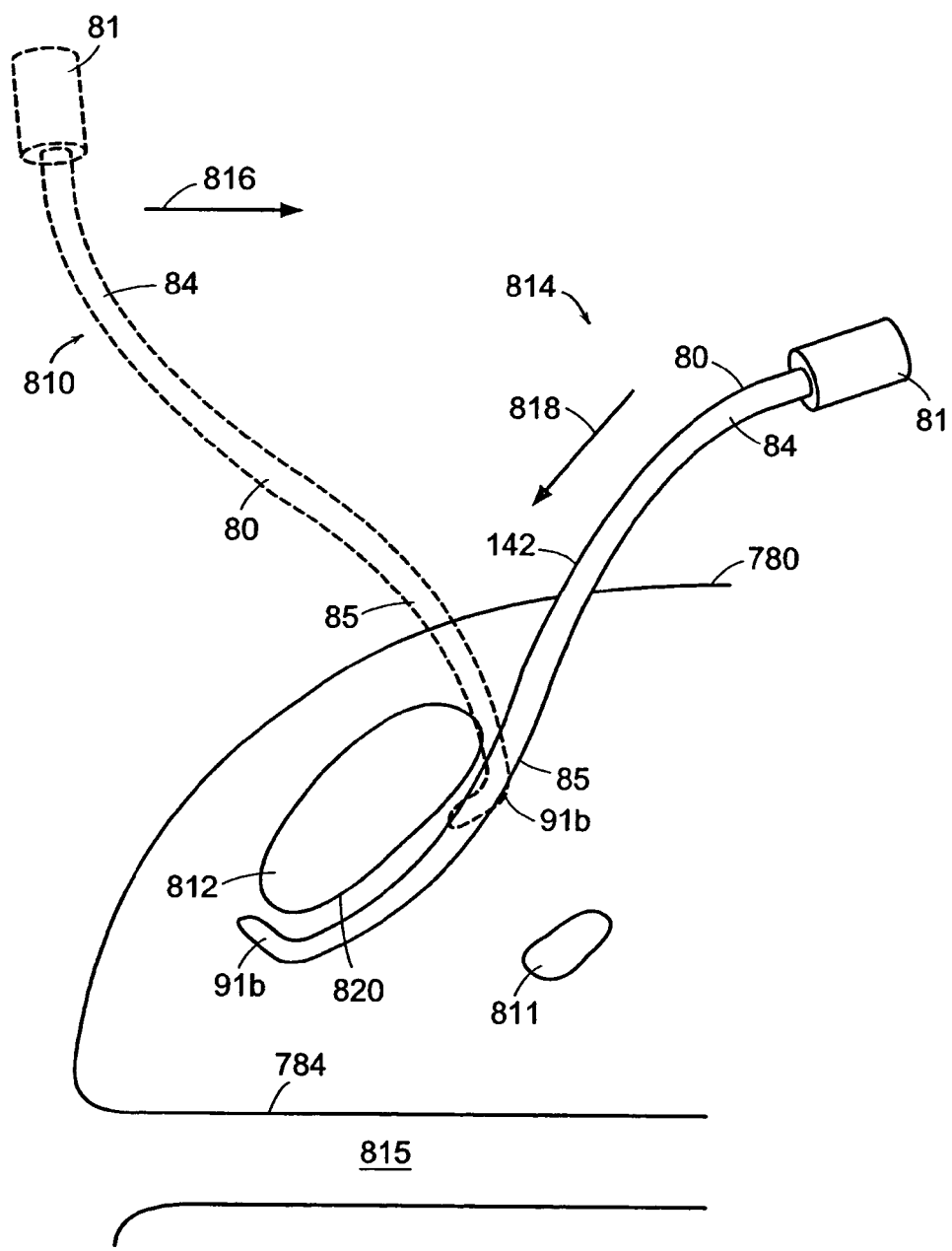
FIG. 74 depicts a schematic view of a suprapubic delivery approach using the shaft of the type shown in FIG. 14 where one previous position of the delivery device is shown in phantom, according to an illustrative embodiment of the invention.

FIG. 74 illustrates, through a schematic side view of the female pelvic area, an illustrative embodiment of the invention casing the delivery device described with respect to FIG. 15. The illustrative shaft 80 is attached to the handle 81. The shaft 80 includes at least two arcs 84 and 85. The shaft 80 also optionally includes an angled distal end 91b. The operator grasps the handle 81 and introduces the shaft 80 through the abdominal skin 780, abdominal wall, abdominal fascia, and rectus fascia in the suprapubic region of the pubic area until the distal end 91 of the shaft 80 emerges through the incision on one side of the vaginal wall 784. The arcs 84 and 85 enable the operator to pass through the suprapubic region to the vagina and navigate around internal organs more easily than a single arc/curve configuration. The shaft 80 is inserted at a first position 810 (phantom line) through the abdominal skin 780, abdominal wall, abdominal fascia, to the suprapubic region of the pubic area, near the pubic bone 812. In a preferred embodiment, the distal tip 91b is pointed toward the pubic bone 812, and away from other organs such as the bladder 811 to prevent puncturing them.

The operator moves the shaft 80 from the first position 810 to a second position 814 in a direction indicated by a first arrow 816. The arcs 80 and 82 enable the operator to move the distal tip 91 of the shaft 80 along the contour of the pubic bone 812. From the second position 814, the operator pushes the shaft 80 in the direction indicated by a second arrow 818 and the shaft 80 passes adjacent the posterior side 820 of the pubic bone 812 on its way towards the vagina 815.

With continued reference to FIG. 74, during the procedure, the operator directs the angled distal end 91 along the posterior side 820 of the pubic bone 812 to avoid accidental perforation of other organs while advancing towards the target area. The plurality of arcs in the shaft 80 provides ergonomic benefits. For example, the first arc 80 provides the medical operator with clearance between the medical operator's hand and the patients body while allowing the operator to exert sufficient force onto the shaft 80 to advance the shaft 80 in its intended course, for example, from the second position 814 in the direction indicated by the second arrow 818 during the above-described embodiment of suprapubic approach. The contour of the shaft 80 and the angle of the distal end 91 of the shaft 80 work together to lessen the risk of injuring organs including the urinary bladder 811, which could otherwise be harmed during the surgical procedure. The operator may perform cystoscopy to determine if the bladder had been perforated.

Figure 75:
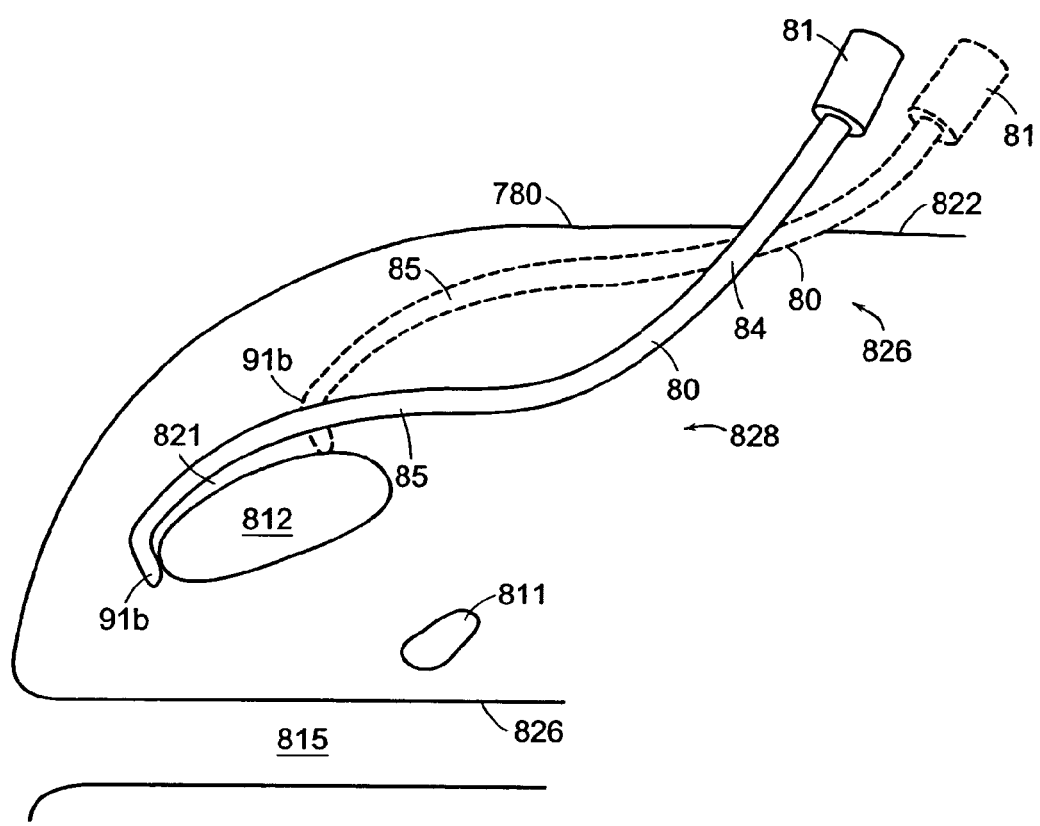
FIG. 75 depicts a schematic view of a prepubic delivery approach using the delivery device of FIG. 74 where one previous position of the delivery device is shown in phantom, according to an illustrative embodiment of the invention.

Referring now to FIG. 75, the operator may opt for the pre-pubic approach, which tunnels between the abdominal skin 780 and the anterior side 821 of the pubic bones 812 to eliminate any chance of perforating the bladder 811. In an illustrative embodiment, the delivery device described with respect to FIG. 15 having the shaft 80 with at least two arcs 84 and 85 is again used as an example to illustrate the principle of this approach, while shafts of other shapes and structures may be used for the pre-pubic approach as well. The medical operator grasps the handle 81 and introduces the shaft 80 through a puncture 822 in the abdominal skin 780, with the angled distal end 91b first, into the abdominal fascia, and through the pre-pubic region of the pubic area until the distal end 91b of the shaft 80 emerges through an incision on the vagina wall 826. Specifically, the shaft 80 passes along the anterior surface 821 of the pubic bone 812, for example, from a first position 826 (shown in phantom) to a second position 828, while the angled distal end 91b of the shaft 80 follows the contour of the anterior surface 821 of the pubic bone 812. Because the bladder 811 and other vital organs are posterior to the pubic bone 812, the operator eliminates the risk of inadvertent perforation of these organs by passing through the pre-pubic region to the vagina 815. Similar to what is described in connection with the suprapubic approach, the plurality of arcs 84 and 85 in the shaft 80 provides ergonomic benefits for the procedure. In the pre-pubic-to-vaginal method, the operator does not need to conduct any cystoscopy to confirm the integrity of the bladder and the urethra.

After a first tunnel from the abdominal skin 780 to the vaginal wall 826 is created through the above steps, the remaining aspects of the pre-pubic approach is the same as the supra-pubic approach described above. The prepubic approach can also be performed with two needles with or without guide tubes.

Figure 76A:
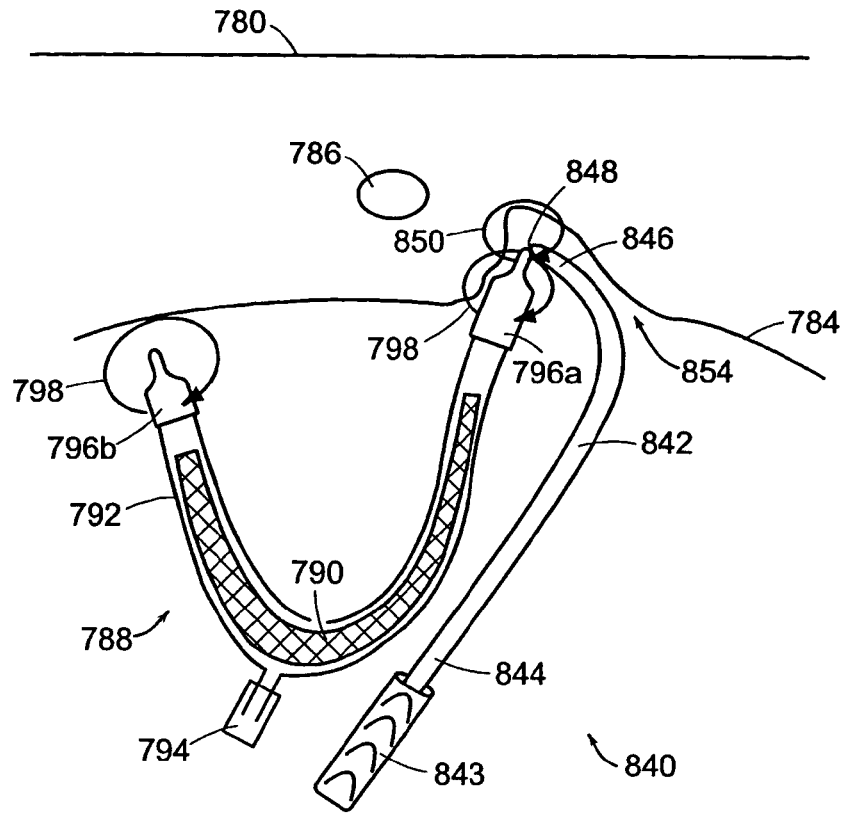
FIGS. 76A and 76B depict schematic views of steps in a transvaginal approach where a medical implant is interconnected to a distal end of a shaft for delivery to an anatomical site in the patient.
Figure 76B:
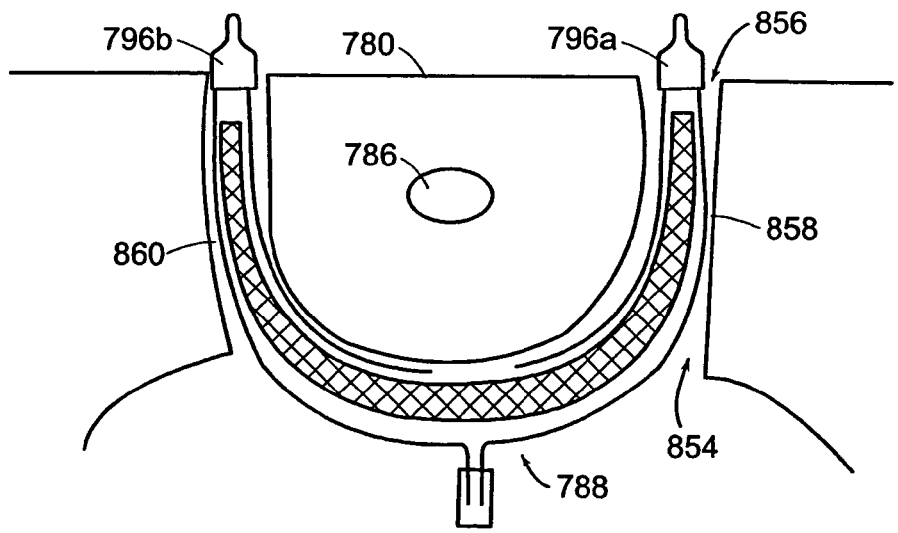

FIGS. 76A and 76B depict steps of a transvaginal approach according to an illustrative embodiment of the invention. Specifically, referring to FIG. 76A, a delivery device 840 includes a shaft 842 attached at a proximal end to a handle 843.

The shaft 842 has a distal end 846 with a distal tip 848. The shaft 842 may be curved or straight or include both curved and straight sections. As in the case of the shaft 762 (FIGS. 73A and 73B), the shaft 842 can be any suitable shaft, including without limitation any of those shafts disclosed herein or in disclosures incorporated by reference. The distal end 846 of the shaft 842 includes a connector 850, marked in general with a circle. The connector 850 can be any suitable connector, including without-limitation, any of those disclosed herein or in disclosures incorporated by reference.

As in the case of the suprapubic and prepubic approaches of FIGS. 73A-73E, the delivery device 840 may be any suitable delivery device, including without limitation, any of those delivery devices disclosed herein or in the disclosures incorporated by reference.

As in the case of the procedures of FIGS. 73A-73E, the procedures of FIGS. 76A and 76B employ the sling assembly 788. In use, the medical operator interfits or interconnects the sling assembly end 796a to the shaft 842, for example, by way of the shaft connector 850 and sling assembly connector 798a. Alternatively, in embodiments where the sling assembly 788 attaches to dilator tubes, such as the dilator tubes 735a and 735b of FIG. 72, the operator slidably interfits the shaft 842 through the dilator tube 735a or 735b, without any interconnection. Next, the operator grasps the proximal end 844 of the shaft 842 or the handle 843, and introduces the shaft 842 tip 848 first, into a puncture 854 in the vaginal wall 784 on one side of the urethra. The operator, using the shaft 842, tunnels transvaginally through the rectus fascia, abdominal fascia, and abdominal wall in the region of the pubic tubercle until the distal end 846 of the shaft 842 emerges through a puncture 856 on one side of the abdominal skin 780, creating a first tunnel 858 between the vaginal puncture 854 and the abdominal puncture 856. Similar to the suprapubic and prepubic approaches, the shaft 842 (where a dilator tube is not employed) or the sleeve 792 preferably exhibits a visibly discernable optical property such that the shaft 842 can be distinguished from the surrounding tissue during a cystoscopy.

The operator then separates the shaft connector 850 from the sling assembly connector 798a. The operator keeps the sling assembly end 796a from slipping back into the abdominal puncture 856 using, for example, a clamp. The operator proceeds to create a second tunnel 860 on the contralateral side of the urethra 786 by repeating the above steps with the sling assembly end 796*b*. The same shaft 842 or a second shaft may be used.

After both ends 796*a* and 796*b* have emerged on the abdominal side, and the cystoscopy confirms that the bladder and the urethra 786 have not been perforated, the operator then adjusts the position and tension in the sling assembly 788 to finish the delivery and implanting process as described earlier in connection with the suprapubic approach.

Figure 77:
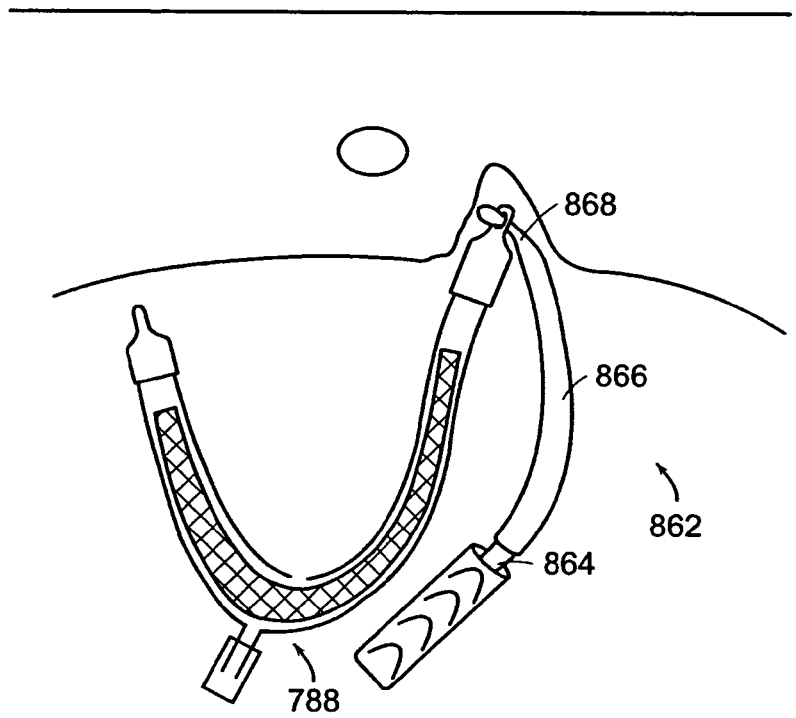
FIG. 77 depicts a schematic view of steps in a transvaginal approach where the implant is interconnected to a distal end of a guide tube for delivery to an anatomical site in the patient.

Referring now to FIG. 77, in another illustrative transvaginal approach, a distal end 868 of a guide tube 866 attaches to an implant such as a sling assembly. This approach is essentially the same as the approach of FIGS. 76A and 76B except that the interconnection is between the sling assembly and the distal end 868 of the guide tube 866. An advantage of this embodiment is that two guide tubes may be placed, one on each side of the urethra, using a single shaft. Once both guide tubes are placed a single cystoscopy may be performed to verify placement. A pusher assembly such as the pusher assembly 30 of FIG. 72 may be employed to facilitate removal of the dilator tubes from the shaft 864.

Figure 78A:
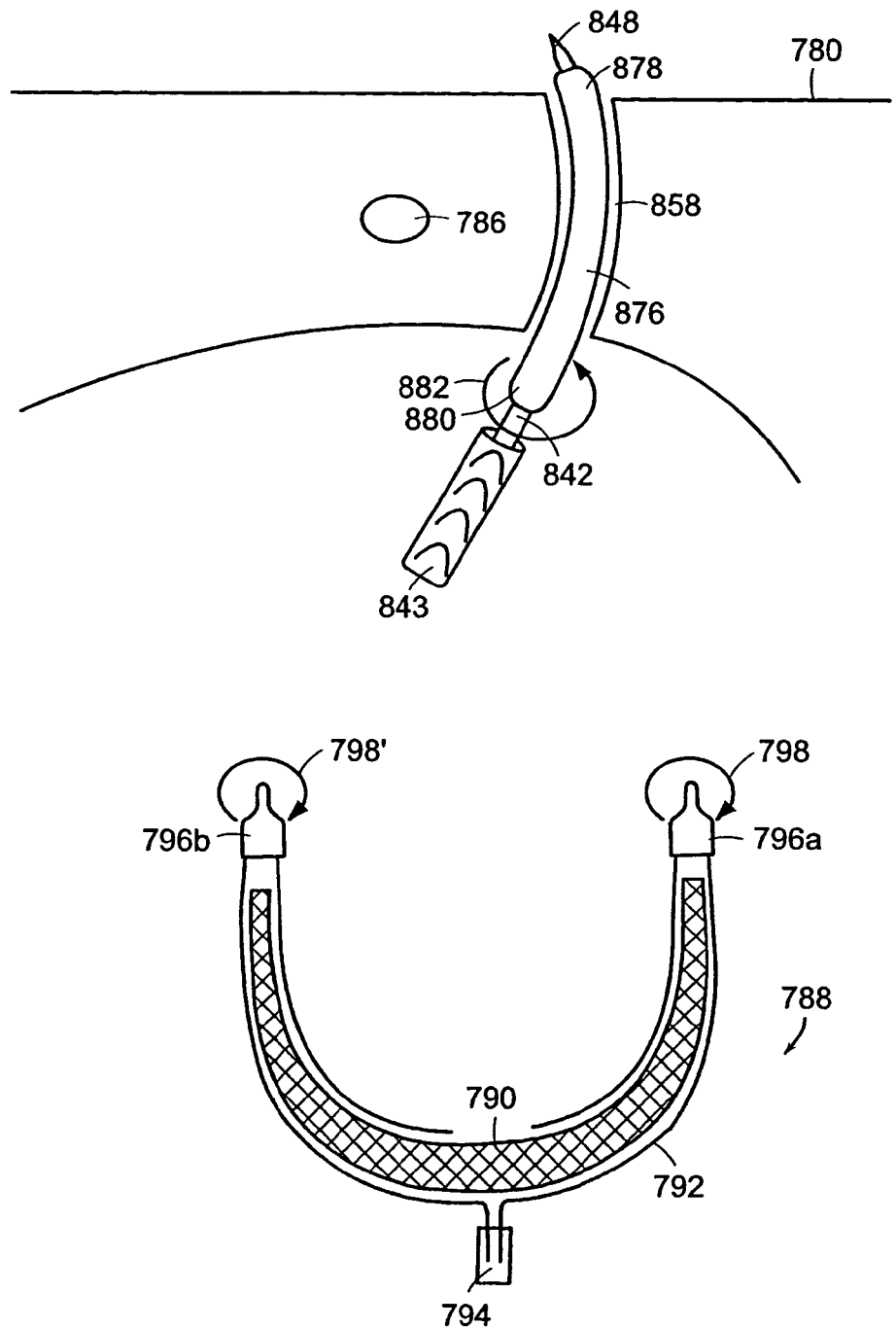
FIGS. 78A and 78B depict schematic views of steps in a transvaginal approach where the implant is interconnected to a proximal end of a guide tube for delivery to an anatomical site in the patient.

Referring now to FIG. 78A, in another illustrative transvaginal approach, a proximal end 880 of a guide tube 876 attaches to the sling assembly end 796*a*. The interconnection between the sling assembly connector 798*a* and the proximal end connector 882 on the guide tube 876 may be made prior to insertion of the guide tube 876 into the body, as shown in FIG. 72, or subsequent to guide tube insertion, as shown in FIG. 78A. The delivery device 870 may also include a pusher assembly such as that shown in FIG. 72, and as described in connection with FIGS. 3-6, for axially actuating the guide tube 876 off the shaft 842. One example of the guide tube 876 is described in connection with FIGS. 63A-63D and 64. Another exemplary guide tube is described with respect to FIG. 72 where a proximal end of the guide tube is interconnected, for example, through heat bonding, with an end of a sling assembly. As in the embodiments, the distal tip 848 of the shaft 842 extends outside the distal end 878 of the guide tube 876 for piercing through the tissue. The operator, using the shaft 842 sheathed in the guide tube 876, tunnels transvaginally to create the first tunnel 858 as described in connection with FIGS. 76A and 76B.

Figure 78B:
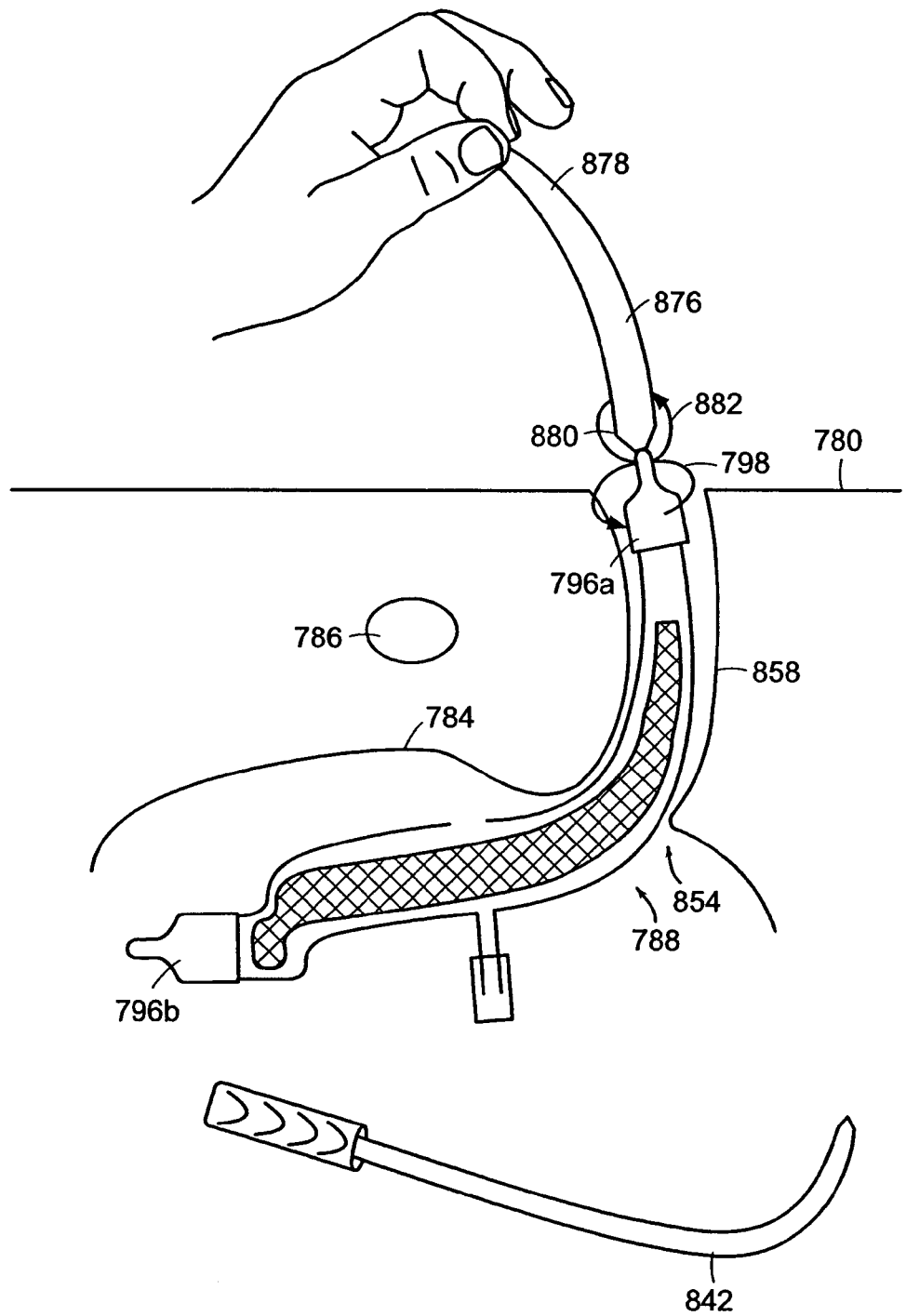

Referring also to FIG. 78B, if a pusher assembly such as the pusher assembly 30 with respect to FIG. 72 is employed, the operator actuates in the distal direction to edge enough of the guide tube 876 off the shaft 842 so that the operator can grasp the distal end 878 of the guide tube 876 by hand or with the assistance of an instrument. Once the guide tube 876 is grasped, the operator withdraws the remainder of the shaft 842 from the first tunnel 858 by pulling it out of the vaginal puncture 854. With the guide tube 876 remaining in the tunnel 858, the operator can clamp its distal end 878 to stop the tip 878 from slipping back into the tunnel 858. The operator can perform a cystoscopy and remove the guide tube 876 at this point (as shown in FIG. 78B) or repeats the above steps on the contralateral side of the urethra 786 and creates a second tunnel from the vaginal wall 784 to the abdominal skin 780, substituting the first guide tube 876 with a second substantially identical guide tube. The operator can use the same shaft 842 or a different one. If two shafts are used, cystoscopy may be done in series, or both tubes may be inserted on both side before single cystoscopy is performed. Once the contralateral guide tube is placed and placement is verified, both guide tubes can be pulled through the respective vaginal incisions to position the sling assembly 788. Then the guide tubes can be separated from the sling assembly 788 by, for example, cutting.

Figure 79A:
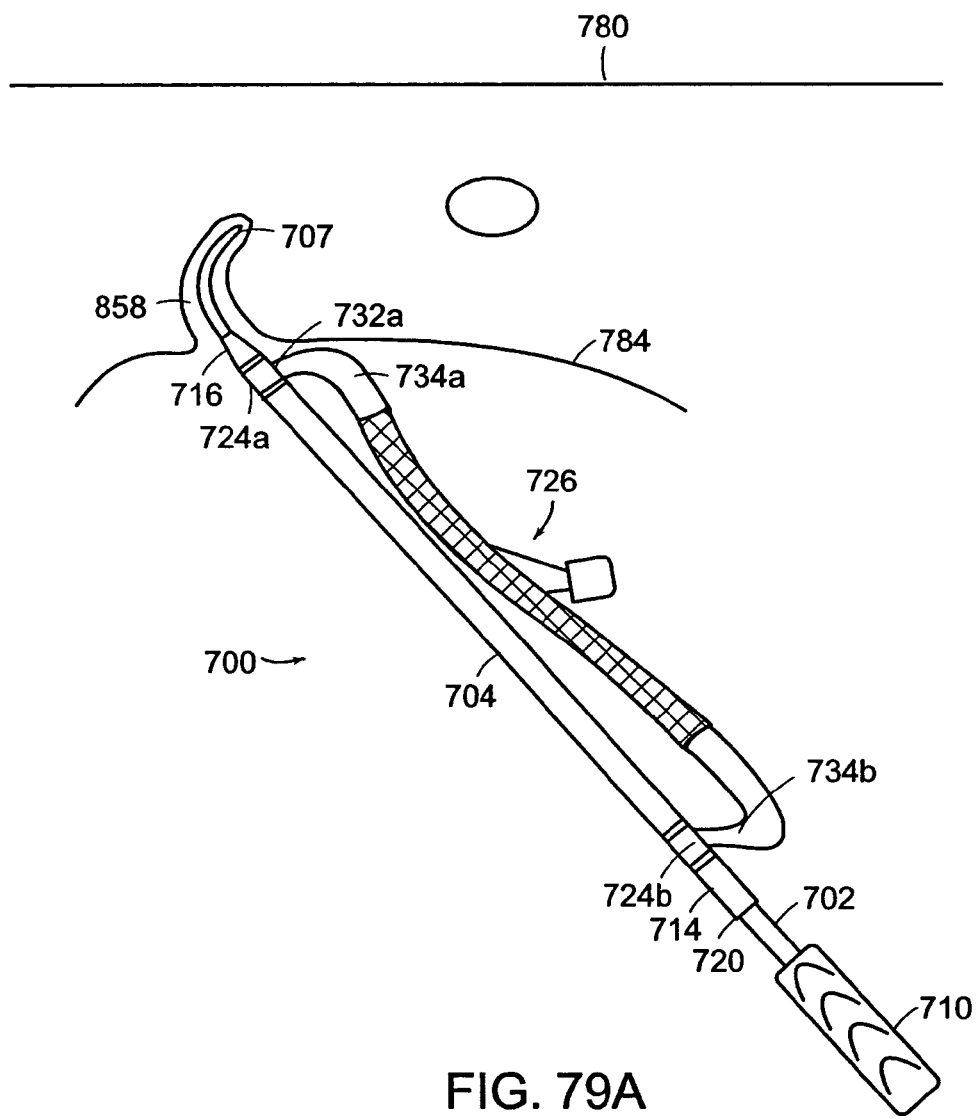
FIGS. 79A and 79B depict schematic views of steps in a transvaginal approach where the implant is interconnected to both distal and proximal ends of a guide tube for delivery to an anatomical site in the patient.
Figure 79B:
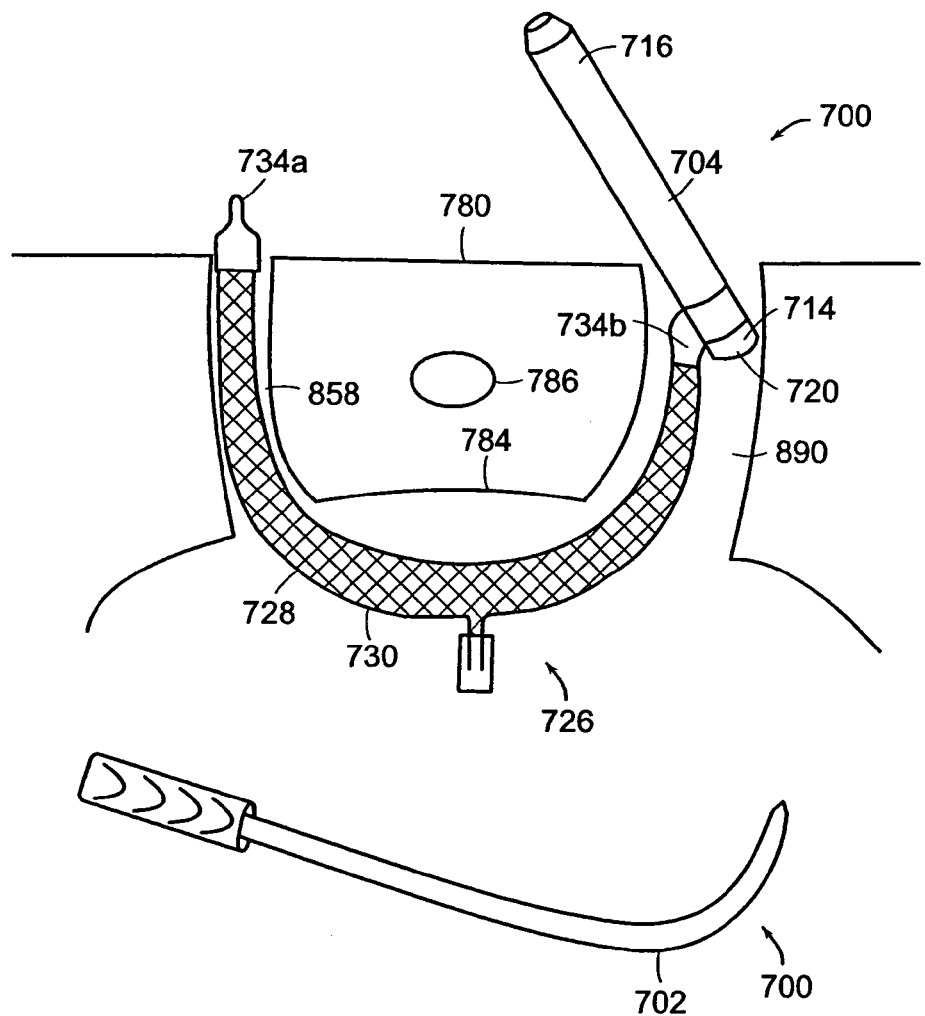

FIGS. 79A and 79B illustrate another transvaginal approach, in which both distal and proximal ends of the guide tube 704 are attached to the sling assembly 726. The delivery system 700 is described in connection with FIGS. 68 and 69, and includes the shaft 702 and the guide tube 704. The guide tube 704 has the first connector 724*a* at the distal end 716 and the second connector 724*b* at the proximal end 714, for connecting to the two ends of the sling assembly 726. Two sleeve ends 734*a* and 734*b* of the sling assembly 726 are interconnected with the distal end 716 and the proximal end 714 of the guide tube 704, respectively. As in previously discussed guide tube embodiments where the guide tube does not connect to the handle, the guide tube 704 slidably interfits over the shaft 702 without interconnection. The operator, using the shaft 702 slidably interfitted in the guide tube 704, tunnels transvaginally to create the first tunnel 858 as described in connection with FIGS. 76A and 76B, until the distal end 716 of the guide tube 704 and its interconnected sleeve end 734*a* of the sleeve assembly 726 both emerge from the abdominal skin 780.

Referring also to FIG. 79B, the operator then separates the sleeve end 734*a* from the distal end 716 of the guide tube 704, and withdraws the delivery device 700 out of the vaginal wall 784 via the first tunnel 858. The sleeve end 734*a* of the sling assembly 726 remains outside the abdominal skin 780 with part of the sling assembly 726 residing inside the first tunnel 858. The other sleeve end 734*b* remains interconnected to the proximal end 714 of the guide tube 704. The operator creates a second tissue tunnel 890 from the vaginal wall 784 to the abdominal skin 780 on the contralateral side of the urethra 786, similar to the first tunnel 858, using the delivery device 700. After the distal end 716 of the guide tube 704 emerges from the abdominal skin 780, the operator slides the shaft 702 out of the proximal opening 720 of the guide tube 704, and withdraws the shaft 702 out of the vaginal wall 784 via the second tunnel 890. The operator grasps the distal end 716 of the guide tube 704 and pulls the guide tube 704 and its interconnected sleeve end 734*b* out of the abdominal skin 780 via the second tunnel 890. Once the sleeve end 734*b* of the sling assembly 726 emerges out of the abdominal skin 780, the operator separates it from the proximal end 714 of the guide tube 704. The operator further adjusts the position and tension in the sling assembly 726 before removing the sleeve member 730 from the sling 728 for implanting.

Figure 80A:
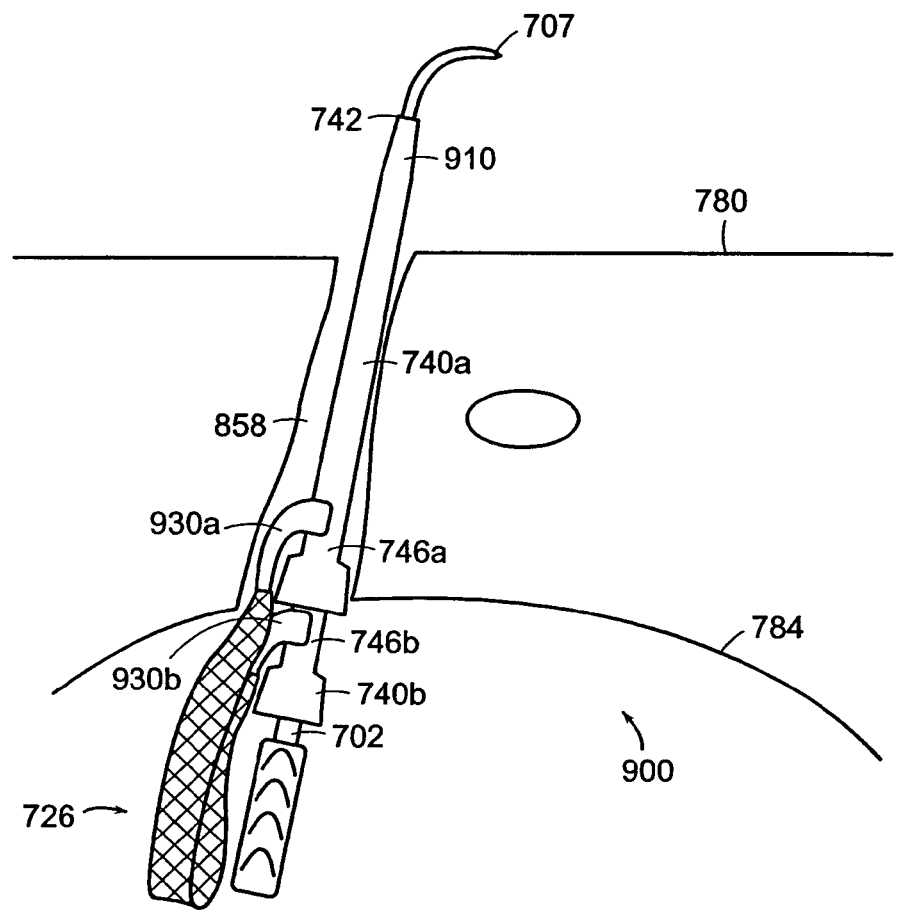
FIGS. 80A and 80B depict schematic views of steps in a transvaginal approach where the implant is interconnected to two guide tubes simultaneously for delivery to an anatomical site in the patient.
Figure 80B:
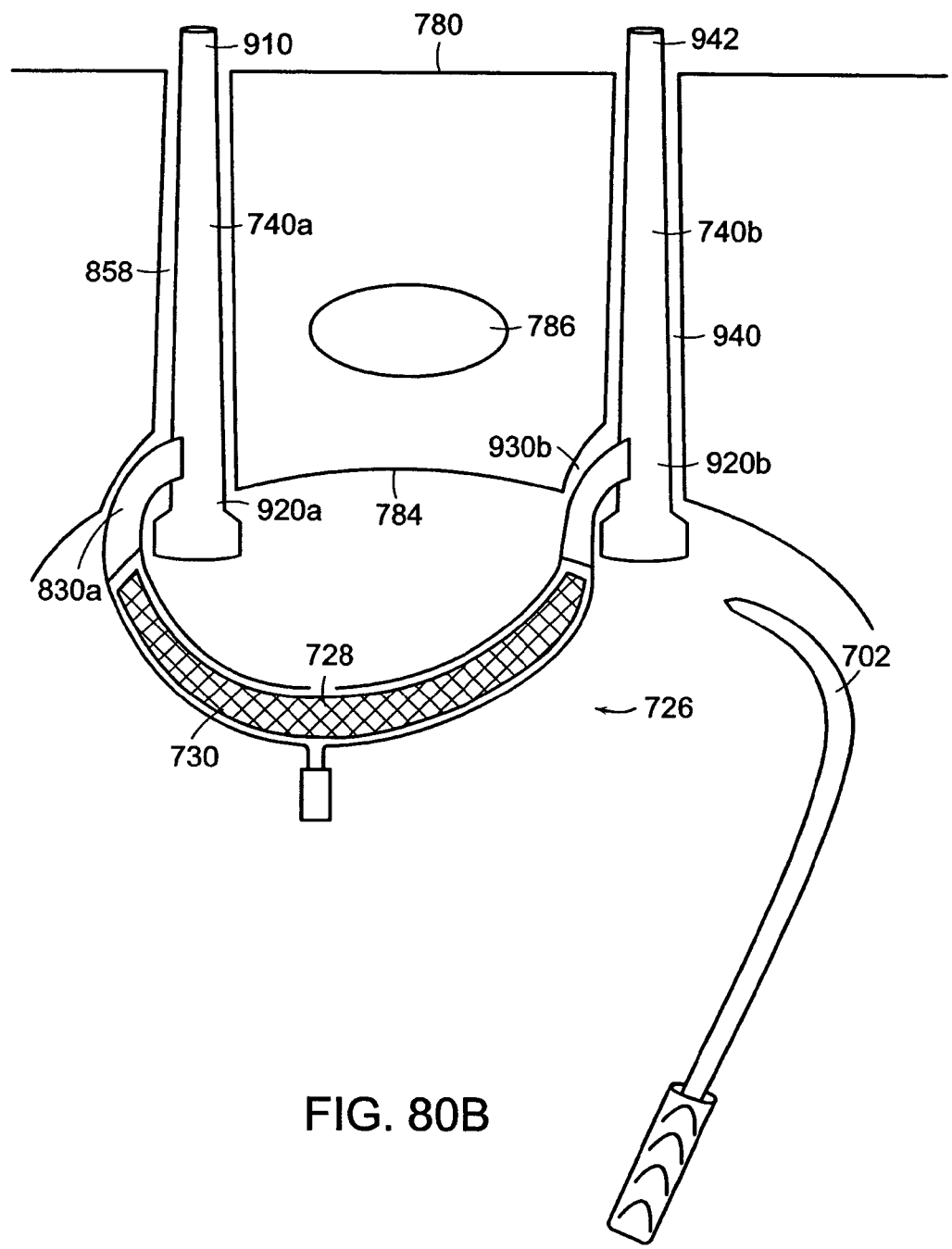

FIGS. 80A and 80B illustrate another transvaginal approach, which employs the delivery system of FIG. 70 or 71. As described previously, the sling assembly 726 is interconnected to the proximal end 746*a* of the first guide tube 740*a* and to the proximal end 746*b* of the second guide tube 740*b*. The second guide tube 740*b* slidably interfits over the shaft 702 via proximal opening 750 (FIG. 70A), or via the side port 754*b* (FIG. 71). The first guide tube 740*a* slidably interfits over the second guide tube 740*b* via the proximal opening 744 (FIG. 70), or via the side port 754*b* (FIG. 71). The distal tip 707 of the shaft 702 extends through a distal opening 742 of the first guide tube 740*a*.

In use, the operator tunnels transvaginally to create the first tunnel 858 as described in connection with FIGS. 76A and 76B, until the distal end 910 of the first guide tube 740*a* emerges from the abdominal skin 780. The operator then slides the second guide tube 740*b* from inside the first guide tube 740*a*, and withdraws the second guide tube 740*b* out of the vaginal wall 784 via the first tunnel 858. The distal end 910 of the first guide tube 740a is clamped outside the abdominal skin 780 with the rest of the first guide tube 740a remaining inside the first tunnel 858. The end 930a of the sling assembly 726 remains interconnected with the proximal end 746a of the guide tube 740a. The operator then creates a second tissue tunnel 940 from the vaginal wall 784 to the abdominal skin 780 on the contralateral side of the urethra 786, similar to the first tunnel 858, using the shaft 702 slidingly interfitted through the second guide tube 740b. After a distal end 942 of the second guide tube 740b emerges from the abdominal skin 780, the operator slides the shaft 702 out of the second guide tube 740b, and withdraws the shaft 702 out of the vaginal wall 784 via the second tunnel 940. Subsequent to cystoscopy, the operator grasps both distal ends 910 and 942 of the first and second guide tubes 740a and 740b, and pulls the two guide tubes 740a and 740b out of the abdominal skin 780 via the first and second tunnels 858 and 940. Once the ends 930a and 930b of the sling assembly 726 emerge out of the abdominal skin 780, the operator separates the ends 930a and 930b from the proximal tube ends 920a and 920b, respectively. The operator further adjusts the position and tension in the sling assembly 726 before removing the sleeve member 730 from the body of the patient. Cystoscopy can be performed while the guide tubes are in the tunnel before being pulled through.

Figure 81A:
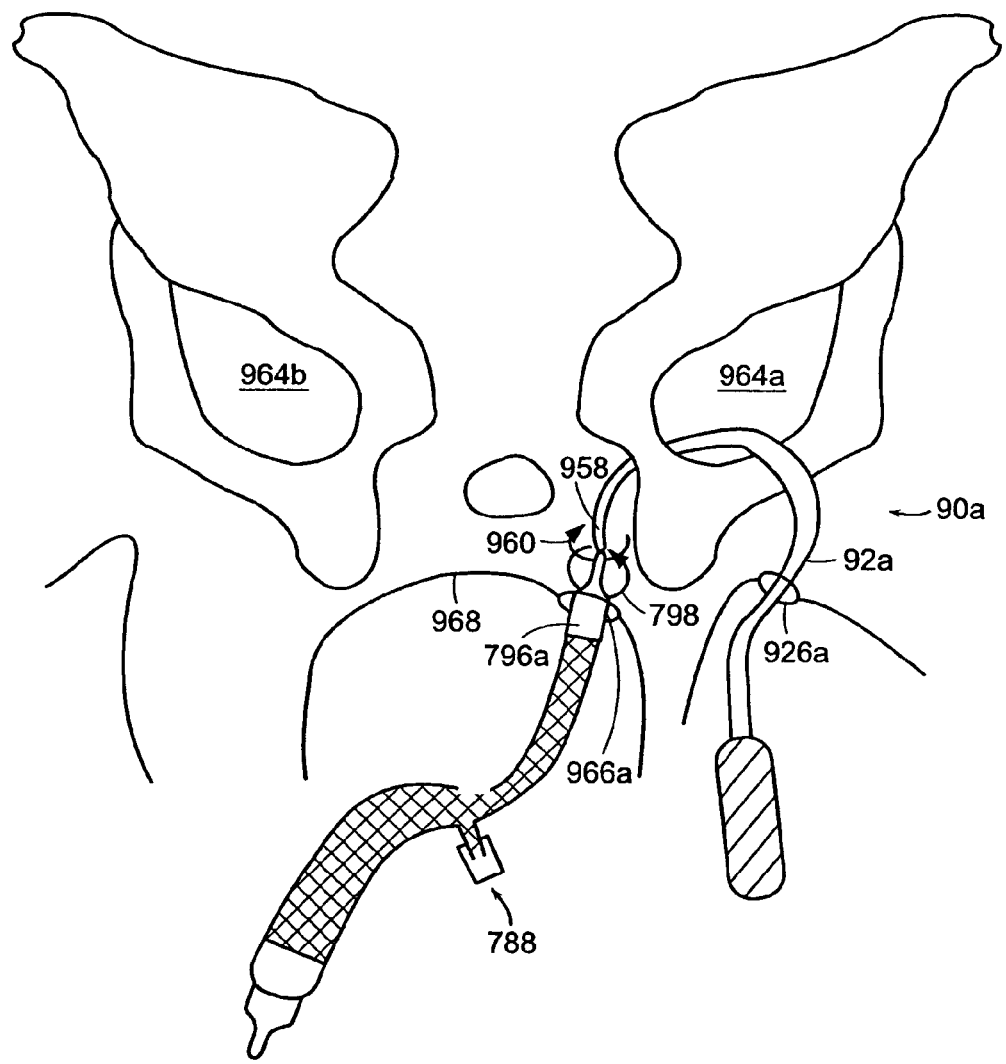
FIGS. 81A and 81B depict schematic views of steps in a trans-obturator approach to deliver a medical implant to an anatomical site in the patient, according to another illustrative embodiments of the invention.
Figure 81B:
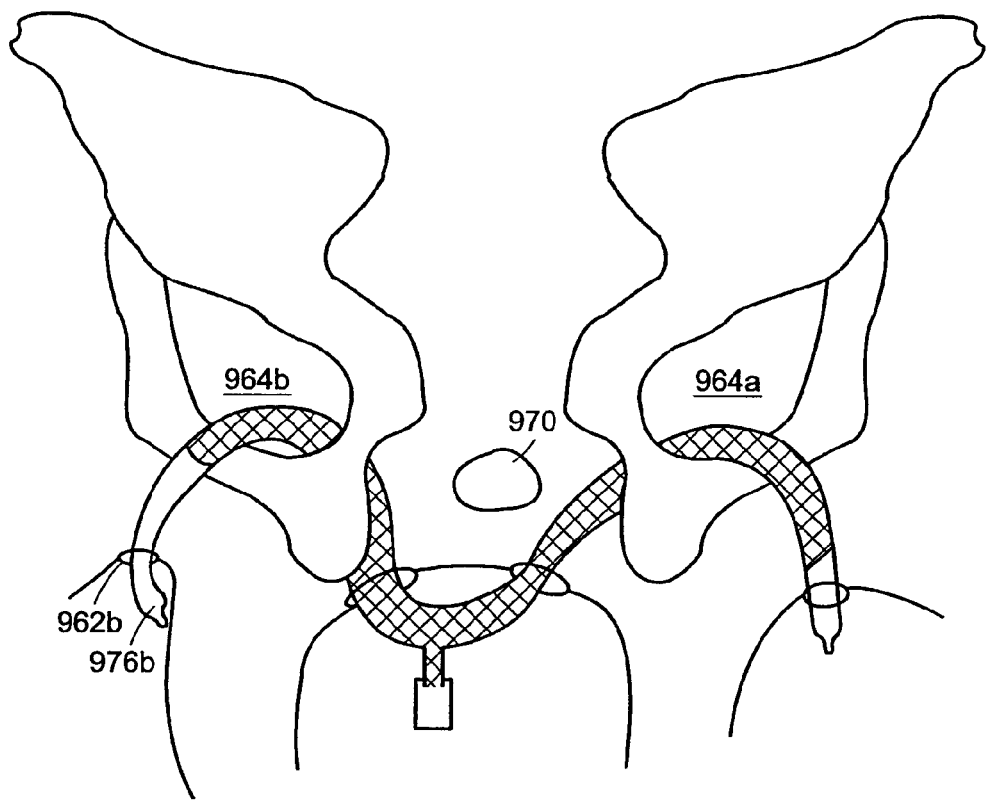

FIGS. 81A and 81B depict an illustrative trans-obturator approach using the delivery device 90a of FIG. 17 or the delivery device 90b of FIG. 18. Other embodiments of delivery devices including those described here or incorporated by reference can also be used for this approach. Taking the delivery device 90a as an example: as previously described, the delivery device 90a includes a shaft 92a and a handle 93a. The shaft 92a, at least in part, describes an arc of a substantial degree, for example, no less than about 45, about 60, or about 90 degrees in various embodiments. In one embodiment, the curve in the shaft 92a forms a "C" configuration. In the alternative delivery device embodiment 90b described previously with respect to FIG. 18, the needle shaft 92b describes the helical curve 94.

According to one exemplary embodiment of the trans-obturator approach using the delivery device embodiment 90a, a first incision 962a is made on the inside of the patient's thigh, for example, about 1 cm outside the external margin of the labia majora. The operator inserts the shaft 92a, tip first, into the first incision 962a on the thigh and continues to penetrate a first obturator foramen 964a. With a rotating wrist motion, the shaft is guided along the posterior ischiopubic ramus to a first vaginal incision 966a on the vaginal wall 968. After a distal portion 958 of the shaft 92a emerges out of the vaginal wall 968, the operator interconnects a first connector 960 attached to the shaft distal end 958, with a second connector 798 attached to the sleeve end 796a. Alternatively, a guide tube such as previously described and having a connector attached to a distal end, can be slid over the shaft 952 before the incision, and the connector on the guide tube can interconnect with the sleeve end 796a. Then, the operator withdraws the delivery device 90a back out of the obturator foramen 964a, bringing the sleeve end 796a of the sling assembly 788 out of the first thigh incision 962a.

Referring also to FIG. 81B, the operator repeats the above steps on the contralateral side of the urethra 970 and threads or tunnels the other sleeve end 796b through the other obturator foramen 964b and out of a second thigh incision 962b. After proper adjustment of the position, the thigh incisions may be closed. In some embodiments the sling ends are anchored to the pelvic bones. However, in other embodiments, the sling ends remain unanchored. Alternatively, the operator can reverse the direction in the trans-obturator approach by starting from a vaginal incision and tunneling through the obturator foramen to the thigh incision using the same embodiments described above.

V. Guide Member

According to one aspect of the invention, an implant, for example, a sling assembly, can be equipped with guide members that facilitate the delivery of the implant. The guide members can have a male insertive feature or a female receptive feature. The guide member can be solid or hollow and may include laterally placed apertures. Various illustrative guide member embodiments will now be discussed.

Figure 82:
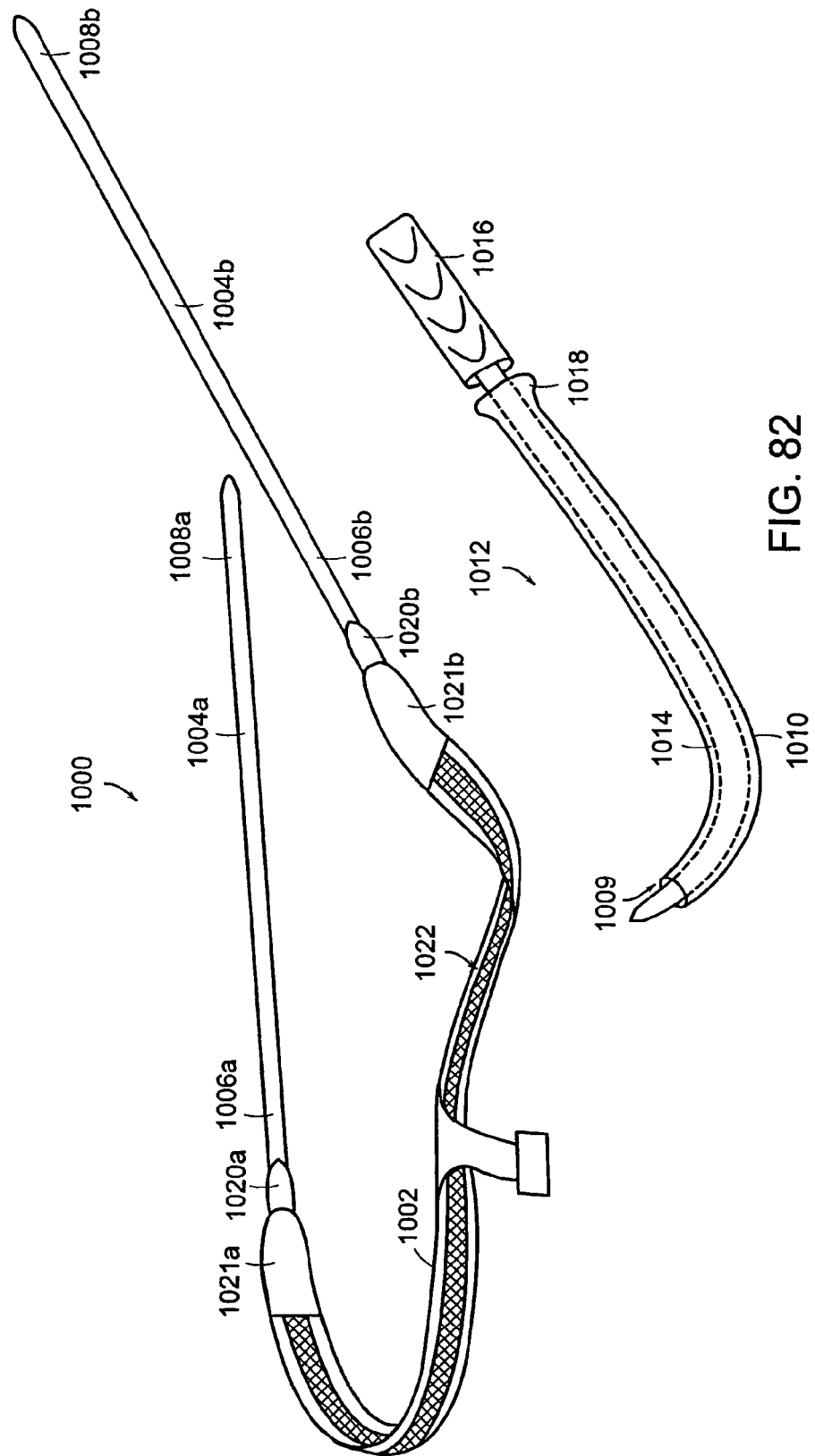
FIG. 82 depicts a side perspective view of a sling assembly with two male guide members, and a delivery device, according to an illustrative embodiment of the invention.

FIG. 82 depicts an illustrative sling assembly 1000. The sling assembly 1000 includes a sling 1002, and two guide members 1004a and 1004b. In this embodiment, the guide members 1004a and 1004b are formed as solid rods, each having a first end (1006a, 1006b) and a second end (1008a, 1008b). However, in other embodiments, the guide members 1004a and 1004b may be hollow. In one embodiment, the second ends 1008a and 1008b taper and are advantageous in performing insertive functions. In some configurations, the distal ends 1008a and 1008b terminate in conical tips capable of tissue piercing functions. Alternatively, the guide members 1004a and 1004b have a substantially constant diameter. The guide members 1004a and 1004b are shaped and sized to slidably move within an axial lumen 1009 of a guide tube 1010.

The illustrated guide members 1004a and 1004b are substantially straight and made from flexible materials that permit them to flex. In one embodiment, the guide members 1004a and 1004b have enough flexibility to negotiate a curve, for example, a curve in the lumen 1009 of the guide tube 1010. According to another feature, the outer diameter of the guide members 1004a and 1004b are less than the inner diameter of the lumen 1009 of the guide tube 1010. In one embodiment, the first ends 1006a and 1006b of the guide members 1004a and 1004b are adjacent dilators 1020a and 1020b, respectively. In one embodiment, the guide members 1004a and 1004b are longer than the guide tube 1010. However, the guide members 1004a and 1004b may be of any suitable length, including less than or equal to that of the guide tube 1010.

With continued reference to FIG. 82, the sling assembly 1000 may include a sleeve member 1022 that at least partly encloses the sling 1002. The first end 1006a of the guide member 1004a secures to the sleeve assembly end 1021a, for example, by heat bonding or other suitable mechanism. Similarly, the first end 1006b of the guide member 1004b attaches to the sling assembly end 1021b. In some embodiments, the guide members 1004a and 1004b interconnect with the sleeve assembly ends 1021a and 1021b through connectors such as those previously described and/or incorporated by reference in this application.

Figure 83:
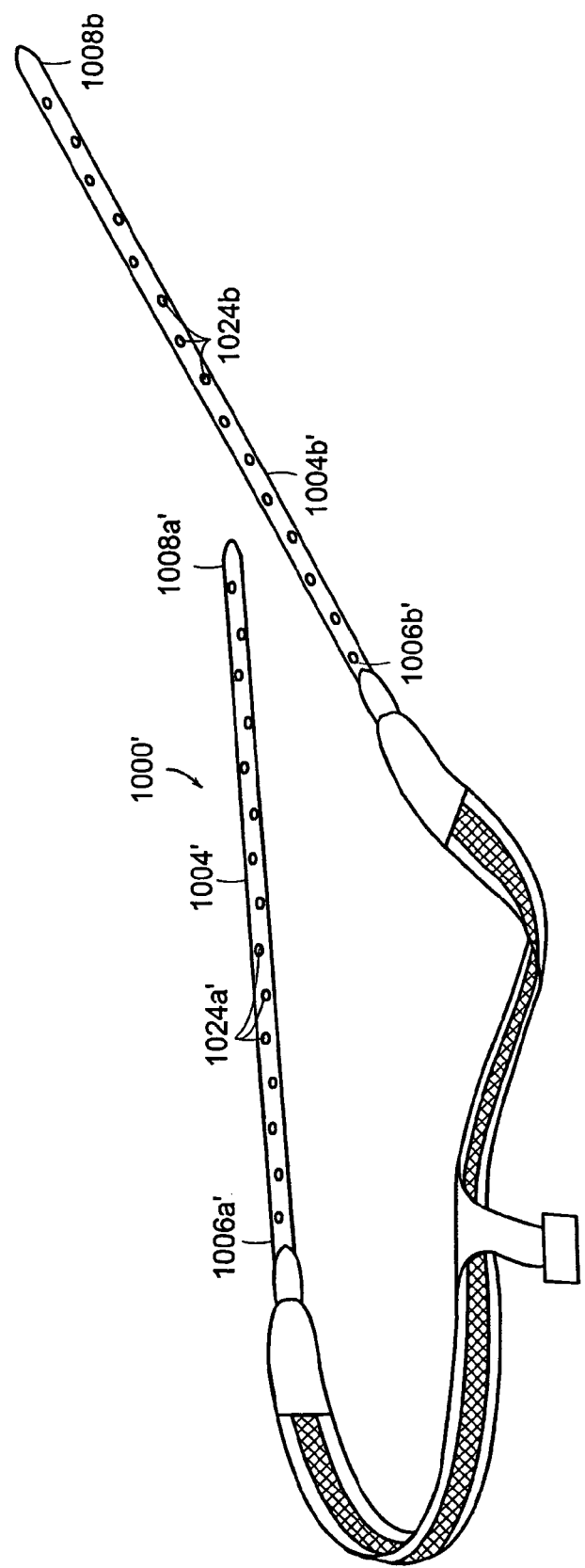
FIG. 83 depicts a side perspective view of an alternative embodiment to the male guide members of FIG. 82, according to an embodiment of the invention.

FIG. 83 depicts a sling assembly 1000' employing an alternative embodiment of the guide members 1004a and 1004b. More particularly, the sling assembly 1000' includes two guide member 1004a' and 1004b', which each have an axial lumen extending from a first end (1006a', 1006b') a second end (1008a', 1008b'). Optionally, the guide members 1004a' and 1004b' each include one or more apertures 1024a and 1024b, respectively, which are in fluid communication with the axial lumen. As described previously in connection with FIGS. 10A, 10B and 11, the apertures 1024a and 1024b are advantageous in alerting the operator of any perforation in an organ, such as the bladder, during the delivery procedure. The guide members 1004*a*' and 1004*b*' may or may not have a distal opening that is communicative with the axial lumen.

Figure 84B:
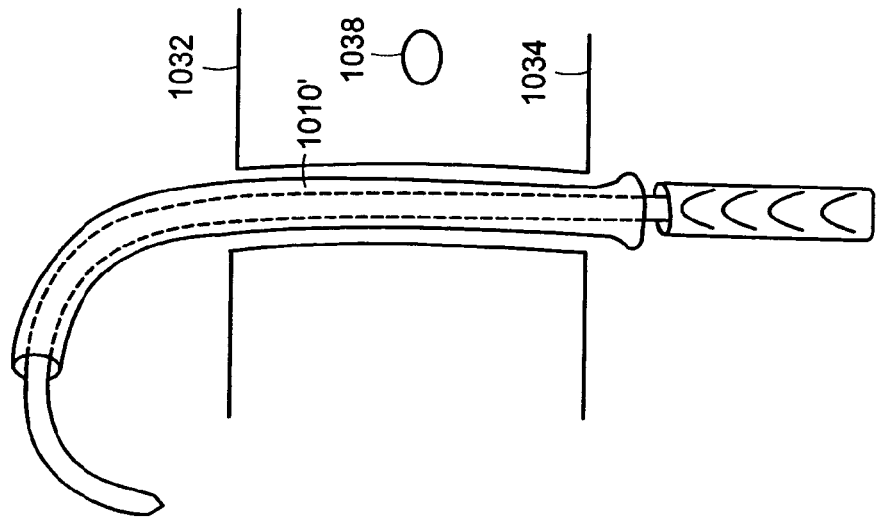
FIG. 84B depicts a schematic view of steps in a transvaginal delivery approach using the delivery device shown in FIG. 84A.
Figure 84A:
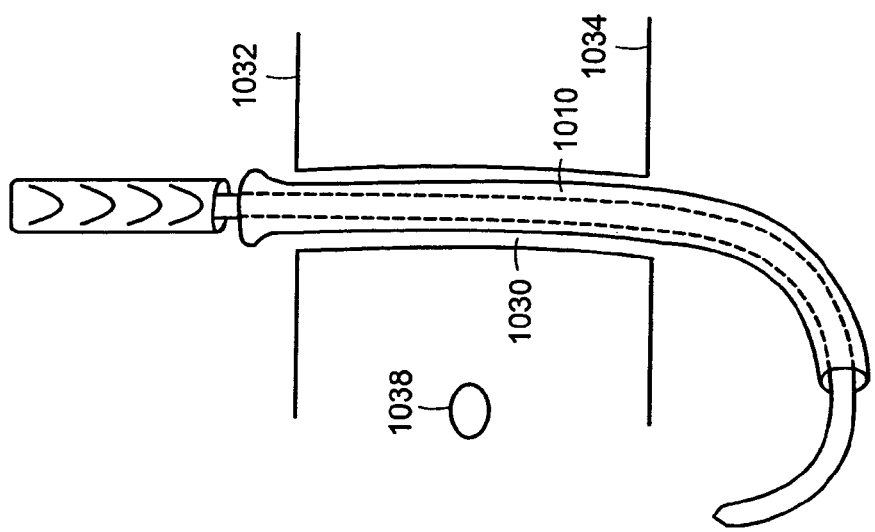
FIG. 84A depicts a schematic view of steps in a suprapubic or prepubic delivery approach using a delivery device including a shaft and a guide tube.

The guide members, which are interconnected with the sling assembly 1022, can facilitate the delivery of the sling assembly to an anatomical site, whether in a suprapubic, prepubic, transvaginal, or trans-obturator approach. In a preferred embodiment, the guide members are used in conjunction with a guide tube. Referring to FIGS. 84A and 84B, in one illustrative embodiment, the guide tube 1010 and 1010' are installed between the vaginal wall 1034 and the abdominal skin 1032 on either side of the urethra using any suitable transvaginal, suprapubic or prepubic.

Figure 84C:
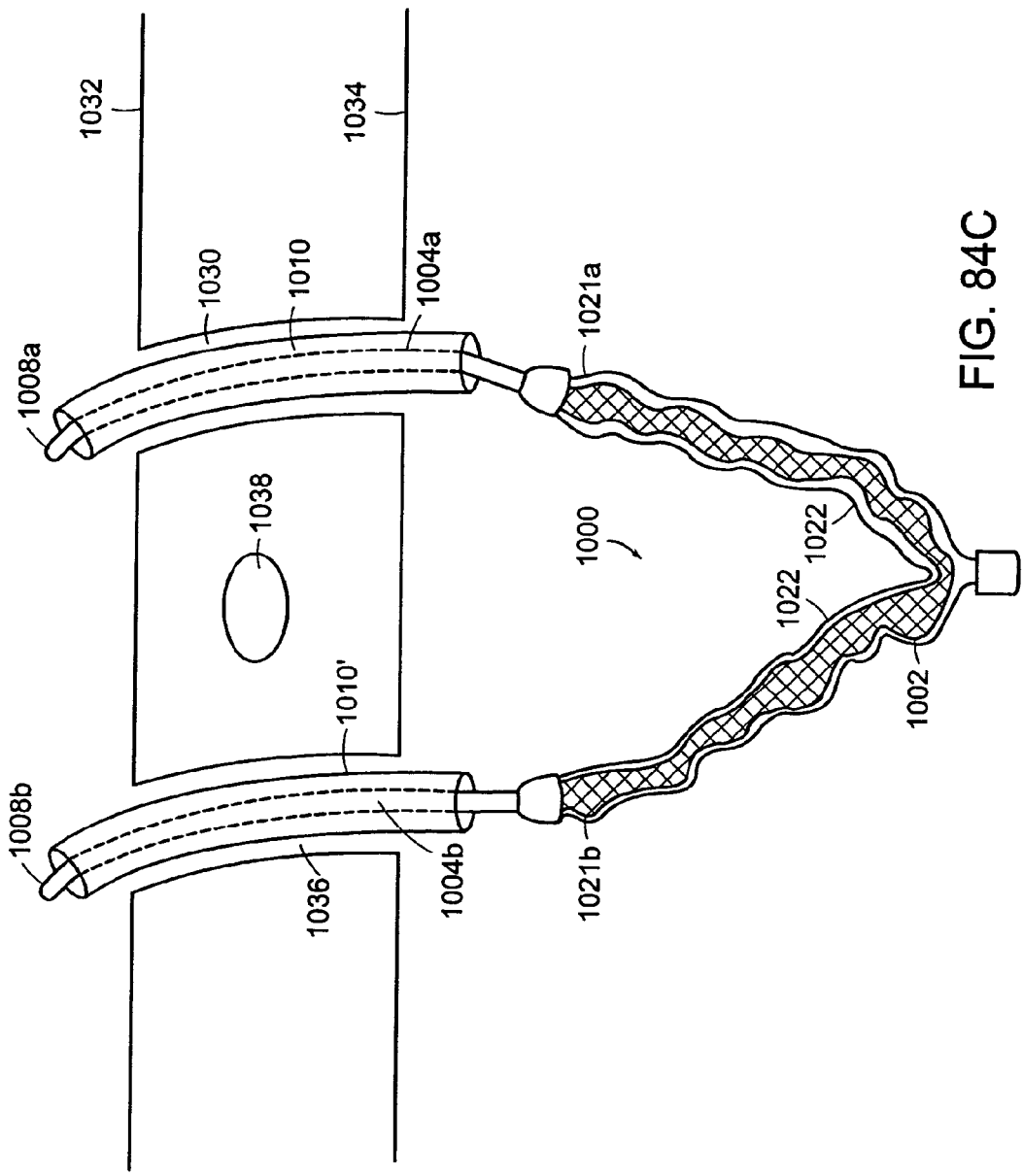
FIG. 84C depicts a schematic view of steps using the male guide members of the general type shown in FIG. 82 subsequent to steps shown in FIG. 84A or 84B.

Referring to FIG. 84C, the guide members 1004*a* and 1004*b* can then be inserted transvaginally through the guide tubes 1010 and 1010', respectively. The operator pulls the second ends 1008*a* and 1008*b* of the guide members 1004*a* and 1004*b* and the respective guide tubes 1010 and 1010' from the first and second tunnels 1030 and 1036 until the sleeve ends 1021*a* and 1021*b* emerge from the abdominal skin 1032. The operator then grasps the sleeve ends 1021*a* and 1021*b* and adjusts the position and tension of the sleeve member 1022. Once positioned, the sleeve member 1022 is removed from the patient's body as previously described, leaving the sling 1002 in place.

Figure 85:
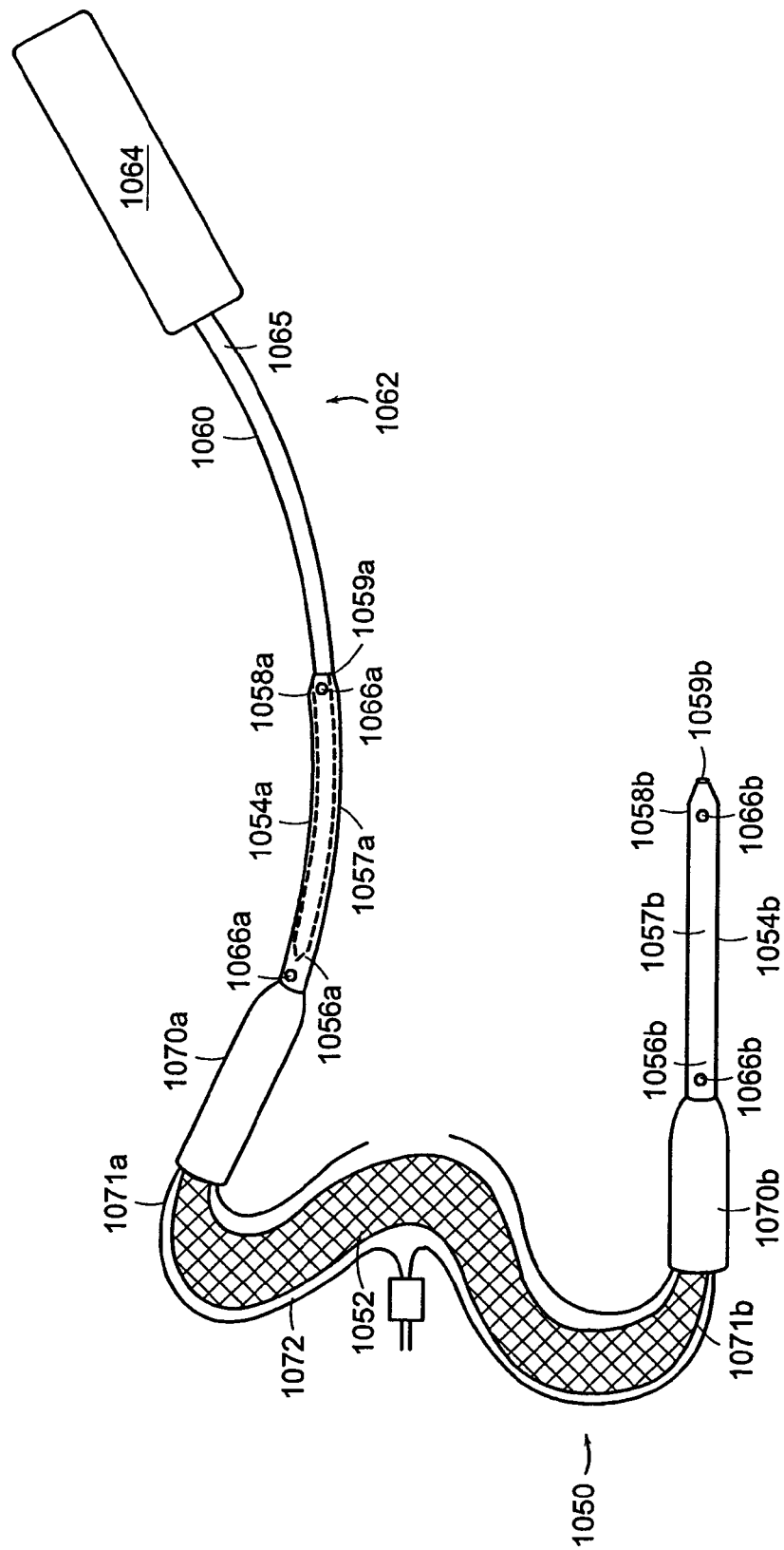
FIG. 85 depicts a side perspective view of an implant delivery system including two female guide members, according to an illustrative embodiment of the invention.

FIG. 85 depicts an illustrative embodiment of a sling assembly 1050 including guide members 1054*a* and 1054*b* having receptacle connectors at their free ends 1058*a*, 1058*b*. Each of the guide members 1054*a* and 1054*b* has a first end 1056*a*, 1056*b*) and a second, free end 1058*a*, 1058*b*. A receptacle 1057*a*, 1057*b* extends from a terminal opening 1059*a*, 1059*b* of the guide members 1054*a* and 1054*b* and terminates anywhere along the length of the guide members 1054*a* and 1054*b*. According to one feature, the guide members 1054*a* and 1054*b* have a tubular structure with openings at both the first end (1056*a*, 1056*b*) and the second end (1058*a*, 1058*b*) that are in fluid communication with the axial lumen (1057*a*, 1057*b*). In one embodiment, the free ends 1058*a* and 1058*b* of the guide members 1054*a* and 1054*b* taper axially inward and are advantageous in performing tissue dilation. Alternatively, the guide members 1054*a* and 1054*b* have a substantially constant diameter. The receptacles 1057*a* and 1057*b* are shaped and sized to slidably fit over a distal end of a delivery shaft 1060. The shaft 1060 attaches at a proximal end 1065 to a handle 1064. Optionally, each of the guide members 1054*a* and 1054*b* may have one or more apertures 1066*a* and 1066*b*, respectively, that are in fluid communication with the receptacles 1057*a* and 1057*b*, respectively.

The illustrated guide members 1054*a* and 1054*b* may be made sufficiently rigid to slide over the shaft 1060 against the pressure from surrounding tissue inside a tissue tunnel. For example, in one embodiment, the guide members 1054*a* and 1054*b* are made of stainless steel. In one feature, the first end (1056*a*, 1056*b*) of the guide members 1054*a* and 1054*b* are adjacent to an optional dilator (1070*a*, 1070*b*). In one embodiment, the guide members 1054*a* and 1054*b* are longer than the shaft 1060. However, the guide members 1054*a* and 1054*b* may be of any suitable length, including less than or equal to that of the shaft 1060.

With continued reference to FIG. 85, the sling assembly 1050 may include a sleeve member 1072 that at least partly encloses the sling 1052. The guide members 1054*a* and 1054*b* may be secured to the sleeve ends 1071*a* and 1071*b*, respectively, via the dilators 1070*a* and 1070*b*, for example, by heat bonding or other suitable mechanism. Alternatively, the guide members 1054*a* and 1054*b* can be interconnected with the sleeve ends 1071*a* and 1071*b*, respectively, via connectors such as those described previously.

Figure 86A:
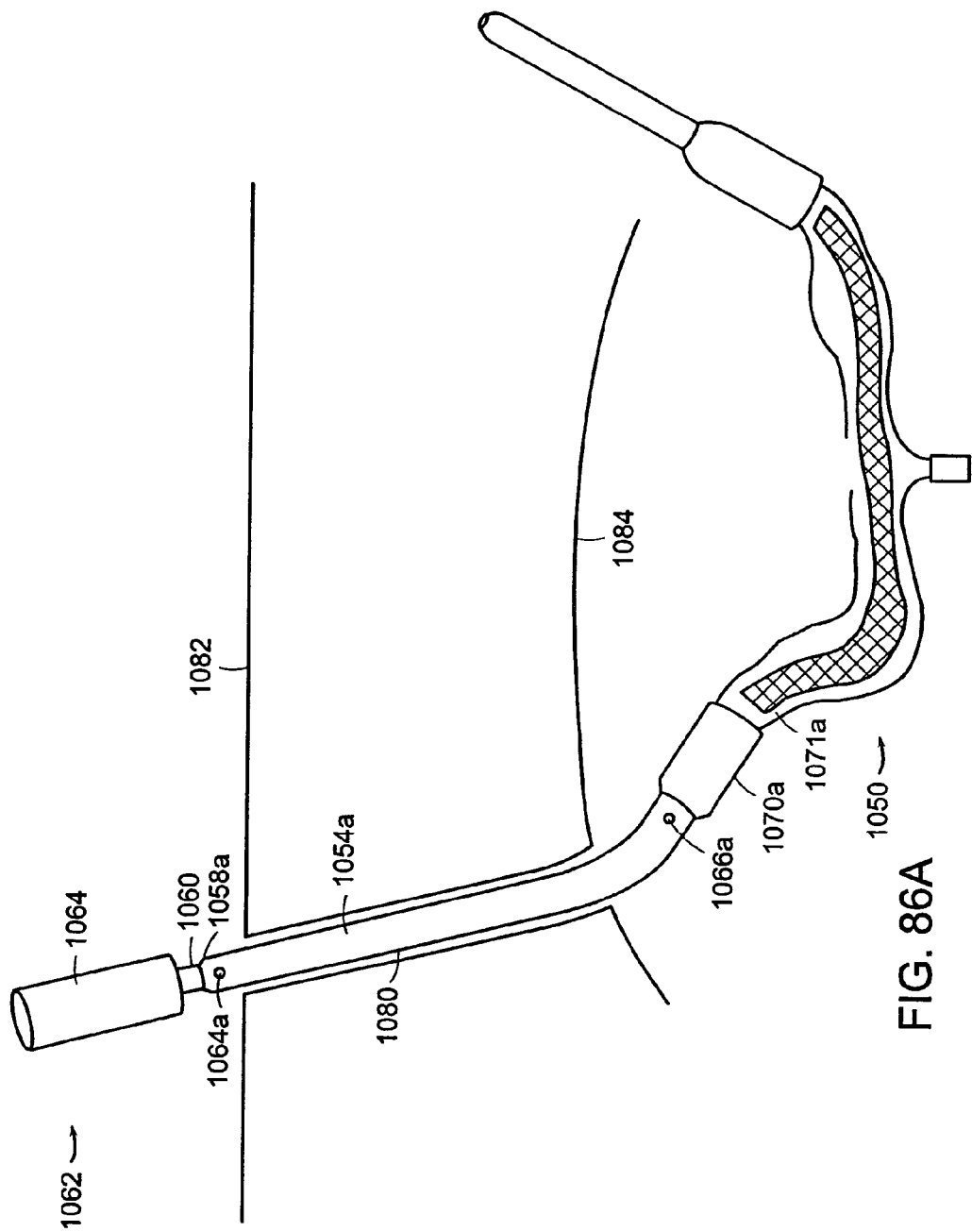
FIGS. 86A and 86B depict schematic views of steps in a suprapubic or prepubic delivery approach using the delivery device of FIG. 85.

The guide members 1054*a* and 1054*b* can facilitate the delivery of the sling assembly 1050 to an anatomical site using a suprapubic, prepubic, transvaginal, trans-obturator, or any other approach. Referring to FIG. 86A, in an illustrative embodiment of both the suprapubic and prepubic approaches, a first tunnel 1080 between the abdominal skin 1082 and the vaginal wall 1084 is created by the insertion of the delivery device 1062 from the abdominal side to the vaginal side as described above in other method embodiments. Once the operator has determined that the bladder has not been perforated, the operator slides the receptacle 1057*a* of the first guide member 1054*a* onto the shaft 1060. The operator proceeds to advance the first guide member 1054*a* inside the first tunnel 1080 onto the shaft 1060 until the second end 1058*a* of the first guide member 1054*a* emerges from the patient's abdominal skin 1082. The optional tapering feature at the second end 1058*a* of the first guide member 1054*a* is advantageous for the advancing step as the first guide member 1054*a* dilates the first tunnel 1080 to advance. If the first guide member 1054*a* includes the optional apertures 1066*a*, fluid seeping through the apertures 1066*a* will alert the operator to perforation of the bladder.

Figure 86B:
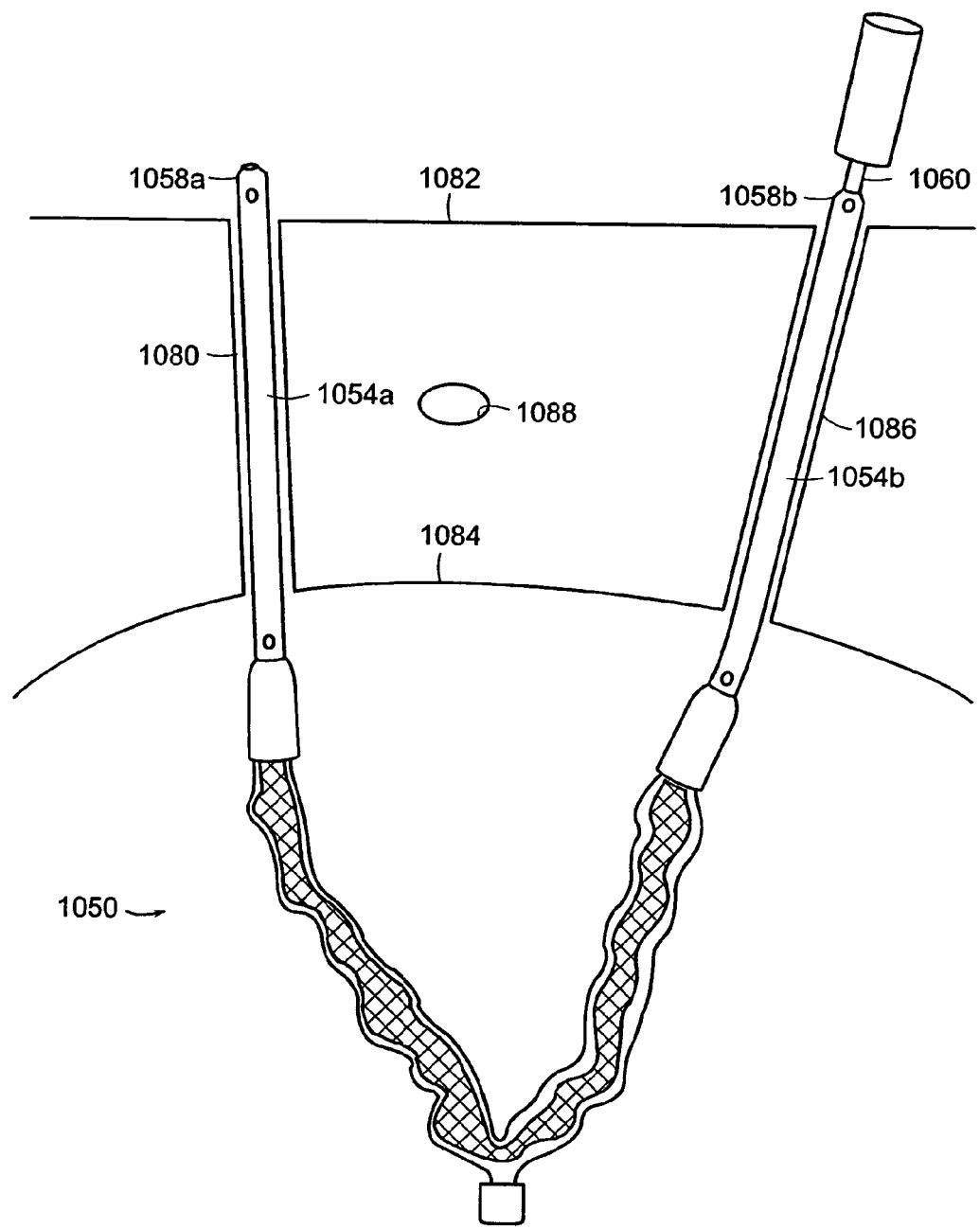

Referring also to FIG. 86B, the operator withdraws the shaft 1060, leaving the first guide member 1054*a* in the first tunnel 1080 with the first end 1058*a* outside the abdominal skin 1082. The operator then uses the same shaft 1060 or a second shaft to create a second tunnel 1086 in a similar fashion on the contralateral side of the urethra 1088. The operator, repeating the steps with respect to the first guide member 1054*a*, advances the second guide member 1054*b* inside the second tunnel 1086 over the shaft 1060 until the second end 1058*b* of the second guide member 1054*b* emerges from the abdominal skin 1082. The operator then pulls the first and second guide members 1054*a* and 1054*b* from the patient's tissues through the first 1080 and second 1086 tunnels, respectively, and out of the abdominal skin 1082, and completes the delivery procedure as described above.

In an alternative embodiment, the shaft 1086 interfits tightly into the receptacles 1057*a* and 1057*b*, and the operator withdraws the shaft 1086 to withdraw the respective sleeve ends 1071*a* and 1071*b* through the abdominal incisions.

Figure 87A:
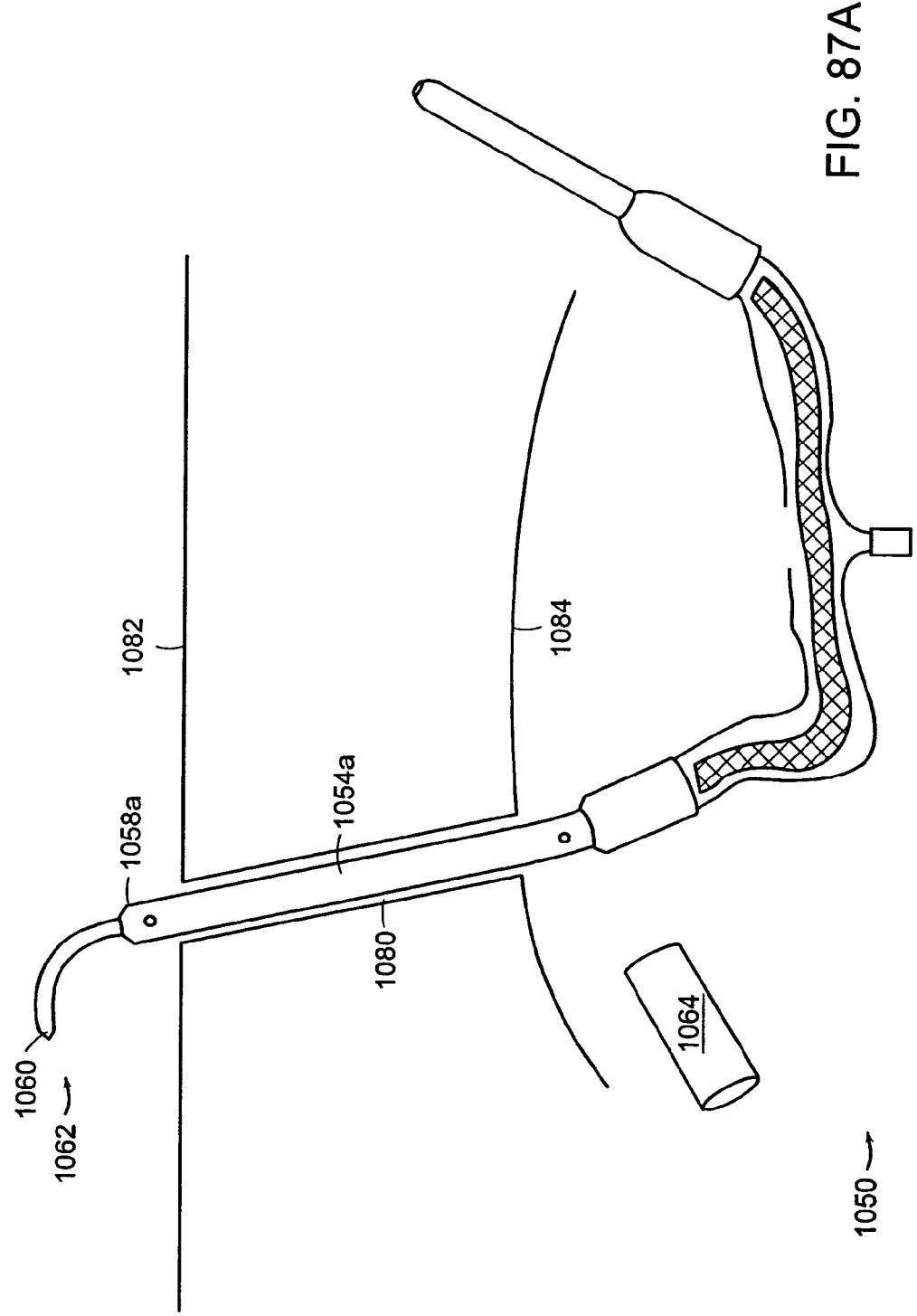
FIGS. 87A and 87B depict schematic views of steps in a transvaginal delivery approach using the delivery device of FIG. 85.

Referring now to FIG. 87A, in an illustrative embodiment of a transvaginal approach, the first tunnel 1080 between the vaginal wall 1084 and the abdominal skin 1082 is created by the insertion of the delivery device 1062 from the vaginal wall 1084 to get to the abdominal skin 1082 as described above in other method embodiments. The handle 1064, which is reversibly associated with the shaft 1060, is taken off the proximal end 1065 of the shaft 1060 (FIG. 85). The operator slides the first guide member 1054*a* over the proximal end 1065 of the shaft 1060 (FIG. 85), and advances the first guide member 1054*a* in the first tunnel 1080 until the second end 1058*a* of the first guide member 1054*a* emerges from the abdominal skin 1082.

Figure 87B:
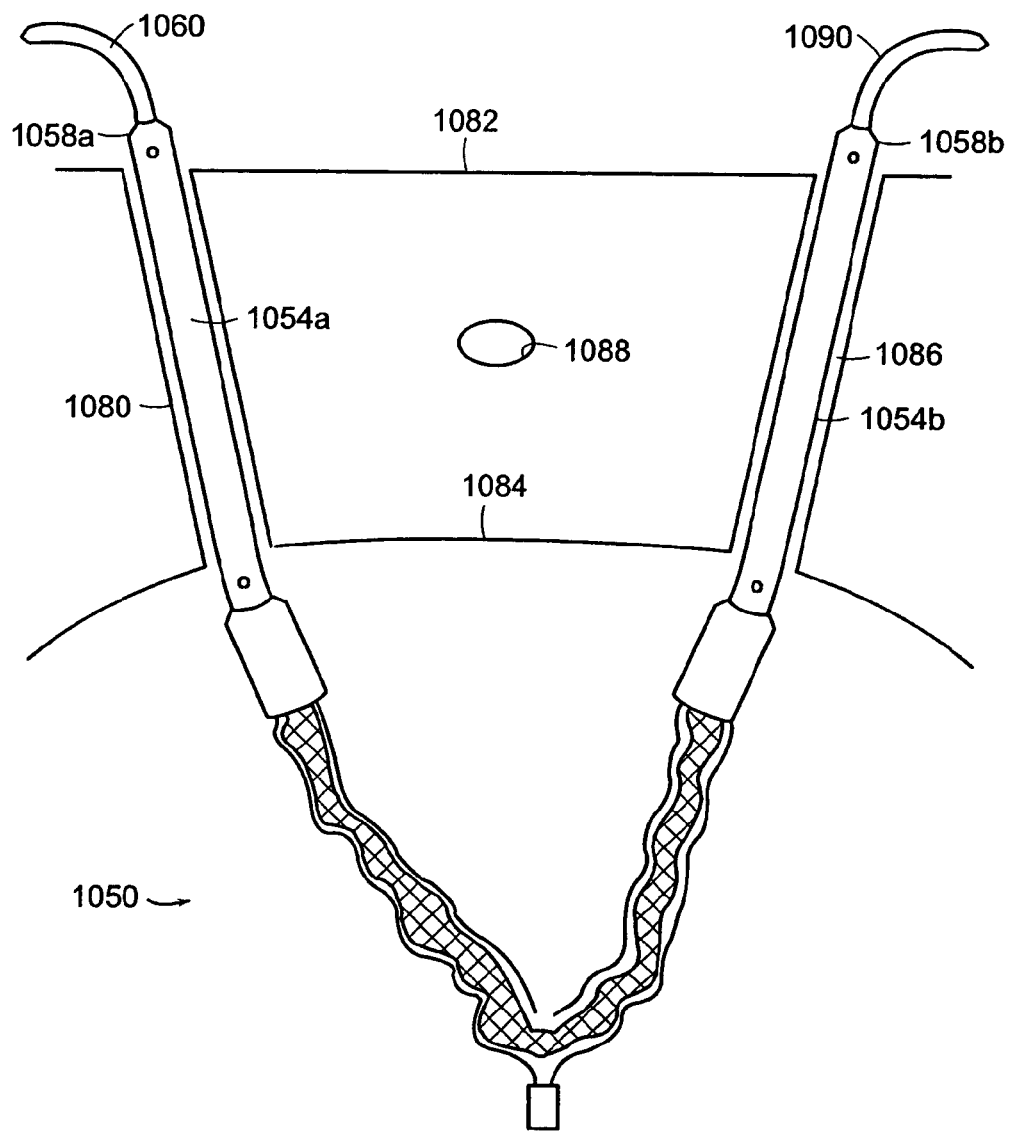

Referring also to FIG. 87B, the operator then uses a second shaft 1090 to create the second tunnel 1086 in a similar fashion on the contralateral side of the urethra 1088. The operator, repeating the steps with respect to the first guide member 1054*a*, removes the handle 1064 and slides the second guide member 1054*b* over a proximal end of the second shaft 1090. The operator advances the second guide member 1054*b* inside the second tunnel 1086 over the second shaft 1090 until the distal end 1058*b* of the second guide member 1054b emerges from the abdominal skin 1082. The operator then pulls the first and second guide members 1054s and 1054b, with the first and second shafts 1060 and 1090, out of the patient's body through the first 1080 and second 1086 tunnels, respectively. After the first and second guide members 1054a and 1054b are out of the abdominal skin 1082, the operator completes the delivery procedure as described above.

Variations, modifications, and other implementations of what is described may be employed without departing from the spirit and the scope of the invention. More specifically, any of the method, system and device features described above or incorporated by reference may be combined with any other suitable method, system or device features disclosed herein or incorporated by reference, and is within the scope of the contemplated inventions.

What is claimed is:

1. A connector pair for attaching a medical implant to a delivery device, the connector pair comprising,
    a substantially rigid closed loop connector located at an end of a medical implant, the closed loop connector including a base portion, a neck portion, and a loop portion, and
    a slotted connector formed in a distal end of a shaft of a delivery device for interfitting with the closed loop connector of the medical implant, the slotted connector including a first leg, a second leg, a first channel, and a second channel, the first leg extending radially into the shaft and the second leg extending axially in a distal direction along the shaft, the first channel and the second channel extending from the second leg,
    the neck portion of the closed loop connector configured to lock into the first channel and the second channel.

2. The connector pair of claim 1, wherein the closed loop connector is shaped to track the distal end of the shaft.

3. The connector pair of claim 1, wherein the base portion extends from the end of the medical implant to the neck portion, the neck portion tapering radially outward and extending axially from the base portion to the loop portion, the loop portion being curved.

4. The connector pair of claim 1, wherein the distal end of the shaft is tapered for interfitting with the neck portion of the closed loop connector.

5. The connector pair of claim 1, wherein the first channel and the second channel are located substantially diametrically opposite each other in the distal end of the shaft.

6. The connector pair of claim 1, wherein the closed loop connector and the slotted connector are sized for end to end interconnection between the medical implant and the shaft of the delivery device.

7. The connector pair of claim 1, wherein the closed loop connector interfits within the second leg of the slotted connector.

8. A connector pair for attaching a medical implant to a delivery device, the connector pair comprising,
    a closed loop connector located at an end of a medical implant, the closed loop connector including a base portion, a neck portion, and a loop portion, and
    a slotted connector formed in a distal end of a shaft of a delivery device for interfitting with the closed loop connector of the medical implant, the slotted connector including a first leg, a second leg, a first channel, and a second channel, the first leg extending radially into the shaft and the second leg extending axially in a distal direction along the shaft and includes a narrowing for locking the looped connector into the second leg,
    the neck portion of the closed loop connector configured to lock into with the first channel and the second channel.

9. The connector pair of claim 8, wherein the second leg of the slotted connector is longer than the first leg of the slotted connector.

10. The connector pair of claim 8, wherein the second leg of the slotted connector extends distally at about a 90 degree angle relative to the first leg of the slotted connector.

11. The connector pair of claim 8, wherein the narrowing is formed where the second leg initially extends from the first leg.

12. The connector pair of claim 8, wherein the second leg at the narrowing has a width of less than that of the loop portion of the closed loop connector.

13. The connector pair of claim 8, wherein the narrowing includes a protuberance in a wall of the second leg.

14. The connector pair of claim 13, wherein the protuberance forms a substantially flat shoulder facing a distal most end of the shaft.

15. A connector pair for attaching a medical implant to a delivery device, the connector pair comprising,
    a closed loop connector located at an end of a medical implant, the closed loop connector including a base portion, a neck portion, and a loop portion, and
    a slotted connector formed in a distal end of a shaft of a delivery device for interfitting with the closed loop connector of the medical implant, the slotted connector including a first, a leg, a first channel, and a second channel, the first leg extending radially into the shaft and the second leg extending axially in a distal direction along the shaft, wherein the second leg is substantially spherical in shape having an opening for accepting the looped connector at an intersection with the first leg,
    the neck portion of the closed loop connector configured to lock into with the first channel and the second chan.

16. The connector pair of claim 15, wherein the opening in the second leg has a width of less than that of the loop portion of the closed loop connector.

* * * * *